(12) United States Patent
Tsou et al.

(10) Patent No.: US 11,878,986 B2
(45) Date of Patent: Jan. 23, 2024

(54) POLY HETEROCYCLIC CONJUGATES AND THEIR PHARMACEUTICAL USES

(71) Applicant: National Health Research Institutes, Miaoli County (TW)

(72) Inventors: Lun Kelvin Tsou, Miaoli County (TW); Kuan-Hsun Huang, Miaoli County (TW); Chiung-Tong Chen, Miaoli County (TW); Chuan Shih, Carmel, IN (US)

(73) Assignee: National Health Research Institutes, Miaoli County (TW)

( * ) Notice: Subject to any disclaimer, the term of this patent is extended or adjusted under 35 U.S.C. 154(b) by 213 days.

(21) Appl. No.: 17/349,140

(22) Filed: Jun. 16, 2021

(65) Prior Publication Data

US 2021/0403483 A1 Dec. 30, 2021

Related U.S. Application Data

(60) Provisional application No. 63/042,276, filed on Jun. 22, 2020.

(51) Int. Cl.
| | | |
|---|---|---|
| C07D 493/04 | (2006.01) | |
| C07D 498/14 | (2006.01) | |
| C07D 498/18 | (2006.01) | |
| A61K 47/55 | (2017.01) | |
| A61P 35/00 | (2006.01) | |

(52) U.S. Cl.
CPC ............ *C07D 498/14* (2013.01); *A61K 47/55* (2017.08); *A61P 35/00* (2018.01)

(58) Field of Classification Search
CPC .. C07D 493/04; C07D 498/14; C07D 498/18; A61K 47/55; A61P 35/00
See application file for complete search history.

(56) References Cited

U.S. PATENT DOCUMENTS

| | | |
|---|---|---|
| 2014/0271490 A1 | 9/2014 | Matosziuk et al. |
| 2019/0167704 A1 | 6/2019 | Ponte et al. |
| 2019/0263935 A1 | 8/2019 | Kellogg et al. |

FOREIGN PATENT DOCUMENTS

WO WO-2015/179299 A1 11/2015

OTHER PUBLICATIONS

Liu et al "Targeting Tumor Associated Phosphatidylserine with New Zinc Dipicolylamine-Based Drug Conjugates" Bioconjugate Chemistry, 2017.
Plaunt et al "Library Synthesis, Screening, and Discovery of Modified Zinc(II)-Bis(Dipicolylamine) Probe for Enhanced Molecular Imaging of Cell Death" Bioconjugate Chemistry vol. 25, pp. 724-737, 2014.
Reddy et al "Folate Receptor-Specific Antitumor Activity of EC131, a Folate-Maytansinoid Conjugate" Cancer Research vol. 67, pp. 6376-6382, 2007.

*Primary Examiner* — Brenda L Coleman
(74) *Attorney, Agent, or Firm* — Morse, Barnes-Brown & Pendleton, P.C.; Martin Z. Zhang, Esq.

(57) ABSTRACT

Compounds of Formula (I) shown below and a pharmaceutical composition containing one of the compounds:

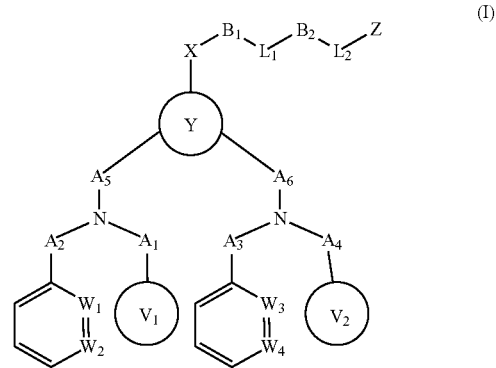

Each of the variables is defined herein. Also disclosed is a method of treating a condition associated with uncontrolled cell growth with a compound of Formula (I).

15 Claims, 3 Drawing Sheets

POLY HETEROCYCLIC CONJUGATES AND THEIR PHARMACEUTICAL USES

CROSS REFERENCE TO RELATED APPLICATION

This application claims priority of U.S. Provisional Application No. 63/042,276, filed on Jun. 22, 2020.

BACKGROUND

Phospholipid phosphatidylserine (PS), abundant on the external surfaces of cancer cells, is an established target molecule for cancer therapy. See Yin et al., Cancer Immunol Res 2013, 1, 256-268.

Ligand-targeted therapeutics offer enormous potential to enhance the precision and efficacy of anticancer therapies. See Srinivasarao et. al., Chem Rev 2017, 117, 12133-12164; Srinivasarao et. al., Nat Rev Drug Discov 2015, 14, 203-219; and Allen et. al., Science 2004, 303, 1818-1822. One strategy is to covalently link chemotherapeutic agents to antibodies that selectively recognize tumor antigens. However, antibody-drug conjugates have many drawbacks, including poor in vitro and in vivo stability, high antigenicity, difficult conjugation chemistry, high manufacturing cost, and low solid tumor penetration.

There is a need to develop new compounds for delivering therapeutic agents that associate with PS without the above-described drawbacks.

SUMMARY

The present invention is based on a discovery that certain small molecule drug conjugates are effective in delivering therapeutic agents to cancer cells that have phosphatidylserine on the external surfaces of their cell membranes.

This invention relates to compounds of Formula (I) shown below:

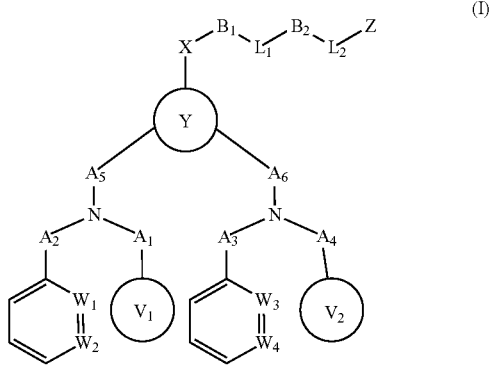

(I)

In this formula, each of $A_1$, $A_2$, $A_3$, $A_4$, $A_5$, and $A_6$, independently, is a $C_1$-$C_6$ bivalent aliphatic radical; $B_1$ is a bond, $C_1$-$C_6$ bivalent aliphatic radical, a $C_1$-$C_6$ bivalent heteroaliphatic radical, a bivalent aryl radical, a bivalent heteroaryl radical, or CHC(O)$R_1$, in which $R_1$ is a $C_1$-$C_6$ monovalent aliphatic radical, a $C_1$-$C_6$ monovalent heteroaliphatic radical, a monovalent aryl radical, a monovalent heteroaryl radical, a $C_1$-$C_{14}$ monovalent aralkyl radical, or a $C_1$-$C_{14}$ monovalent heteroaralkyl radical; $B_2$ is a bond, a $C_1$-$C_6$ bivalent aliphatic radical, a $C_1$-$C_6$ bivalent heteroaliphatic radical, a bivalent aryl radical, a bivalent heteroaryl radical, $D_1$-$NR_2$—C(O)-$D_2$, $D_1$-$NR_2$—C(O)-$D_2$-C(O)$NR_2'$-$D_3$, $D_1$-C(O)$NR_2$-$D_2$-$NR_2'$—C(O)-$D_3$, $D_1$-C(O)$NR_2$-$D_2$-$NR_2'$-$D_3$, $D_1$-$D_2$-C(O)—$NR_2$—C(O)-$D_3$, or $D_1$-$D_2$-$D_3$, each of $D_1$, $D_2$, $D_3$, independently, being a $C_1$-$C_6$ bivalent aliphatic radical, a $C_1$-$C_6$ bivalent heteroaliphatic radical, a bivalent aryl radical, a bivalent heteroaryl radical, a $C_1$-$C_{10}$ bivalent aralkyl radical, or a $C_1$-$C_{10}$ bivalent heteroaralkyl radical, and each of $R_2$ and $R_2'$, independently, being H, a $C_1$-$C_6$ bivalent heteroaliphatic radical, a bivalent aryl radical, a bivalent heteroaryl radical, a $C_1$-$C_{10}$ bivalent aralkyl radical, or C(O)$R_2''$, in which $R_2''$ is a $C_1$-$C_6$ monovalent aliphatic radical, a $C_1$-$C_6$ monovalent heteroaliphatic radical, a monovalent aryl radical, a monovalent heteroaryl radical, a $C_1$-$C_{14}$ monovalent aralkyl radical, or a $C_1$-$C_{14}$ monovalent heteroaralkyl radical; $L_1$ is a bond, $NR_3$, $NR_3$C(O), $NR_3$C(S), $NR_3$C$R_4$$R_5$, $NR_3$SO$_2$, $NR_3$C(O)$NR_4$, or $NR_3$C(S)$NR_4$, each of $R_3$, $R_4$, and $R_5$, independently, being H, a $C_1$-$C_6$ monovalent aliphatic radical, a $C_1$-$C_6$ monovalent heteroaliphatic radical, a monovalent aryl radical, a monovalent heteroaryl radical, a $C_1$-$C_{14}$ monovalent aralkyl radical, a $C_1$-$C_{14}$ monovalent heteroaralkyl radical, C(S)R', or C(O)R', in which R' is a $C_1$-$C_6$ monovalent aliphatic radical, a $C_1$-$C_6$ monovalent heteroaliphatic radical, a monovalent aryl radical, a monovalent heteroaryl radical, a $C_1$-$C_{14}$ monovalent aralkyl radical, or a $C_1$-$C_{14}$ monovalent heteroaralkyl radical; $L_2$ is a bond, $SR_6$, $SSR_6$, C(O)$SR_6$, $NR_6$, $NR_6$C(O), $NR_6$C(S), $NR_6$C$R_7$$R_8$, $NR_6$SO$_2$, $NR_6$C(O)$NR_7$, or $NR_6$C(S)$NR_7$, each of $R_6$, $R_7$, and $R_8$, independently, being H, a $C_1$-$C_6$ monovalent aliphatic radical, a $C_1$-$C_6$ monovalent heteroaliphatic radical, a monovalent aryl radical, a monovalent heteroaryl radical, a $C_1$-$C_{14}$ monovalent aralkyl radical, a $C_1$-$C_{14}$ monovalent heteroaralkyl radical, C(S)R', or C(O)R', in which R' is a $C_1$-$C_6$ monovalent aliphatic radical, a $C_1$-$C_6$ monovalent heteroaliphatic radical, a monovalent aryl radical, a monovalent heteroaryl radical, a $C_1$-$C_{14}$ monovalent aralkyl radical, or a $C_1$-$C_{14}$ monovalent heteroaralkyl radical; each of $W_1$, $W_2$, $W_3$, and $W_4$, independently, is N or C$R_5$, $R_5$ being H, halo, cyano, amino, hydroxyl, nitro, sulfhydryl, a $C_1$-$C_6$ aliphatic radical, a $C_1$-$C_6$ heteroaliphatic radical, a haloaliphatic radical, NHC(O)$R_9$, or NHC(O)NH$R_9$, in which $R_9$ is a $C_1$-$C_6$ monovalent aliphatic radical, a $C_1$-$C_6$ monovalent heteroaliphatic radical, a monovalent aryl radical, a monovalent heteroaryl radical, a $C_1$-$C_{14}$ monovalent aralkyl radical, or a $C_1$-$C_{14}$ monovalent heteroaralkyl radical; X is a bond, O, S, or $NR_6$, $R_6$ being H, a $C_1$-$C_6$ monovalent aliphatic radical, a $C_1$-$C_6$ monovalent heteroaliphatic radical, a monovalent aryl radical, a monovalent heteroaryl radical, a $C_1$-$C_{14}$ monovalent aralkyl radical, or a $C_1$-$C_{14}$ monovalent heteroaralkyl radical; Y is an aryl ring or a heteroaryl ring; each of $V_1$ and $V_2$, independently, is an aryl ring or a heteroaryl ring; and Z is an anticancer therapeutic moiety.

Each of the aliphatic radical, the heteroaliphatic radical, the aralkyl radical, and the heteroaralkyl radical is unsubstituted or substituted with halo, cyano, amino, hydroxyl, nitro, sulfhydryl, $C_1$-$C_6$ alkoxy, $C_1$-$C_6$ alkylamino, $C_1$-$C_{12}$ dialkylamino, or $C_1$-$C_6$ haloalkyl; and each of the aryl radical and the heteroaryl radical is unsubstituted or substituted with halo, cyano, amino, hydroxyl, nitro, sulfhydryl, a $C_1$-$C_6$ aliphatic radical, a $C_1$-$C_6$ heteroaliphatic radical, or a haloaliphatic radical.

The term "aliphatic" herein refers to a saturated or unsaturated, linear or branched, acyclic, cyclic, or polycyclic hydrocarbon moiety. Examples include, but are not limited to, alkyl, alkylene, alkenyl, alkenylene, alkynyl, alkynylene, cycloalkyl, cycloalkylene, cycloalkenyl, cycloalkenylene, cycloalkynyl, and cycloalkynylene moieties. The term "heteroaliphatic" herein refers to an aliphatic moiety containing at least one heteroatom selected from N, O, P, B, S, Si, Sb, Al, Sn, As, Se, and Ge. The term "haloaliphatic" herein refers to an aliphatic moiety substituted with one or more halogen atoms. The term "alkyl" herein refers to a straight or branched hydrocarbon group, containing 1-20 (e.g., 1-10 and 1-6) carbon atoms. Examples include methyl, ethyl, n-propyl, i-propyl, n-butyl, i-butyl, and t-butyl. The term "alkylene" refers to bivalent alkyl. Examples include —$CH_2$—, —$CH_2CH_2$—, —$CH_2CH_2CH_2$—, —$CH_2(CH_3)$ $CH_2$—, and —$CH_2CH_2CH_2CH_2$—. The term "haloalkyl" refers to alkyl substituted with one or more halogen (chloro, fluoro, bromo, or iodo) atoms. Examples include trifluoromethyl, bromomethyl, and 4,4,4-trifluorobutyl. The term "haloalkylene" refers to bivalent haloalkyl.

The term "heteroalkylene" refers to a bivalent alkyl group, in which one or more carbon atoms are replaced by a heteroatom (e.g., O, N, P, and S). The term "alkoxy" refers to an —O-alkyl group. Examples include methoxy, ethoxy, propoxy, and isopropoxy. The term "haloalkoxy" refers to alkoxy substituted with one or more halogen atoms.

The term "alkenyl" refers to a straight or branched hydrocarbon group, containing 2-20 (e.g., 2-10 and 2-6) carbon atoms and one or more double bonds.

The term "cycloalkyl" refers to a saturated and partially unsaturated monocyclic, bicyclic, tricyclic, or tetracyclic hydrocarbon group having 3 to 12 carbons. Examples of cycloalkyl groups include, but are not limited to, cyclopropyl, cyclobutyl, cyclopentyl, cyclopentenyl, cyclohexyl, cyclohexenyl, cycloheptyl, and cyclooctyl. The term "cycloalkylene" refers to bivalent cycloalkyl.

The term "heterocycloalkyl" refers to a nonaromatic 5-8 membered monocyclic, 8-12 membered bicyclic, or 11-14 membered tricyclic ring system having one or more heteroatoms (e.g., O, N, P, and S). Examples of heterocycloalkyl groups include, but are not limited to, piperazinyl, imidazolidinyl, azepanyl, pyrrolidinyl, dihydrothiadiazolyl, dioxanyl, morpholinyl, tetrahydropuranyl, and tetrahydrofuranyl. The term "heterocycloalkylene" refers to bivalent heterocycloalkyl.

The term "aryl" refers to a 6-carbon monocyclic, 10-carbon bicyclic, 14-carbon tricyclic aromatic ring system wherein each ring may have 1 to 5 substituents. Examples of aryl groups include phenyl, naphthyl, and anthracenyl. The term "arylene" refers to bivalent aryl. The term "aralkyl" refers to alkyl substituted with an aryl group. The term "aralkenyl" refers to alkenyl substituted with an aryl group.

The term "heteroaryl" refers to an aromatic 5-8 membered monocyclic, 8-12 membered bicyclic, or 11-14 membered tricyclic ring system having one or more heteroatoms (e.g., O, N, P, and S). Examples include triazolyl, oxazolyl, thiadiazolyl, tetrazolyl, pyrazolyl, pyridyl, furyl, imidazolyl, benzimidazolyl, pyrimidinyl, thienyl, quinolinyl, indolyl, thiazolyl, and benzothiazolyl. The term "heteroaralkyl" refers to an alkyl group substituted with a heteroaryl group. The term "heteroaralkenyl" refers to an alkenyl group substituted with a heteroaryl group. The term "heteroarylene" refers to bivalent heteroaryl.

The term "halo" refers to a fluoro, chloro, bromo, or iodo radical. The term "amino" refers to a radical derived from amine, which is unsubstituted or mono-/di-substituted with alkyl, aryl, cycloalkyl, heterocycloalkyl, or heteroaryl. The term "alkylamino" refers to alkyl-NH—. The term "dialkylamino" refers to alkyl-N(alkyl)-.

The term "acyl" refers to —C(O)-alkyl, —C(O)-aryl, —C(O)-cycloalkyl, —C(O)— heterocycloalkyl, or —C(O)-heteroaryl.

Alkyl, cycloalkyl, heterocycloalkyl, aryl, heteroaryl, aralkyl, heteroaralkyl, alkoxy, and aryloxy mentioned herein include both substituted and unsubstituted moieties. Examples of substituents include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cycloalkyl, and heterocycloalkyl, in which alkyl, alkenyl, alkynyl, alkyloxy, aryl, heteroaryl cycloalkyl, and heterocycloalkyl may further substituted.

The term "compound", when referring to a compound of Formula (I), also covers its salts, solvates, and metal complexes. A salt can be formed between an anion and a positively charged group (e.g., amino) on a compound; examples of a suitable anion include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. A salt can also be formed between a cation and a negatively charged group; examples of a suitable cation include sodium ion, potassium ion, magnesium ion, calcium ion, and an ammonium cation such as tetramethylammonium ion. A salt further includes those containing quaternary nitrogen atoms. A solvate refers to a complex formed between an active compound and a pharmaceutically acceptable solvent. Examples of a pharmaceutically acceptable solvent include water, ethanol, isopropanol, ethyl acetate, acetic acid, and ethanolamine. A metal complex can be formed of a compound and a metal ion. The metal ion is a cation having two or more charges. The metal complex is typically formed via chelation of a metal ion and a compound of Formula (I). Examples of the metal ion include $Zn^{2+}$, $Cu^{2+}$, $Ca^{2+}$, $Mg^{2+}$, $Mn^{2+}$, $Ni^{2+}$, $CO^{2+}$, $Fe^{2+}$, $Cd^{2+}$, and a combination thereof.

For use of a compound of this invention, an effective amount of the compound in a pharmaceutical composition is administered to a subject in need of PS-related cancer treatment.

The pharmaceutical composition further contains a pharmaceutically acceptable carrier. The carrier must be "acceptable" in the sense that it is compatible with the active ingredient of the composition (and preferably, capable of stabilizing the active ingredient) and not deleterious to the subject to be treated.

The details of one or more embodiments of the invention are set forth in the description below. Other features, objects, and advantages of the invention will be apparent from the description and from the claims.

DETAILED DESCRIPTION

Figure 1:
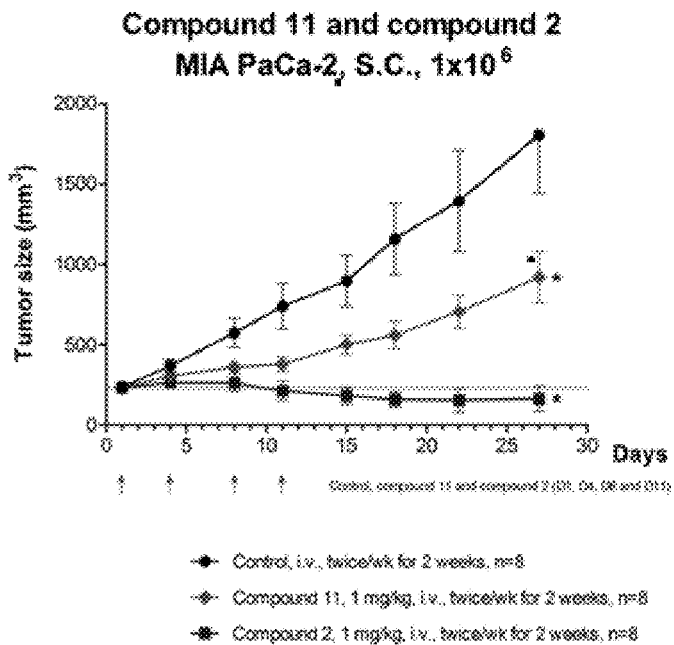
FIG. 1 shows efficacy of compounds 2 and 11 in inhibiting the growth of human pancreatic cancer cells lines MIA PaCa-2.

Described in detail below are compounds of this invention, their syntheses, and their anticancer potency.

Referring back to Formula (I) set forth in the SUMMARY section above,

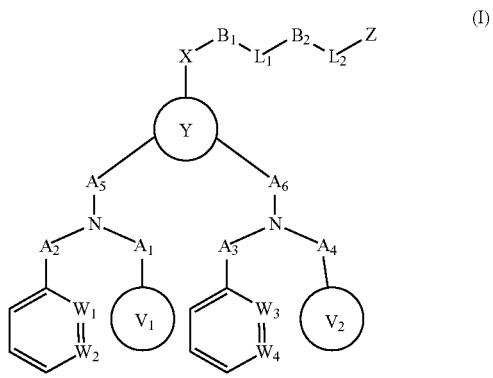

it is preferred that Z is:

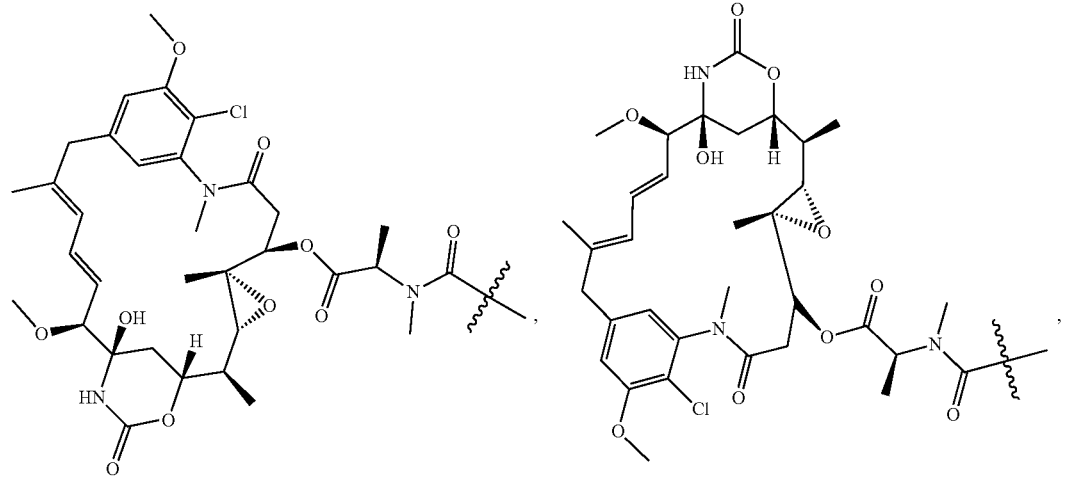

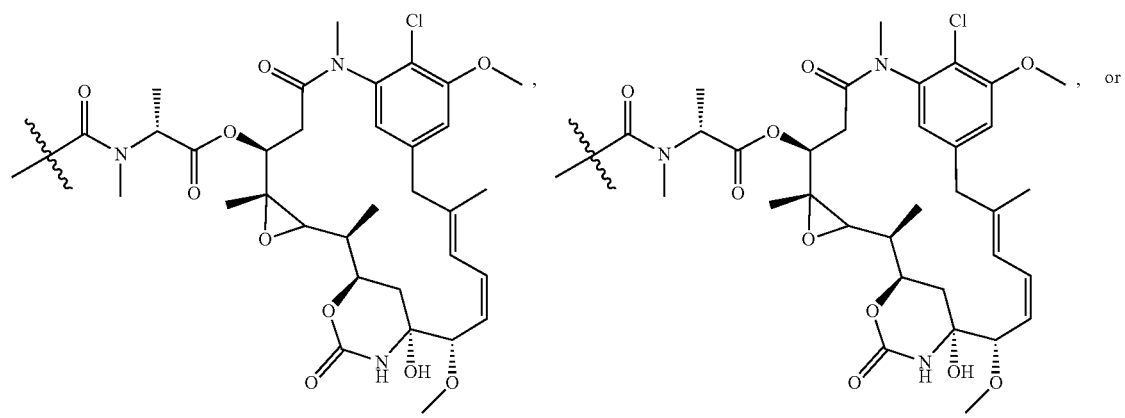

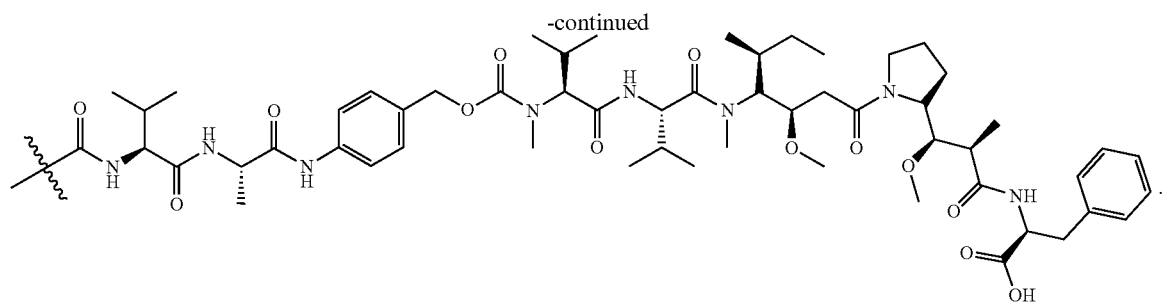

In a preferred set of compounds of Formula (I), each of $A_1, A_2, A_3, A_4, A_5$, and $A_6$ is methylene; $B_1$ is $C_1$-$C_6$ bivalent aliphatic radical, a $C_1$-$C_6$ bivalent heteroaliphatic radical, or $CHC(O)R_1$; $B_2$ is a bond, a $C_1$-$C_6$ bivalent aliphatic radical, a bivalent aryl radical, $D_1$-$NR_2$—$C(O)$-$D_2$, $D_1$-$NR_2$—$C(O)$-$D_2$-$C(O)NR_2'$-$D_3$, $D_1$-$C(O)NR_2$-$D_2$-$NR_2'$—$C(O)$-$D_3$, $D_1$-$C(O)NR_2$-$D_2$-$NR_2'$-$D_3$, $D_1$-$D_2$-$C(O)$—$NR_2$—$C(O)$-$D_3$, or $D_1$-$D_2$-$D_3$; $L_1$ is a bond, $NR_3C(O)$, or $NR_3C(O)NR_4$; more preferably, B2 is

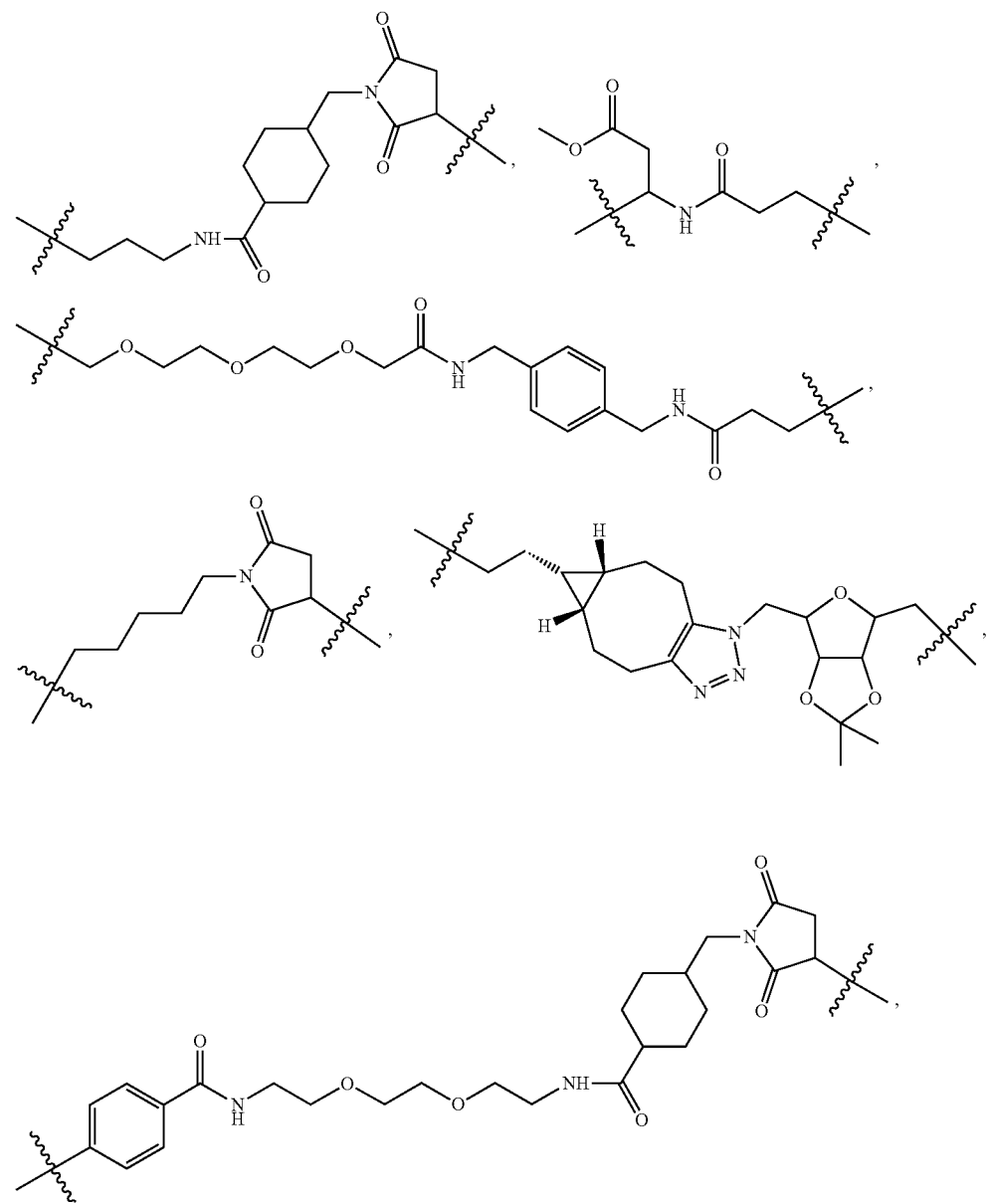

-continued
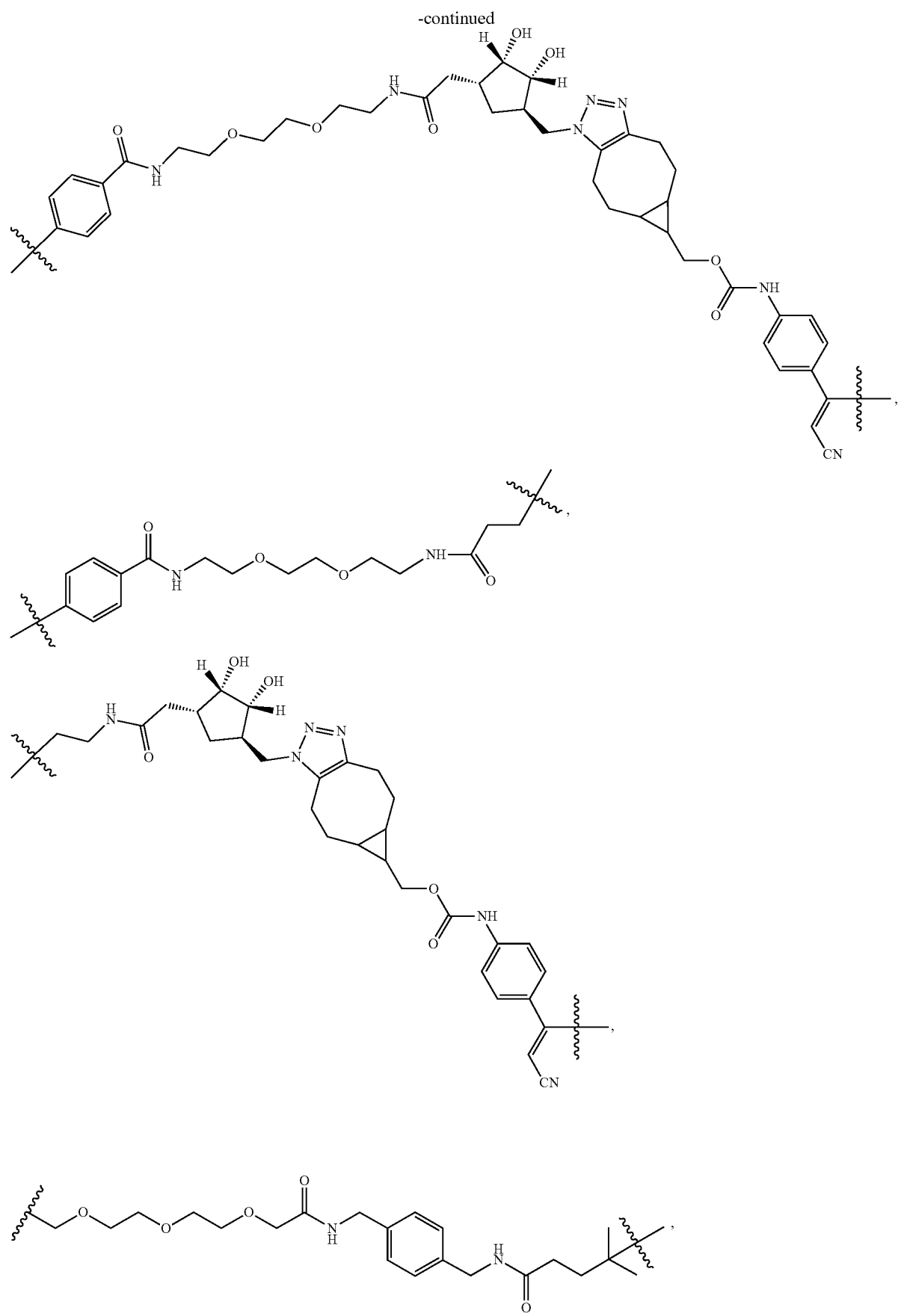

-continued
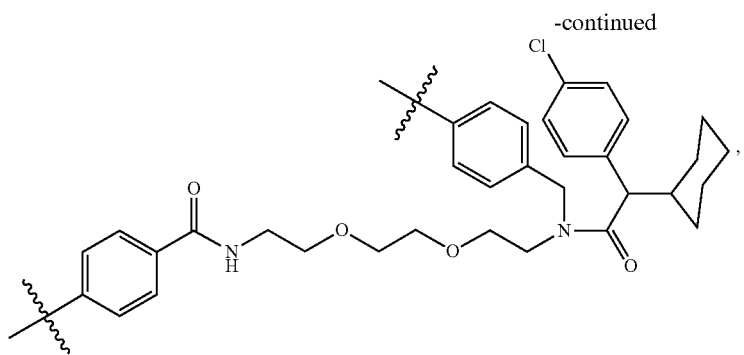
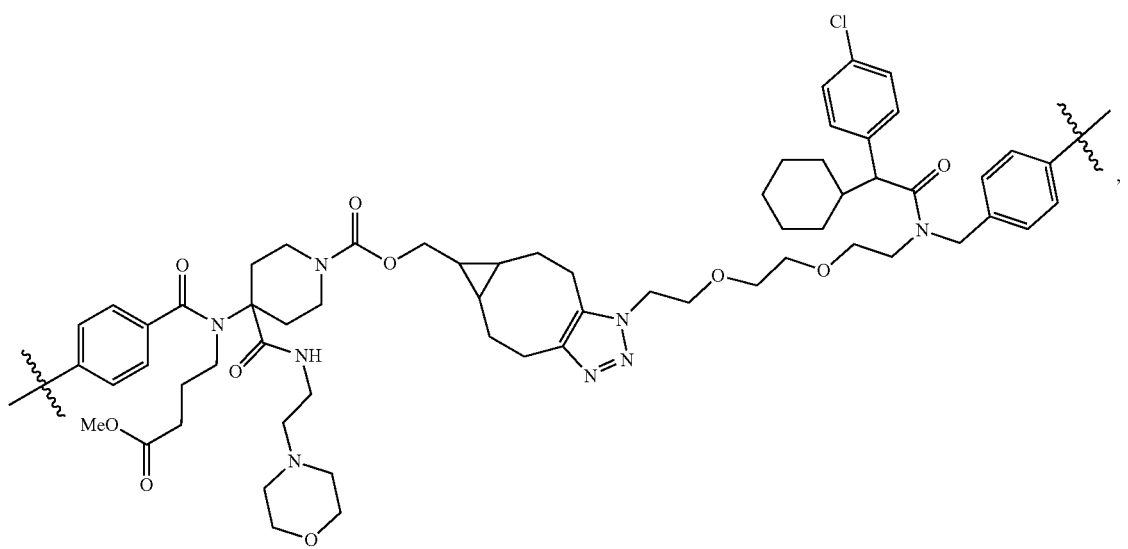
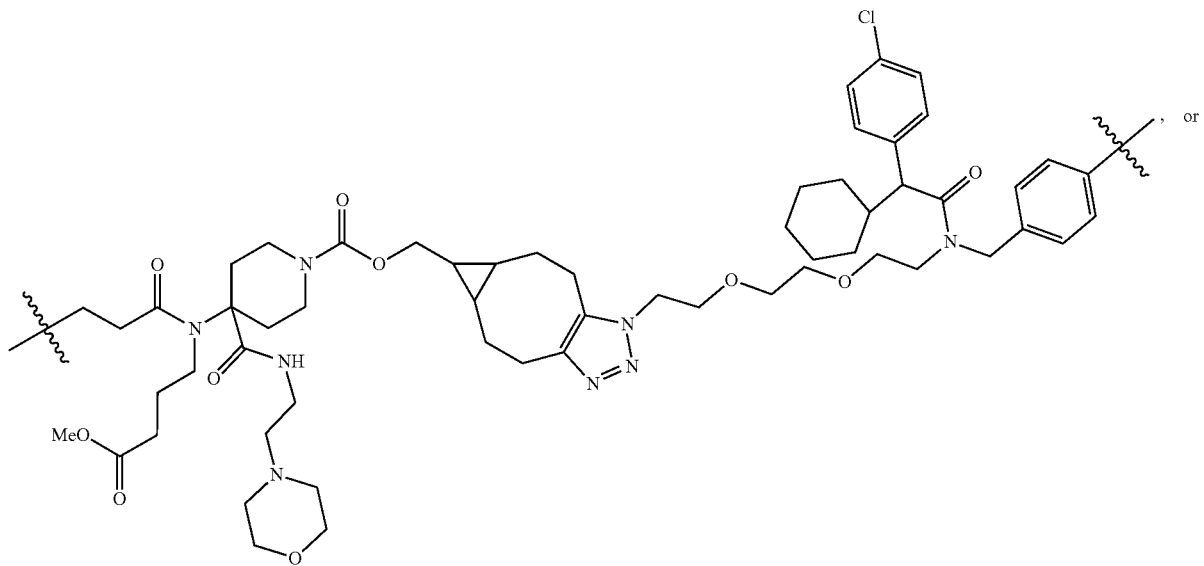

-continued

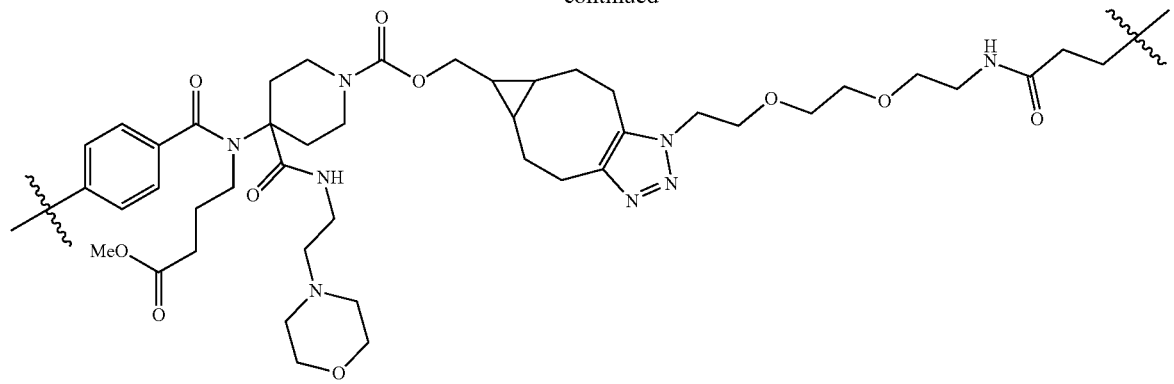

$L_2$ is a bond, $SR_6$, $SSR_6$, or $C(O)SR_6$; more preferably, $L_2$ is a bond,

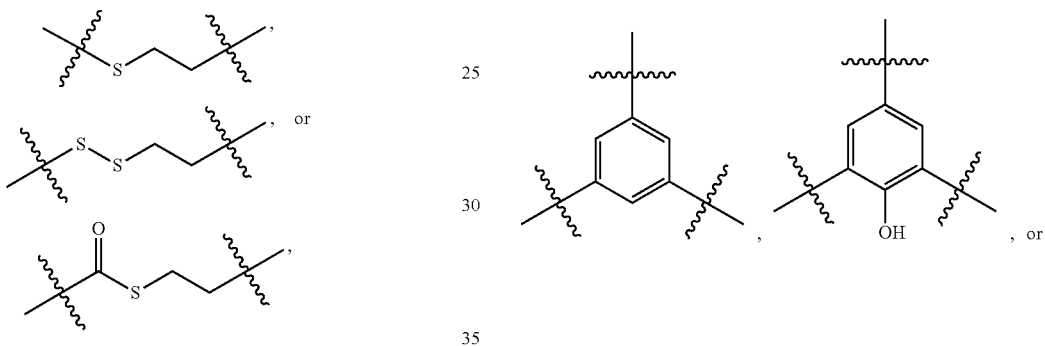

each of $W_1$, $W_2$, $W_3$, and $W_4$, independently, is N or $CR_5$, $R_5$ being H, $NHC(O)R_9$, or $NHC(O)NHR_9$; more preferably, each of $W_2$ and $W_4$, independently, is $CR_5$, $R_9$ being a $C_4$-$C_6$ monovalent aliphatic radical, phenyl,

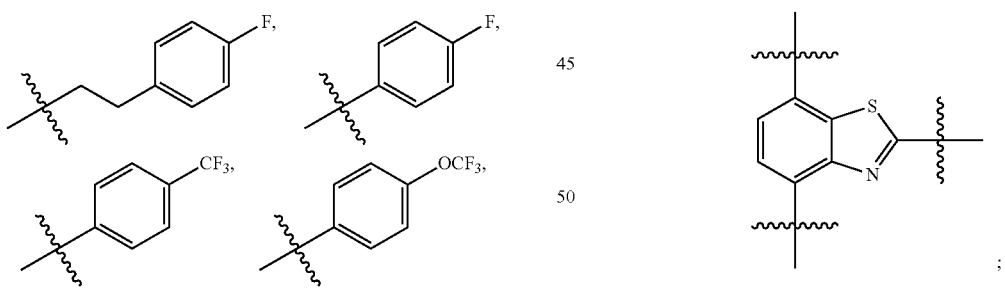

Cl,

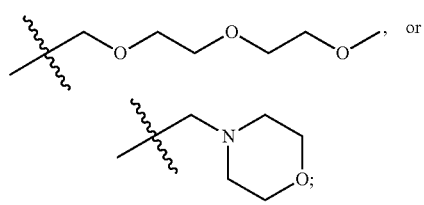

X is a bond, O, or NH; Y is each of $V_1$ and $V_2$, independently, is a phenyl ring, a five-member heteroaryl ring, or a six-member heteroaryl ring.

In another preferred set of compounds covered by Formula (I), each of $A_1$, $A_2$, $A_3$, $A_4$, $A_5$, and $A_6$ is methylene; $B_1$ is a $C_1$-$C_6$ bivalent aliphatic radical or a $C_1$-$C_6$ bivalent heteroaliphatic radical; $B_2$ is $D_1$-$C(O)NR_2$-$D_2$-$NR_2'$—$C(O)$-$D_3$ or $D_1$-$C(O)NR_2$-$D_2$-$NR_2'$-$D_3$; more preferably, $B_2$ is

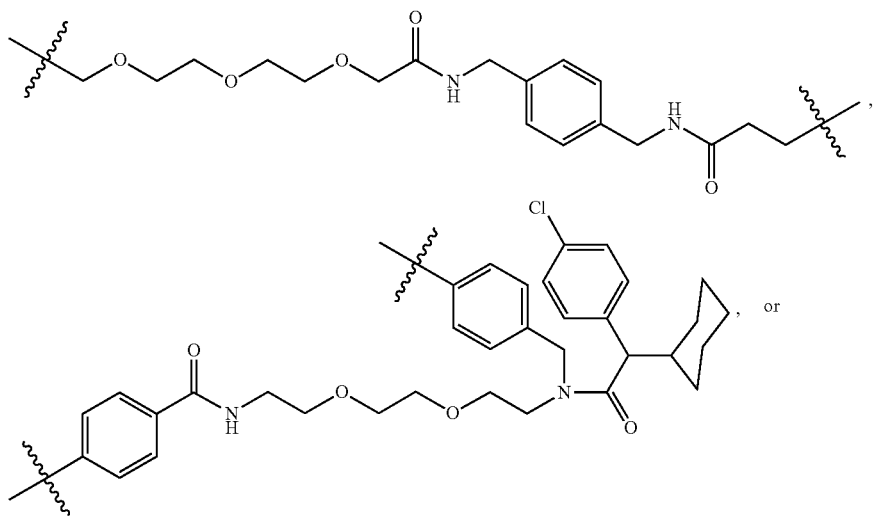

$L_1$ is $NR_3C(O)$; $L_2$ is $SSR_6$ or $C(O)SR_6$; more preferably, $L_2$ is

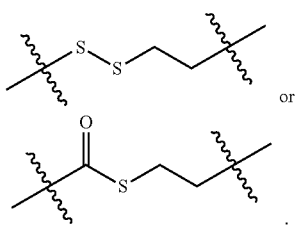

each of $W_1$, $W_2$, $W_3$, and $W_4$, independently, is N or $CR_5$, $R_5$ being H or $NHC(O)R_9$, $R_9$ being a $C_1$-$C_6$ monovalent aliphatic radical; more preferably, each of $W_2$ and $W_4$, independently, is $CR_5$; X is O; Y is

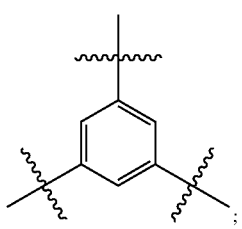 [SMILES: *c1cc(*)cc(*)c1]

each of $V_1$ and $V_2$, independently, is a pyridine ring; and Z is

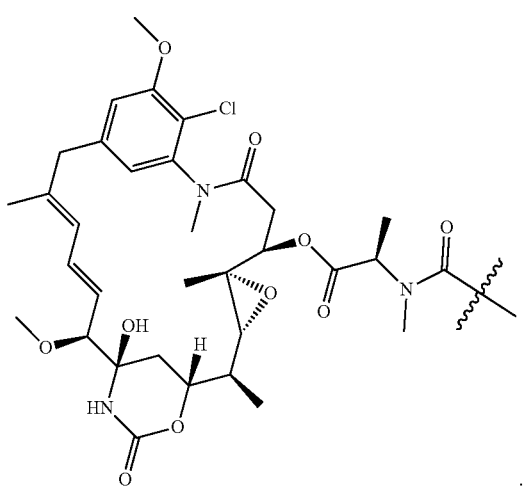 [SMILES: *C(=O)N(C)[C@H](C)C(=O)O[C@@H]1CC(=O)N(C)c2cc(cc(OC)c2Cl)C/C(C)=C/C=C/[C@H](OC)[C@]2(O)C[C@@H](OC(=O)N2)[C@H](C)[C@H]2O[C@@]21C]

Shown below are the structures of 27 exemplary compounds of this invention:

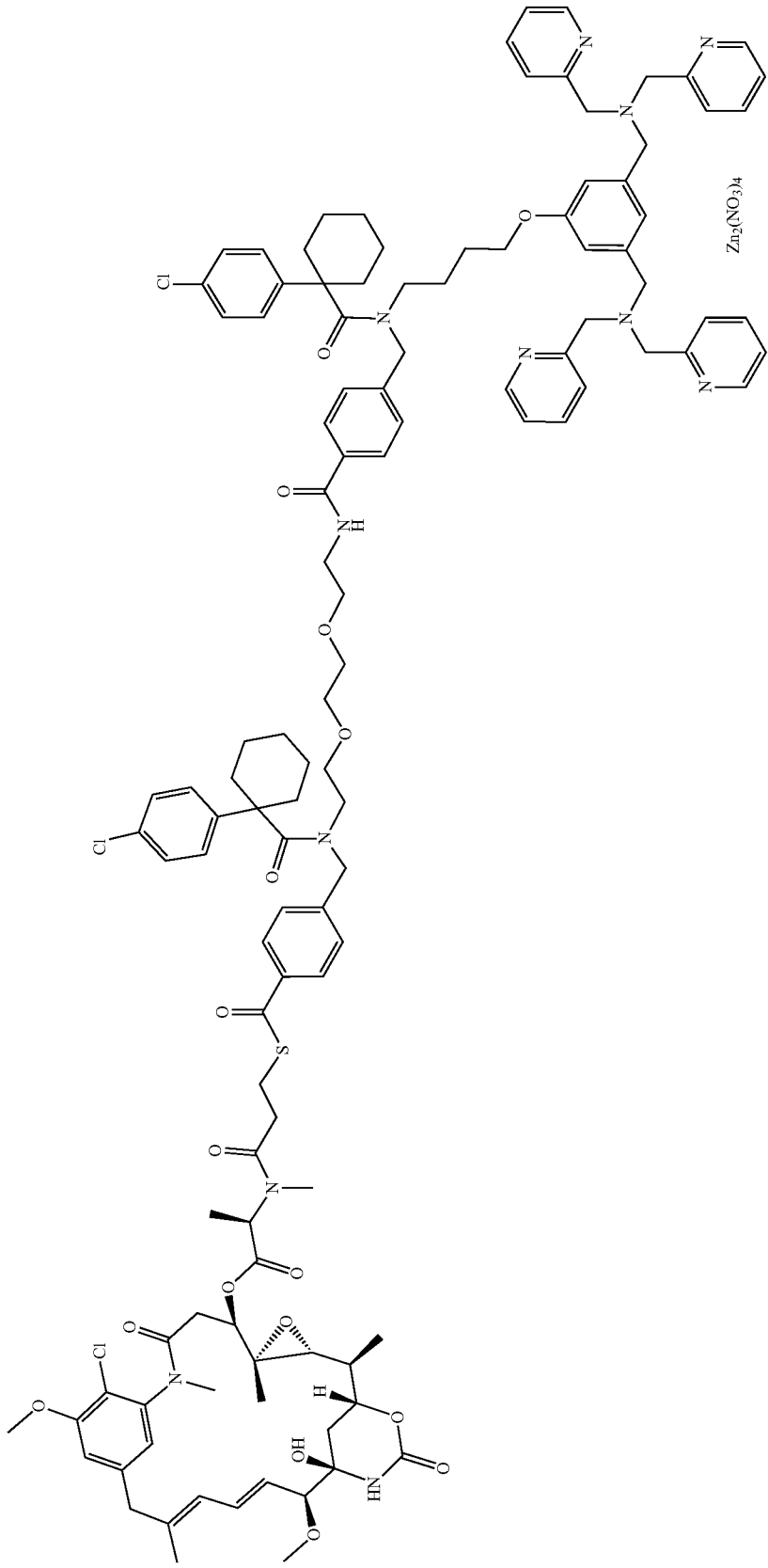

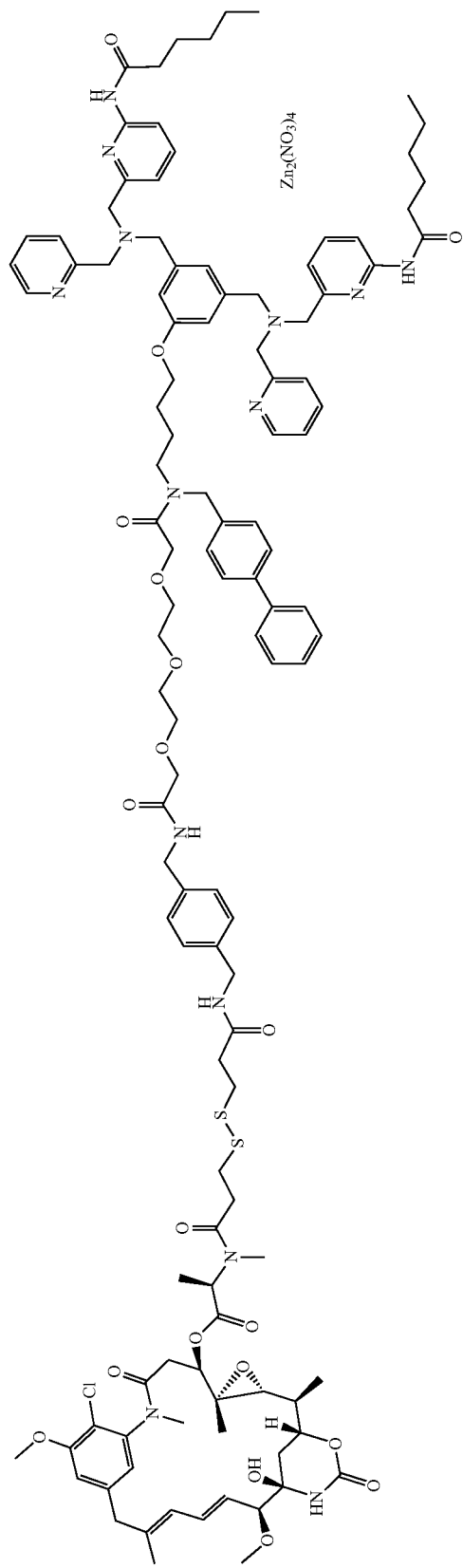

-continued
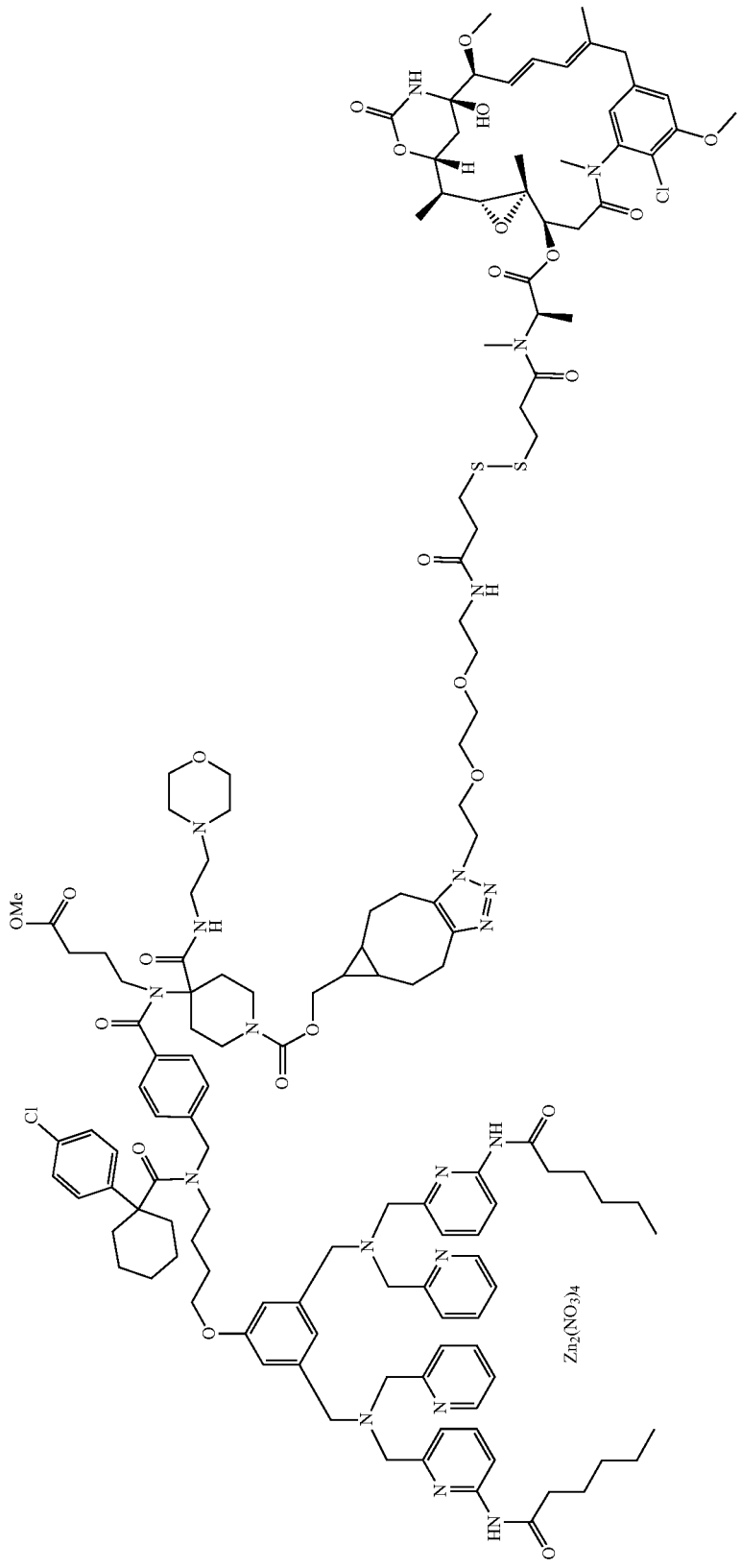

-continued
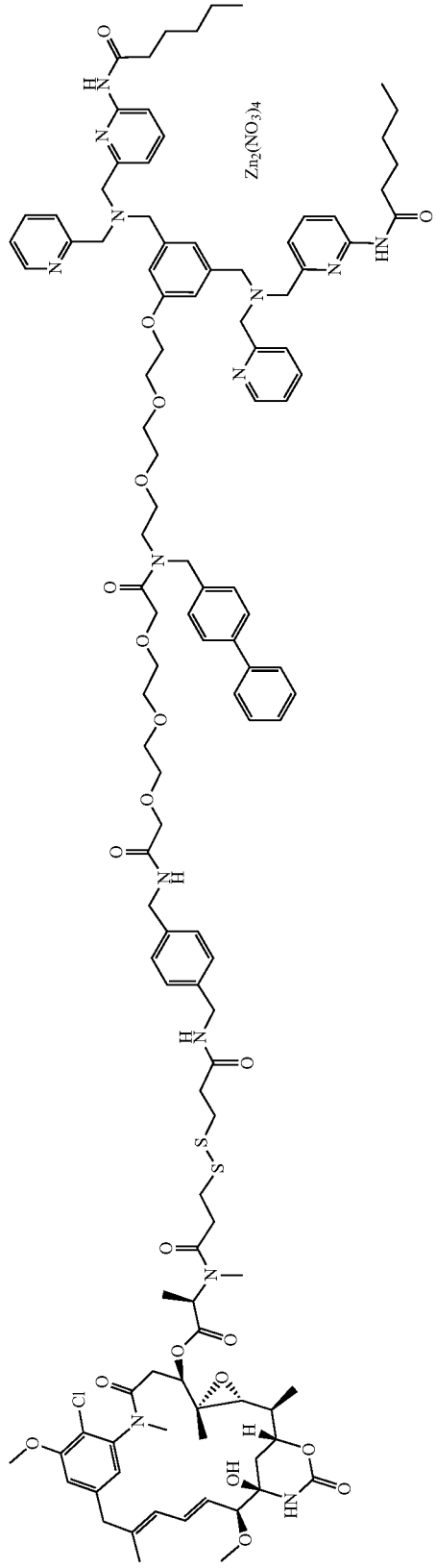
4
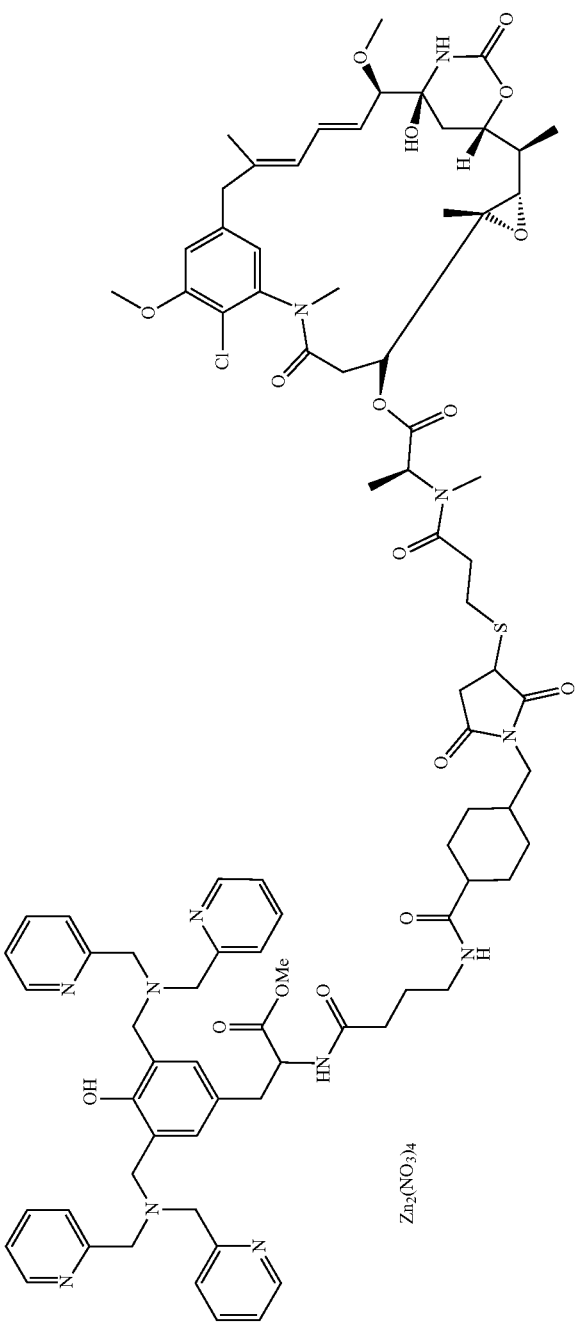
5

6
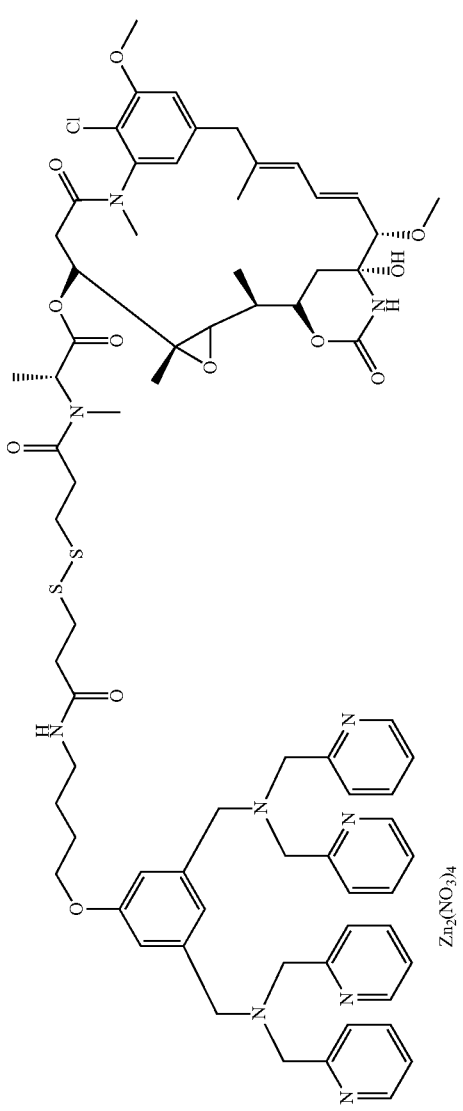
7
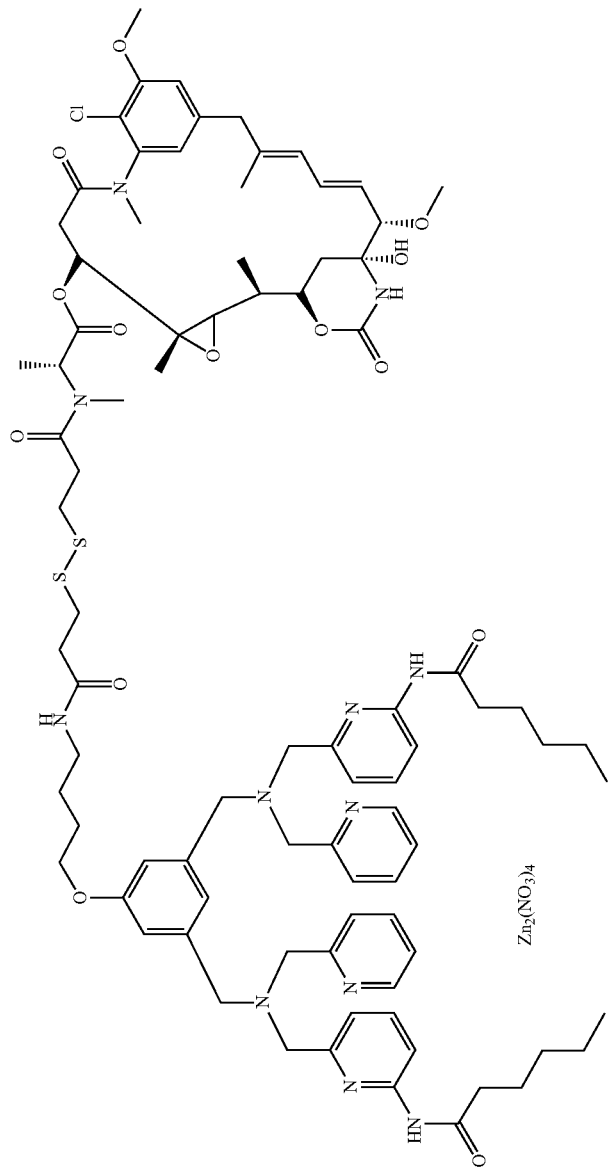

-continued
8
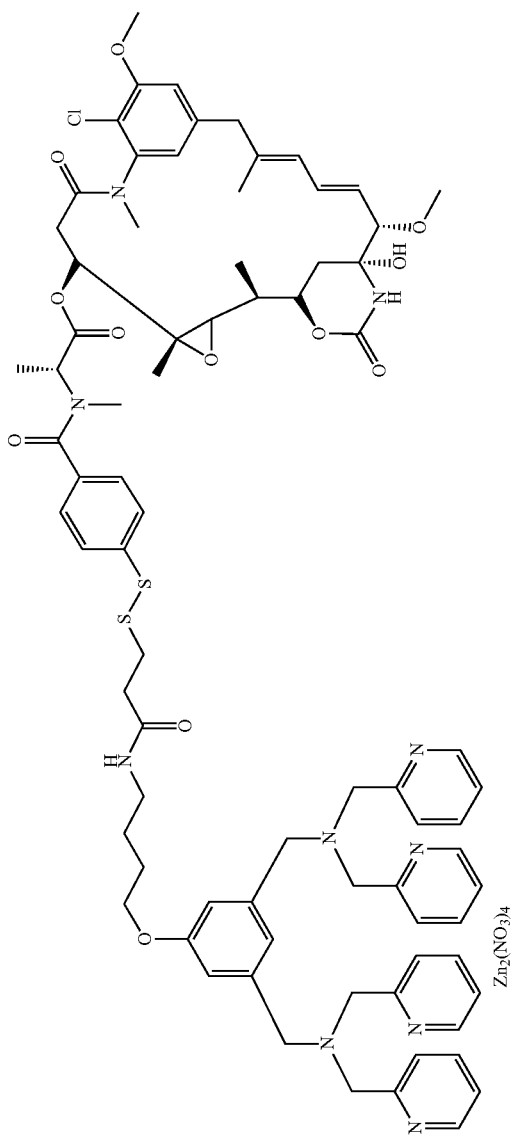
9
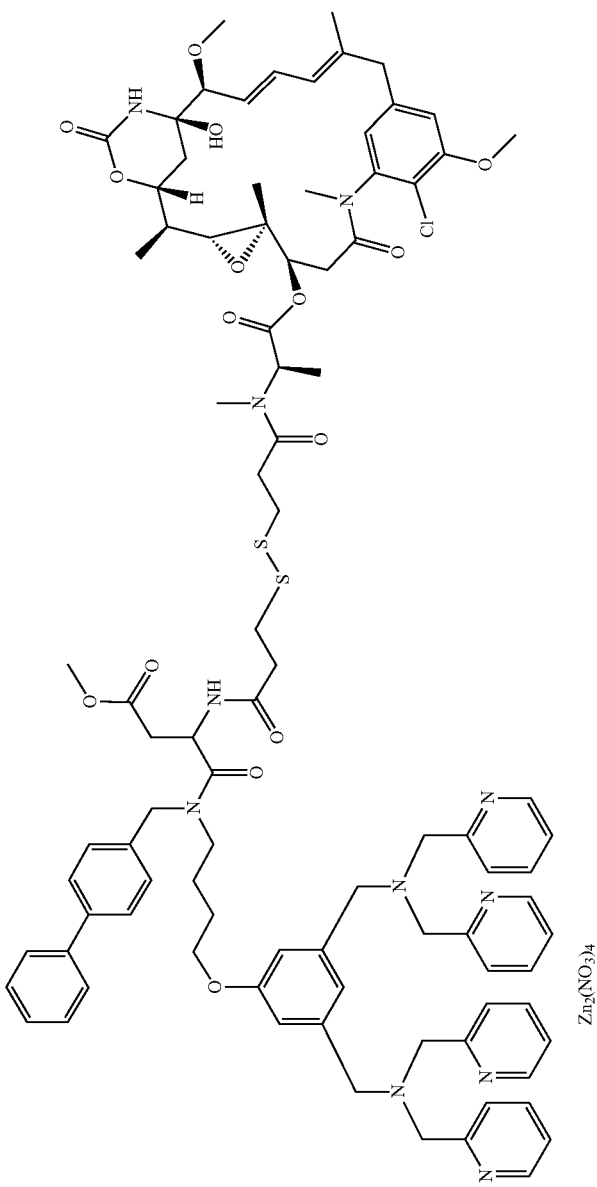

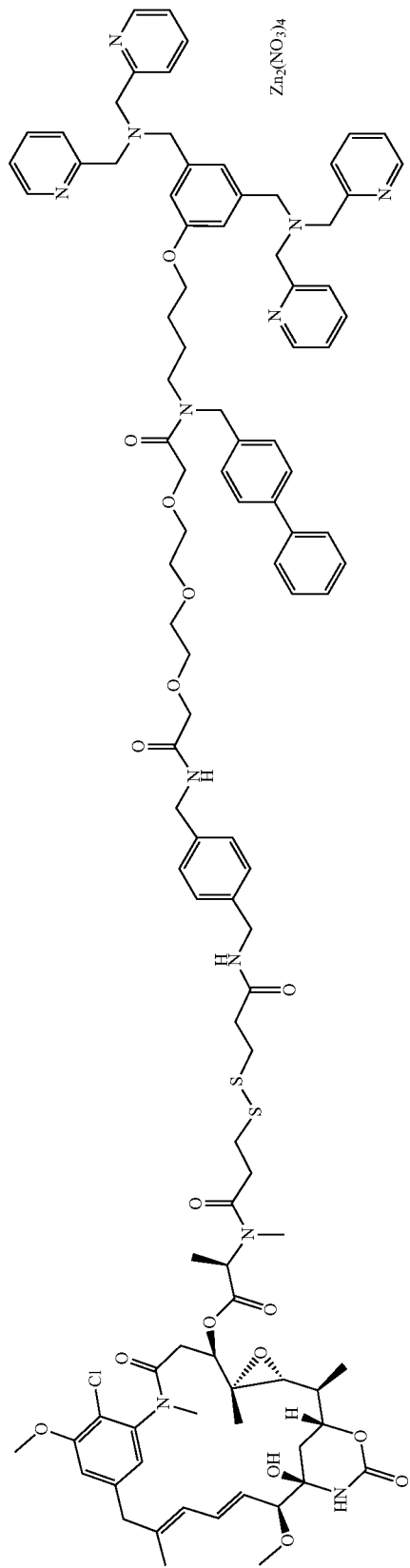

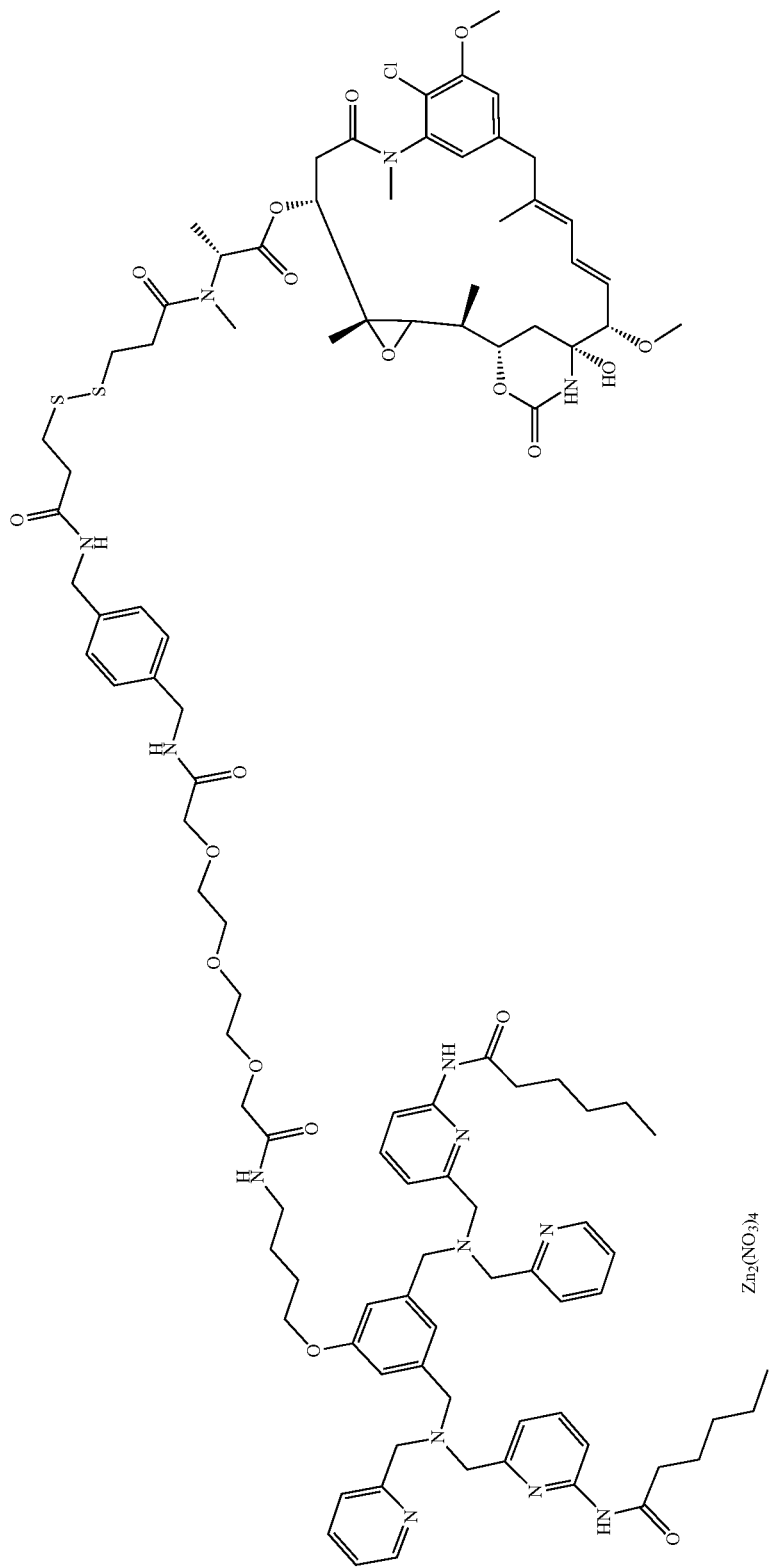

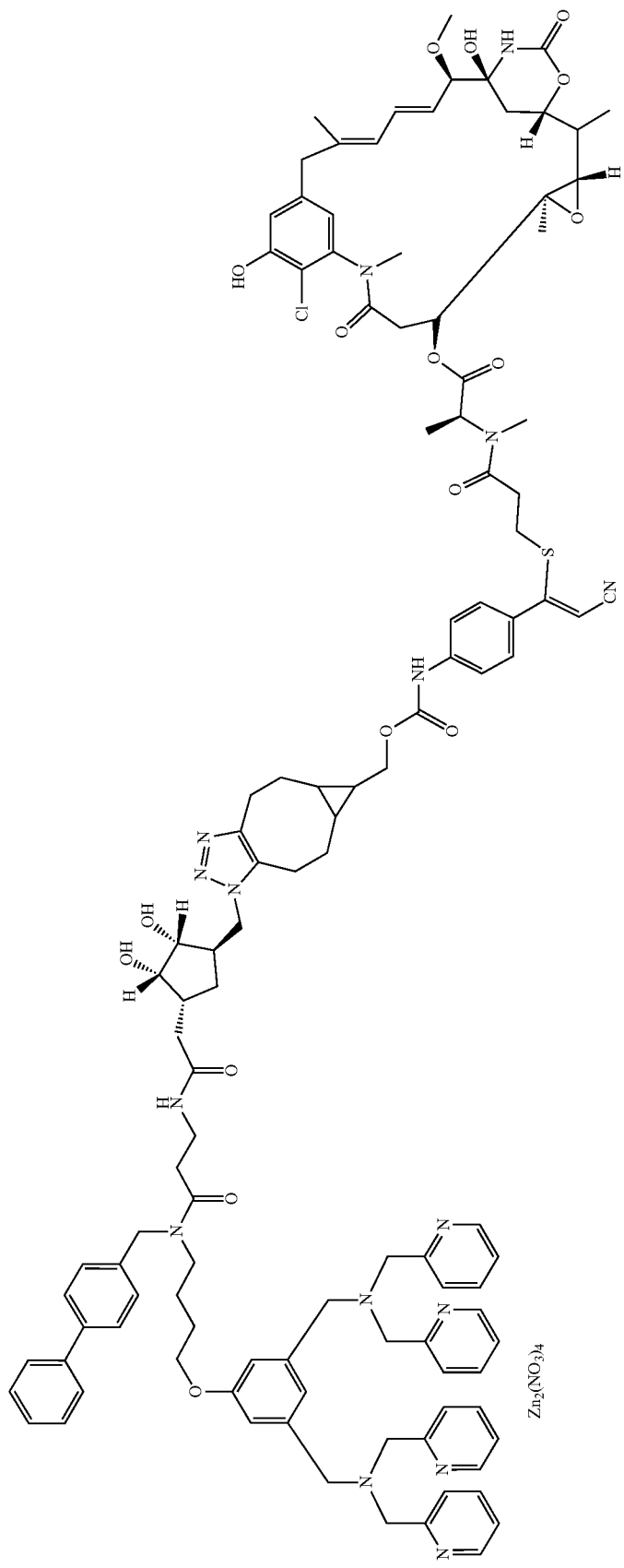

13
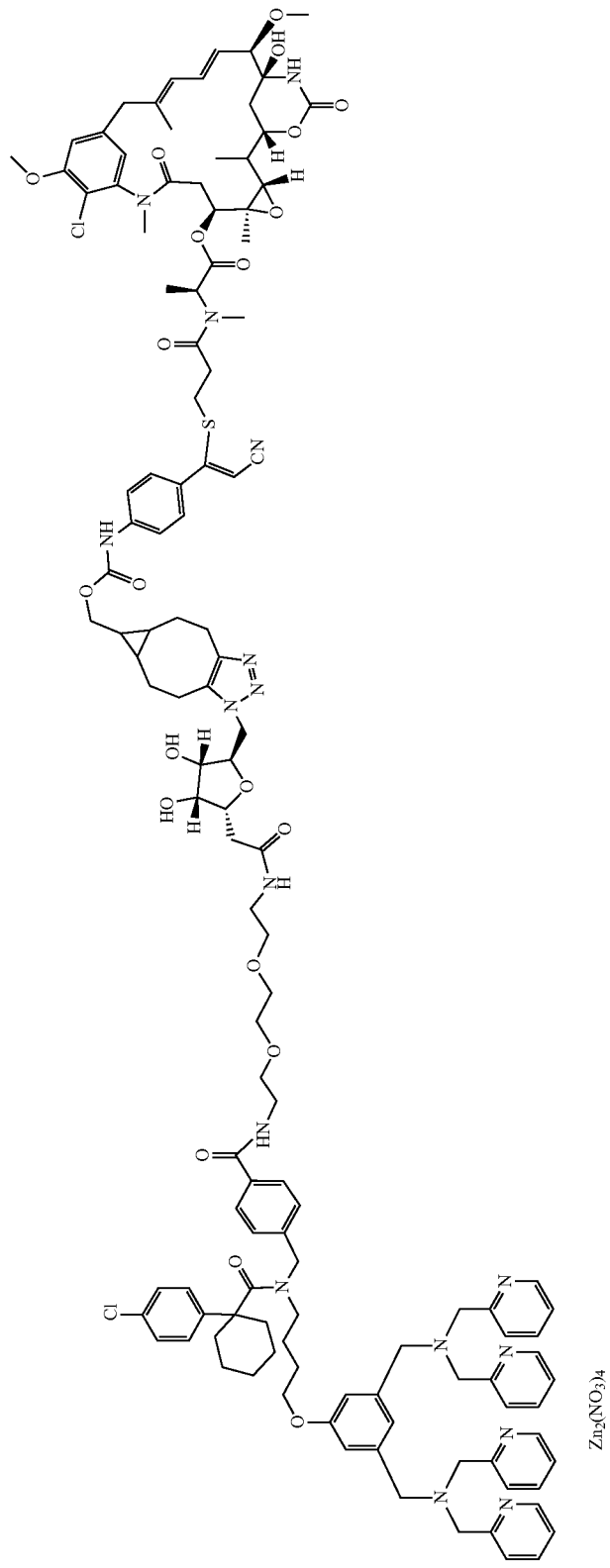
Zn₂(NO₃)₄

14
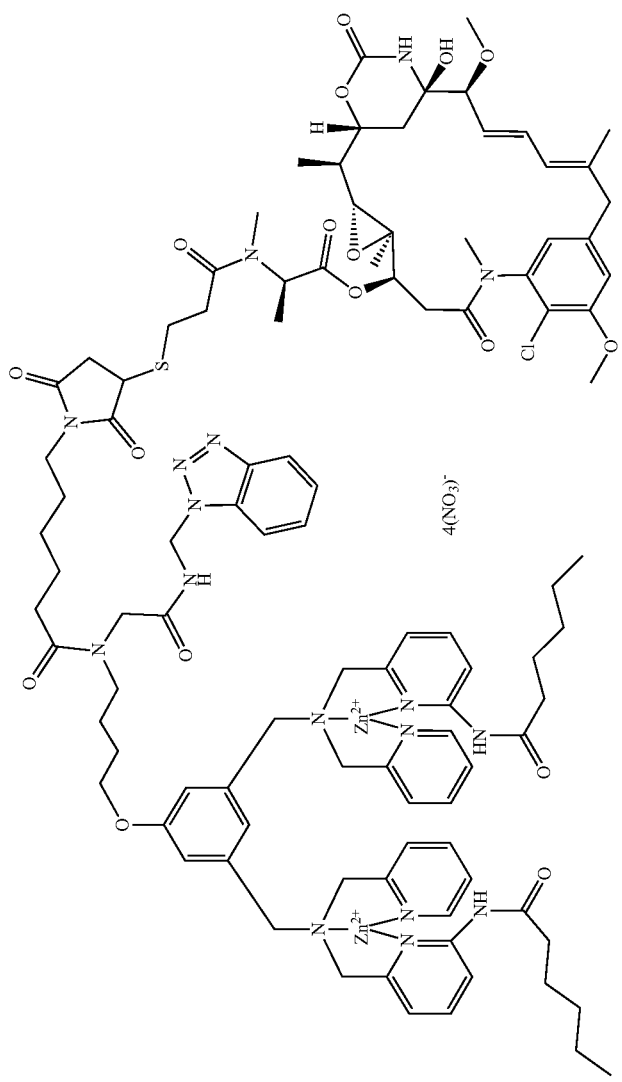

15
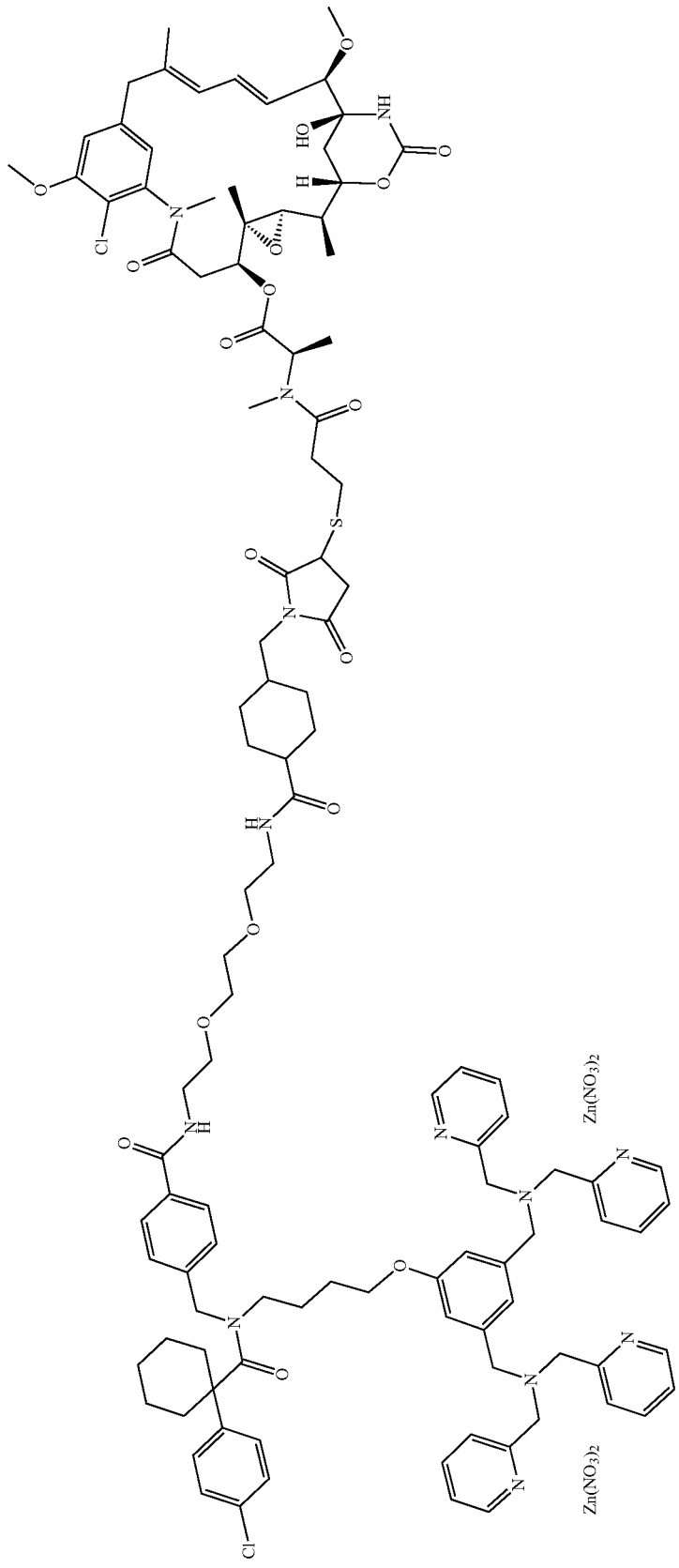

16
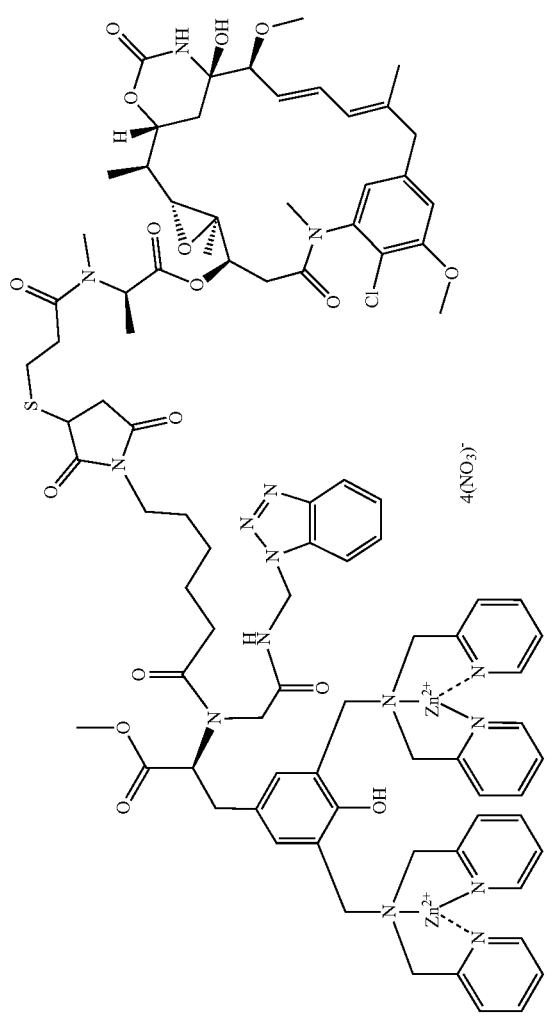

17
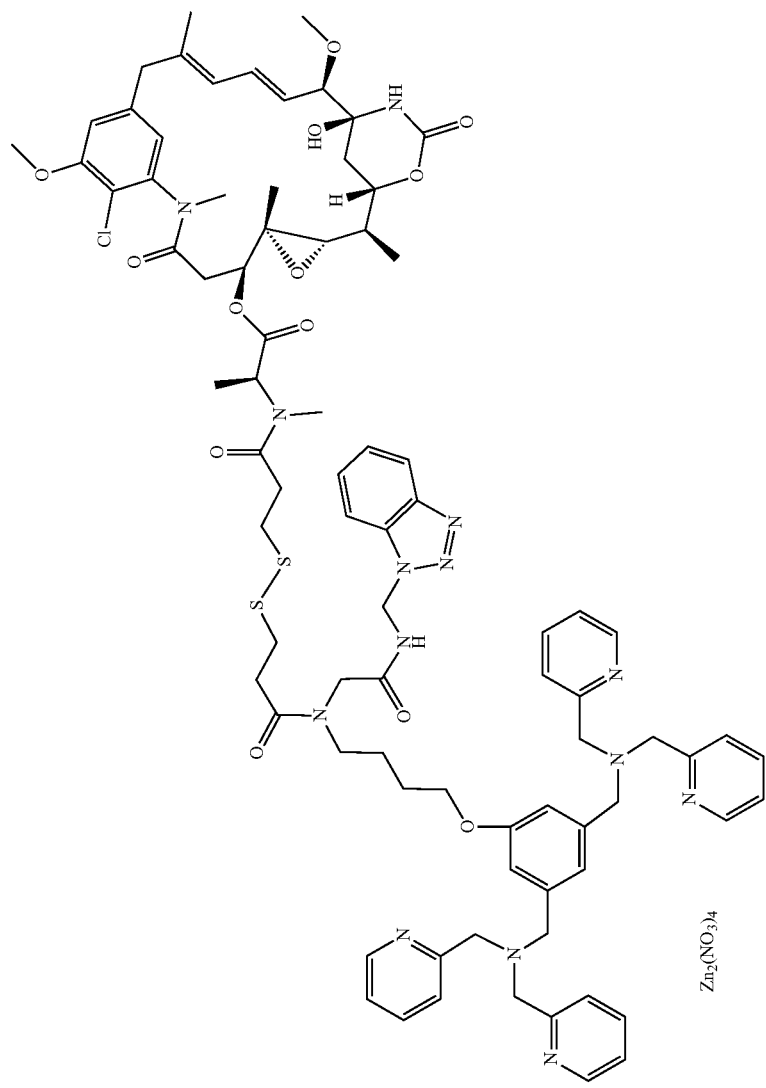
Zn2(NO3)4

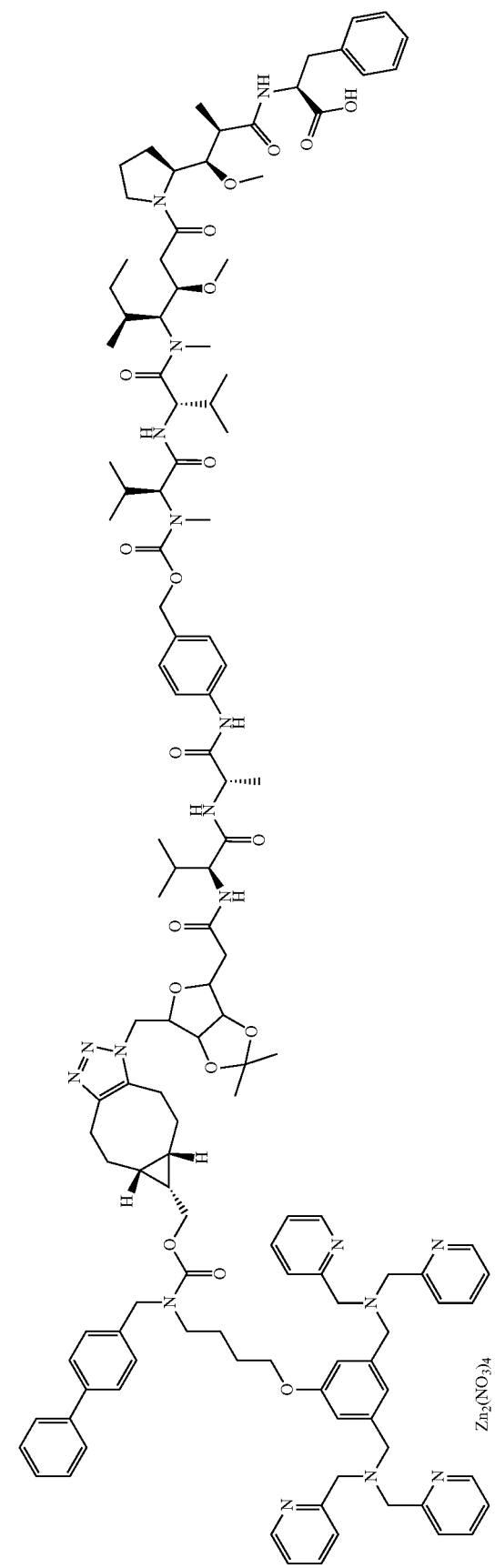

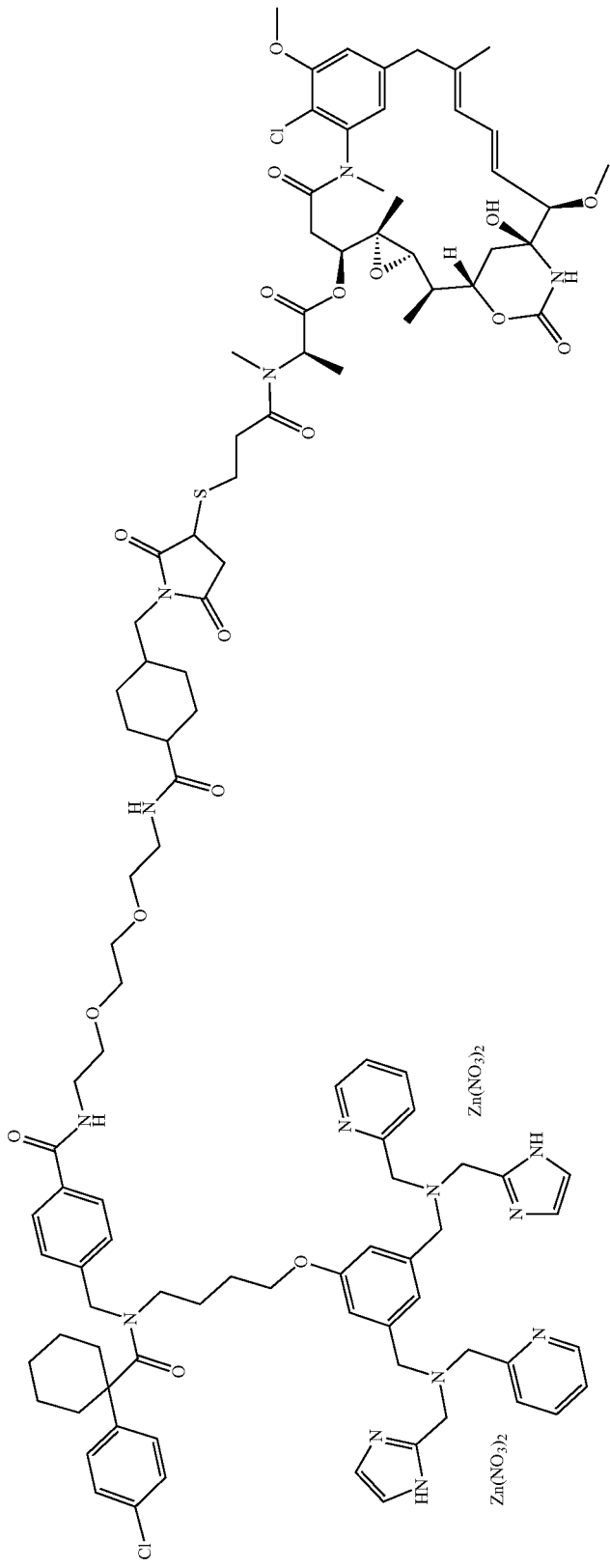

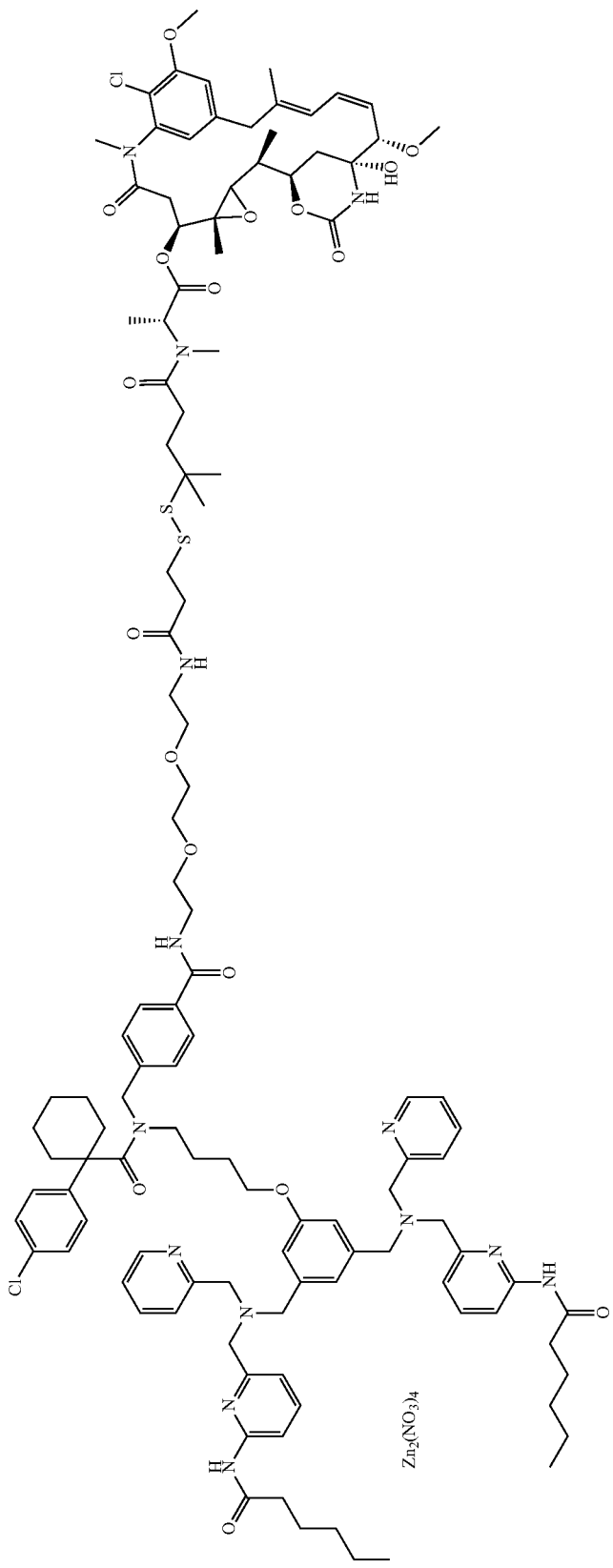

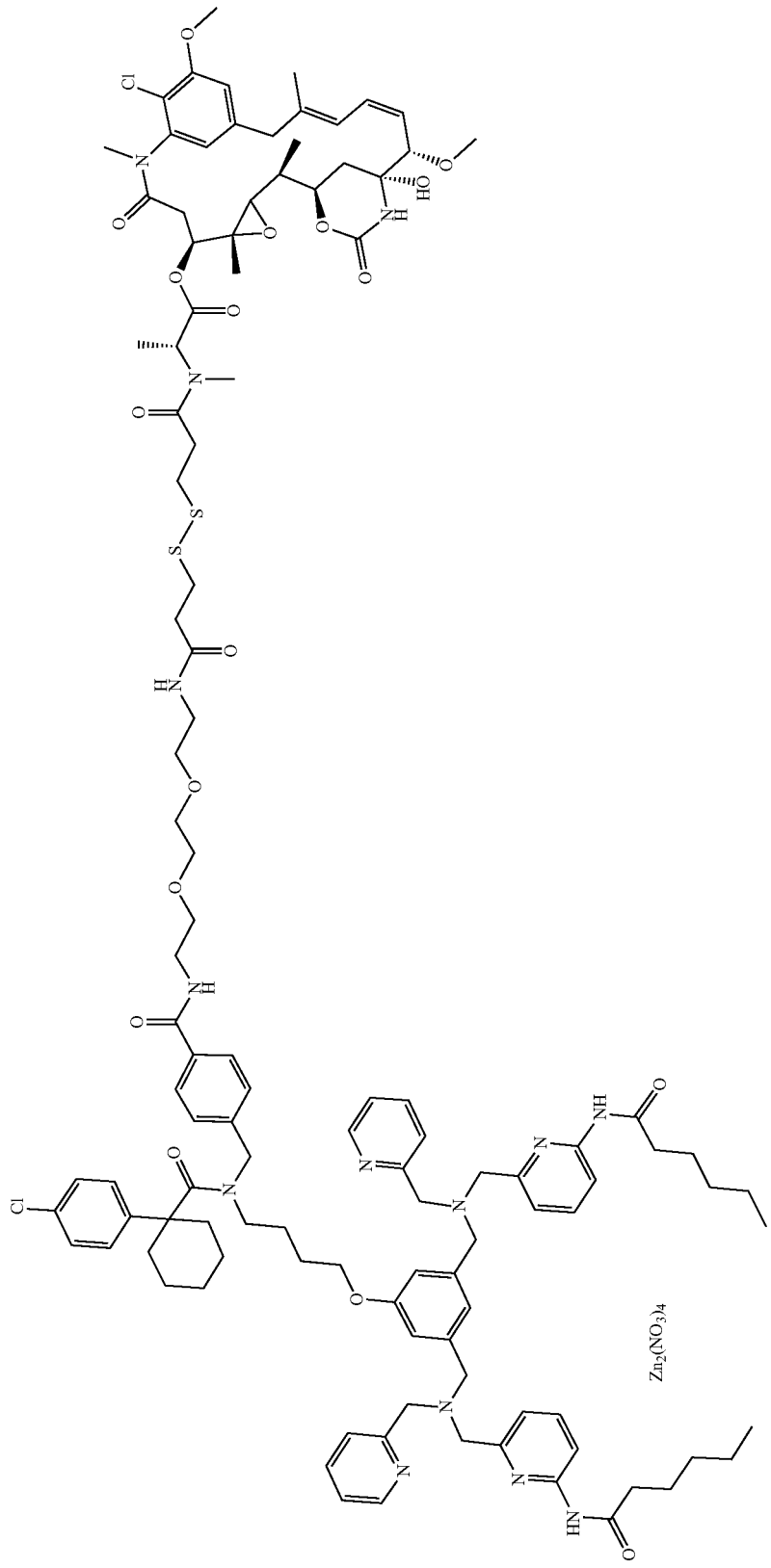

-continued
22
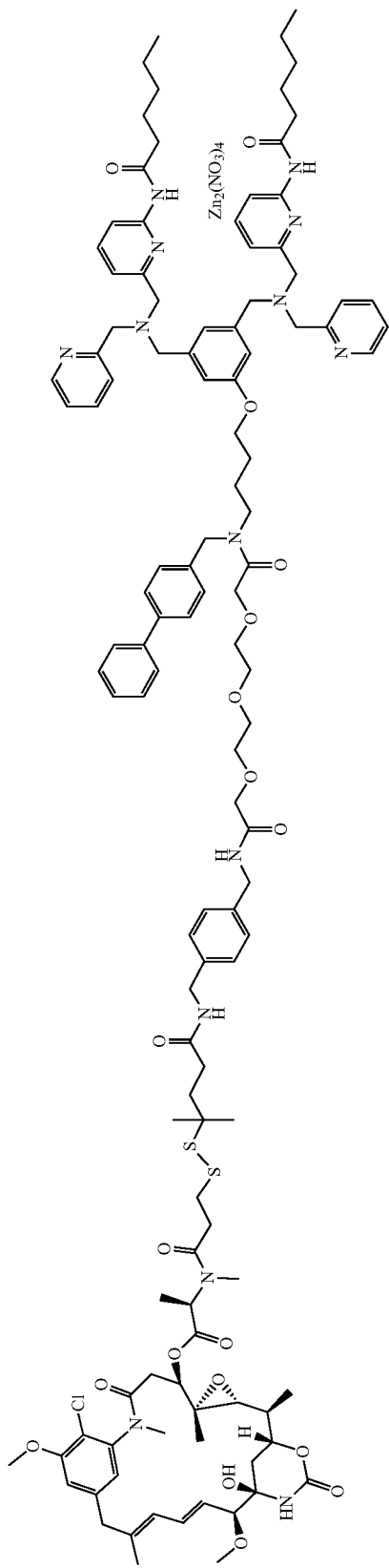
23
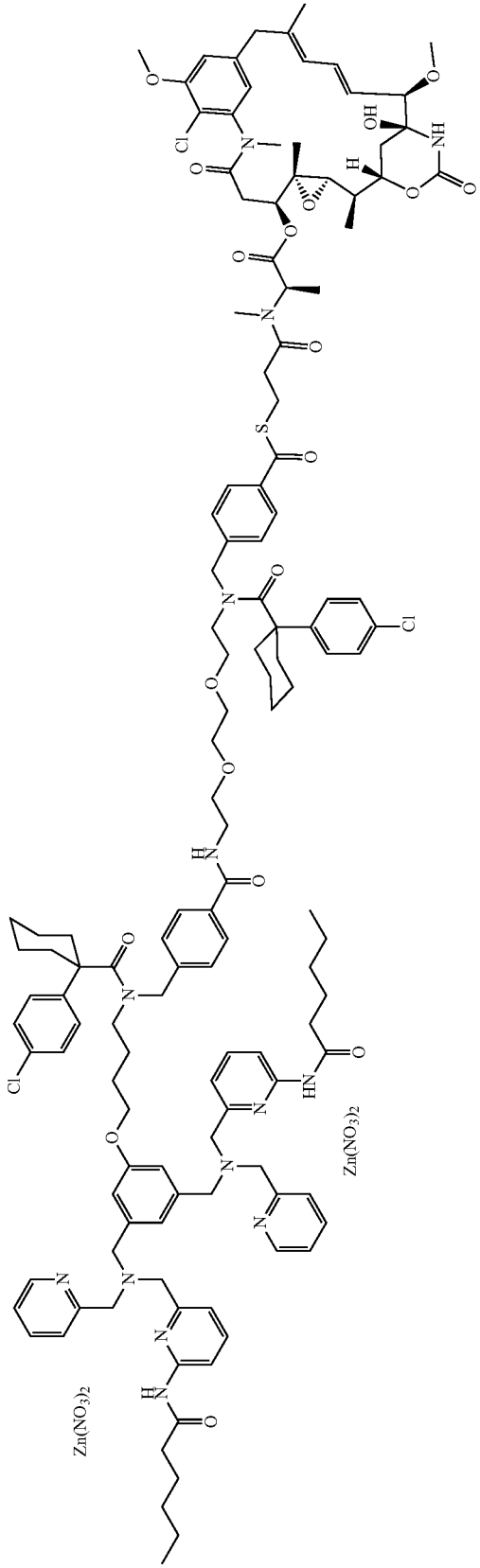

24
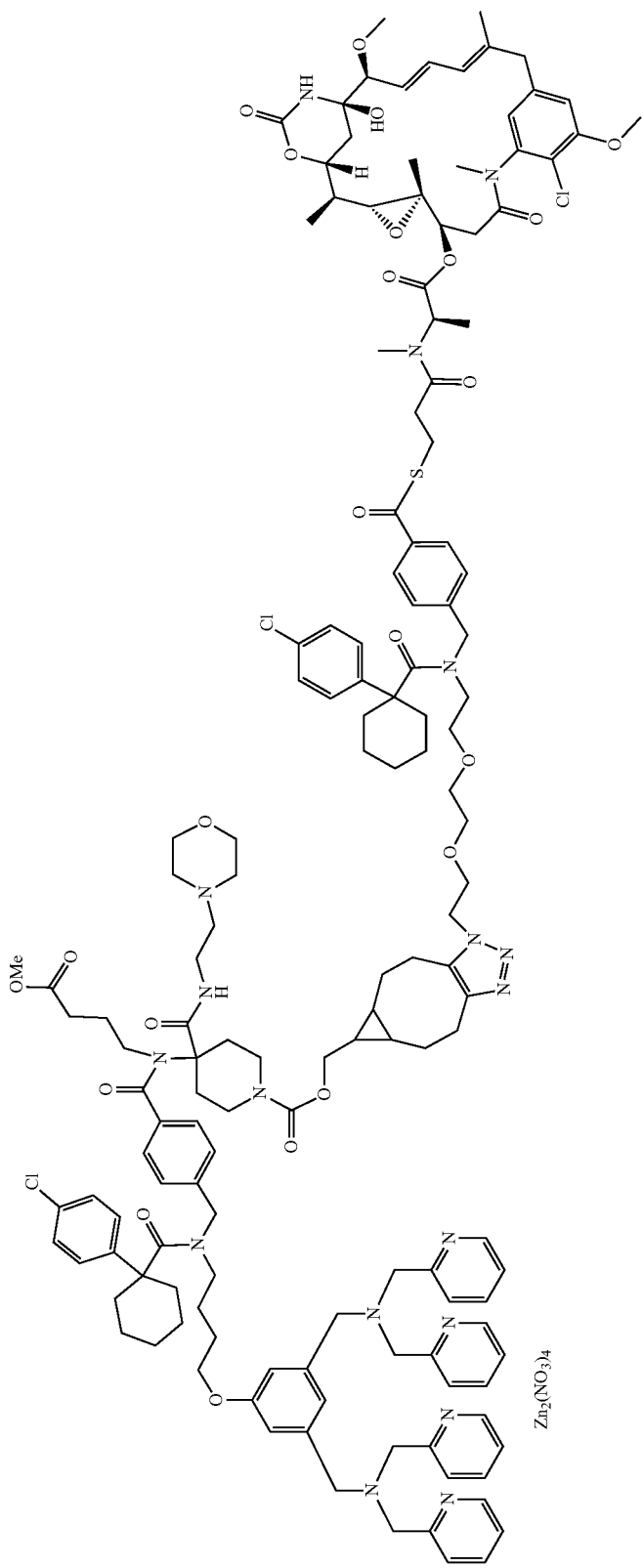

-continued
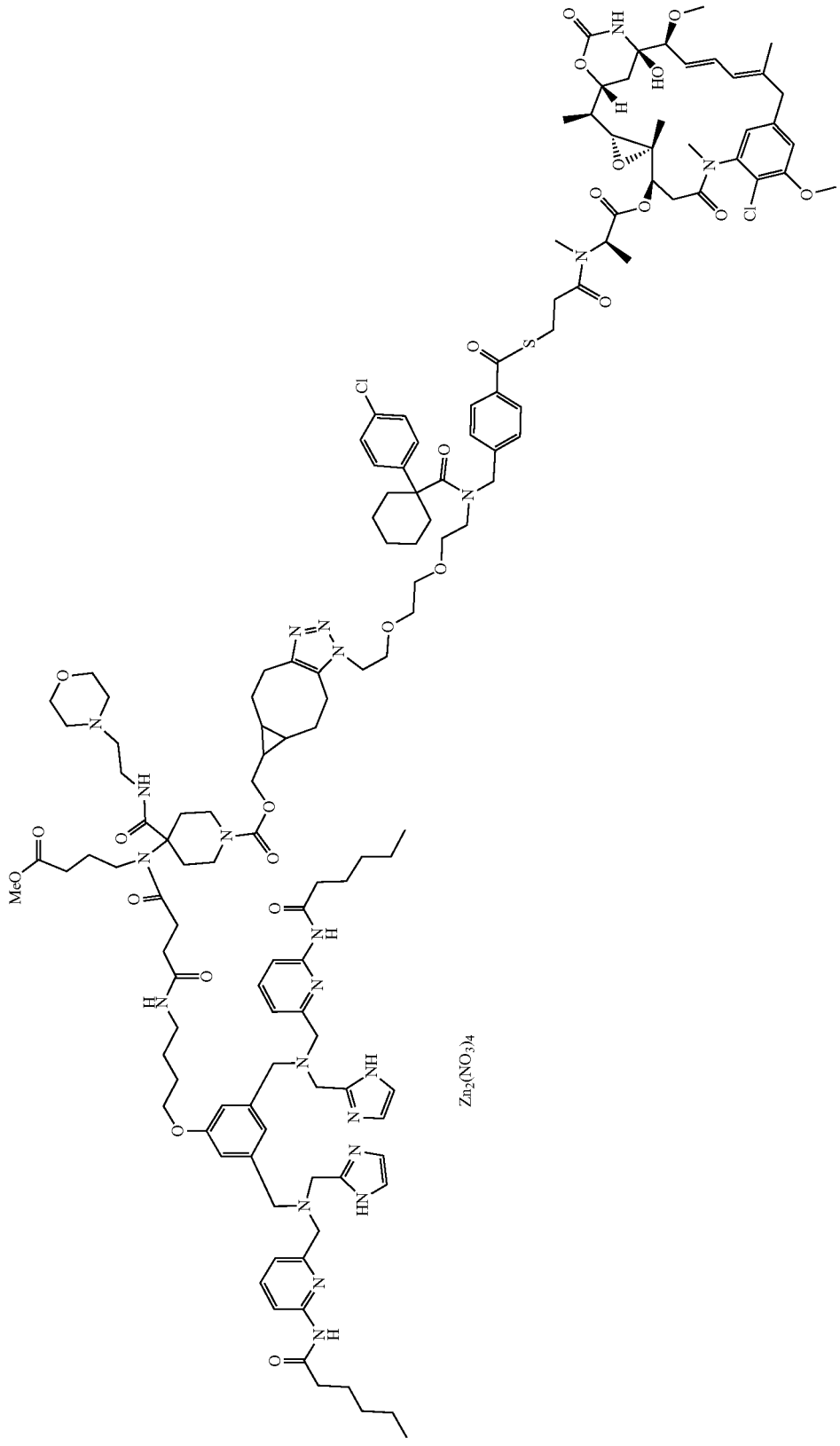

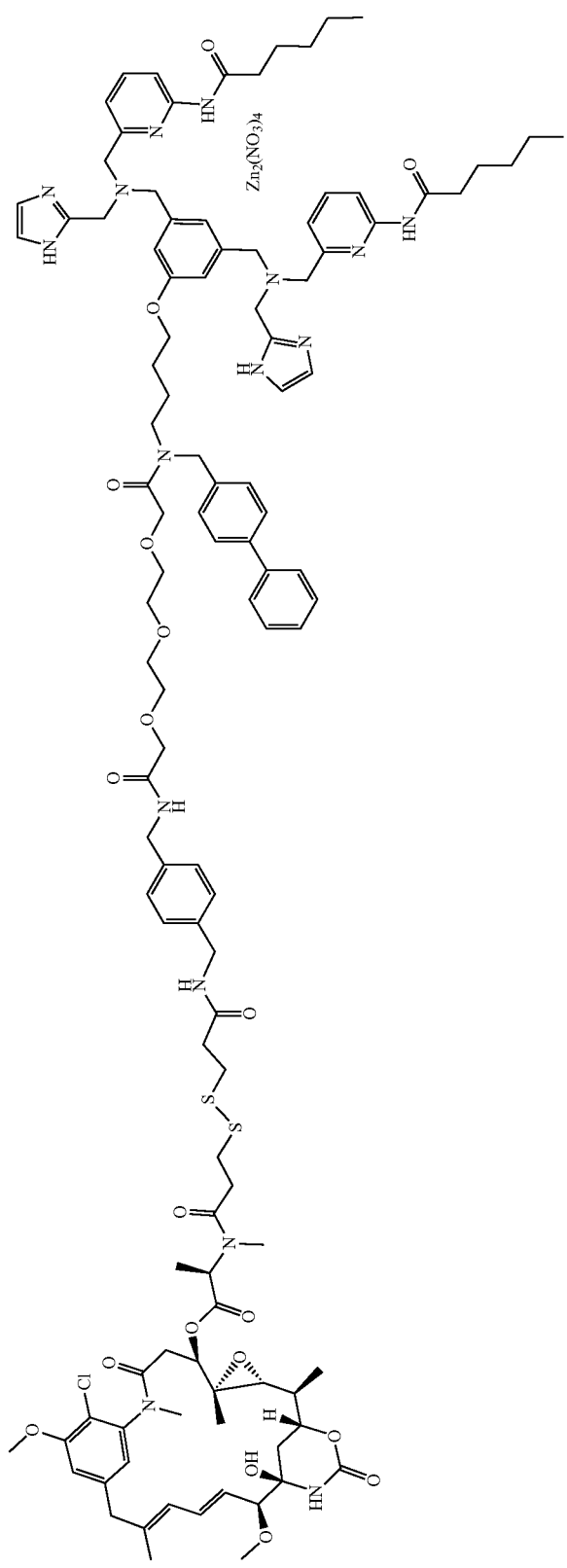
26
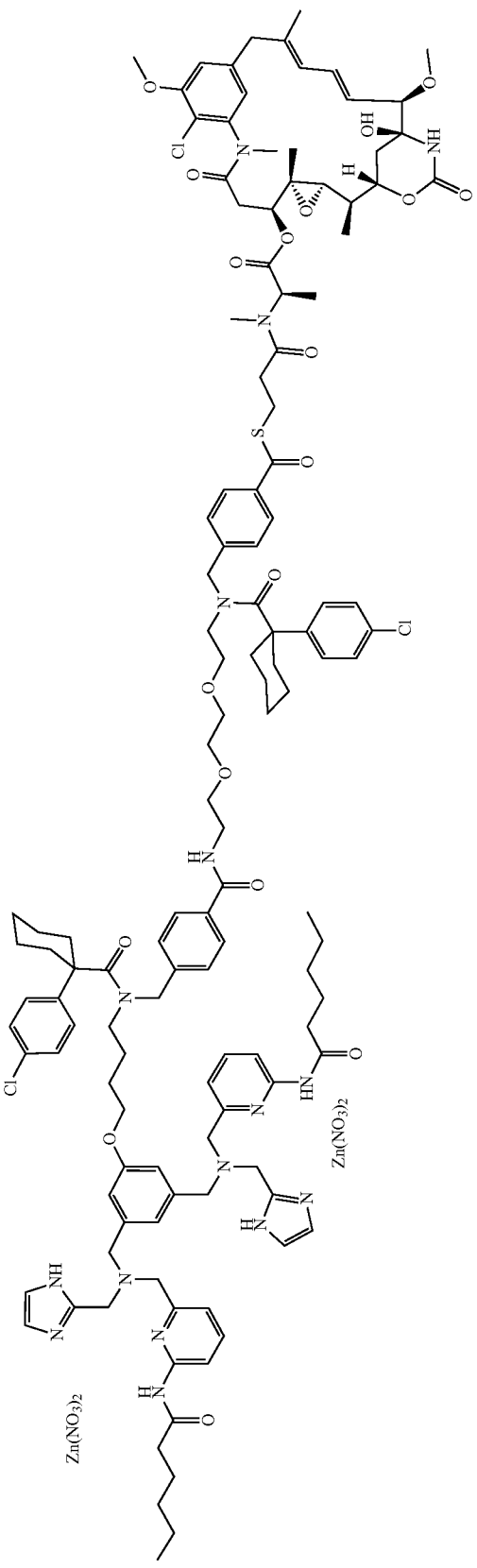
27

The compounds of this invention can be prepared by synthetic methods well known in the art. See R. Larock, Comprehensive Organic Transformations (2$^{nd}$ Ed., VCH Publishers 1999); P. G. M. Wuts and T. W. Greene, Greene's Protective Groups in Organic Synthesis (4, Ed., John Wiley and Sons 2007); L. Fieser and M. Fieser, Fieser and Fieser's Reagents for Organic Synthesis (John Wiley and Sons 1994); and L. Paquette, ed., Encyclopedia of Reagents for Organic Synthesis (2$^{nd}$ ed., John Wiley and Sons 2009) and subsequent editions thereof.

Synthesis of compounds of this invention and determination of their anticancer activities are described in the examples below.

The following examples are to be construed as merely illustrative and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Example 1: Synthesis of Eighteen Head Groups

Syntheses of head groups BPRDP0101, BPRDP0102, BPRDP0103, BPRDP0104, BPRDP0105, BPRDP0106, BPRDP0107, BPRDP0109, and BPRDP0111

Head groups BPRDP0101, BPRDP0102, BPRDP0103, BPRDP0104, BPRDP0105, BPRDP0106, BPRDP0107, BPRDP0109, and BPRDP0111 were prepared according to the schemes shown below.

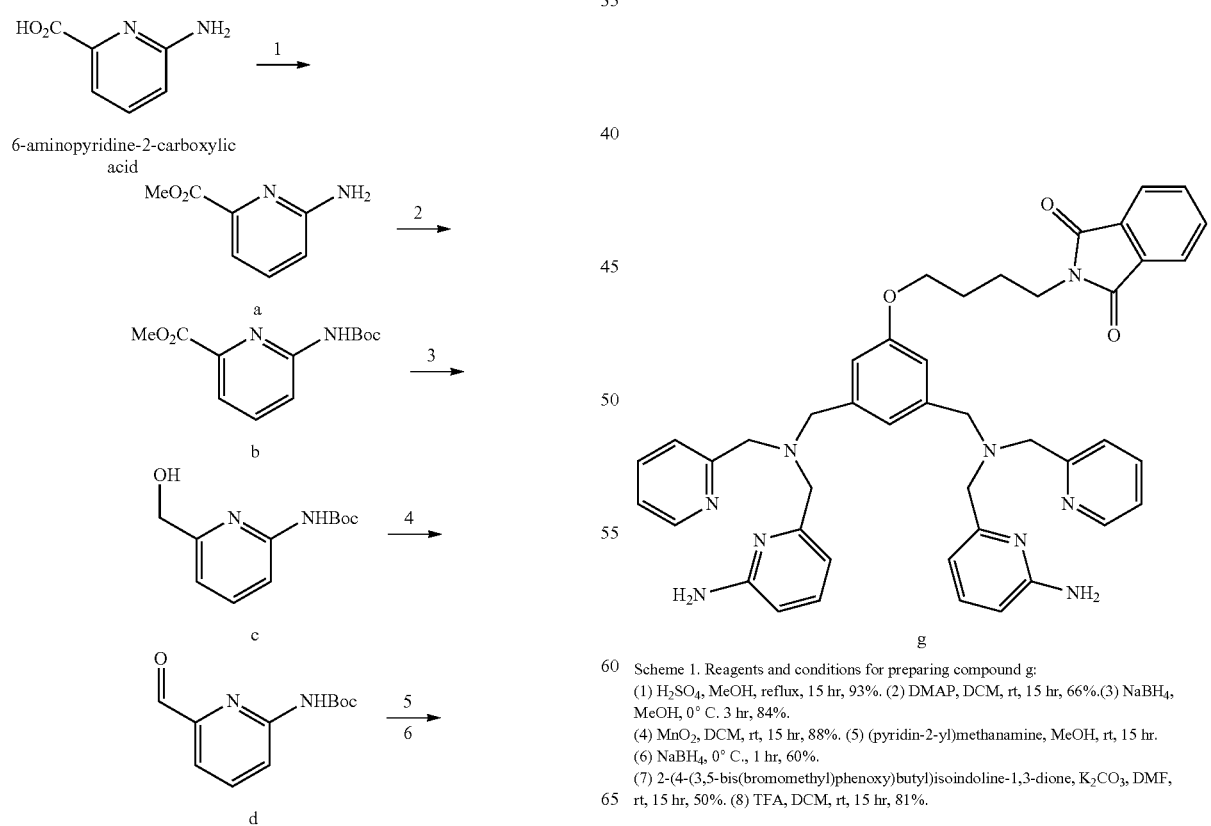

Scheme 1. Reagents and conditions for preparing compound g:
(1) H$_2$SO$_4$, MeOH, reflux, 15 hr, 93%. (2) DMAP, DCM, rt, 15 hr, 66%.(3) NaBH$_4$, MeOH, 0° C. 3 hr, 84%.
(4) MnO$_2$, DCM, rt, 15 hr, 88%. (5) (pyridin-2-yl)methanamine, MeOH, rt, 15 hr.
(6) NaBH$_4$, 0° C., 1 hr, 60%.
(7) 2-(4-(3,5-bis(bromomethyl)phenoxy)butyl)isoindoline-1,3-dione, K$_2$CO$_3$, DMF, rt, 15 hr, 50%. (8) TFA, DCM, rt, 15 hr, 81%.

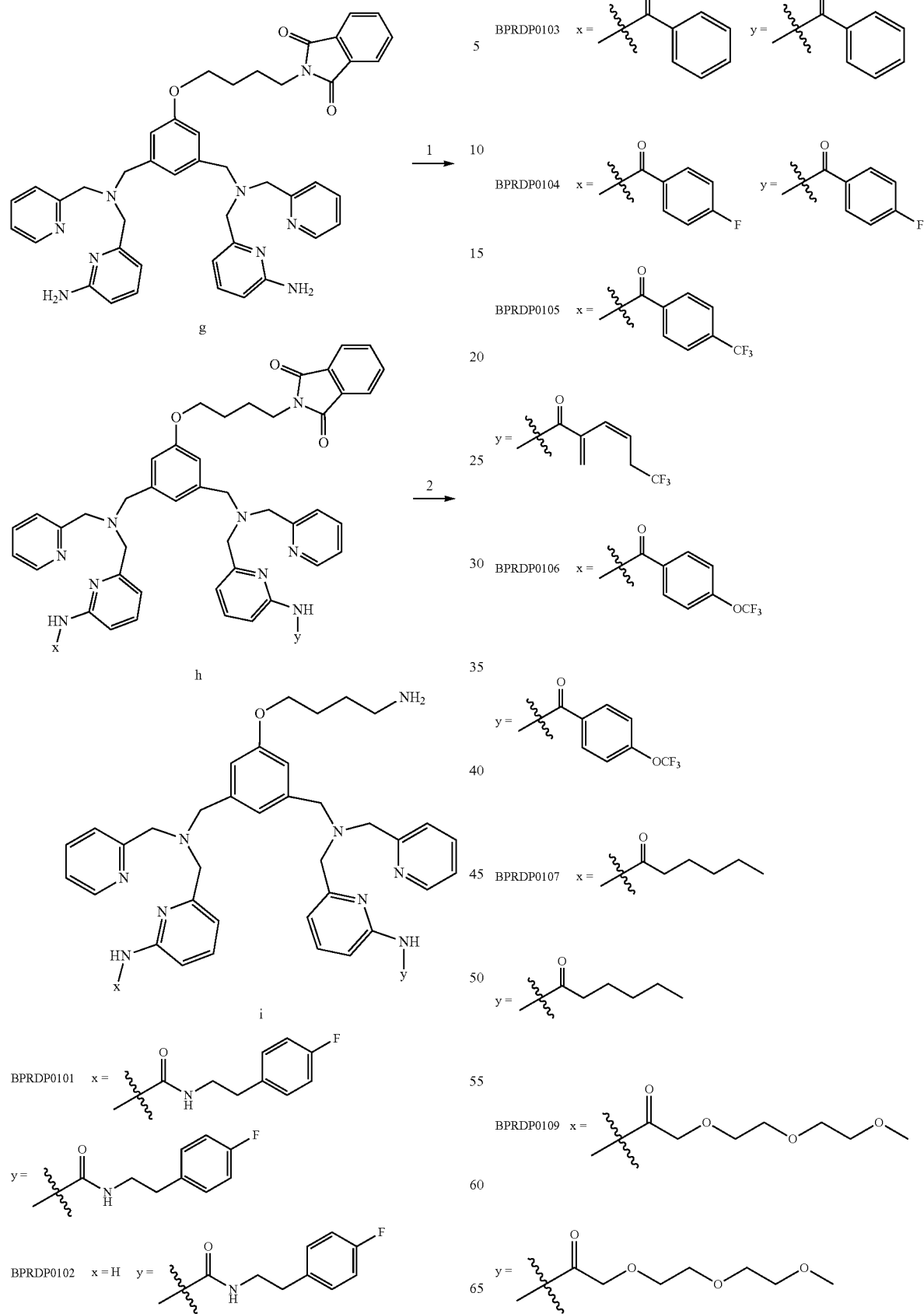

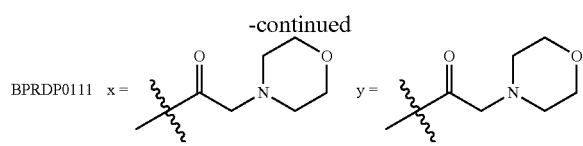

Scheme 2. Reagents and conditions for preparing head group BPRDP0101: (1) 1-fluoro-4-(2-isocyanatoethyl)benzene, DCM, rt, 15 hr, 42%. (2) Hydrazine hydrate, EtOH, DCM, rt, 15 hr, 85%.
Reagents and conditions for preparing head group BPRDP0102: (1) 1-fluoro-4-(2-isocyanatoethyl)benzene, DCM, rt, 15 hr, 45%. (2) Hydrazine hydrate, EtOH, DCM, rt, 15 hr, 79%.
Reagents and conditions for preparing head group BPRDP0103: (1) benzoic acid, EDCI, DMAP, DMF, rt, 15 hr, 66%. (2) Hydrazine hydrate, EtOH, DCM, rt, 15 hr, 81%.
Reagents and conditions for preparing head group BPRDP0104: (1) 4-fluorobenzoic acid, EDCI, DMAP, DMF, rt, 15 hr, 57%. (2) Hydrazine hydrate, EtOH, DCM, rt, 15 hr, 83%.
Reagents and conditions for preparing head group BPRDP0105: (1) 4-(trifluoromethyl)benzoic acid, EDCI, DMAP, DMF, rt, 15 hr, 55%. (2) Hydrazine hydrate, EtOH, DCM, rt, 15 hr, 74%.
Reagents and conditions for preparing head group BPRDP0106: (1) 4-(trifluoromethoxy)benzoic acid, EDCI, DMAP, DMF, rt, 15 hr, 55%. (2) Hydrazine hydrate, EtOH, DCM, rt, 15 hr, 79%.
Reagents and conditions for preparing head group BPRDP0107: (1) hexanoic acid, EDCI, DMAP, DMF, rt, 15 hr, 60%. (2) Hydrazine hydrate, EtOH, DCM, rt, 15 hr, 87%.
Reagents and conditions for preparing head group BPRDP0109: (1) 2-(2-(2-methoxyethoxy)ethoxy)acetic acid, PyBop, DIPEA, DMF, rt, 48 hr, 49%. (2) Hydrazine hydrate, EtOH, DCM, rt, 15 hr, 82%.
Reagents and conditions for preparing head group BPRDP0111: (1) 2-morpholinoacetic acid, PyBop, DIPEA, DMF, rt, 15 hr, 49%. (2) Hydrazine hydrate, EtOH, DCM, rt, 15 hr, 86%.

Preparation of Compound g

Methyl 6-aminopyridine-2-carboxylate (compound a): To a stirred solution of 6-aminopyridine-2-carboxylic acid (10 g, 72 mmol) in 300 mL of Methanol (MeOH) at 0° C., sulfuric acid ($H_2SO_4$, 10 mL) was slowly added. The resultant reaction mixture was stirred for 1 hour and refluxed for 15 hours. MeOH was removed and the resultant residue was extracted with $CH_2Cl_2$ (200 mL). The $CH_2Cl_2$ solution was then washed with a saturated aqueous solution of $NaHCO_3$ (200 mL) and water (200 mL), dried over $MgSO_4$, and concentrated under reduced pressure to yield compound a (10.3 g, 93%). $^1$H NMR (300 MHz, CDCl$_3$): δ 7.55-7.45 (m, 2H), 6.65 (d, J=8.7 Hz, 1H), 3.93 (s, 3H).

Tert-butyl 6-(methoxycarbonyl)pyridin-2-ylcarbamate (compound b): To a stirred solution of compound a (1 g, 6.58 mmol, 1 eq.) in 50 mL of dry dichloromethane (DCM) at room temperature, Di-tert-butyl dicarbonate (1.3 g, 5.92 mmol, 0.9 eq.) and DMAP (0.8 g, 6.58 mmol, 1 eq.) were slowly added. The resultant reaction mixture was stirred for 15 hours. The resultant residue was extracted with $CH_2Cl_2$ (100 mL). The $CH_2Cl_2$ extract was then washed with water (100 mL), dried over $MgSO_4$, and concentrated under reduced pressure. The resultant residue was purified by flash chromatography over silica gel with Ethyl acetate/Hexane (1/4) to yield compound b (1.1 g, 66%). $^1$H NMR (300 MHz, CDCl$_3$): δ 8.16-8.13 (m, 1H), 7.80-7.78 (m, 2H), 3.97 (s, 3H), 1.50 (s, 9H).

Tert-butyl 6-(hydroxymethyl)pyridin-2-ylcarbamate (compound c): To a stirred solution of compound b (1 g, 3.97 mmol, 1 eq.) in 50 mL of Methanol (MeOH) at 0° C., sodium borohydride (2.26 g, 59.5 mmol, 15 eq.) was slowly added. The resultant reaction mixture was stirred at 0° C. for 3 hours. After removal of MeOH, the residue was extracted with $CH_2Cl_2$ (200 mL). The $CH_2Cl_2$ extract was washed with a saturated ammonium chloride aqueous solution twice (2×200 mL), dried over $MgSO_4$, and concentrated under reduced pressure to yield compound c (750 mg, 84%). $^1$H NMR (300 MHz, CDCl$_3$): δ 7.81 (d, J=8.4 Hz, 1H), 7.67-7.62 (m, 1H), 6.88 (d, J=7.5 Hz, 1H), 4.64 (s, 2H), 1.53 (s, 9H).

Tert-butyl 6-formylpyridin-2-ylcarbamate (compound d): To a stirred solution of compound c (800 mg, 3.57 mmol, 1 eq.) in 100 mL of dry dichloromethane (DCM) at room temperature, $MnO_2$ (2.26 g, 59.5 mmol, 15 eq.) was slowly added. The resultant reaction mixture was stirred at room temperature for 15 hours, filtered with celite, and washed with $CH_2Cl_2$. The $CH_2Cl_2$ solution was concentrated under reduced pressure to yield compound d (700 mg, 88%). $^1$H NMR (300 MHz, CDCl$_3$): δ 9.89 (s, 1H), 8.20 (d, J=8.1 Hz, 1H), 7.87-7.81 (m, 1H), 7.61 (d, J=7.2 Hz, 1H), 1.53 (s, 9H).

Tert-butyl 6-(((pyridin-2-yl)methylamino)methyl)pyridin-2-ylcarbamate (compound e): To a stirred solution of compound d (1 g, 4.5 mmol, 1.3 eq.) in 50 mL of MeOH at room temperature, (pyridine-2-yl)methanamine (380 mg, 3.46 mmol, 1 eq.) was slowly added. The resultant reaction mixture was stirred at room temperature for 15 hours and then cooled down to 0° C. Sodium borohydride (2 g, 52 mmol, 15 eq.) was added. The mixture was stirred at 0° C. for 1 hour. After removal of MeOH, the resultant residue was extracted with $CH_2Cl_2$ (200 mL). The $CH_2Cl_2$ extract was washed with a saturated ammonium chloride aqueous solution (200 mL), dried over $MgSO_4$, and concentrated under reduced pressure. The resultant residue was purified by flash chromatography over silica gel with Ethyl acetate/Hexane (5/95) to yield compound e (650 mg, 60%). $^1$H NMR (300 MHz, CDCl$_3$): δ 8.55 (d, J=5.7 Hz, 1H), 7.76 (d, J=8.7 Hz, 1H), 7.66-7.57 (m, 2H), 7.33 (d, J=7.8 Hz, 1H), 7.17-7.13 (m, 1H), 6.96 (d, J=7.2 Hz, 1H), 3.94 (s, 2H), 3.84 (s, 2H), 1.51 (s, 9H).

Di-tert-butyl (((((5-(4-(1,3-dioxoisoindolin-2-yl)butoxy)-1,3-phenylene)bis(methylene))bis((pyridin-2-ylmethyl)azanediyl))bis(methylene))bis(pyridine-6,2-diyl))dicarbamate (compound f): To a stirred solution of compound e (500 mg, 1.59 mmol, 2 eq.) in 5 mL of dry dimethylformamide (DMF) at room temperature, 2-(4-(3,5-bis(bromomethyl)phenoxy)butyl)isoindoline-1,3-dione (380 mg, 0.795 mmol, 1 eq.) and $K_2CO_3$ (544 mg, 4 mmol, 5 eq.) were slowly added. The resultant reaction mixture was stirred at room temperature for 15 hours and extracted with $CH_2Cl_2$ (100 mL). The $CH_2Cl_2$ extract was washed with water (5×100 mL), dried over $MgSO_4$, and concentrated under reduced pressure. The resultant residue was purified by flash chromatography over silica gel with Ethyl acetate/Hexane (7/3) to yield compound f (380 mg, 50%). $^1$H NMR (300 MHz, CDCl$_3$): δ 8.47 (d, J=5.1 Hz, 2H), 7.85-7.80 (m, 4H), 7.70-7.68 (m, 2H), 7.65-7.60 (m, 2H), 7.53-7.49 (m, 4H), 7.43 (s, 1H), 7.13-7.07 (m, 4H), 6.69 (s, 2H), 3.95 (t, J=5.7 Hz, 2H), 3.78-3.73 (m, 6H), 3.72 (s, 4H), 3.54 (s, 4H), 1.90-1.79 (m, 4H), 1.31 (s, 18H).

2-(4-(3,5-bis((((6-aminopyridin-2-yl)methyl)(pyridin-2-ylmethyl)amino)methyl) phenoxy)butyl)isoindoline-1,3-dione (compound g): To a stirred solution of compound f (500 mg, 0.53 mmol) in 50 ml of dry DCM at room temperature, trifluoroacetic acid (TFA) was slowly added. The reaction mixture was stirred at room temperature for 15 hours and extracted with $CH_2Cl_2$ (200 mL). The $CH_2Cl_2$ extract was washed with a saturated aqueous solution of $NaHCO_3$ (200 mL), dried over $MgSO_4$, and concentrated under reduced pressure to yield compound g (320 mg, 81%). $^1$H NMR (300 MHz, CDCl$_3$): δ 8.49 (d, J=3.9 Hz, 2H), 7.85-7.82 (m, 2H), 7.72-7.69 (m, 2H), 7.62-7.61 (m, 4H), 7.40-7.35 (m, 2H), 7.13-7.08 (m, 2H), 7.06 (s, 1H), 6.93 (d, J=7.5 Hz, 2H), 6.82 (s, 2H), 6.35 (d, J=7.8 Hz, 2H), 3.96 (t, J=6.3 Hz, 2H), 3.80 (s, 4H), 3.77-3.74 (m, 2H), 3.61 (s, 8H), 1.90-1.83 (m, 4H).

Synthesis of Head Group BPRDP0101
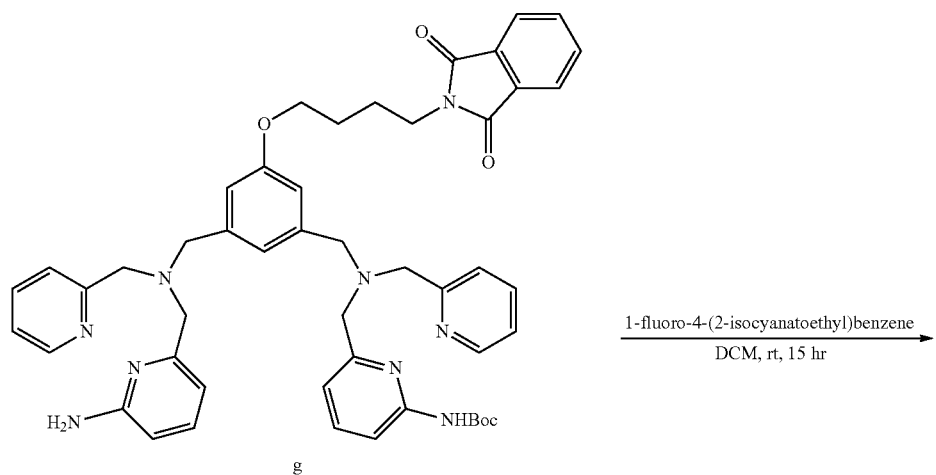
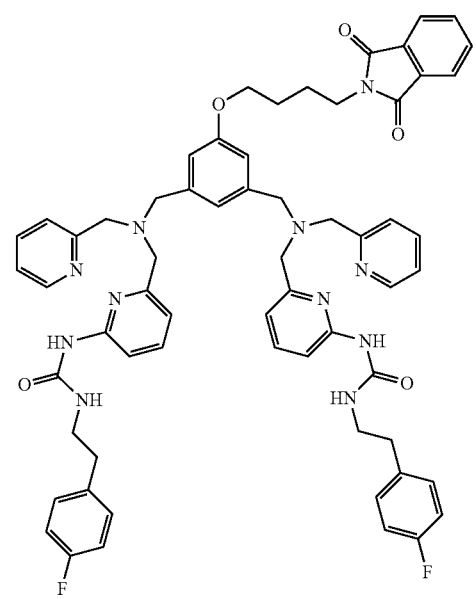

1,1'-(((((5-(4-(1,3-dioxoisoindolin-2-yl)butoxy)-1,3-phenylene)bis(methylene))bis ((pyridin-2-ylmethyl)azanediyl)) bis(methylene))bis(pyridine-6,2-diyl))bis(3-(4-fluorophenethyl)urea) (compound h101): To a stirred solution of compound g (200 mg, 0.267 mmol, 1 eq.) in 20 mL of dry DCM at room temperature, 1-fluoro-4-(2-isocyanatoethyl) benzene (264 mg, 1.6 mmol, 6 eq.) was slowly added. The reaction mixture was stirred at room temperature for 15 hours and concentrated under reduced pressure. The resultant residue was purified by flash chromatography over silica gel with MeOH/DCM (5/95) to yield compound h101 (120 mg, 42%). $^1$H NMR (300 MHz, CDCl$_3$): δ 8.5 (d, J=4.2 Hz, 2H), 7.85-7.82 (m, 2H), 7.72-7.69 (m, 2H), 7.64-7.58 (m, 2H), 7.53-7.49 (m, 4H), 7.17-7.10 (m, 8H), 6.99 (s, 1H), 6.96-6.88 (m, 4H), 6.83 (s, 2H), 6.52 (d, J=7.8 Hz, 2H), 3.96 (t, J=5.7 Hz, 2H), 3.77-3.75 (m, 2H), 3.73 (s, 4H), 3.65-3.58 (m, 4H), 3.57 (s, 4H), 3.43 (s, 4H), 2.84 (t, J=7.2 Hz, 4H), 1.88-1.83 (m, 4H). ESI-MS C$_{62}$H$_{61}$F$_2$N$_{11}$O$_5$: 1077.4825, found 540 [(EM+2H$^+$)/2.

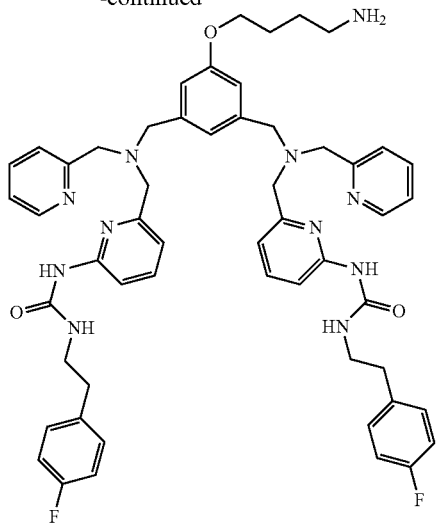

BPRDP0101

1,1'-(6,6'-((((5-(4-aminobutoxy)-1,3-phenylene)bis(methylene))bis((pyridin-2-ylmethyl)azanediyl))bis(methylene)) bis(pyridine-6,2-diyl))bis(3-(4-fluorophenethyl)urea) (head group BPRDP0101): To a stirred solution of compound h101 (200 mg, 0.185 mmol, 1 eq.) in 3 mL EtOH and 1 mL dry DCM at room temperature, hydrazine hydrate (120 mg, 3.7 mmol, 20 eq.) was slowly added. The resultant reaction mixture was stirred at room temperature for 15 hours. EtOH and DCM were removed and the resultant residue was extracted with CH$_2$Cl$_2$ (200 mL). The CH$_2$Cl$_2$ extract was washed with H$_2$O (200 mL), dried over MgSO$_4$, and concentrated under reduced pressure to yield BPRDP0101 (150 mg, 85%). $^1$H NMR (400 MHz, CDCl$_3$): δ 8.51 (d, J=4.0 Hz, 2H), 7.62-7.58 (m, 2H), 7.49-7.41 (m, 4H), 7.15-7.09 (m, 6H), 6.99 (d, J=7.2 Hz, 2H), 6.91-6.87 (m, 5H), 6.76 (d, J=8.0 Hz, 2H), 6.72 (s, 2H), 3.84 (m, 2H), 3.76 (s, 4H), 3.61-3.57 (m, 4H), 3.55 (s, 4H), 3.43 (s, 4H), 2.90 (m, 2H), 2.81 (t, J=6.8 Hz, 4H), 1.77 (m, 4H). ESI-MS C$_{54}$H$_{59}$F$_2$N$_{11}$O$_3$: 947.477, found 538 [(EM+2Zn$^{2+}$)+2]/2.

Synthesis of Head Group BPRDP0102

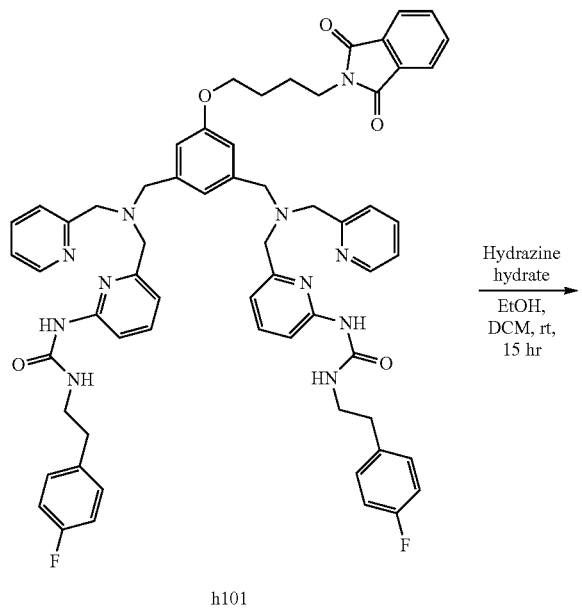

h101

Hydrazine hydrate
EtOH, DCM, rt, 15 hr

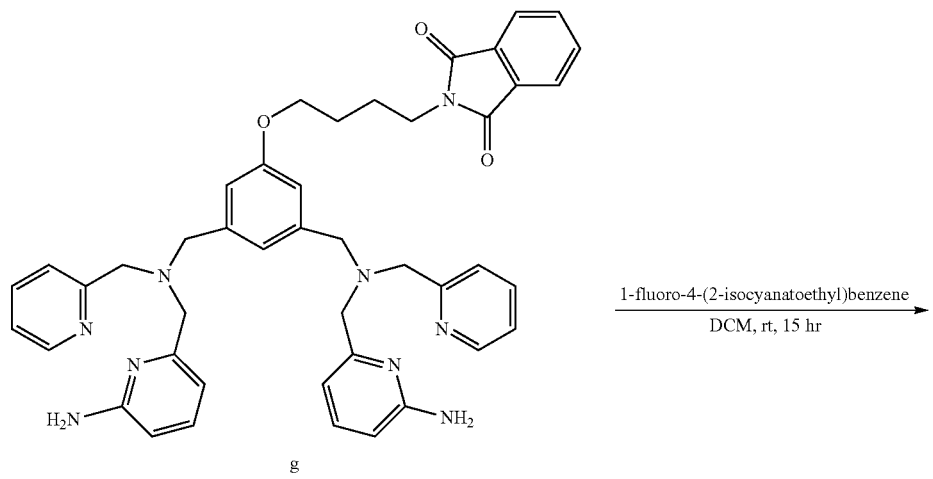

g 1-fluoro-4-(2-isocyanatoethyl)benzene
DCM, rt, 15 hr

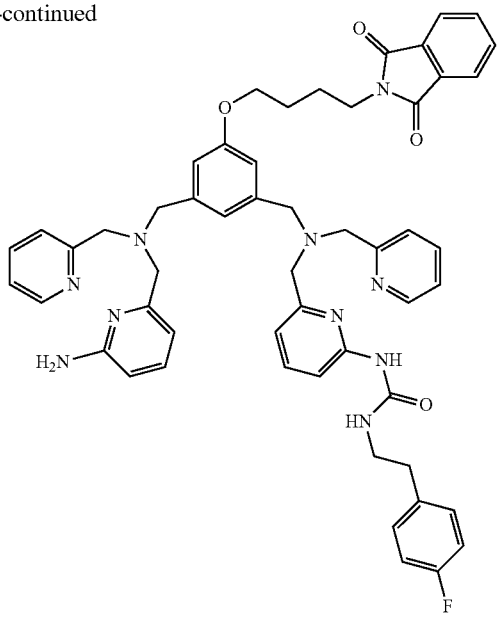

h102

1-(6-(((3-(((((6-aminopyridin-2-yl)methyl)(pyridin-2-yl-methyl)amino)methyl)-5-(4-(1,3-dioxoisoindolin-2-yl)butoxy)benzyl)(pyridin-2-ylmethyl)amino)methyl) pyridin-2-yl)-3-(4-fluorophenethyl)urea (compound h102): To a stirred solution of compound g (200 mg, 0.267 mmol, 1 eq.) in 20 mL of dry DCM at room temperature, 1-fluoro-4-(2-isocyanatoethyl)benzene (264 mg, 1.6 mmol, 6 eq.) was slowly added. The reaction mixture was stirred at room temperature for 15 hours and concentrated under reduced pressure. The resultant residue was purified by flash chromatography over silica gel with MeOH/DCM (5/95) to yield compound h102 (110 mg, 45%). $^1$H NMR (400 MHz, CDCl$_3$): δ 8.51-8.48 (m, 2H), 7.85-7.82 (m, 2H), 7.72-7.70 (m, 2H), 7.64-7.59 (m, 4H), 7.55-7.47 (m, 1H), 7.39-7.35 (m, 1H), 7.17-7.09 (m, 5H), 7.03 (s, 1H), 6.95-6.91 (m, 3H), 6.84 (s, 1H), 6.80 (s, 1H), 6.52 (d, J=8.0 Hz, 1H), 6.35 (d, J=8.4 Hz, 1H), 3.96 (t, J=6.0 Hz, 2H), 3.80-3.74 (m, 6H), 3.64-3.59 (m, 6H), 3.56 (s, 2H), 3.44 (s, 2H), 2.84 (t, J=6.8 Hz, 2H), 1.91-1.80 (m, 4H).

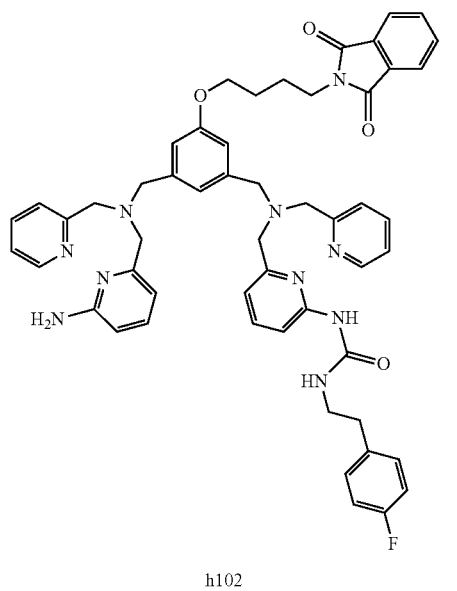

h102

Hydrazine hydrate
EtOH, DCM, rt, 15 hr
⟶

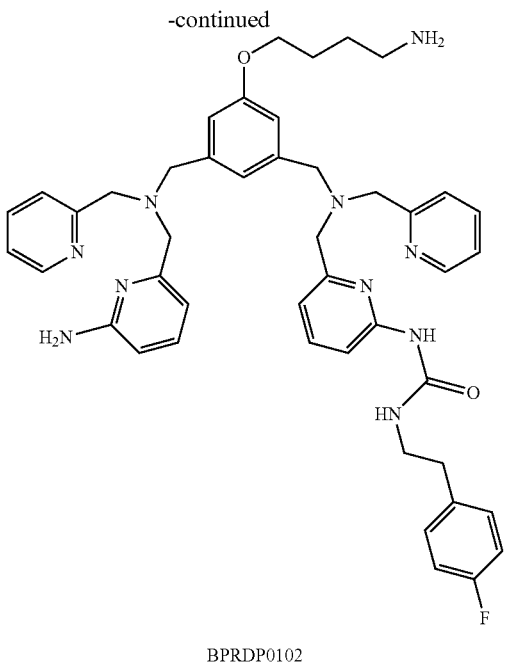

BPRDP0102

1-(6-{[(3-(4-Amino-butoxy)-5-1{[(6-amino-pyridin-2-ylmethyl)-pyridin-2-ylmethyl-amino]-methyl}-benzyl)-pyridin-2-ylmethyl-amino]-methyl}-pyridin-2-yl)-3-[2-(4-fluoro-phenyl)-ethyl]-urea (head group BPRDP0102): To a stirred solution of compound h102 (200 mg, 0.219 mmol, 1 eq.) in 3 mL EtOH and 1 mL dry DCM at room temperature, hydrazine hydrate (140 mg, 4.4 mmol, 20 eq.) was slowly added. The resultant reaction mixture was stirred at room temperature for 15 hours. Removal of EtOH and DCM gave a crude residue. The resultant residue was extracted with CH$_2$Cl$_2$ (200 mL). The CH$_2$Cl$_2$ solution was then washed with H$_2$O (200 mL), dried over MgSO$_4$, and concentrated under reduced pressure to yield BPRDP0102 (135 mg, 79%). $^1$H NMR (400 MHz, CDCl$_3$): δ 8.51-8.48 (m, 2H), 7.62-7.57 (m, 3H), 7.53-7.45 (m, 2H), 7.38-7.34 (m, 1H), 7.16-7.07 (m, 5H), 7.02 (s, 1H), 6.94-6.90 (m, 3H), 6.84-6.79 (m, 2H), 6.63 (d, J=8.4 Hz, 1H), 6.33 (d, J=8.0 Hz, 1H), 3.93 (t, J=6.0 Hz, 2H), 3.79-3.75 (m, 4H), 3.64-3.57 (m, 8H), 3.44 (s, 2H), 2.84 (t, J=7.2 Hz, 2H), 2.77 (t, J=6.8 Hz, 2H), 1.82-1.75 (m, 2H), 1.66-1.59 (m, 2H). ESI-MS $C_{45}H_{51}FN_{10}O_2$: 782.418, found 456 [(EM+2Zn$^{2+}$)+2]/2.

Synthesis of Head Group BPRDP0103

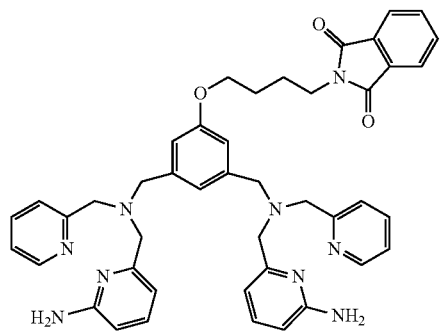

g

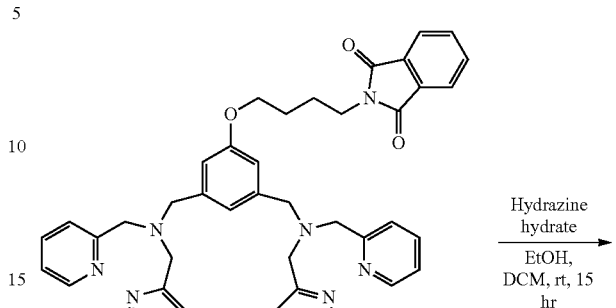

h103

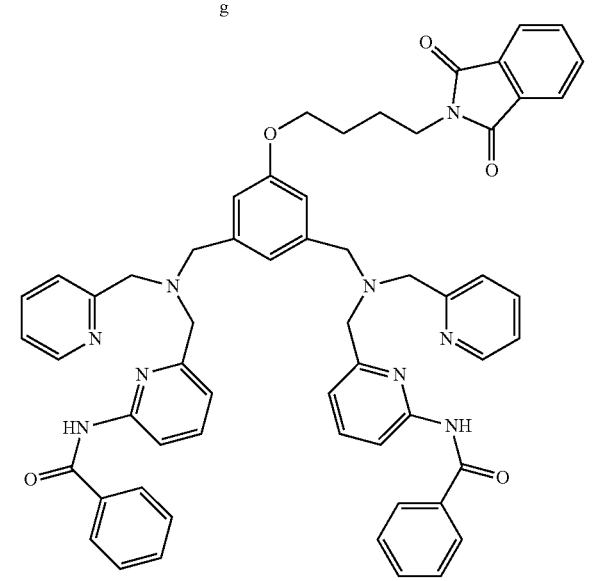

h103

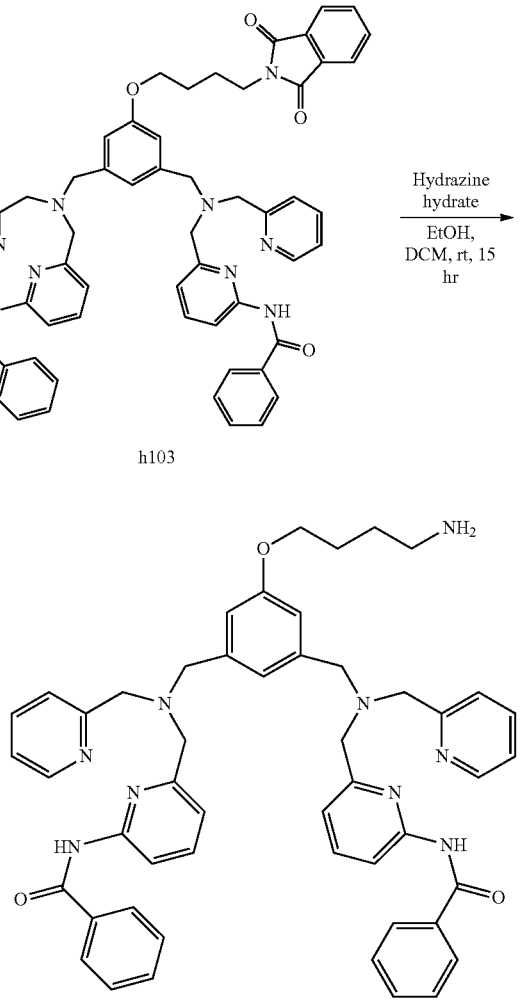

BPRDP0103

N,N'-(((((5-(4-(1,3-dioxoisoindolin-2-yl)butoxy)-1,3-phenylene)bis(methylene)) bis((pyridin-2-ylmethyl)azanediyl))bis(methylene))bis(pyridine-6,2-diyl))dibenzamide (compound h103): To a stirred solution of compound g (200 mg, 0.267 mmol, 1 eq.) in 4 ml of dry DMF at room temperature, benzoic acid (130 mg, 1.07 mmol, 4 eq.), EDCI (310 mg, 1.6 mmol, 6 eq), and DMAP (33 mg, 0.267 mmol, 1 eq.) were slowly added. The reaction mixture was stirred at room temperature for 15 hours and extracted with $CH_2Cl_2$ (200 mL). The $CH_2Cl_2$ extract was washed with a saturated aqueous solution of NaHCO$_3$ (200 mL), dried over MgSO$_4$, and concentrated under reduced pressure. The resultant residue was purified by flash chromatography over silica gel with MeOH/Ethyl acetate (2/98) to yield compound h103 (170 mg, 66%). $^1$H NMR (400 MHz, CDCl$_3$): δ 8.47 (d, J=4.4 Hz, 2H), 8.27 (d, J=8.4 Hz, 2H), 7.83-7.81 (m, 2H), 7.79-7.77 (m, 4H), 7.73-7.68 (m, 4H), 7.58-7.52 (m, 4H), 7.48-7.44 (m, 2H), 7.37-7.33 (m, 4H), 7.28 (d, J=7.2 Hz, 2H), 7.16 (s, 1H), 7.12-7.09 (m, 2H), 6.77 (s, 2H), 3.96 (t, J=6.0 Hz, 2H), 3.77-3.73 (m, 6H), 3.60 (s, 8H), 1.89-1.78 (m, 4H). ESI-MS $C_{58}H_{53}N_9O_5$: 955.479, found 956 [EM+H$^+$].

N,N'-(6,6'-(((((5-(4-aminobutoxy)-1,3-phenylene)bis(methylene))bis((pyridin-2-ylmethyl)azanediyl))bis(methylene))bis(pyridine-6,2-diyl))dibenzamide (head group BPRDP0103): To a stirred solution of compound h103 (200 mg, 0.209 mmol, 1 eq.) in 3 mL EtOH and 1 mL dry DCM at room temperature, hydrazine hydrate (134 mg, 4.2 mmol, 20 eq.) was slowly added. The resultant reaction mixture was stirred at room temperature for 15 hours. Removal of EtOH and DCM gave a residue. The residue was extracted with $CH_2Cl_2$ (200 mL). The $CH_2Cl_2$ solution was then washed with H$_2$O (200 mL), dried over MgSO$_4$, and concentrated under reduced pressure to yield BPRDP0103 (140 mg, 81%). $^1$H NMR (400 MHz, CDCl$_3$): δ 8.47 (d, J=4.8 Hz, 2H), 8.27 (d, J=8.0 Hz, 2H), 7.79 (d, J=6.8 Hz, 4H), 7.73-7.69 (m, 2H), 7.58-7.45 (m, 6H), 7.37-7.33 (m, 4H), 7.27 (d, J=8.4 Hz, 2H), 7.16 (s, 1H), 7.12-7.09 (m, 2H), 6.77 (s, 2H), 3.94 (t, J=6.4 Hz, 2H), 3.77 (s, 4H), 3.61 (s, 4H), 3.60 (s, 4H), 2.74 (t, J=6.8 Hz, 2H), 1.82-1.75 (m, 2H), 1.63-1.55 (m, 2H). ESI-MS $C_{50}H_{51}N_9O_3$: 825.4115, found 477 [(M+2Zn$^{2+}$)+2]/2.

Synthesis of Head Group BPRDP0104

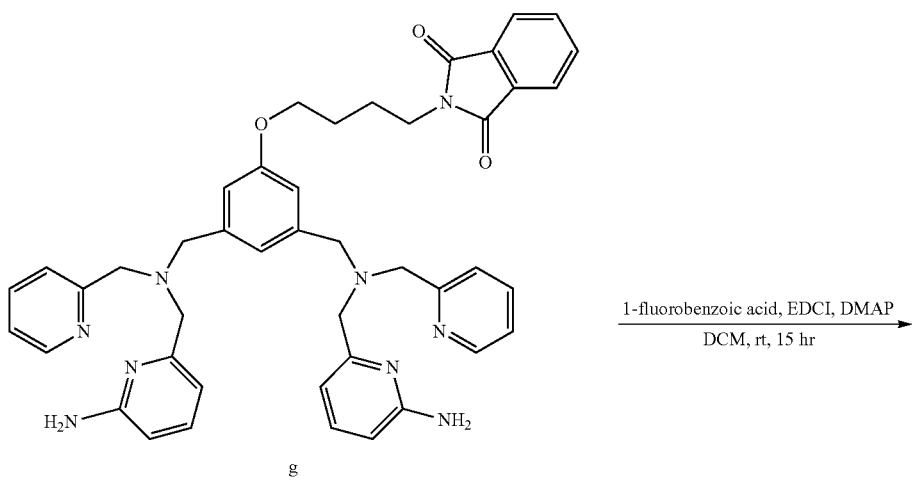

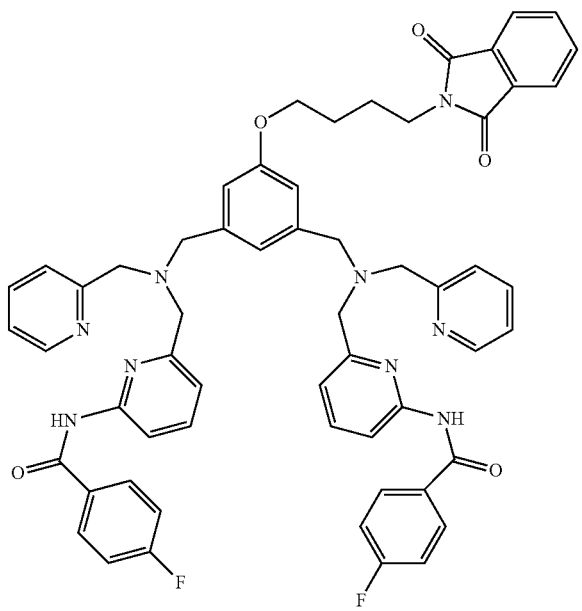

N,N'-(((((5-(4-(1,3-dioxoisoindolin-2-yl)butoxy)-1,3-phenylene)bis(methylene)) bis((pyridin-2-ylmethyl)azanediyl))bis(methylene))bis(pyridine-6,2-diyl))bis(4-fluorobenzamide) (compound h104): To a stirred solution of compound g (200 mg, 0.267 mmol, 1 eq.) in 4 ml of dry DMF at room temperature, 4-fluorobenzoic acid (150 mg, 1.07 mmol, 4 eq.), EDCI (310 mg, 1.6 mmol, 6 eq.), and DMAP (33 mg, 0.267 mmol, 1 eq.) were slowly added. The resultant reaction mixture was stirred at room temperature for 15 hours and then extracted with $CH_2Cl_2$ (200 mL). The $CH_2Cl_2$ extract was washed with a saturated aqueous solution of $NaHCO_3$ (200 mL), dried over $MgSO_4$, and concentrated under reduced pressure. The resultant residue was purified by flash chromatography over silica gel with MeOH/Ethyl acetate (2/98) to yield compound h104 (150 mg, 57%). $^1$H NMR (400 MHz, $CDCl_3$): δ 8.48 (d, J=4.8 Hz, 2H), 8.23 (d, J=8.0 Hz, 2H), 7.83-7.76 (m, 6H), 7.74-7.68 (m, 4H), 7.59-7.55 (m, 2H), 7.52-7.49 (m, 2H), 7.27 (d, J=8.0 Hz, 2H), 7.16 (s, 1H), 7.13-7.10 (m, 2H), 7.03-6.98 (m, 4H), 6.76 (s, 2H), 3.96 (t, J=6.0 Hz, 2H), 3.78-3.73 (m, 6H), 3.61 (s, 4H), 3.60 (s, 4H), 1.89-1.79 (m, 4H).

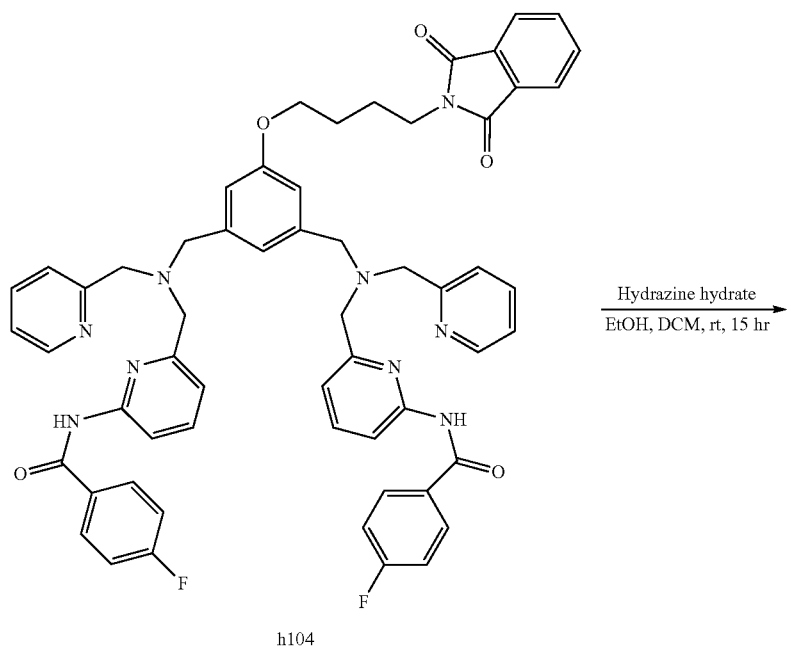

h104

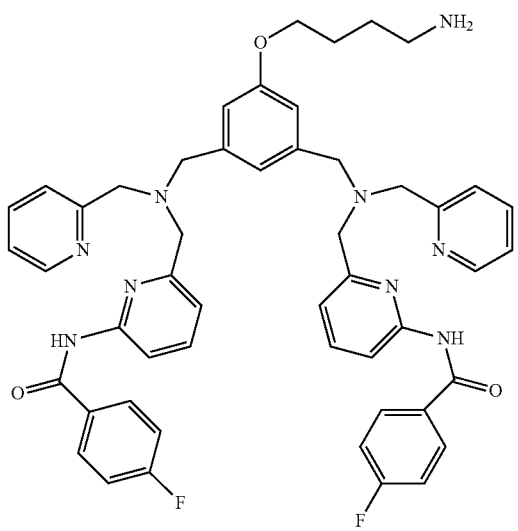

BPRDP0104

N,N'-(6,6'-(((((5-(4-aminobutoxy)-1,3-phenylene)bis(methylene))bis((pyridin-2-ylmethyl)azanediyl))bis(methylene))bis(pyridine-6,2-diyl))bis(4-fluorobenzamide) (head group BPRDP0104): To a stirred solution of compound h104 (200 mg, 0.202 mmol, 1 eq.) in 3 mL EtOH and 1 mL dry DCM at room temperature, hydrazine hydrate (129 mg, 4.04 mmol, 20 eq.) was slowly added. The resultant reaction mixture was stirred at room temperature for 15 hours. EtOH and DCM were removed and the resultant residue was extracted with $CH_2Cl_2$ (200 mL). The $CH_2Cl_2$ solution was then washed with $H_2O$ (200 mL), dried over $MgSO_4$, and concentrated under reduced pressure to yield BPRDP0104 (145 mg, 83%). $^1H$ NMR (400 MHz, $CDCl_3$): δ 8.47 (d, J=4.8 Hz, 2H), 8.23 (d, J=8.4 Hz, 2H), 7.81-7.77 (m, 4H), 7.72-7.69 (m, 2H), 7.58-7.53 (m, 2H), 7.50-7.48 (m, 2H), 7.26 (d, J=7.2 Hz, 2H), 7.14 (s, 1H), 7.12-7.09 (m, 2H), 7.00 (t, J=8.4 Hz, 4H), 6.74 (s, 2H), 3.92 (t, J=6.4 Hz, 2H), 3.76 (s, 4H), 3.59 (s, 4H), 3.58 (s, 4H), 2.77 (t, J=7.2 Hz, 2H), 1.81-1.74 (m, 2H), 1.65-1.60 (m, 2H). ESI-MS $C_{50}H_{49}F_2N_9O_3$: 861.3926, found 884 (M+Na$^+$).

Synthesis of Head Group BPRDP0105

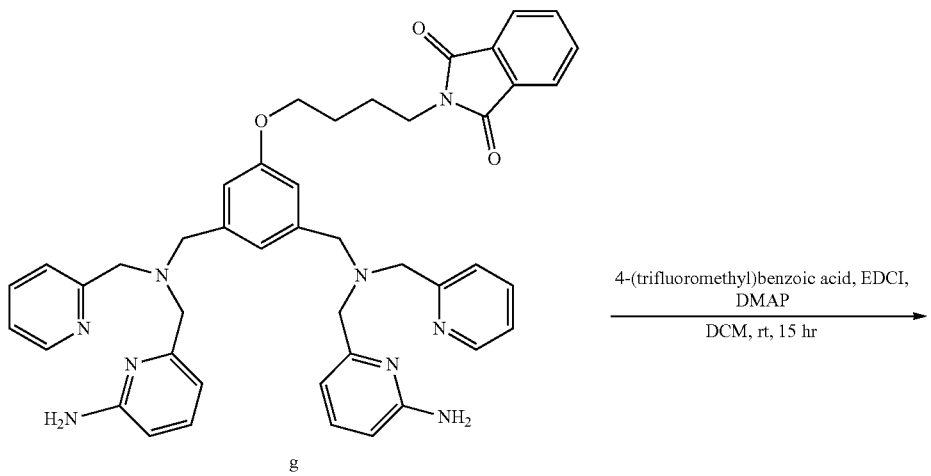

4-(trifluoromethyl)benzoic acid, EDCI, DMAP
―――――――――――――――――――→
DCM, rt, 15 hr

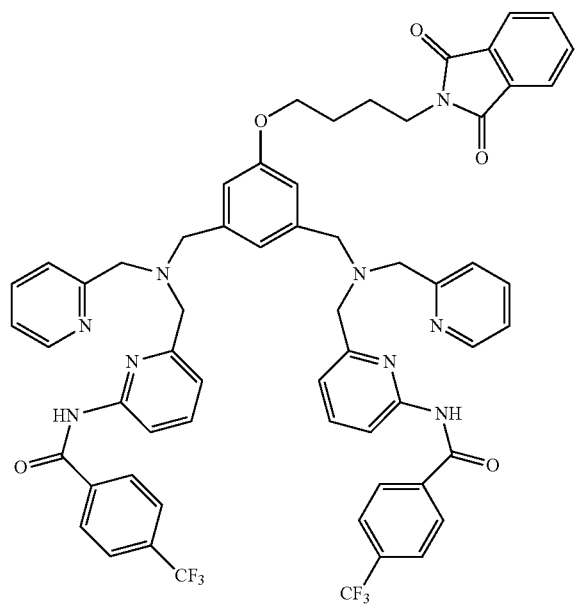

h105

N,N'-(((((5-(4-(1,3-dioxoisoindolin-2-yl)butoxy)-1,3-phenylene)bis(methylene)) bis((pyridin-2-ylmethyl) azanediyl))bis(methylene))bis(pyridine-6,2-diyl))bis(4-(trifluoromethyl)benzamide) (compound h105): To a stirred solution of compound g (200 mg, 0.267 mmol, 1 eq.) in 4 mL dry DMF at room temperature, 4-(trifluoromethyl)benzoic acid (203 mg, 1.07 mmol, 4 eq.), EDCI (310 mg, 1.6 mmol, 6 eq.), and DMAP (33 mg, 0.267 mmol, 1 eq.) were slowly added. The resultant reaction mixture was stirred at room temperature for 15 hours and the solvent was removed. The resultant residue was extracted with $CH_2Cl_2$ (200 mL). The $CH_2Cl_2$ solution was then washed with a saturated aqueous solution of $NaHCO_3$ (200 mL), dried over $MgSO_4$, and concentrated under reduced pressure. The resultant residue was purified by flash chromatography over silica gel with MeOH/Ethyl acetate (2/98) to yield compound h105 (160 mg, 55%). $^1$H NMR (400 MHz, $CDCl_3$): δ 8.48 (d, J=5.6 Hz, 2H), 8.26 (d, J=8.4 Hz, 2H), 7.83-7.80 (m, 6H), 7.76-7.72 (m, 2H), 7.70-7.68 (m, 2H), 7.58-7.54 (m, 6H), 7.49 (d, J=8.0 Hz, 2H), 7.27 (d, J=6.0 Hz, 2H), 7.21 (s, 1H), 7.14-7.10 (m, 2H), 6.74 (s, 2H), 3.96 (t, J=6.0 Hz, 2H), 3.77-3.73 (m, 6H), 3.58 (s, 4H), 3.55 (s, 4H), 1.89-1.79 (m, 4H).

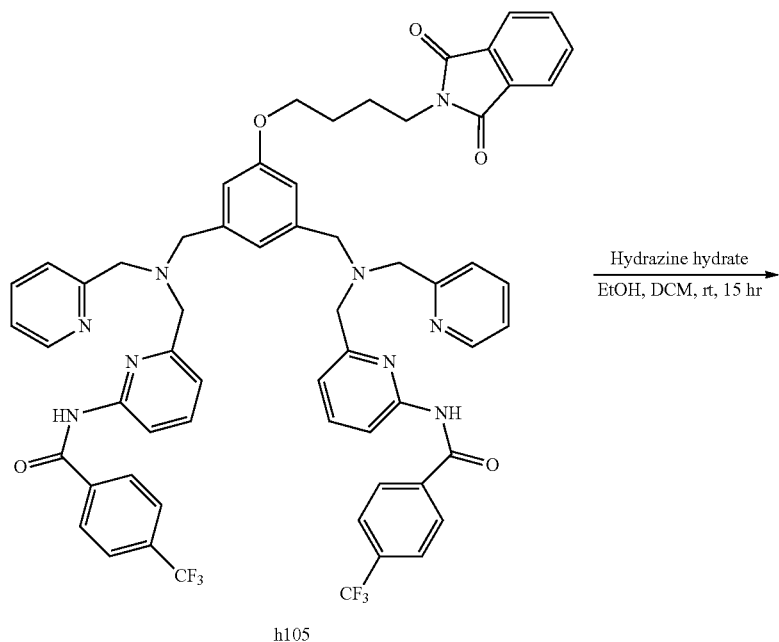

h105

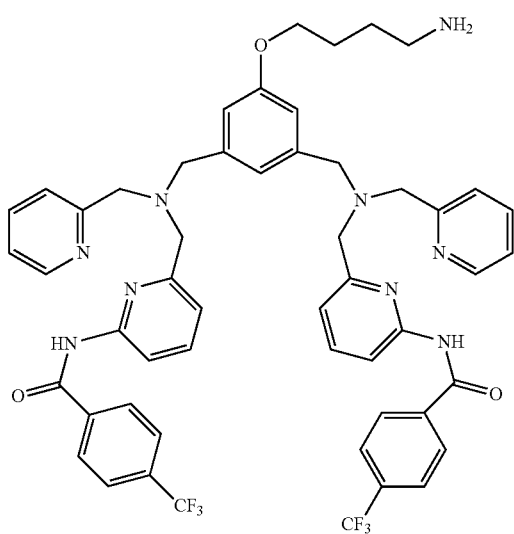

BPRDP0105

N,N'-(6,6'-((((5-(4-aminobutoxy)-1,3-phenylene)bis(methylene))bis((pyridin-2-ylmethyl)azanediyl))bis(methylene))bis(pyridine-6,2-diyl))bis(4-(trifluoromethyl)benzamide) (head group BPRDP0105): To a stirred solution of compound h105 (200 mg, 0.183 mmol, 1 eq.) in 3 mL EtOH and 1 mL dry DCM at room temperature, hydrazine hydrate (117 mg, 3.66 mmol, 20 eq.) was slowly added. The resultant reaction mixture was stirred at room temperature for 15 hours. Removal of EtOH and DCM gave a residue. The residue was extracted with $CH_2Cl_2$ (200 mL). The $CH_2Cl_2$ solution was then washed with $H_2O$ (200 mL), dried over $MgSO_4$, and concentrated under reduced pressure to yield BPRDP0105 (130 mg, 74%). $^1$H NMR (400 MHz, $CDCl_3$): δ 8.47 (d, J=4.0 Hz, 2H), 8.25 (d, J=8.4 Hz, 2H), 7.82 (d, J=8.0 Hz, 4H), 7.75-7.71 (m, 2H), 7.58-7.54 (m, 6H), 7.47 (d, J=7.6 Hz, 2H), 7.25 (d, J=8.0 Hz, 2H), 7.18 (s, 1H), 7.13-7.10 (m, 2H), 6.72 (s, 2H), 3.92 (t, J=6.0 Hz, 2H), 3.74 (s, 4H), 3.58 (s, 4H), 3.54 (s, 4H), 2.82 (t, J=6.8 Hz, 2H), 1.80-1.77 (m, 2H), 1.69-1.66 (m, 2H). ESI-MS $C_{52}H_{49}F_6N_9O_3$: 961.3863, found 962 (EM+H$^+$).

Synthesis of Head Group BPRDP0106

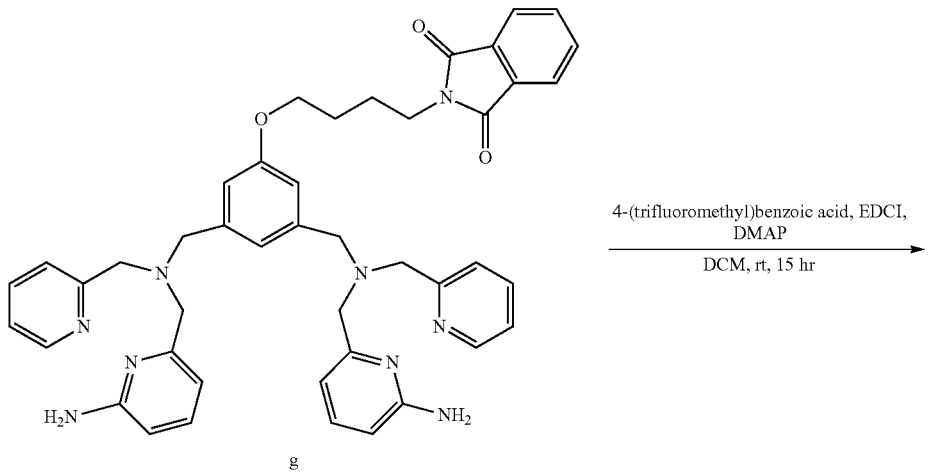

g

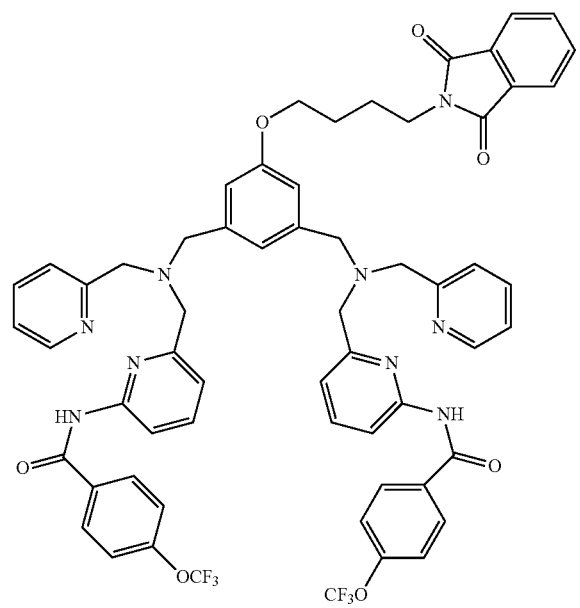

h106

N,N'-(((((5-(4-(1,3-dioxoisoindolin-2-yl)butoxy)-1,3-phenylene)bis(methylene)) bis((pyridin-2-ylmethyl)azanediyl))bis(methylene))bis(pyridine-6,2-diyl))bis(4-(trifluoromethoxy)benzamide) (compound h106): To a stirred solution of compound g (200 mg, 0.267 mmol, 1 eq.) in 4 ml of dry DMF at room temperature, 4-(trifluoromethoxy)benzoic acid (220 mg, 1.07 mmol, 4 eq.), EDCI (310 mg, 1.6 mmol, 6 eq.), and DMAP (33 mg, 0.267 mmol, 1 eq.) were slowly added. The resultant reaction mixture was stirred at room temperature for 15 hours and the solvent was removed. To the residue, $CH_2Cl_2$ (200 mL) was added. The $CH_2Cl_2$ solution was washed with a saturated aqueous solution of $NaHCO_3$ (200 mL), dried over $MgSO_4$, and concentrated under reduced pressure. The resultant residue was purified by flash chromatography over silica gel with MeOH/Ethyl acetate (2/98) to yield compound h106 (165 mg, 55%). $^1$H NMR (300 MHz, $CDCl_3$): δ 8.46 (d, J=4.8 Hz, 2H), 8.24 (d, J=8.1 Hz, 2H), 7.82-7.79 (m, 2H), 7.76-7.71 (m, 6H), 7.69-7.66 (m, 2H), 7.58-7.52 (m, 2H), 7.49-7.46 (m, 2H), 7.25 (d, J=7.5 Hz, 2H), 7.19 (s, 1H), 7.12-7.08 (m, 6H), 6.73 (s, 2H), 3.95 (t, J=5.7 Hz, 2H), 3.76-3.71 (m, 6H), 3.56 (s, 4H), 3.53 (s, 4H), 1.88-1.77 (m, 4H).

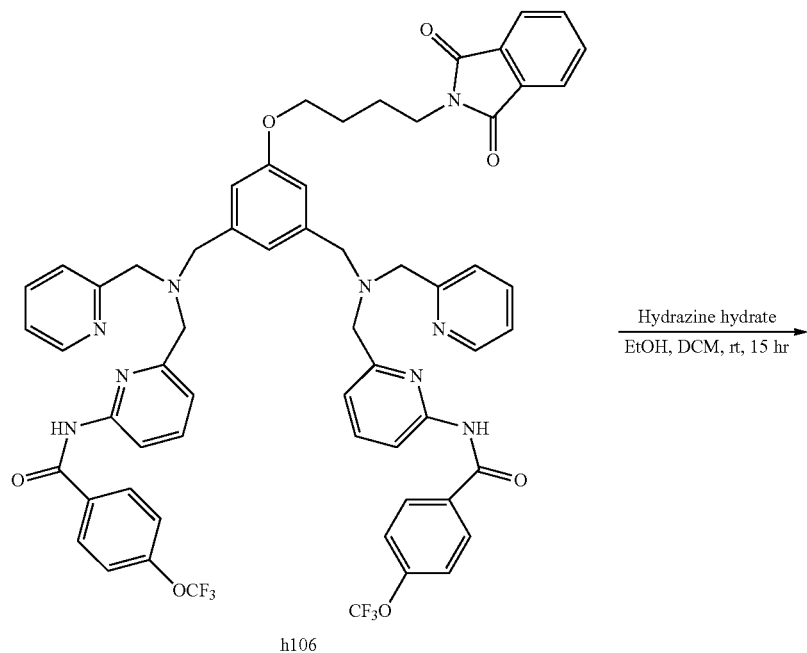

h106

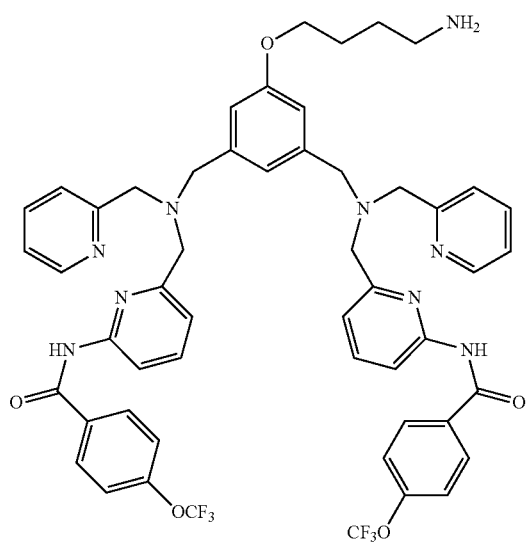

BPRDP0106

N,N'-(6,6'-((((5-(4-aminobutoxy)-1,3-phenylene)bis(methylene))bis((pyridin-2-ylmethyl)azanediyl))bis(methylene))bis(pyridine-6,2-diyl))bis(4-(trifluoromethoxy)benzamide) (head group BPRDP0106): To a stirred solution of compound 106 (200 mg, 0.178 mmol, 1 eq.) in 3 mL EtOH and 1 mL of dry dichloromethane (DCM) at room temperature, hydrazine hydrate (114 mg, 3.56 mmol, 20 eq.) was slowly added. The resultant reaction mixture was stirred at room temperature for 15 hours. EtOH and DCM were removed. To the resultant residue $CH_2Cl_2$ (200 mL) was added. The $CH_2Cl_2$ solution was washed with $H_2O$ (200 mL), dried over $MgSO_4$, and concentrated under reduced pressure to yield BPRDP0106 (140 mg, 79%). $^1$H NMR (300 MHz, $CDCl_3$): δ 8.47 (d, J=4.2 Hz, 2H), 8.26-8.23 (m, 2H), 7.77-7.69 (m, 6H), 7.58-7.53 (m, 2H), 7.48-7.46 (m, 2H), 7.25 (d, J=7.5 Hz, 2H), 7.19 (s, 1H), 7.13-7.11 (m, 6H), 6.72 (s, 2H), 3.92 (t, J=6.0 Hz, 2H), 3.74 (s, 4H), 3.57 (s, 4H), 3.54 (s, 4H), 2.81 (t, J=6.9 Hz, 2H), 1.81-1.75 (m, 2H), 1.71-1.64 (m, 2H). ESI-MS $C_{52}H_{49}F_6N_9O_5$: 993.3761, found 561 [(M+2Zn$^{2+}$)+2]/2.

Synthesis of Head Group BPRDP0107

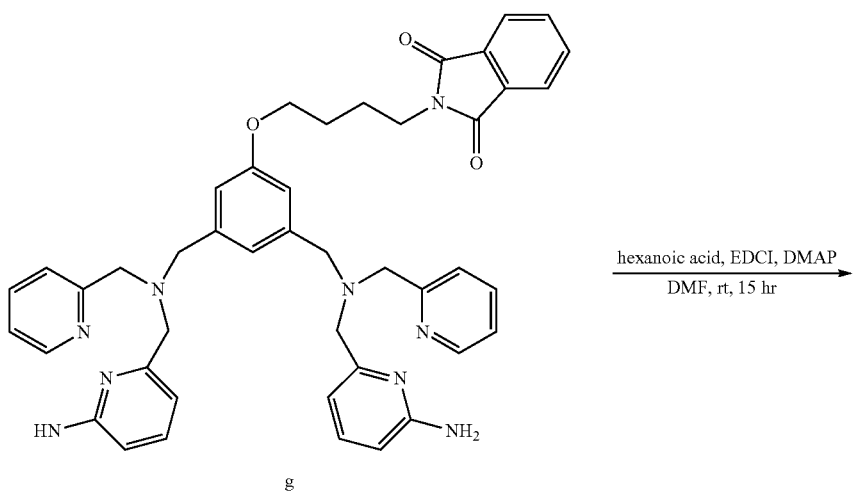

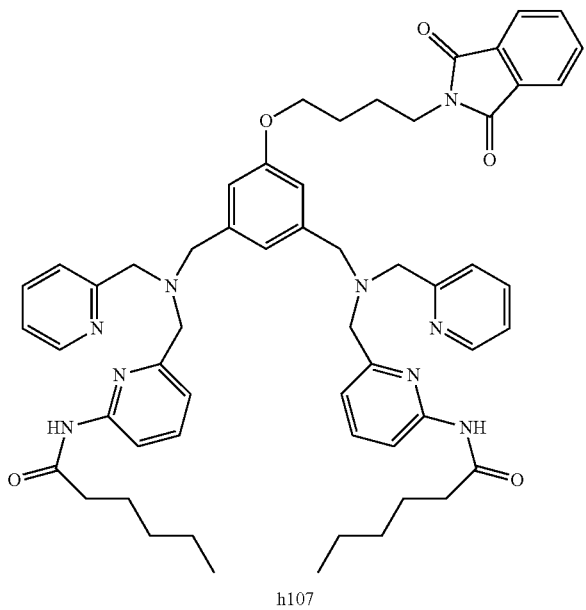

N,N'-(((((5-(4-(1,3-dioxoisoindolin-2-yl)butoxy)-1,3-phenylene)bis(methylene)) bis((pyridin-2-ylmethyl)azanediyl))bis(methylene))bis(pyridine-6,2-diyl))dihexanamide (compound h107): To a stirred solution of compound g (200 mg, 0.267 mmol, 1 eq.) in 4 mL of dry dimethylformamide (DMF) at room temperature, hexanoic acid (124 mg, 1.07 mmol, 4 eq.), EDCI (310 mg, 1.6 mmol, 6 eq.) and DMAP (33 mg, 0.267 mmol, 1 eq.) were slowly added. The resultant reaction mixture was stirred at room temperature for 15 hours and then concentrated. To the resultant residue $CH_2Cl_2$ (200 mL) was added. The $CH_2Cl_2$ solution was then washed with a saturated aqueous solution of $NaHCO_3$ (200 mL), dried over $MgSO_4$, and concentrated under reduced pressure. The resultant residue was purified by flash chromatography over silica gel with MeOH/Ethyl acetate (2/98) to yield compound h107 (150 mg, 60%). $^1$H NMR (300 MHz, $CDCl_3$): δ 8.48 (d, J=4.5 Hz, 2H), 8.11 (d, J=8.4 Hz, 2H), 7.83-7.81 (m, 2H), 7.70-7.64 (m, 4H), 7.58-7.53 (m, 2H), 7.48 (d, J=7.5 Hz, 2H), 7.26-7.23 (m, 3H), 7.14-7.09 (m, 2H), 6.73 (s, 2H), 3.95 (t, J=5.7 Hz, 2H), 3.77-3.73 (m, 6H), 3.68 (s, 4H), 3.56 (s, 4H), 2.07 (t, J=7.2 Hz, 4H), 1.89-1.79 (m, 4H), 1.59-1.49 (m, 4H), 1.24-1.13 (m, 8H), 0.82 (t, J=6.9 Hz, 6H). ESI-MS $C_{56}H_{65}N_9O_5$: 943.5109, found 945 [EM+H$^+$].

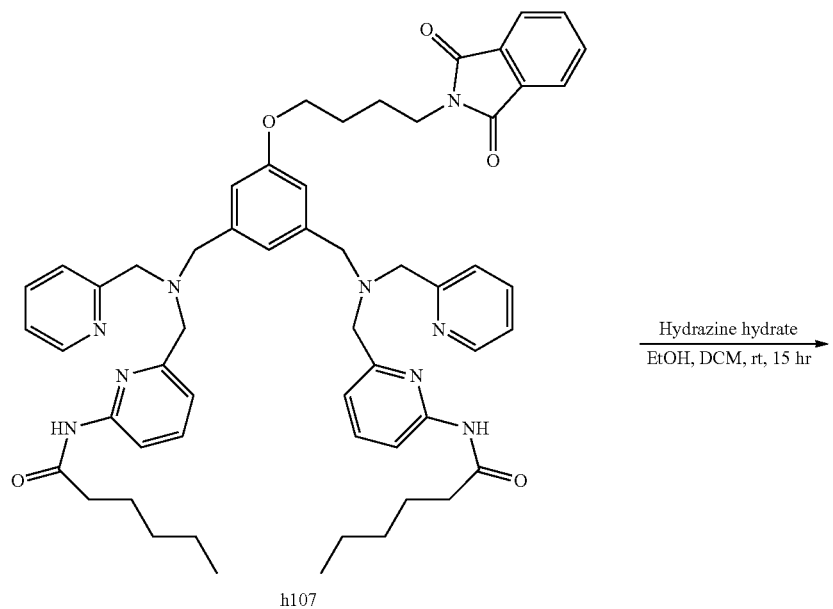

h107

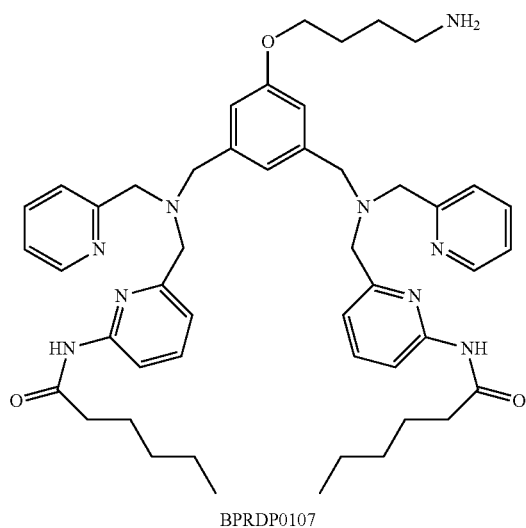

BPRDP0107

Hexanoic acid (6-{[(3-(4-amino-butoxy)-5-{[(6-hexanoylamino-pyridin-2-ylmethyl)-pyridin-2-ylmethyl-amino]-methyl}-benzyl)-pyridin-2-ylmethyl-amino]-methyl}-pyridin-2-yl)-amide (head group BPRDP0107): To a stirred solution of compound h107 (200 mg, 0.212 mmol, 1 eq.) in 3 ml EtOH and 1 mL dry DCM at room temperature, hydrazine hydrate (136 mg, 4.24 mmol, 20 eq.) was slowly added. The resultant reaction mixture was stirred at room temperature for 15 hours. Removal of EtOH and DCM gave a residue. The residue was extracted with $CH_2Cl_2$ (200 mL). The $CH_2Cl_2$ solution was then washed with $H_2O$ (200 mL), dried over $MgSO_4$, and concentrated under reduced pressure to yield BPRDP0107 (150 mg, 87%). $^1$H NMR (400 MHz, $CDCl_3$): δ 8.49 (d, J=4.0 Hz, 2H), 8.11 (d, J=8.4 Hz, 2H), 7.68-7.64 (m, 2H), 7.58-7.54 (m, 2H), 7.47 (d, J=8.0 Hz, 2H), 7.23-7.21 (m, 3H), 7.14-7.11 (m, 2H), 3.93 (t, J=6.0 Hz, 2H), 3.77 (s, 4H), 3.68 (s, 4H), 3.56 (s, 4H), 2.83 (t, J=6.8 Hz, 2H), 2.10 (t, J=7.2 Hz, 4H), 1.84-1.77 (m, 2H), 1.73-1.66 (m, 2H), 1.58-1.51 (m, 4H), 1.24-1.14 (m, 8H), 0.82 (t, J=6.8 Hz, 6H). ESI-MS $C_{48}H_{63}N_9O_3$: 813.5054, found 814 (EM+H$^+$).

Synthesis of Head Group BPRDP0109
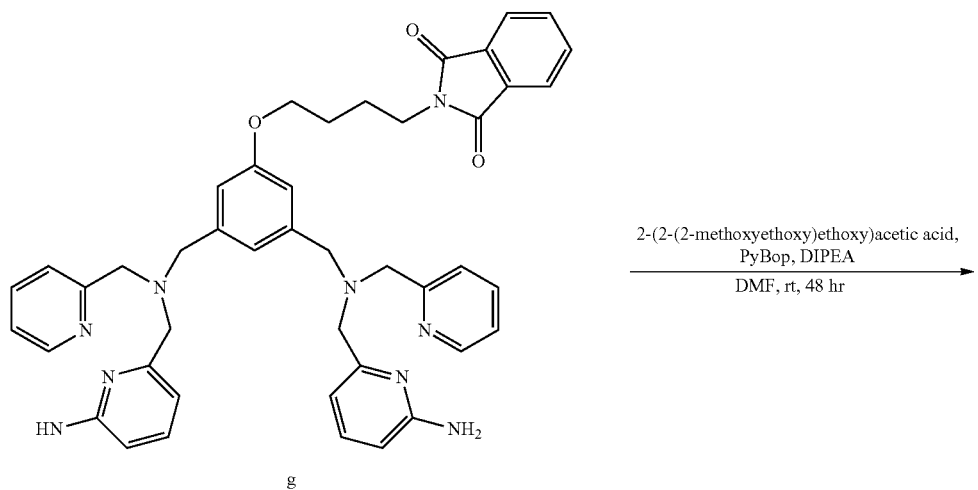
2-(2-(2-methoxyethoxy)ethoxy)acetic acid, PyBop, DIPEA
―――――――――――――――――――→
DMF, rt, 48 hr
g
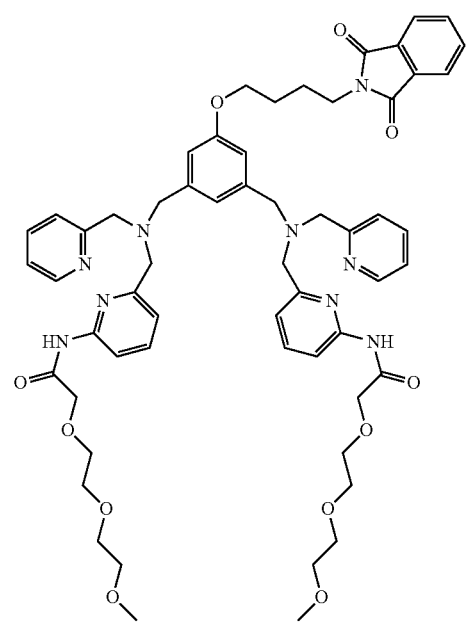
h109

N,N'-(((((5-(4-(1,3-dioxoisoindolin-2-yl)butoxy)-1,3-phenylene)bis(methylene))bis((pyridin-2-ylmethyl)azanediyl))bis(methylene))bis(pyridine-6,2-diyl))bis(2-(2-(2-methoxyethoxy)ethoxy)acetamide) (compound h109): To a stirred solution of compound g (200 mg, 0.267 mmol, 1 eq.) in 4 mL of dry dimethylformamide (DMF) at room temperature, 2-(2-(2-methoxyethoxy)ethoxy)acetic acid (190 mg, 1.07 mmol, 4 eq.), PyBOP (556 mg, 1.07 mmol, 4 eq.), and DIPEA (276 mg, 2.14 mmol, 8 eq.) were slowly added. The resultant reaction mixture was stirred at room temperature for 48 hours and then concentrated. $CH_2Cl_2$ (200 mL) was added to the resultant residue. The $CH_2Cl_2$ solution was then washed with a saturated ammonium chloride aqueous solution (200 mL), dried over $MgSO_4$, and concentrated under reduced pressure. The resultant residue was purified by flash chromatography over silica gel with MeOH/Ethyl acetate (2/98) to yield compound h109 (140 mg, 49%). $^1$H NMR (400 MHz, $CDCl_3$): δ 8.47 (d, J=5.6 Hz, 2H), 8.05 (d, J=7.6 Hz, 2H), 7.83-7.81 (m, 2H), 7.70-7.68 (m, 2H), 7.66-7.59 (m, 4H), 7.55 (d, J=8.0 Hz, 2H), 7.35 (d, J=7.2 Hz, 2H), 7.13-7.09 (m, 2H), 7.01 (s, 1H), 6.82 (s, 2H), 4.11 (s, 4H), 3.96 (t, J=6.0 Hz, 2H), 3.77-3.74 (m, 8H), 3.71-3.65 (m, 12H), 3.60 (s, 4H), 3.57-3.54 (m, 4H), 3.82 (s, 6H), 3.16-3.12 (m, 2H), 1.89-1.81 (m, 4H). ESI-MS $C_{58}H_{69}N_9O_{11}$: 1067.5117, found 538 [EM+2H$^+$]/2.

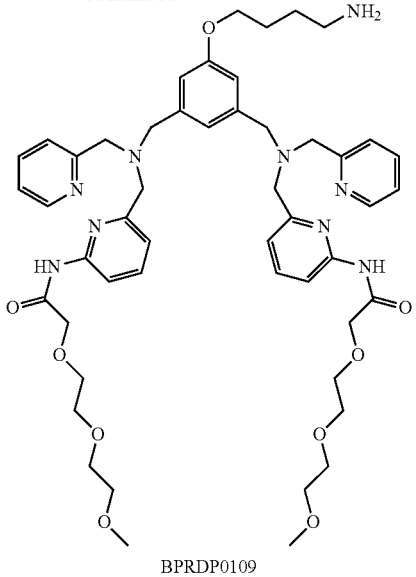

BPRDP0109

N-(6-{[(3-(4-Amino-butoxy)-5-{[(6-{2-[2-(2-methoxy-ethoxy)-ethoxy]-acetylamino}-pyridin-2-ylmethyl)-pyridin-2-ylmethyl-amino]-methyl}-benzyl)-pyridin-2-ylmethyl-amino]-methyl}-pyridin-2-yl)-2-[2-(2-methoxy-ethoxy)-ethoxy]-acetamide (head group BPRDP0109): To a stirred solution of compound h109 (200 mg, 0.187 mmol, 1 eq.) in 3 mL EtOH and 1 mL dry DCM at room temperature, hydrazine hydrate (120 mg, 3.74 mmol, 20 eq.) was slowly added. The resultant reaction mixture was stirred at room temperature for 15 hours. Removal of EtOH and DCM gave a residue, which was extracted with $CH_2Cl_2$ (200 mL). The $CH_2Cl_2$ solution was then washed with $H_2O$ (200 mL), dried over $MgSO_4$, and concentrated under reduced pressure to yield BPRDP0109 (145 mg, 82%). $^1$H NMR (300 MHz, $CD_3OD$): δ 8.68 (d, J=5.4 Hz, 2H), 8.08-8.03 (m, 4H), 7.63-7.59 (m, 2H), 7.53-7.49 (m, 2H), 7.42 (d, J=8.1 Hz, 2H), 7.34-7.31 (m, 2H), 7.19 (s, 1H), 7.00 (s, 2H), 4.47 (s, 2H), 4.46 (s, 2H), 4.41-4.28 (m, 4H), 4.08-3.93 (m, 8H), 3.87-3.83 (m, 4H), 3.78-3.75 (m, 4H), 3.72-3.69 (m, 4H), 3.58-3.55 (m, 4H), 3.31-3.29 (m, 2H), 3.09 (t, J=7.5 Hz, 2H), 1.93-1.88 (m, 4H). ESI-MS $C_{50}H_{67}N_9O_9$: 937.5062, found 533 [(M+2Zn$^{2+}$)+2]/2.

Synthesis of Head Group BPRDP0111

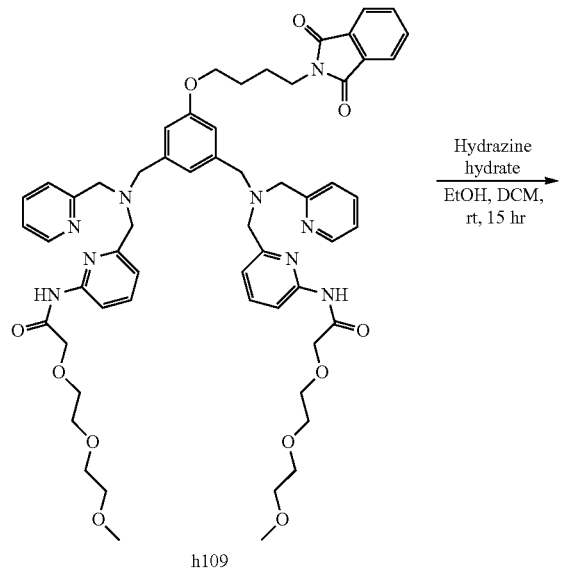

h109

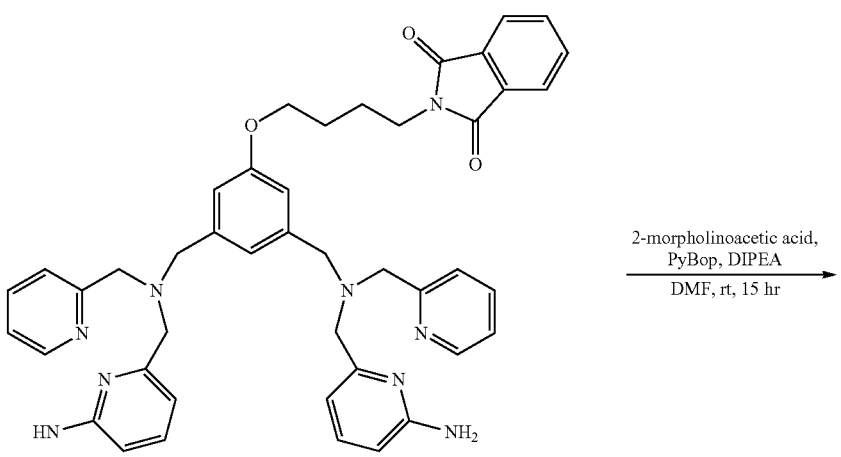

g

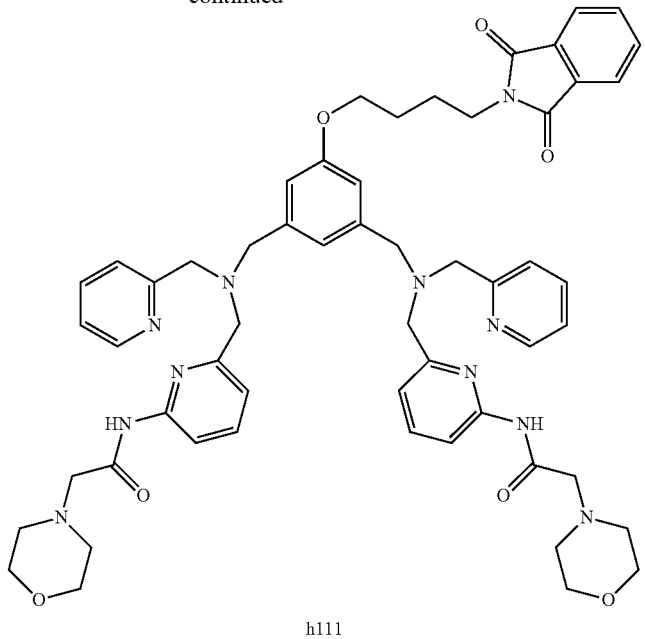

h111

N,N'-(((((5-(4-(1,3-dioxoisoindolin-2-yl)butoxy)-1,3-phenylene)bis(methylene)) bis((pyridin-2-ylmethyl)azanediyl))bis(methylene))bis(pyridine-6,2-diyl))bis (2-morpholinoacetamide) (compound h11): To a stirred solution of compound g (200 mg, 0.267 mmol, 1 eq.) in 4 mL of dry DMF at room temperature, 2-morpholinoacetic acid (155 mg, 1.07 mmol, 4 eq.), PyBOP (556 mg, 1.07 mmol, 4 eq.), and DIPEA (276 mg, 2.14 mmol, 8 eq.) were slowly added. The resultant reaction mixture was stirred at room temperature for 48 hours and then concentrated. To the resultant residue was added $CH_2Cl_2$ (200 mL). The $CH_2Cl_2$ solution was then washed with a saturated ammonium chloride aqueous solution (200 mL), dried over $MgSO_4$, and concentrated under reduced pressure. The resultant residue was purified by flash chromatography over silica gel with MeOH/Ethyl acetate (2/98) to yield compound h111 (130 mg, 49%). $^1$H NMR (300 MHz, $CDCl_3$): δ 8.50 (d, J=4.8 Hz, 2H), 8.05 (d, J=8.4 Hz, 2H), 7.85-7.82 (m, 2H), 7.72-7.57 (m, 8H), 7.35 (d, J=7.8 Hz, 2H), 7.15-7.11 (m, 2H), 7.03 (s, 1H), 6.84 (s, 2H), 3.97 (t, J=5.7 Hz, 2H), 3.80-3.74 (m, 14H), 3.70 (s, 4H), 3.63 (s, 4H), 3.13 (s, 4H), 2.61-2.58 (m, 8H), 1.87-1.79 (m, 4H).

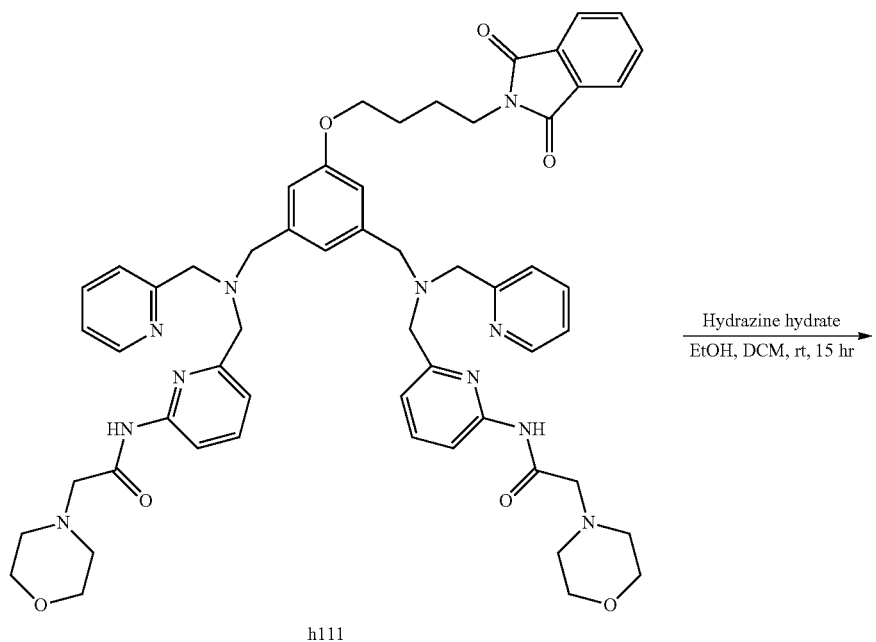

h111

Hydrazine hydrate
EtOH, DCM, rt, 15 hr

-continued

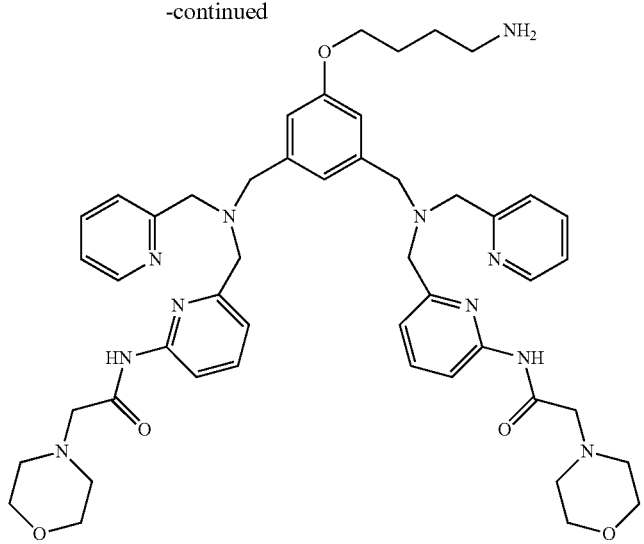

BPRDP0111

N-[6-({[3-(4-Amino-butoxy)-5-({[6-(2-morpholin-4-yl-acetylamino)-pyridin-2-ylmethyl]-pyridin-2-ylmethyl-amino}-methyl)-benzyl]-pyridin-2-ylmethyl-amino}-methyl)-pyridin-2-yl]-2-morpholin-4-yl-acetamide (head group BPRDP0111): To a stirred solution of compound h111 (200 mg, 0.200 mmol, 1 eq.) in 3 mL EtOH and 1 mL dry DCM at room temperature, hydrazine hydrate (128 mg, 4.0 mmol, 20 eq.) was slowly added. The resultant reaction mixture was stirred at room temperature for 15 hours. Removal of EtOH and DCM gave a residue, which was then diluted with $CH_2Cl_2$ (200 mL). The $CH_2Cl_2$ solution was then washed with $H_2O$ (200 mL), dried over $MgSO_4$, and concentrated under reduced pressure to yield BPRDP0111 (150 mg, 86%). $^1H$ NMR (300 MHz, $CDCl_3$): δ 8.50 (d, J=4.2 Hz, 2H), 8.04 (d, J=7.5 Hz, 2H), 7.67-7.54 (m, 6H), 7.33 (d, J=7.2 Hz, 2H), 7.15-7.11 (m, 2H), 7.01 (s, 1H), 6.83 (s, 2H), 3.94 (t, J=5.7 Hz, 2H), 3.80-3.75 (m, 12H), 3.71 (s, 4H), 3.64 (s, 4H), 3.14 (s, 4H), 2.84 (t, J=7.2 Hz, 2H), 2.59 (t, J=4.5 Hz, 8H), 1.84-1.78 (m, 2H), 1.74-1.67 (m, 2H). ESI-MS $C_{48}H_{61}N_{11}O_5$: 871.4857, found 500 [(M+2Zn$^{2+}$)+2]/2.

Synthesis of Head Group BPRDP0108

Head group BPRDP0108 was prepared according to the scheme shown below.

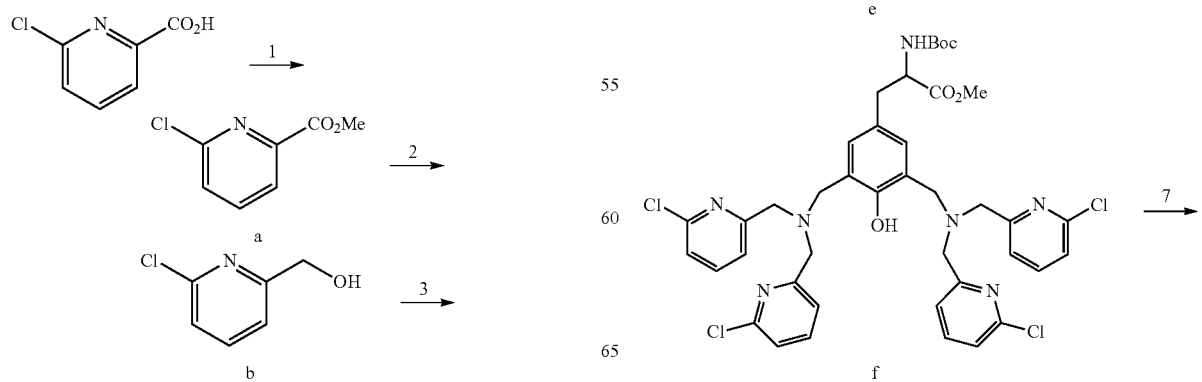

-continued

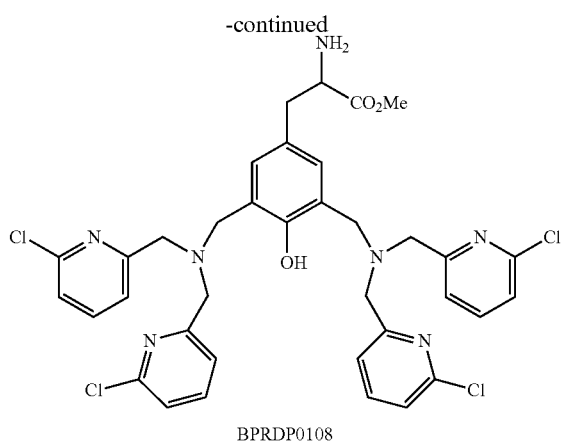

BPRDP0108

Scheme 3. Reagents and conditions for preparing head group BPRDP0108: (1) HOBt, EDCI, N-Methylmorpholine, MeOH, 65° C., 15 hr, 88%. (2) NaBH$_4$, MeOH, 0° C., 2 hr, 90%. (3) PBr$_3$, DCM, rt, 15 hr, 68%. (4) 2-Nitrobenzenesulfonamide, K$_2$CO$_3$, DMF, rt, 15 hr, 59%. (5) thiophenol, K$_2$CO$_3$, DMF, rt, 3 hr, 56%. (6) tert-butyl 1-(methoxycarbonyl)-2-(4-hydroxyphenyl) ethylcarbamate, Formaldehyde, HCl(2N), H$_2$O, EtOH, reflux, 15 hr, 44%. (7) TFA, DCM, rt, 15 hr, 80%.

To a stirred solution of 6-chloropyridine-2-carboxylic acid (1 g, 6.33 mmol, 1 eq.) in 100 mL of Methanol at room temperature, HOBt (1.7 g, 12.66 mmol, 2 eq.), EDCI (2.4 g, 12.66 mmol, 2 eq.), and N-Methylmorpholine (1.3 g, 12.66 mmol, 2 eq.) were slowly added.

The resultant reaction mixture was stirred for 0.5 hour at room temperature and then heated at 65° C. for 15 hours. MeOH was removed and the resultant residue was diluted with CH$_2$Cl$_2$ (200 mL). The CH$_2$Cl$_2$ solution was then washed with a saturated aqueous solution of NaHCO$_3$ (200 mL) and water (200 mL), dried over MgSO$_4$, and concentrated under reduced pressure to yield compound a (950 mg, 88%).

To a stirred solution of compound a (500 mg, 2.92 mmol, 1 eq.) in 20 mL of Methanol at 0° C., NaBH$_4$ (550 mg, 14.6 mmol, 5 eq.) was slowly added. The resultant reaction mixture was stirred at 0° C. for 2 hours. MeOH was removed and the resultant residue was diluted with CH$_2$Cl$_2$ (200 mL). The CH$_2$Cl$_2$ solution was then washed with a saturated ammonium chloride aqueous solution twice (2×200 mL), dried over MgSO$_4$, and concentrated under reduced pressure to yield compound b (380 mg, 90%).

To a stirred solution of PBr$_3$ (12.4 g, 45.8 mmol, 2 eq.) in 660 mL of dry DCM at room temperature, compound b (3.3 g, 22.9 mmol, 1 eq.) was slowly added. The resultant reaction mixture was stirred at room temperature for 15 hours and concentrated. The resultant residue was diluted with CH$_2$Cl$_2$ (100 mL). The CH$_2$Cl$_2$ solution was then washed with a saturated aqueous solution of NaHCO$_3$ (100 mL) and water (100 mL), dried over MgSO$_4$, and concentrated under reduced pressure to yield compound c (3.2 g, 68%).

To a stirred solution of compound c (500 mg, 2.43 mmol, 2 eq.) in 50 mL of dry DMF at room temperature, K$_2$CO$_3$ (838 mg, 6.08 mmol, 5 eq.) and 2-Nitrobenzenesulfonamide (245 mg, 1.22 mmol, 1 eq.) were slowly added. The resultant reaction mixture was stirred at room temperature for 15 hours and then concentrated. The resultant residue was diluted with CH$_2$Cl$_2$ (100 mL). The CH$_2$Cl$_2$ solution was washed with a saturated aqueous solution of water (5×100 mL), dried over MgSO$_4$, and concentrated under reduced pressure. The resultant residue was purified by flash chromatography over silica gel with Ethyl acetate/Hexane (3/7) to yield compound d (650 mg, 59%).

To a stirred solution of compound d (600 mg, 1.32 mmol, 1 eq.) in 60 mL of dry DMF at room temperature, K$_2$CO$_3$ (910 mg, 6.6 mmol, 5 eq.) and thiophenol (0.6 mL) were slowly added. The resultant reaction mixture was stirred at room temperature for 3 hours and then concentrated. The resultant residue was diluted with CH$_2$Cl$_2$ (100 mL). The CH$_2$Cl$_2$ solution was then washed with a saturated aqueous solution of water (5×100 mL), dried over MgSO$_4$, and concentrated under reduced pressure. The resultant residue was purified by flash chromatography over silica gel with MeOH/Ethyl acetate (3/97) to yield compound e (200 mg, 56%). $^1$H NMR (300 MHz, CDCl$_3$): δ 7.64-7.59 (m, 4H), 7.30 (d, J=7.5 Hz, 2H), 7.20 (d, J=7.5 Hz, 2H), 3.92 (s, 4H). ESI-MS C$_{12}$H$_{11}$Cl$_2$N$_3$: 267.033, found 268 [EM+H$^+$].

To a stirred solution of compound e (4 g, 14.9 mmol, 2 eq.) in EtOH (25 mL) and H$_2$O (60 mL) at room temperature, 2 N HCl (2 mL), formaldehyde (1 g), and (tert-butyl 1-(methoxycarbonyl)-2-(4-hydroxyphenyl)Ethylcarbamate (2.2 g, 7.45 mmol, 1 eq.) were slowly added. The resultant reaction mixture was stirred at room temperature for 1 hour and then refluxed for 15 hours. EtOH was removed and the resultant residue was diluted with CH$_2$Cl$_2$ (200 mL). The CH$_2$Cl$_2$ solution was washed with a saturated aqueous solution of NaHCO$_3$ (200 mL), dried over MgSO$_4$, and concentrated under reduced pressure. The resultant residue was purified by flash chromatography over silica gel with MeOH/DCM (7/93) to yield compound f (2.8 g, 44%). $^1$H NMR (400 MHz, CDCl$_3$): δ 7.62-7.60 (m, 4H), 7.43 (d, J=7.2 Hz, 4H), 7.17 (d, J=7.2 Hz, 4H), 6.92 (s, 2H), 3.81 (s, 8H), 3.76 (s, 4H), 3.65 (m, 4H), 2.99-2.94 (m, 2H), 1.34 (s, 9H).

2-Amino-3-(3,5-bis-{[bis-(6-chloro-pyridin-2-ylmethyl)-amino]-methyl}-4-hydroxy-phenyl)-propionic acid methyl ester (head group BPRDP0108): To a stirred solution of compound f (500 mg, 0.584 mmol) in 50 mL of dry DCM at room temperature, TFA (5 mL) was slowly added. The resultant reaction mixture was stirred at room temperature for 15 hours. The resultant residue was extracted with CH$_2$Cl$_2$ (200 mL). The CH$_2$Cl$_2$ solution was then washed with a saturated aqueous solution of NaHCO$_3$ (200 mL), dried over MgSO$_4$, and concentrated under reduced pressure to yield BPRDP0108 (340 mg, 77%). $^1$H NMR (400 MHz, CDCl$_3$): δ 7.62-7.58 (m, 4H), 7.44 (d, J=7.2 Hz, 4H), 7.17 (d, J=7.2 Hz, 4H), 6.96 (s, 2H), 3.81 (s, 8H), 3.77 (s, 4H), 3.69-3.65 (m, 4H), 2.99-2.94 (m, 1H), 2.78-2.73 (m, 1H). ESI-MS C$_{36}$H$_{35}$Cl$_4$N$_7$O$_3$: 755.5202, found 756 (M+H$^+$).

Syntheses of Head Groups BPRDP0115 and BPRDP0117

Head groups BPRDP0115 and BPRDP0117 were prepared according to the schemes shown below.

Scheme 4

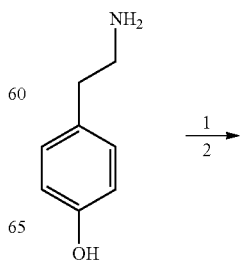

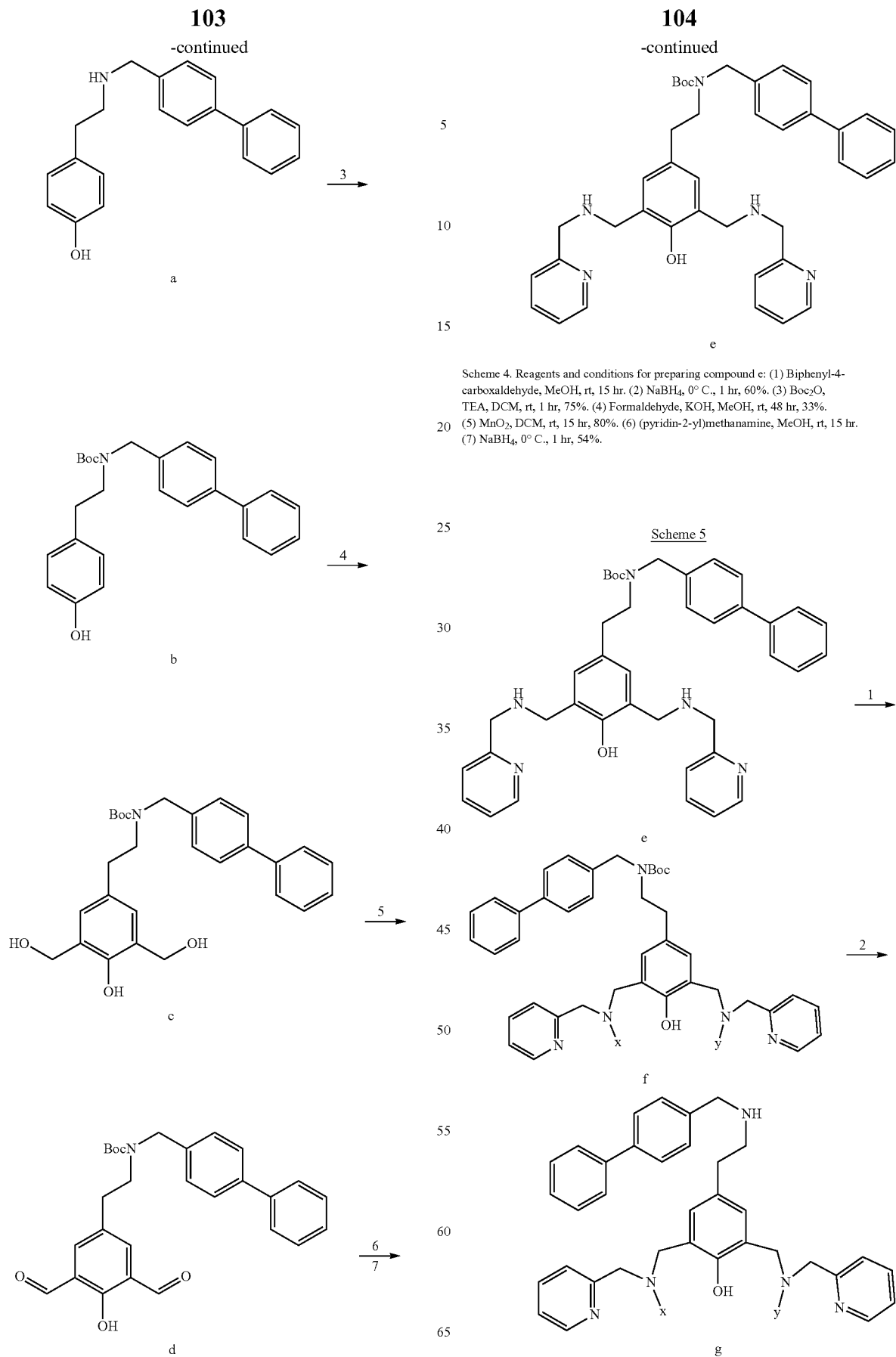
Scheme 4. Reagents and conditions for preparing compound e: (1) Biphenyl-4-carboxaldehyde, MeOH, rt, 15 hr. (2) NaBH$_4$, 0° C., 1 hr, 60%. (3) Boc$_2$O, TEA, DCM, rt, 1 hr, 75%. (4) Formaldehyde, KOH, MeOH, rt, 48 hr, 33%. (5) MnO$_2$, DCM, rt, 15 hr, 80%. (6) (pyridin-2-yl)methanamine, MeOH, rt, 15 hr. (7) NaBH$_4$, 0° C., 1 hr, 54%.
Scheme 5

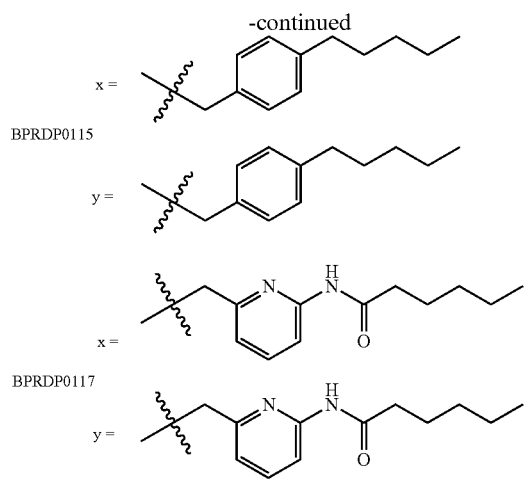

Scheme 5. Reagents and conditions for preparing head group BPRDP0115: (1) 4-pentylbenzaldehyde, NaB(OAc)₃H, DCM, rt, 15 hr, 48%. (2) TFA, DCM, rt, 2 hr, 89%. Reagents and conditions for preparing head group BPRDP0117: (1) N-(6-formylpyridin-2-yl)hexanamide, NaB(OAc)₃H, DCM, rt, 15 hr, 51%. (2) TFA, DCM, rt, 2 hr, 84%.

Preparation of Compound e 4-(2-(([1,1'-biphenyl]-4-ylmethyl)amino)ethyl)phenol (compound a): To a stirred solution of 4-(2-aminoethyl) phenol (300 mg, 2.19 mmol, 1 eq.) in 10 mL of Methanol at room temperature, biphenyl-4-carboxaldehyde (600 mg, 3.3 mmol, 1.5 eq.) was slowly added. The resultant reaction mixture was stirred at room temperature for 15 hours. The reaction mixture was then cooled down to 0° C. and sodium borohydride (830 mg, 21.9 mmol, 10 eq.) was added. The resultant mixture was stirred at 0° C. for 1 hour. MeOH was removed and the resultant residue was diluted with $CH_2Cl_2$ (200 mL). The $CH_2Cl_2$ solution was washed with a saturated ammonium chloride aqueous solution (200 mL), dried over $MgSO_4$, and concentrated under reduced pressure. The resultant residue was purified by flash chromatography over silica gel with Ethyl acetate/Hexane (1/1) to yield compound a (400 mg, 60%). $^1$H NMR (400 MHz, DMSO-$d_6$): δ 7.63 (d, J=8.0 Hz, 2H), 7.57 (d, J=8.4 Hz, 2H), 7.45-7.41 (m, 2H), 7.38-7.31 (m, 3H), 6.96 (d, J=8.4 Hz, 2H), 6.63 (d, J=8.4 Hz, 2H), 3.72 (s, 2H), 2.67-2.58 (m, 4H).

Tert-butyl ([1,1'-biphenyl]-4-ylmethyl)(4-hydroxyphenethyl)carbamate (compound b): To a stirred solution of compound a (100 mg, 0.33 mmol, 1 eq.) in 10 mL of dry DCM at room temperature, di-tert-butyl dicarbonate (150 mg, 0.66 mmol, 2 eq.) and TEA (1 mL) were slowly added. The resultant reaction mixture was stirred for 1 hour and concentrated. The resultant residue was diluted with $CH_2Cl_2$ (100 mL). The $CH_2Cl_2$ solution was washed with a saturated ammonium chloride aqueous solution twice (2×200 mL), dried over $MgSO_4$, and concentrated under reduced pressure. The resultant residue was purified by flash chromatography over silica gel with Ethyl acetate/Hexane (3/7) to yield compound b (100 mg, 75%). $^1$H NMR (300 MHz, CDCl₃): δ 7.59-7.53 (m, 4H), 7.46-7.41 (m, 2H), 7.36-7.31 (m, 1H), 7.28-7.26 (m, 2H), 7.00 (m, 2H), 6.76 (d, J=7.2 Hz, 2H), 4.39 (s, 2H), 3.42-3.34 (m, 2H), 2.74-2.72 (m, 2H), 1.48 (s, 9H).

Tert-butyl ([1,1'-biphenyl]-4-ylmethyl)(4-hydroxy-3,5-bis(hydroxymethyl) phenethyl)carbamate (compound c): To a stirred solution of compound b (480 mg, 1.19 mmol, 1 eq.) in 5 mL of MeOH at room temperature, a mixture of formaldehyde (20 mL) and KOH (0.65 g, 11.9 mmol, 10 eq.) in 20 ml of $H_2O$ were slowly added. The resultant reaction mixture was stirred for 48 hours and concentrated. The resultant residue was diluted with $CH_2Cl_2$ (100 mL). The $CH_2Cl_2$ solution was washed with a saturated ammonium chloride aqueous solution (3×200 mL), dried over $MgSO_4$, and concentrated under reduced pressure. The resultant residue was purified by flash chromatography over silica gel with Ethyl acetate/Hexane (1/3) to yield compound c (180 mg, 33%). $^1$H NMR (300 MHz, CDCl₃): δ 7.59-7.53 (m, 4H), 7.46-7.41 (m, 2H), 7.36-7.31 (m, 1H), 7.28-7.26 (m, 2H), 6.86 (s, 1H), 6.81 (s, 1H), 4.75 (s, 4H), 4.40 (s, 2H), 3.35 (m, 2H), 2.71 (m, 2H), 1.47 (s, 9H).

Tert-butyl ([1,1'-biphenyl]-4-ylmethyl)(3,5-diformyl-4-hydroxyphenethyl) carbamate (compound d): To a stirred solution of compound c (1 g, 2.16 mmol, 1 eq.) in 100 mL of dry DCM at room temperature, $MnO_2$ (3.76 g, 43.2 mmol, 20 eq.) was slowly added. The resultant reaction mixture was stirred at room temperature for 15 hours, filtered through celite, and washed with DCM. The resultant residue was concentrated under reduced pressure to yield compound d (790 mg, 80%). $^1$H NMR (300 MHz, CDCl₃): δ 10.18 (s, 2H), 7.76 (s, 1H), 7.66 (s, 1H), 7.60-7.53 (m, 4H), 7.47-7.41 (m, 2H), 7.37-7.34 (m, 1H), 7.32-7.27 (m, 2H), 4.43 (s, 2H), 3.45 (m, 2H), 2.84 (m, 2H), 1.47 (s, 9H).

Tert-butyl ([1,1'-biphenyl]-4-ylmethyl)(4-hydroxy-3,5-bis(((pyridin-2-ylmethyl) amino)methyl)phenethyl)carbamate (compound e): To a stirred solution of compound d (600 mg, 1.3 mmol, 1 eq.) in 30 mL of methanol at room temperature, (pyridin-2-yl)methanamine (562 mg, 5.2 mmol, 4 eq.) was slowly added. The resultant reaction mixture was stirred at room temperature for 15 hours and cooled down to 0° C. Sodium borohydride (490 mg, 13 mmol, 10 eq.) was added. The mixture was stirred at 0° C. for 1 hour. MeOH was removed and the resultant residue was diluted with $CH_2Cl_2$ (200 mL). The $CH_2Cl_2$ solution was then washed with a saturated ammonium chloride aqueous solution (200 ml), dried over $MgSO_4$, and concentrated under reduced pressure. The resultant residue was purified by flash chromatography over silica gel with MeOH/DCM (1/9) to yield compound e (450 mg, 54%). $^1$H NMR (300 MHz, CDCl₃): δ 8.53 (d, J=4.5 Hz, 2H), 7.70-7.62 (m, 2H), 7.58-7.52 (m, 4H), 7.45-7.40 (m, 2H), 7.35-7.32 (m, 1H), 7.29-7.26 (m, 4H), 7.21-7.17 (m, 2H), 6.89 (s, 1H), 6.82 (s, 1H), 4.41 (s, 2H), 4.00 (s, 4H), 3.99 (s, 4H), 3.35 (m, 2H), 2.69 (m, 2H), 1.48-1.45 (m, 9H).

Synthesis of Head Group BPRDP0115

Tert-butyl ([1,1'-biphenyl]-4-ylmethyl)(4-hydroxy-3,5-bis(((4-pentylbenzyl) (pyridin-2-ylmethyl)amino)methyl) phenethyl)carbamate (compound f115): To a stirred solution of compound e (500 mg, 0.78 mmol, 1 eq.) in 50 mL of dry DCM at room temperature, 4-pentylbenzaldehyde (550 mg, 3.12 mmol, 4 eq.) and NaB(OAc)₃H (1.65 g, 7.8 mmol, 10 eq.) were slowly added. The resultant reaction mixture was stirred at room temperature for 15 hours and concentrated. The resultant residue was diluted with $CH_2Cl_2$ (200 mL). The $CH_2Cl_2$ solution was then washed with a saturated aqueous solution of $NaHCO_3$ (200 mL), dried over $MgSO_4$, and concentrated under reduced pressure. The resultant residue was purified by flash chromatography over silica gel with Ethyl acetate/Hexane (2/3) to yield compound f115 (360 mg, 48%). $^1$H NMR (300 MHz, CDCl₃): δ 8.51 (d, J=5.1 Hz, 2H), 7.62-7.40 (m, 10H), 7.36-7.33 (m, 1H), 7.28-7.25 (m, 6H), 7.13-7.08 (m, 6H), 7.02 (s, 1H), 6.96 (s, 1H), 4.42 (s, 1H), 4.34 (s, 1H), 3.78 (s, 4H), 3.71 (s, 4H), 3.64 (s, 4H), 3.40-3.30 (m, 2H), 2.73-2.70 (m, 2H), 2.54 (t, J=7.8 Hz, 4H), 1.62-1.46 (m, 13H), 1.32-1.27 (m, 8H), 0.88 (t, J=6.6 Hz, 6H). ESI-MS $C_{64}H_{77}N_5O_3$: 963.6026, found 965 (EM+H⁺).

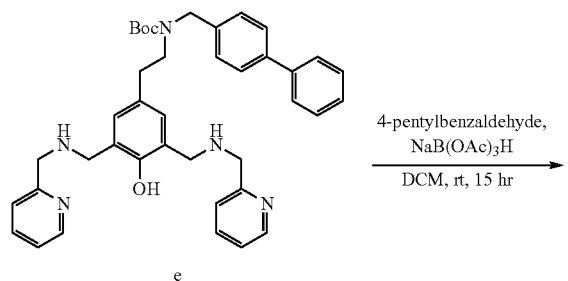

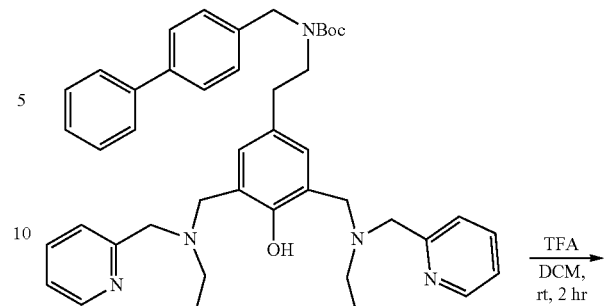

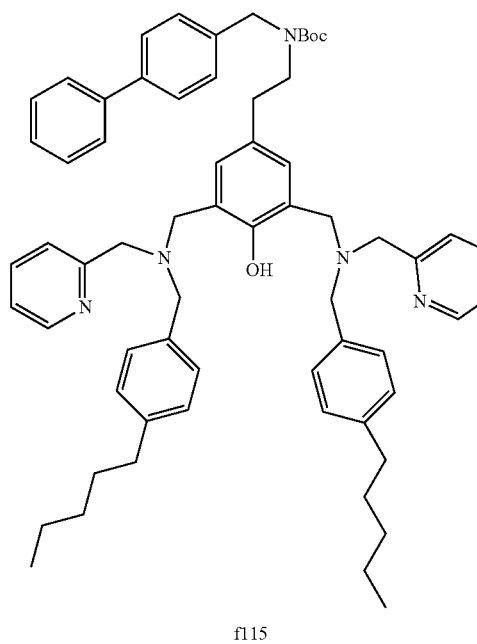

f115

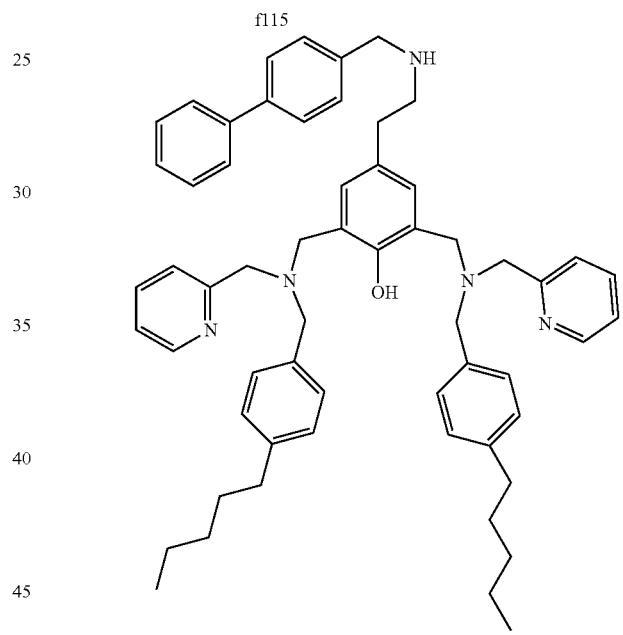

BPRDP0115

4-{2-[(Biphenyl-4-ylmethyl)-amino]-ethyl}-2,6-bis-{[(4-pentyl-benzyl)-pyridin-2-ylmethyl-amino]-methyl}-phenol (head group BPRDP0115): To a stirred solution of compound f115 (500 mg, 0.52 mmol) in 50 mL of dry DCM at room temperature, TFA was slowly added. The resultant reaction mixture was stirred at room temperature for 2 hours and concentrated. The resultant residue was diluted with $CH_2Cl_2$ (200 mL). The $CH_2Cl_2$ solution was then washed with a saturated aqueous solution of $NaHCO_3$ (200 mL), dried over $MgSO_4$, and concentrated under reduced pressure to yield BPRDP0115 (400 mg, 89%). $^1$H NMR (300 MHz, $CDCl_3$): δ 8.50 (d, J=3.9 Hz, 2H), 7.61-7.38 (m, 10H), 7.35-7.31 (m, 3H), 7.27-7.25 (m, 4H), 7.12-7.07 (m, 6H), 7.03 (s, 2H), 3.82 (s, 2H), 3.76 (s, 4H), 3.70 (s, 4H), 3.63 (s, 4H), 2.90 (t, J=6.9 Hz, 2H), 2.78 (t, J=6.3 Hz, 2H), 2.54 (t, J=7.5 Hz, 4H), 1.62-1.52 (m, 4H), 1.31-1.26 (m, 8H), 0.87 (t, J=6.9 Hz, 6H). ESI-MS $C_{59}H_{69}N_5O$: 863.5, found 864 (M+H$^+$).

Synthesis of Head Group BPRDP0117

Tert-butyl ([1,1'-biphenyl]-4-ylmethyl)(3,5-bis((((6-hexanamidopyridin-2-yl) methyl)(pyridin-2-ylmethyl)amino) methyl)-4-hydroxyphenethyl)carbamate (compound f117): To a stirred solution of compound e (500 mg, 0.78 mmol, 1 eq.) in 50 mL of dry DCM at room temperature, N-(6-formylpyridin-2-yl) hexanamide (686 mg, 3.12 mmol, 4 eq.) and NaB(OAc)$_3$H (1.65 g, 7.8 mmol, 10 eq.) were slowly added. The resultant reaction mixture was stirred at room temperature for 15 hours and concentrated. The resultant residue was diluted with $CH_2Cl_2$ (200 mL). The $CH_2Cl_2$ solution was then washed with a saturated aqueous solution of $NaHCO_3$ (200 mL), dried over $MgSO_4$, and concentrated under reduced pressure. The resultant residue was purified by flash chromatography over silica gel with Ethyl acetate/ Hexane (4/1) to yield compound f117 (420 mg, 51%). $^1$H NMR (400 MHz, $CDCl_3$): δ 8.48 (d, J=4.8 Hz, 2H), 8.05 (d, J=8.4 Hz, 2H), 7.59-7.45 (m, 10H), 7.44-7.40 (m, 2H), 7.34-7.31 (m, 1H), 7.21-7.19 (m, 2H), 7.11-7.07 (m, 4H), 6.94 (s, 2H), 4.37 (s, 2H), 3.85 (s, 4H), 3.76 (s, 8H), 3.40-3.30 (m, 2H), 2.70 (m, 2H), 2.31 (t, J=7.6 Hz, 4H), 1.74-1.66 (m, 4H), 1.51-1.44 (m, 9H), 1.39-1.25 (m, 8H), 0.91-0.86 (m, 6H). ESI-MS $C_{64}H_{77}N_9O_5$: 1051.6048, found 527 [EM+2H$^+$]/2.

Hexanoic acid (6-{[(5-{2-[(biphenyl-4-ylmethyl)-amino]-ethyl}-3-{[(6-hexanoylamino-pyridin-2-ylmethyl)-pyridin-2-ylmethyl-amino]-methyl}-2-hydroxy-benzyl)-pyridin-2-ylmethyl-amino]-methyl}-pyridin-2-yl)-amide (head group BPRDP0117): To a stirred solution of compound f117 (500 mg, 0.48 mmol) in 50 mL of dry DCM at room temperature, TFA was slowly added. The reaction mixture was stirred at room temperature for 2 hours and concentrated. The resultant residue was diluted with $CH_2Cl_2$ (200 mL). The $CH_2Cl_2$ solution was then washed with a saturated aqueous solution of NaHCO$_3$ (200 mL), dried over MgSO$_4$, and concentrated under reduced pressure to yield BPRDP0117 (380 mg, 84%). $^1$H NMR (300 MHz, CDCl$_3$): δ 8.49 (d, J=4.5 Hz, 2H), 8.08 (d, J=8.1 Hz, 2H), 7.60-7.53 (m, 4H), 7.49-7.36 (m, 8H), 7.32-7.29 (m, 3H), 7.12-7.07 (m, 4H), 7.00 (s, 2H), 3.87 (s, 2H), 3.83 (s, 4H), 3.72 (s, 8H), 2.93 (t, J=6.6 Hz, 2H), 2.80 (t, J=6.6 Hz, 2H), 2.37 (m, 4H), 1.75-1.65 (m, 4H), 1.35-1.27 (m, 8H), 0.88 (t, J=6.6 Hz, 6H). ESI-MS $C_{59}H_{69}N_9O_3$: 951.5523, found 540 [(M+2Zn$^{2+}$)+2]/2.

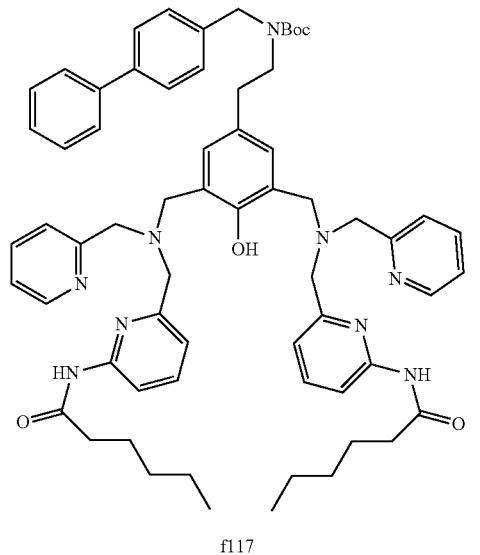

f117

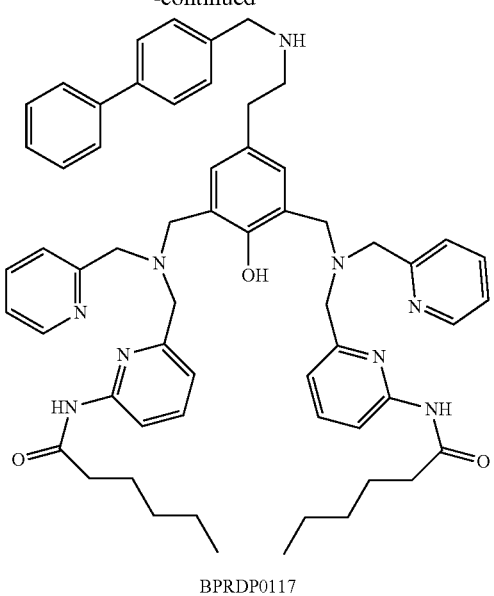

BPRDP0117

Syntheses of Head Groups BPRDP0120 and BPRDP0122

Head groups BPRDP0120 and BPRDP0122 were prepared according to the schemes shown below.

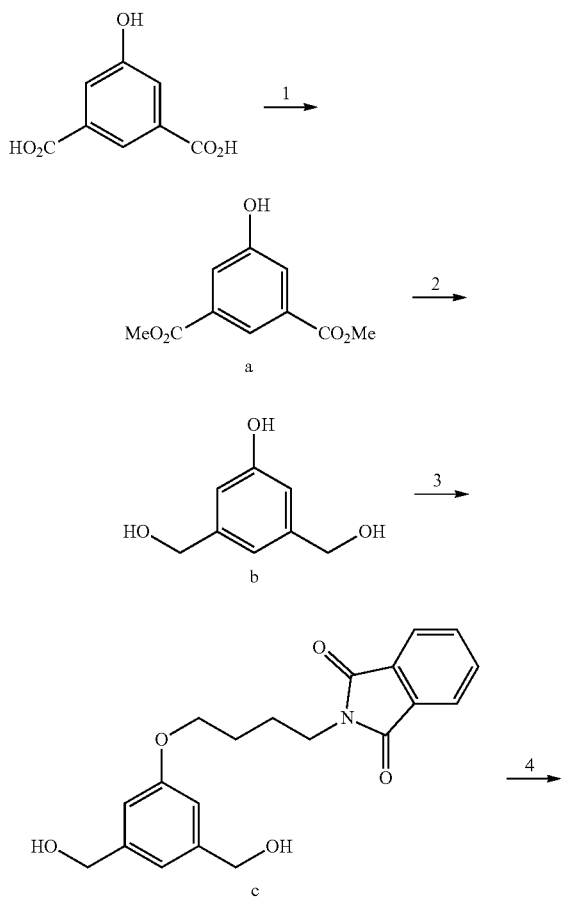

Scheme 6

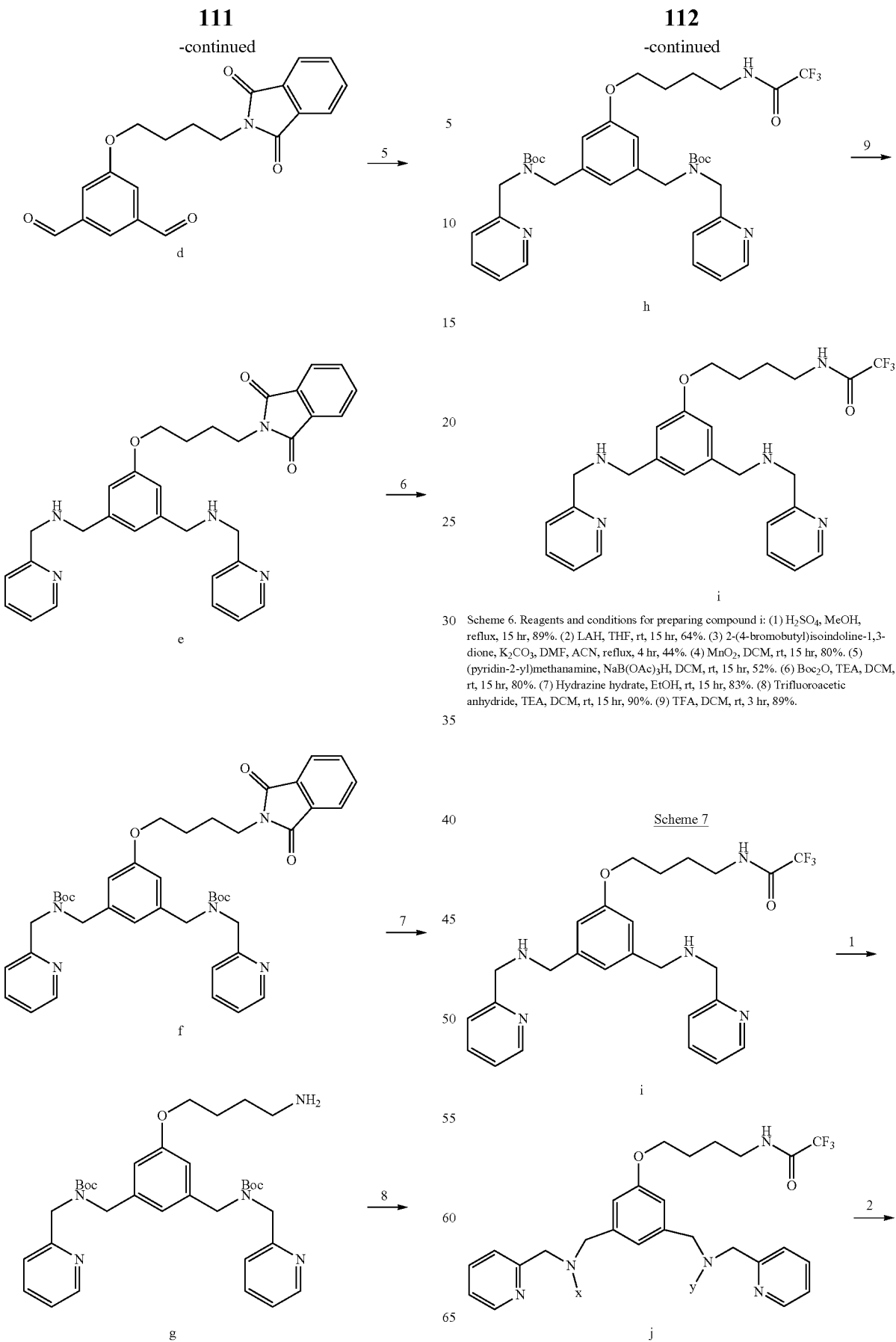
Scheme 6. Reagents and conditions for preparing compound i: (1) H₂SO₄, MeOH, reflux, 15 hr, 89%. (2) LAH, THF, rt, 15 hr, 64%. (3) 2-(4-bromobutyl)isoindoline-1,3-dione, K₂CO₃, DMF, ACN, reflux, 4 hr, 44%. (4) MnO₂, DCM, rt, 15 hr, 80%. (5) (pyridin-2-yl)methanamine, NaB(OAc)₃H, DCM, rt, 15 hr, 52%. (6) Boc₂O, TEA, DCM, rt, 15 hr, 80%. (7) Hydrazine hydrate, EtOH, rt, 15 hr, 83%. (8) Trifluoroacetic anhydride, TEA, DCM, rt, 15 hr, 90%. (9) TFA, DCM, rt, 3 hr, 89%.
Scheme 7

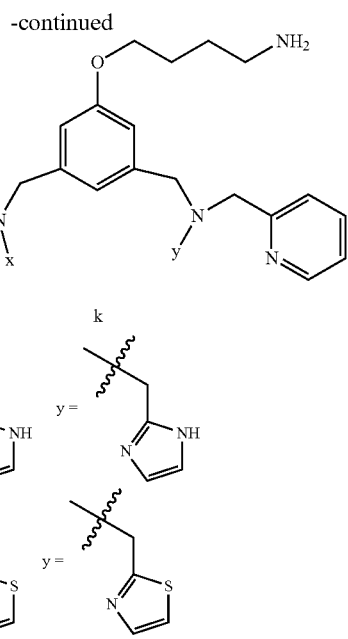

Scheme 7. Reagents and conditions for preparing head group BPRDP0120: (1) 1H-imidazole-2-carbaldehyde, NaB(OAc)₃H, DMF, THF, 40° C., 15 hr, 52%. (2) K₂CO₃, MeOH, rt, 15 hr, 86%. Reagents and conditions for preparing head group BPRDP0122: (1) thiazole-2-carbaldehyde, NaB(OAc)₃H, DCM, rt, 1 hr, 43%. (2) K₂CO₃, MeOH, rt, 15 hr, 85%.

Preparation of Compound i

Dimethyl 5-hydroxybenzene-1,3-dioate (compound a): To a stirred solution of 5-hydroxybenzene-1,3-dioic acid (10 g, 55 mmol) in 500 mL of MeOH at 0° C., sulfuric acid (H₂SO₄, 20 mL) was slowly added. The resultant reaction mixture was stirred at room temperature for 1 hour followed by refluxing for 15 hours. MeOH was removed and the resultant residue was diluted with CH₂Cl₂ (300 mL). The CH₂Cl₂ solution was then washed with a saturated aqueous solution of NaHCO₃ (3×300 mL) and water (200 mL), dried over MgSO₄, and concentrated under reduced pressure to yield compound a (10.2 g, 89%). ¹H NMR (300 MHz, CDCl₃): δ 3.96 (s, 6H), 7.77 (s, 2H), 8.26 (s, 1H).

3,5-Bis(hydroxymethyl)phenol (compound b): To a stirred solution of compound a (10.6 g, 50 mmol, 1 eq.) in 500 mL of dry THF at 0° C., LAH (7.5 g, 0.2 mol, 4 eq.) was slowly added. The resultant reaction mixture was stirred at room temperature for 15 hours and then cooled down to 0° C. Ammonium chloride aqueous solution (50 mL) was slowly added. The mixture was stirred at 0° C. for 1 hour, filtered through celite, and washed with THF. The resultant residue was concentrated under reduced pressure to yield compound b (5 g, 64%). ¹H NMR (400 MHz, CDCl₃): δ 4.57 (s, 6H), 6.71 (s, 2H), 6.80 (s, 1H). 2-(4-(3,5-Bis(hydroxymethyl)phenoxy)butyl)isoindoline-1,3-dione (compound c): To a stirred solution of compound b (7.8 g, 50.6 mmol, 1 eq.) in ACN (200 mL) and DMF (30 mL) at room temperature, 2-(4-bromobutyl)isoindoline-1,3-dione (21 g, 76 mmol, 1.5 eq.) and K₂CO₃ (34 g, 0.25 mol, 5 eq.) were slowly added. The resultant reaction mixture was stirred at room temperature for 1 hour and refluxed for 4 hours. MeOH and ACN were removed and the resultant residue was diluted with CH₂Cl₂ (200 mL). The CH₂Cl₂ solution was then washed with water (200 mL), dried over MgSO₄, and concentrated under reduced pressure. The resultant residue was purified by flash chromatography over silica gel with Ethyl acetate/Hexane (1/1) to yield compound c (8 g, 44%). ¹H NMR (400 MHz, CDCl₃): δ 1.67-1.65 (m, 2H), 1.86-1.81 (m, 2H), 3.75 (t, J=5.6 Hz, 2H), 4.00 (t, J=6.0 Hz, 2H), 4.63 (s, 2H), 4.64 (s, 2H), 6.81 (s, 2H), 6.91 (s, 1H), 7.71-7.69 (m, 2H), 7.84-7.82 (m, 2H).

5-(4-(1,3-Dioxoisoindolin-2-yl)butoxy)isophthalaldehyde (compound d): To a stirred solution of compound c (500 mg, 1.41 mmol, 1 eq.) in 100 mL of dry DCM at room temperature, MnO₂ (1.84 g, 21.1 mmol, 15 eq.) was slowly added. The resultant reaction mixture was stirred at room temperature for 15 hours, filtered through celite, and washed with DCM. The resultant residue was concentrated under reduced pressure to yield compound d (395 mg, 80%). ¹H NMR (400 MHz, CDCl₃): δ 10.04 (s, 2H), 7.94 (s, 1H), 7.86-7.83 (m, 2H), 7.73-7.71 (m, 2H), 7.62 (s, 2H), 4.12 (t, J=5.6 Hz, 2H), 3.79 (t, J=6.4 Hz, 2H), 1.95-1.86 (m, 4H).

2-(4-(3,5-Bis(((pyridin-2-ylmethyl)amino)methyl)phenoxy)butyl)isoindoline-1,3-dione (compound e): To a stirred solution of compound d (500 mg, 1.42 mmol, 1 eq.) in 50 mL of dry DCM at room temperature, (pyridin-2-yl)methanamine (613 mg, 5.68 mmol, 4 eq.) and NaB(OAc)₃H (1.2 g, 5.68 mmol, 4 eq.) were slowly added. The resultant reaction mixture was stirred at room temperature for 15 hours and concentrated. The resultant residue was diluted with CH₂Cl₂ (200 mL). The CH₂Cl₂ solution was then washed with a saturated aqueous solution of NaHCO₃ (200 mL), dried over MgSO₄, and concentrated under reduced pressure. The resultant residue was purified by flash chromatography over silica gel with MeOH/DCM (1/9) to yield compound e (400 mg, 52%). ¹H NMR (300 MHz, CDCl₃): δ 8.55 (d, J=5.7 Hz, 2H), 7.85-7.82 (m, 2H), 7.73-7.69 (m, 2H), 7.66-7.61 (m, 2H), 7.31 (d, J=7.5 Hz, 2H), 7.18-7.13 (m, 2H), 6.92 (s, 1H), 6.81 (s, 1H), 6.80 (s, 1H), 3.99 (t, J=5.7 Hz, 2H), 3.93 (s, 4H), 3.80 (s, 4H), 3.76 (t, J=6.9 Hz, 2H), 1.90-1.79 (m, 4H). ESI-MS C₃₂H₃₃N₅O₃: 535.2583, found 536 (EM+H⁺).

Di-tert-butyl ((5-(4-(1,3-dioxoisoindolin-2-yl)butoxy)-1,3-phenylene)bis (methylene))bis((pyridin-2-ylmethyl)carbamate) (compound f): To a stirred solution of compound e (500 mg, 0.93 mmol, 1 eq.) in 10 mL of dry dichloromethane (DCM) at room temperature, di-tert-butyl dicarbonate (813 mg, 3.73 mmol, 4 eq.) and TEA (1 mL) were slowly added. The resultant reaction mixture was stirred for 15 hours and concentrated. The resultant residue was diluted with CH₂Cl₂ (100 mL). The CH₂Cl₂ solution was then washed with a saturated ammonium chloride aqueous solution (200 mL), dried over MgSO₄, and concentrated under reduced pressure. The resultant residue was purified by flash chromatography over silica gel with Ethyl acetate/Hexane (4/1) to yield compound f (550 mg, 80%). ¹H NMR (300 MHz, CDCl₃): δ 8.51 (d, J=4.2 Hz, 2H), 7.86-7.83 (m, 2H), 7.72-7.69 (m, 2H), 7.66-7.61 (m, 2H), 7.23 (m, 1H), 7.17-7.13 (m, 3H), 6.67-6.62 (m, 3H), 4.54 (s, 2H), 4.48 (s, 2H), 4.42 (s, 2H), 4.40 (s, 2H), 3.91 (t, J=5.7 Hz, 2H), 3.76 (t, J=6.9 Hz, 2H), 1.89-1.82 (m, 4H), 1.47 (s, 9H), 1.40 (s, 9H).

Di-tert-butyl ((5-(4-aminobutoxy)-1,3-phenylene)bis (methylene))bis ((pyridin-2-ylmethyl)carbamate) (compound g): To a stirred solution of compound f (280 mg, 0.38 mmol, 1 eq.) in 6 ml EtOH at room temperature, hydrazine hydrate (240 mg, 7.6 mmol, 20 eq.) was slowly added. The resultant reaction mixture was stirred at room temperature for 15 hours. Removal of EtOH gave a residue, which was diluted with CH₂Cl₂ (200 mL). The CH₂Cl₂ solution was then washed with H₂O (200 mL), dried over MgSO₄, and concentrated under reduced pressure to yield compound g (190 mg, 83%). ¹H NMR (300 MHz, CDCl₃): δ 8.51 (d, J=4.2 Hz, 2H), 7.66-7.61 (m, 2H), 7.23 (m, 1H), 7.17-7.13 (m, 3H), 6.70-6.64 (m, 3H), 4.54 (s, 2H), 4.49 (s, 2H), 4.43

(s, 2H), 4.41 (s, 2H), 3.91 (t, J=6.0 Hz, 2H), 2.78 (t, J=6.9 Hz, 2H), 1.83-1.76 (m, 2H), 1.67-1.57 (m, 2H), 1.47 (s, 9H), 1.40 (s, 9H).

Di-tert-butyl ((5-(4-(2,2,2-trifluoroacetamido)butoxy)-1,3-phenylene)bis (methylene))bis((pyridin-2-ylmethyl)carbamate) (compound h): To a stirred solution of compound g (500 mg, 0.83 mmol, 1 eq.) in 10 mL of dry dichloromethane (DCM) at room temperature, trifluoroacetic anhydride (350 mg, 1.66 mmol, 2 eq.) and TEA (1 mL) were slowly added. The resultant reaction mixture was stirred for 15 hours and concentrated. The resultant residue was diluted with CH$_2$Cl$_2$ (100 mL). The CH$_2$Cl$_2$ solution was then washed with a saturated ammonium chloride aqueous solution (200 mL), dried over MgSO$_4$, and concentrated under reduced pressure to yield compound h (520 mg, 90%). $^1$H NMR (300 MHz, CDCl$_3$): δ 8.51 (d, J=4.2 Hz, 2H), 7.68-7.63 (m, 2H), 7.26 (m, 1H), 7.19-7.15 (m, 3H), 6.70-6.63 (m, 3H), 4.54 (s, 2H), 4.48 (s, 2H), 4.43 (s, 2H), 4.41 (s, 2H), 3.95-3.93 (m, 2H), 3.48-3.44 (m, 2H), 1.87-1.77 (m, 4H), 1.48 (s, 9H), 1.41 (s, 9H). ESI-MS C$_{36}$H$_{46}$F$_3$N$_5$O$_6$: 701.34, found 702 (EM+H$^+$).

N-(4-(3,5-bis(((pyridin-2-ylmethyl)amino)methyl)phenoxy)butyl)-2,2,2-trifluoroacetamide (compound i): To a stirred solution of compound h (500 mg, 0.71 mmol) in 50 ml of dry DCM at room temperature, TFA was slowly added. The resultant reaction mixture was stirred at room temperature for 3 hours and concentrated. The resultant residue was diluted with CH$_2$Cl$_2$ (200 mL). The CH$_2$Cl$_2$ solution was then washed with a saturated aqueous solution of NaHCO$_3$ (200 mL), dried over MgSO$_4$, and concentrated under reduced pressure to yield compound i (320 mg, 89%). $^1$H NMR (300 MHz, CDCl$_3$): δ 8.55 (d, J=5.1 Hz, 2H), 7.69-7.63 (m, 2H), 7.32 (d, J=7.5 Hz, 2H), 7.21-7.17 (m, 2H), 6.94 (s, 1H), 6.89 (s, 2H), 4.03 (t, J=5.7 Hz, 2H), 3.96 (s, 4H), 3.84 (s, 4H), 3.77-3.72 (m, 2H), 1.87-1.79 (m, 4H). ESI-MS C$_{26}$H$_{30}$F$_3$N$_5$O$_2$: 501.2352, found 502 (EM+H$^+$).

Synthesis of Head Group BPRDP0120

N-(4-(3,5-bis((((1H-imidazol-2-yl)methyl)(pyridin-2-ylmethyl)amino)methyl)phenoxy)butyl)-2,2,2-trifluoroacetamide (compound j120): To a stirred solution of compound i (500 mg, 0.996 mmol, 1 eq.) in DMF (25 ml) and THF (25 mL) at room temperature, 1H-imidazole-2-carbaldehyde (382 mg, 3.98 mmol, 4 eq.) and NaB(OAc)$_3$H (844 mg, 3.98 mmol, 4 eq.) were slowly added. The resultant reaction mixture was stirred at room temperature for 1 hour, heated at 40° C. for 15 hours, and then concentrated. The resultant residue was diluted with CH$_2$Cl$_2$ (200 mL). The CH$_2$Cl$_2$ solution was washed with a saturated aqueous solution of NaHCO$_3$ (200 mL), dried over MgSO$_4$, and concentrated under reduced pressure. The resultant residue was purified by flash chromatography over silica gel with MeOH/DCM (7/93) to yield compound j120 (340 mg, 52%). $^1$H NMR (400 MHz, CDCl$_3$): δ 8.59 (d, J=4.8 Hz, 2H), 7.74-7.70 (m, 2H), 7.57 (d, J=7.6 Hz, 2H), 7.25-7.20 (m, 3H), 7.01 (m, 4H), 6.71 (s, 2H), 4.00 (t, J=5.2 Hz, 2H), 3.84 (s, 4H), 3.75 (s, 4H), 3.61 (s, 4H), 3.49-3.45 (m, 2H), 1.84-1.80 (m, 4H). ESI-MS C$_{34}$H$_{38}$F$_3$N$_9$O$_2$: 661.3101, found 662 (EM+H$^+$).

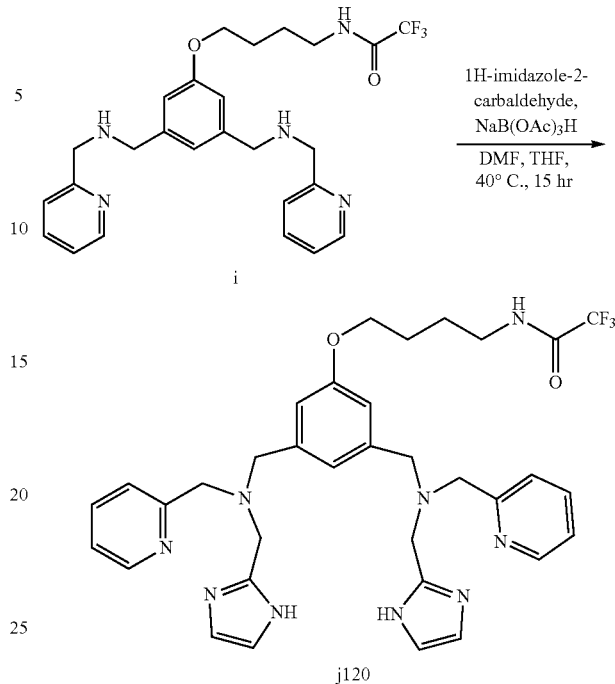

4-(3,5-Bis-{[(1H-imidazol-2-ylmethyl)-pyridin-2-ylmethyl-amino]-methyl}-phenoxy)-butylamine (head group BPRDP0120): To a stirred solution of compound j120 (300 mg, 0.45 mmol, 1 eq.) in 30 mL of MeOH at room temperature, K$_2$CO$_3$ (620 mg, 4.5 mmol, 10 eq.) was slowly added. The resultant reaction mixture was stirred at room temperature for 15 hours. After removal of MeOH, the mixture was filtered through celite and washed with DCM. The filtrate residue was concentrated under reduced pressure to yield BPRDP0120 (220 mg, 86%). $^1$H NMR (300 MHz, CDCl$_3$): δ 8.56 (d, J=6.9 Hz, 2H), 7.69-7.63 (m, 2H), 7.56 (d, J=8.1 Hz, 2H), 7.35 (s, 1H), 7.22-7.17 (m, 2H), 7.02-7.00 (m, 4H), 6.71 (s, 2H), 3.94 (t, J=6.0 Hz, 2H), 3.80 (s, 4H), 3.69 (s, 4H), 3.59 (s, 4H), 2.76 (t, J=6.6 Hz, 2H), 1.85-1.76 (m, 2H), 1.66-1.58 (m, 2H). ESI-MS C$_{32}$H$_{39}$N$_9$O: 565.3278, found 566 (M+H$^+$).

Synthesis of Head Group BPRDP0122

N-(4-(3,5-bis(((pyridin-2-ylmethyl)(thiazol-2-ylmethyl)amino)methyl)phenoxy)butyl)-2,2,2-trifluoroacetamide (compound j122): To a stirred solution of compound i (500 mg, 0.996 mmol, 1 eq.) in 50 mL of dry DCM at room temperature, thiazole-2-carbaldehyde (450 mg, 3.98 mmol, 4 eq.) and NaB(OAc)$_3$H (844 mg, 3.98 mmol, 4 eq.) were slowly added. The resultant reaction mixture was stirred for 1 hour and concentrated. The resultant residue was diluted with CH$_2$Cl$_2$ (200 mL). The CH$_2$Cl$_2$ solution was then washed with a saturated aqueous solution of NaHCO$_3$ (200 mL), dried over MgSO$_4$, and concentrated under reduced pressure. The resultant residue was purified by flash chromatography over silica gel with MeOH/DCM (7/93) to yield compound j122 (300 mg, 43%). $^1$H NMR (300 MHz, CDCl$_3$): δ 8.51 (d, J=5.4 Hz, 2H), 7.71-7.62 (m, 6H), 7.28 (d, J=3.3 Hz, 2H), 7.19-7.15 (m, 2H), 7.10 (s, 1H), 6.91 (s, 2H), 4.03 (t, J=5.4 Hz, 2H), 3.99 (s, 4H), 3.87 (s, 4H), 3.71 (s, 4H), 3.49-3.43 (m, 2H), 1.88-1.79 (m, 4H). ESI-MS C$_{34}$H$_{36}$F$_3$N$_7$O$_2$S$_2$: 695.2324, found 696 (EM+H$^+$).

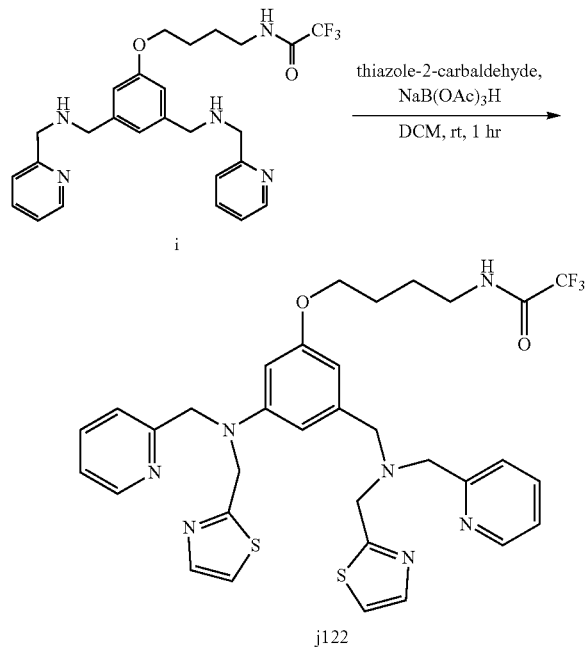

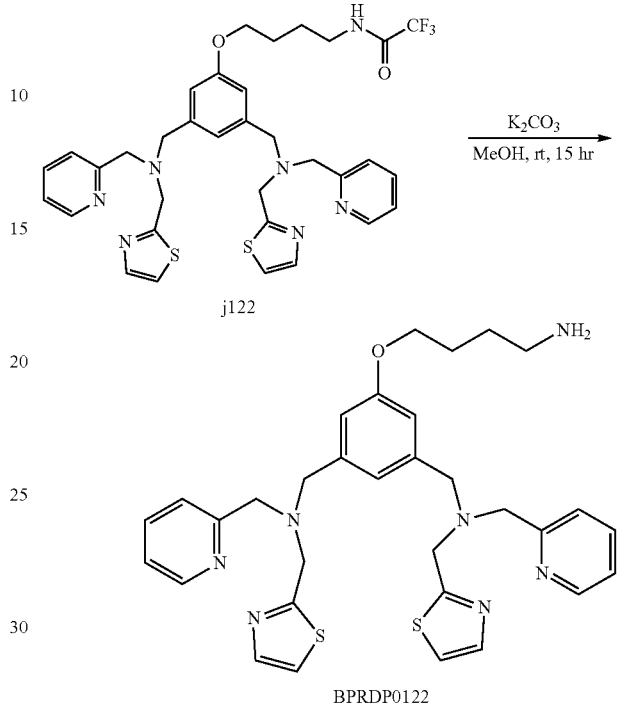

4-{3,5-Bis-[(pyridin-2-ylmethyl-thiazol-2-ylmethyl-amino)-methyl]-phenoxy}-butylamine (head group BPRDP0122): To a stirred solution of compound j122 (300 mg, 0.43 mmol, 1 eq.) in 30 mL of MeOH at room temperature, $K_2CO_3$ (593 mg, 4.3 mmol, 10 eq.) was slowly added. The resultant reaction mixture was stirred at room temperature for 15 hours. MeOH was removed. The residue was filtered through celite and washed with DCM. The filtrate was concentrated under reduced pressure to yield BPRDP0122 (220 mg, 85%). $^1$H NMR (300 MHz, $CDCl_3$): δ 8.51 (d, J=4.5 Hz, 2H), 7.69-7.62 (m, 6H), 7.28-7.26 (m, 2H), 7.17-7.13 (m, 2H), 7.09 (s, 1H), 6.90 (s, 2H), 4.02-3.98 (m, 6H), 3.85 (s, 4H), 3.68 (s, 4H), 2.88 (t, J=6.9 Hz, 2H), 1.88-1.70 (m, 4H). ESI-MS $C_{32}H_{37}N_7OS_2$: 599.2501, found 727 (M+2Zn$^{2+}$)

Syntheses of Head Groups BPRDP0123 and BPRDP0140

Head groups BPRDP0123 and BPRDP0140 were prepared according to the scheme shown below.

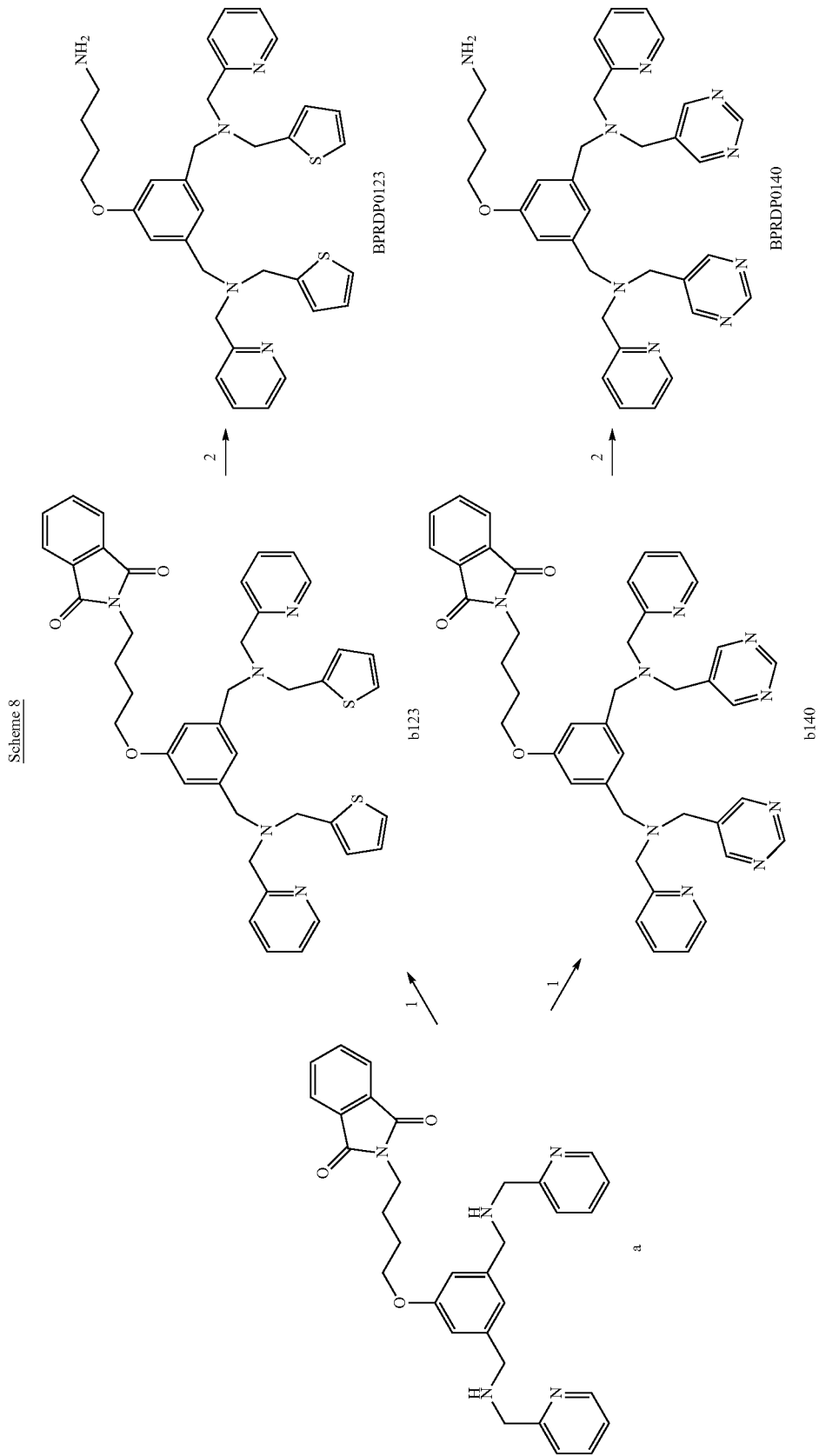
Scheme 8. Reagents and condition for preparing head group BPRDP0123: (1) thiophene-2-carbaldehyde, NaB(OAc)₃H, DCM, rt, 15 hr, 47%. (2) Hydrazine hydrate, EtOH, rt, 15 hr, 80%. Reagents and condition for preparing head group BPRDP0140: (1) pyrimidine-5-carbaldehyde, NaB(OAc)₃H, DCM, DMF, 40°C., 15 hr, 53%. (2) Hydrazine hydrate, EtOH, rt, 15 hr, 83%.

Synthesis of Head Group BPRDP0123

2-(4-(3,5-Bis(((pyridin-2-ylmethyl)(thiophen-2-ylmethyl)amino)methyl)phenoxy) butyl)isoindoline-1,3-dione (compound b123): To a stirred solution of compound a (500 mg, 0.93 mmol, 1 eq.) in 50 mL of dry DCM at room temperature, thiophene-2-carbaldehyde (420 mg, 3.73 mmol, 4 eq.) and NaB(OAc)$_3$H (790 mg, 3.73 mmol, 4 eq.) were slowly added. The resultant reaction mixture was stirred for 15 hours and concentrated. The resultant residue was diluted with CH$_2$Cl$_2$ (200 mL). The CH$_2$Cl$_2$ solution was then washed with a saturated aqueous solution of NaHCO$_3$ (200 mL), dried over MgSO$_4$, and concentrated under reduced pressure. The resultant residue was purified by flash chromatography over silica gel with Ethyl acetate/Hexane (7/3) to yield compound b123 (320 mg, 47%). $^1$H NMR (300 MHz, CDCl$_3$): δ 8.48 (d, J=5.1 Hz, 2H), 7.86-7.81 (m, 2H), 7.73-7.63 (m, 6H), 7.23-7.20 (m, 2H), 7.16-7.11 (m, 2H), 7.07 (s, 1H), 6.94-6.91 (m, 4H), 6.89 (s, 2H), 4.02 (t, J=6.0 Hz, 2H), 3.83-3.76 (m, 10H), 3.63 (s, 4H), 1.92-1.83 (m, 4H).

4-{3,5-Bis-[(pyridin-2-ylmethyl-thiophen-2-ylmethyl-amino)-methyl]-phenoxy}-butylamine (head group BPRDP0123): To a stirred solution of compound b123 (300 mg, 0.41 mmol, 1 eq.) in 6 mL EtOH at room temperature, hydrazine hydrate (265 mg, 8.24 mmol, 20 eq.) was slowly added. The resultant reaction mixture was stirred at room temperature for 15 hours. Removal of EtOH gave a crude residue, which was diluted with CH$_2$Cl$_2$ (200 mL). The CH$_2$Cl$_2$ solution was then washed with H$_2$O (200 mL), dried over MgSO$_4$, and concentrated under reduced pressure to yield BPRDP0123 (197 mg, 80%). $^1$H NMR (300 MHz, CDCl$_3$): δ 8.48 (d, J=4.8 Hz, 2H), 7.68-7.60 (m, 4H), 7.23-7.21 (m, 2H), 7.12-7.09 (m, 3H), 6.94-6.92 (m, 4H), 6.86 (s, 2H), 4.00 (t, J=5.4 Hz, 2H), 3.81 (s, 4H), 3.78 (s, 4H), 3.61 (s, 4H), 2.91 (t, J=6.9 Hz, 2H), 1.89-1.77 (m, 4H). ESI-MS C$_{34}$H$_{39}$N$_5$OS$_2$: 597.2596, found 725 (M+2Zn$^{2+}$).

Synthesis of Head Group BPRDP0140

2-(4-(3,5-Bis(((pyridin-2-ylmethyl)(pyrimidin-5-ylmethyl)amino)methyl)phenoxy)butyl)isoindoline-1,3-dione (compound b140): To a stirred solution of compound a (500 mg, 0.93 mmol, 1 eq.) in DCM (25 ml) and DMF (25 mL) at room temperature, pyrimidine-5-carbaldehyde (403 mg, 3.73 mmol, 4 eq.) and NaB(OAc)$_3$H (790 mg, 3.73 mmol, 4 eq.) were slowly added. The resultant reaction mixture was stirred for 15 hours and concentrated. The resultant residue was diluted with CH$_2$Cl$_2$ (200 mL). The CH$_2$Cl$_2$ solution was then washed with a saturated aqueous solution of NaHCO$_3$ (200 mL), dried over MgSO$_4$, and concentrated under reduced pressure. The resultant residue was purified by flash chromatography over silica gel with MeOH/DCM (4/96) to yield compound b140 (356 mg, 53%). $^1$H NMR (400 MHz, CDCl$_3$): δ 9.07 (s, 2H), 8.74 (s, 4H), 8.53 (d, J=4.0 Hz, 2H), 7.85-7.83 (m, 2H), 7.73-7.70 (m, 4H), 7.50 (d, J=8.0 Hz, 2H), 7.22-7.19 (m, 2H), 6.97 (s, 1H), 6.84 (s, 2H), 3.99 (t, J=6.0 Hz, 2H), 3.80-3.76 (m, 6H), 3.68 (s, 4H), 3.64 (s, 4H), 1.90-1.85 (m, 4H).

4-{3,5-Bis-[(pyridin-2-ylmethyl-pyrimidin-5-ylmethyl-amino)-methyl]-phenoxy}-butylamine (head group BPRDP0140): To a stirred solution of compound b140 (300 mg, 0.42 mmol, 1 eq.) in 6 mL EtOH at room temperature, hydrazine hydrate (267 mg, 8.33 mmol, 20 eq.) was slowly added. The resultant reaction mixture was stirred at room temperature for 15 hours. Removal of EtOH gave a residue, which was diluted with CH$_2$Cl$_2$ (200 mL). The CH$_2$Cl$_2$ solution was then washed with H$_2$O (200 mL), dried over MgSO$_4$, and concentrated under reduced pressure to yield BPRDP0140 (204 mg, 83%). $^1$H NMR (400 MHz, CDCl$_3$): δ 9.01 (s, 2H), 8.72 (s, 4H), 8.51 (d, J=4.8 Hz, 2H), 7.68-7.64 (m, 2H), 7.46 (d, J=7.6 Hz, 2H), 7.17-7.14 (m, 2H), 6.93 (s, 1H), 6.84 (s, 2H), 3.98 (t, J=5.6 Hz, 2H), 3.76 (s, 4H), 3.63 (s, 4H), 3.61 (s, 4H), 2.94 (t, J=7.2 Hz, 2H), 1.89-1.80 (m, 4H). ESI-MS C$_{34}$H$_{39}$N$_9$O: 589.3278, found 590 (M+H$^+$).

Synthesis of Head Group BPRDP0157

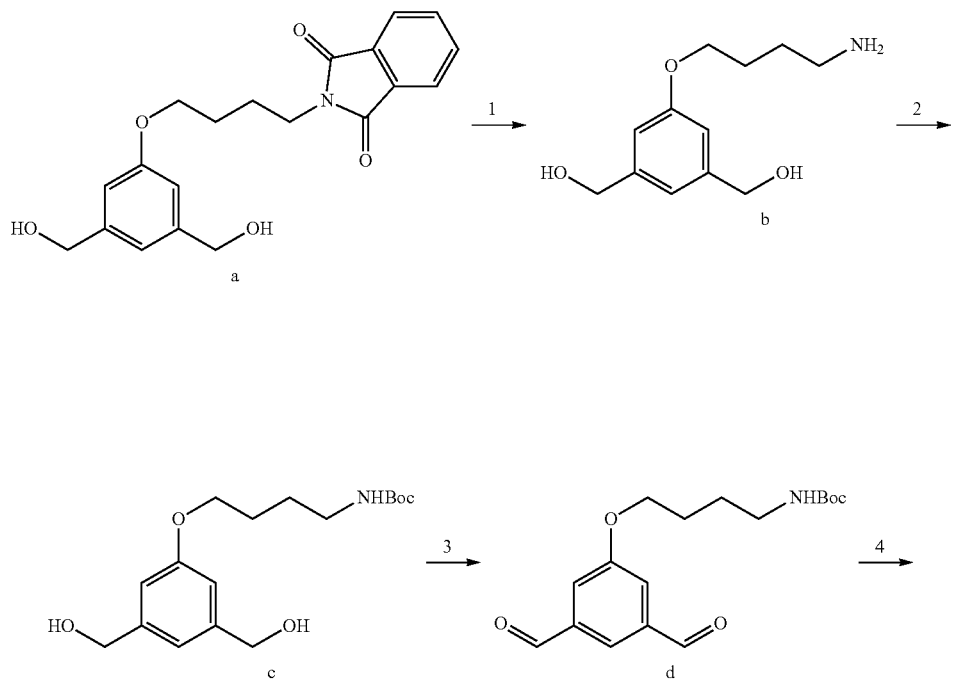

Scheme 9

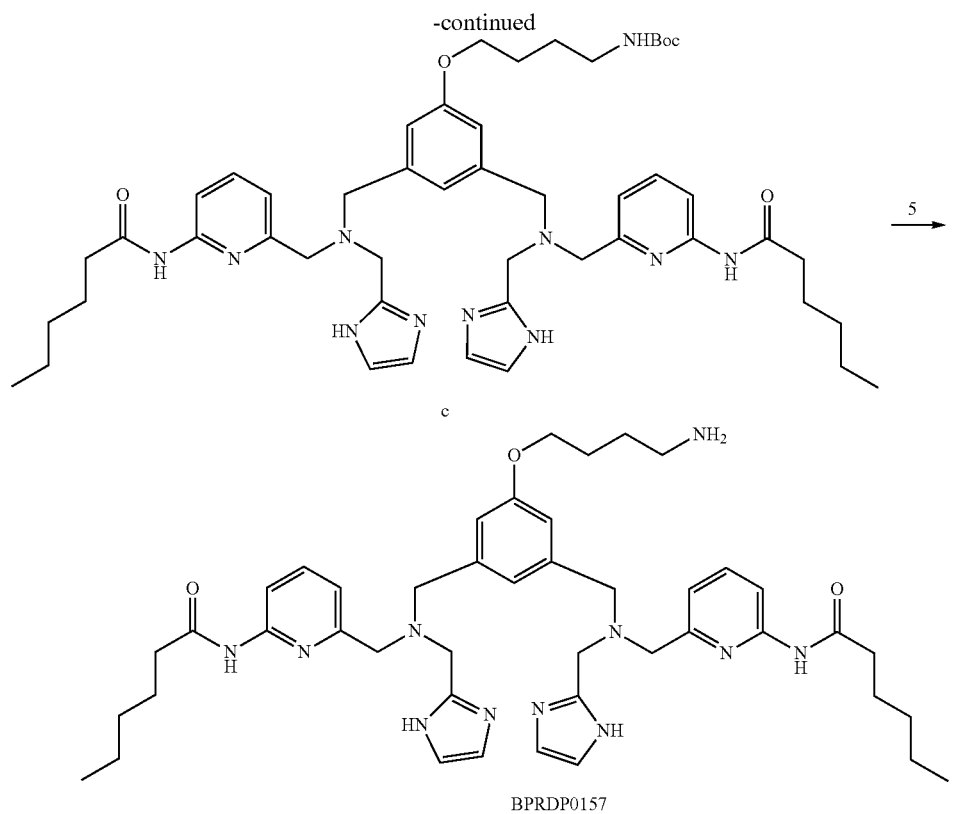

Scheme 9. Reagents and conditions for preparing head group BPRDP0157:
(1) Hydrazine hydrate, EtOH, rt, 15 hr, 85%.
(2) Boc₂O, TEA, THF, DMF, rt, 15 hr, 75%.
(3) MnO₂, DCM, rt, 15 hr, 80%.
(4) N-(6-(((1H-imidazol-2-yl)methylamino)methyl)pyridin-2-yl)hexaniamide, NaB(OAc)₃H, DCM, rt, 15 hr, 40%.
(5) TFA, DCM, 0° C., 3 hr, 90%.

To a stirred solution of compound a (500 mg, 1.41 mmol, 1 eq.) in 20 mL EtOH at room temperature, hydrazine hydrate (900 mg, 28 mmol, 20 eq.) was slowly added. The resultant reaction mixture was stirred at room temperature for 15 hours. EtOH was removed. The resultant residue was diluted with CH$_2$Cl$_2$ (200 mL). The CH$_2$Cl$_2$ solution was then washed with H$_2$O (200 mL), dried over MgSO$_4$, and concentrated under reduced pressure to yield compound b (269 mg, 85%).

Tert-butyl (4-(3,5-bis(hydroxymethyl)phenoxy)butyl)carbamate (compound c): To a stirred solution of compound b (500 mg, 2.22 mmol, 1 eq.) in THF (40 mL) and DMF (5 mL) at room temperature, di-tert-butyl dicarbonate (1.9 g, 8.9 mmol, 4 eq.) and TEA (2 mL) were slowly added. The resultant reaction mixture was stirred for 15 hours and concentrated. The resultant residue was diluted with CH$_2$Cl$_2$ (200 mL). The CH$_2$Cl$_2$ solution was then washed with a saturated ammonium chloride aqueous solution (200 mL) and water (3×200 mL), dried over MgSO$_4$, and concentrated under reduced pressure. The resultant residue was purified by flash chromatography over silica gel with Ethyl acetate/Hexane (7/3) to yield compound c (540 mg, 75%). $^1$H NMR (400 MHz, CDCl$_3$): δ 6.91 (s, 1H), 6.82 (s, 2H), 4.64 (s, 4H), 3.98 (t, J=6.4 Hz, 2H), 3.17 (t, J=7.2 Hz, 2H), 1.83-1.76 (m, 2H), 1.68-1.62 (m, 2H), 1.44 (s, 9H).

Tert-butyl (4-(3,5-diformylphenoxy)butyl)carbamate (compound d): To a stirred solution of compound c (1 g, 3.08 mmol, 1 eq.) in 100 mL of dry DCM at room temperature, MnO$_2$ (7.76 g, 92.4 mmol, 30 eq.) was slowly added. The resultant reaction mixture was stirred at room temperature for 15 hours. The mixture was filtered with celite, washed with DCM. The resultant residue was concentrated under reduced pressure to yield compound d (790 mg, 80%). $^1$H NMR (300 MHz, CDCl$_3$): δ 10.05 (s, 2H), 7.95 (s, 1H), 7.64 (s, 1H), 7.63 (s, 1H), 4.10 (t, J=6.3 Hz, 2H), 3.24-3.18 (m, 2H), 1.90-1.83 (m, 2H), 1.74-1.66 (m, 2H), 1.44 (s, 9H).

N-(6-(((1H-imidazol-2-yl)methylamino)methyl)pyridin-2-yl)hexanamide (compound e): To a stirred solution of compound d (600 mg, 1.87 mmol, 1 eq.) in 60 mL of dry DCM at room temperature, N-(6-(((1H-imidazol-2-yl)methylamino)methyl)pyridin-2-yl)hexanamide (1.68 g, 5.61 mmol, 3 eq.) and NaB(OAc)$_3$H (1.2 g, 5.61 mmol, 3 eq.) were slowly added. The resultant reaction mixture was stirred for 15 hours and concentrated. The resultant residue was diluted with CH$_2$Cl$_2$ (200 mL). The CH$_2$Cl$_2$ solution was then washed with a saturated aqueous solution of NaHCO$_3$ (200 mL), dried over MgSO$_4$, and concentrated under reduced pressure. The resultant residue was purified by flash chromatography over silica gel with MeOH/Ethyl acetate (2/98) to yield compound e (667 mg, 40%). $^1$H NMR (400 MHz, CDCl$_3$): δ 8.05 (d, J=8.0 Hz, 1H), 7.59-7.55 (m, 1H), 6.94 (m, 2H), 6.85 (d, J=7.2 Hz, 1H), 3.91 (s, 2H), 3.72 (s, 2H), 2.40 (t, J=7.2 Hz, 2H), 1.72-1.68 (m, 2H), 1.34-1.31 (m, 4H), 0.90-0.86 (m, 3H). ESI-MS C$_{16}$H$_{23}$N$_5$O: 301.1903, found 302 (EM+H$^+$).

Hexanoic acid (6-{[(3-(4-amino-butoxy)-5-{[(6-hexanoylamino-pyridin-2-ylmethyl)-(1H-imidazol-2-ylmethyl)- amino]-methyl}-benzyl)-(1H-imidazol-2-ylmethyl)-amino]-methyl}-pyridin-2-yl)-amide (head group BPRDP0157): To a stirred solution of compound e (500 mg, 0.56 mmol) in 50 mL of dry DCM at 0° C., TFA was slowly added. The resultant reaction mixture was stirred at 0° C. for 3 hours and concentrated. The resultant residue was diluted with $CH_2Cl_2$ (200 mL). The $CH_2Cl_2$ solution was then washed with a saturated aqueous solution of $NaHCO_3$ (200 mL), dried over $MgSO_4$, and concentrated under reduced pressure to yield BPRDP0157 (400 mg, 90%). $^1$H NMR (400 MHz, DMSO-$d_6$): δ 7.92 (d, J=8.0 Hz, 2H), 7.70-7.66 (m, 2H), 7.35 (d, J=7.6 Hz, 2H), 7.04 (s, 1H), 6.96 (m, 4H), 6.79 (s, 2H), 3.92 (t, J=6.0 Hz, 2H), 3.62 (s, 4H), 3.57 (s, 4H), 3.53 (s, 4H), 2.77 (t, J=7.2 Hz, 2H), 2.32 (t, J=7.2 Hz, 4H), 1.73-1.60 (m, 4H), 1.55-1.49 (m, 4H), 1.24-1.20 (m, 8H), 0.83 (t, J=6.8 Hz, 6H). ESI-MS $C_{44}H_{61}N_{11}O_3$(EM+ H$^+$): 791.4959, found 793. Synthesis of head group BPRDP0170

Scheme 10

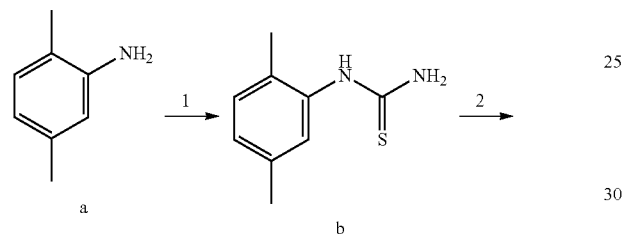

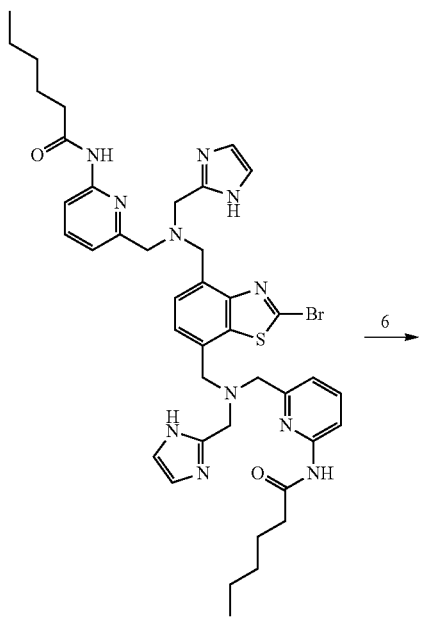

f

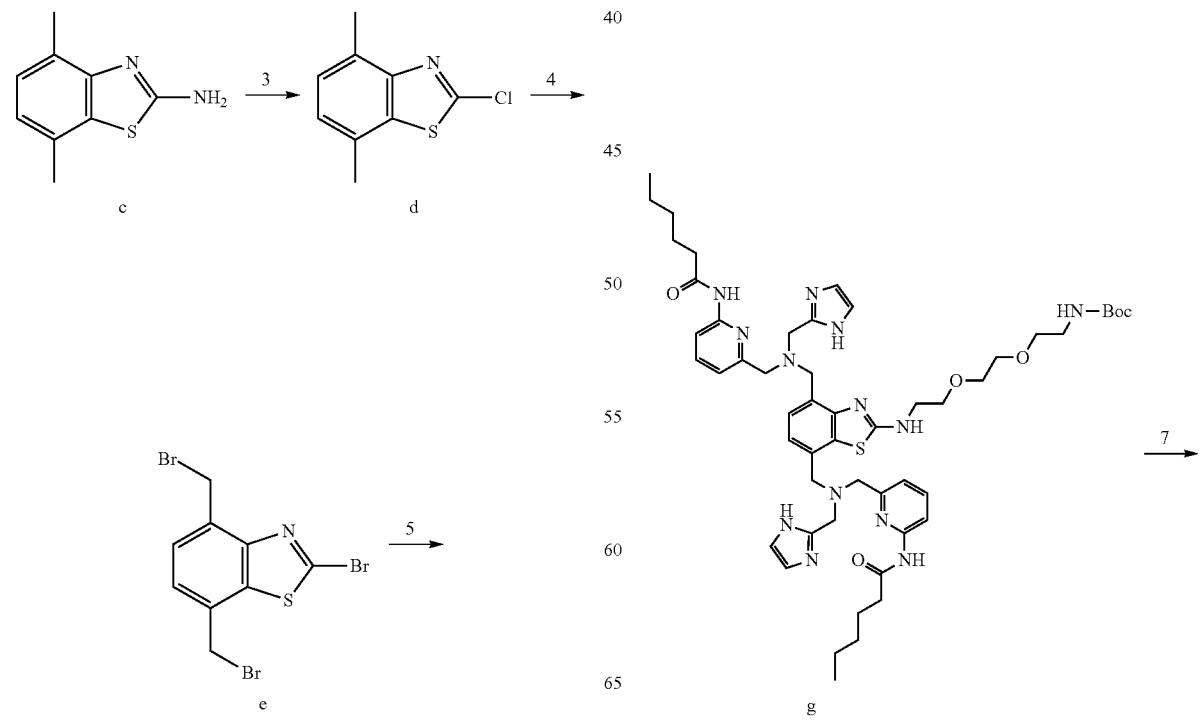

g

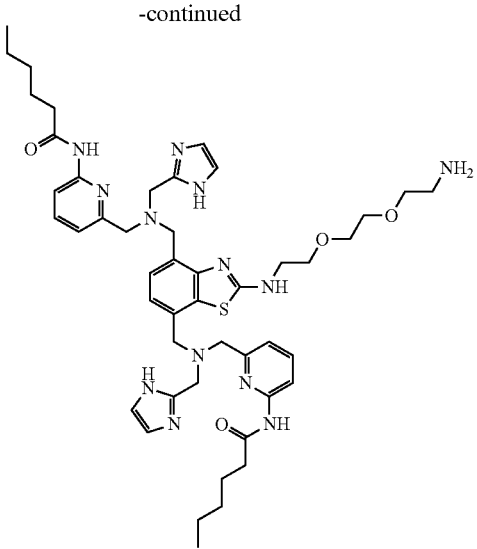

BPRDP0170

Scheme 10. Reagent and conditions for preparing head group BPRDP0170:
(1) NH$_4$SCN, 6 M HCl (aq.) 105° C.
(2) Br$_2$, DCM, 0° C.
(3) 3-Methyl-1-nitrobutane, CuCl$_2$*8H$_2$O, ACN.
(4) NBS, BPO, CCl$_4$.
(5) Hexanoic acid (6-{[(1H-imidazol-2-ylmethyl)-amino]-methyl}-pyridin-2-yl)-amide, K$_2$CO$_3$, ACN.
(6) {2-[2-(2-Amino-ethoxy)-ethoxy]-ethyl}-carbamic acid tert-butyl ester, K$_2$CO$_3$, DMF.
(7) TFA, DCM.

A solution of compound a (5 g, 41 mmol) in 6 M HCl$_{(aq.)}$ was heated at 105° C. for 30 min. Ammonium thiocyanate (3.7 g, 48 mmol) was then added and the resultant mixture was refluxed for 3 hours. The reaction solution was quenched with 100 mL NaHCO$_{3(aq.)}$ and extracted with 100 mL Ethyl acetate. The extract was condensed and the resultant residue was purified by flash chromatography over silica gel to afford compound b (4.1 g, 22 mmol, 53%).

To a solution of compound b (3.4 g, 18 mmol) in DCM was added Br$_{2(l)}$ (3 g, 18 mmol) at 0° C. in a 2-hour period. The reaction solution was then quenched with a Na$_2$S$_2$O$_3$ (2.3 g, 63 mmol) aqueous solution. The organic and aqueous phases were separated. The organic phase solution was concentrated and the resultant residue was washed with Ethyl acetate to give compound c (3.4 g, 18 mmol, 100%).

To a solution of compound c (5 g, 28 mmol) in ACN was added 3-Methyl-1-nitrobutane (4 g, 34 mmol) and CuCl$_2$*5H$_2$O (6 g, 26 mmol) at room temperature in a 3-hour period. The reaction solution was then quenched with 100 mL water and extracted with 100 mL Ethyl acetate. The organic extract was concentrated and the resultant residue was purified by recrystallizing from Hexane to give compound d (2 g, 10 mmol, 35%).

To a solution of compound d (600 mg, 3 mmol) in CCl$_4$ was added BPO (100 mg, 0.3 mmol) and NBS (1.6 g, 9 mmol). The reaction mixture was heated at 85° C. for 3 hours and then concentrated to give a crude residue. The crude residue was purified by flash chromatography over silica gel to give compound e (500 mg, 1 mmol, 33%).

To a solution of compound e (200 mg, 0.5 mmol) in ACN was added hexanoic acid (6-{[(1H-imidazol-2-ylmethyl)-amino]-methyl}-pyridin-2-yl)-amide (200 mg, 1.2 mmol) and K$_2$CO$_3$ (250 mg, 1.8 mmol) at room temperature. The reaction solution was stirred for 3 hours, quenched with 100 mL H$_2$O, and extracted with 100 mL Ethyl acetate. The extract was concentrated and the resultant crude residue was purified by flash chromatography over silica gel to give compound f (90 mg, 0.1 mmol, 20%).

To a solution of compound f (90 mg, 0.1 mmol) in ACN was added {2-[2-(2-Amino-ethoxy)-ethoxy]-ethyl}-carbamic acid tert-butyl ester (80 mg, 0.2 mmol) and DIPEA. The resultant reaction solution was stirred at 130° C. for 72 hours and then concentrated. The residue was purified by flash chromatography over silica gel to give compound g (90 mg, 0.08 mmol, 80%).

To a solution of compound g (90 mg, 0.08 mmol) in 100 mL CH$_2$Cl$_2$ was added 100 mL 1 M HCl$_{(aq.)}$. The organic and aqueous phases were separated. The aqueous solution was neutralized and extracted with 100 mL CH$_2$Cl$_2$. The extract was concentrated and the resultant residue was purified by flash chromatography over silica gel to give compound BPRDP0170 (35 mg, 0.03 mmol, 40%). $^1$H NMR (300 MHz, cd$_3$od) δ 7.82-7.70 (m, 1H), 7.70-7.57 (m, 1H), 7.56-7.42 (m, 6H), 7.28 (d, J=7.6 Hz, 1H), 7.06 (dd, J=10.9, 7.5 Hz, 2H), 6.96 (d, J=7.4 Hz, 1H), 4.26 (s, 2H), 4.11 (s, 4H), 3.87 (d, J=4.3 Hz, 4H), 3.81-3.53 (m, 14H), 3.16-2.99 (m, 2H), 2.47 (td, J=7.5, 5.3 Hz, 4H), 1.83-1.62 (m, 4H), 1.38 (tt, J=7.0, 3.6 Hz, 9H), 1.17 (t, J=7.0 Hz, 1H), 0.93 (t, J=7.0 Hz, 6H). ESI-MS C$_{47}$H$_{65}$N$_{13}$O$_4$S$^+$: 907.50, found: 908.78 (M$^+$). HPLC purity: 96%

Example 2: Synthesis of Compounds 1-27

Synthesis of Compound 1

Scheme 11

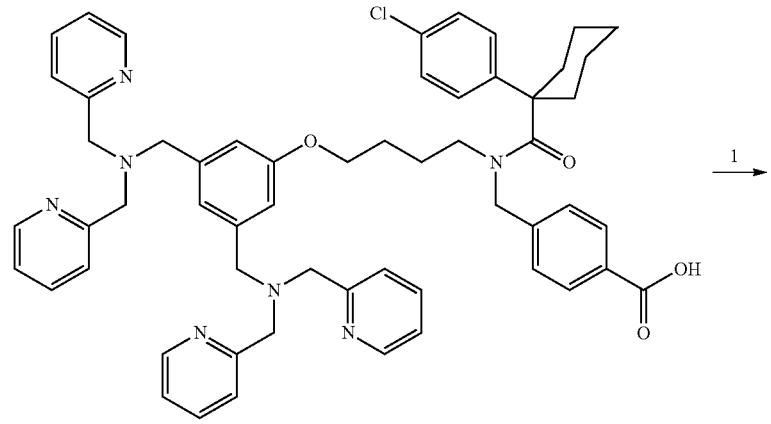

1-1

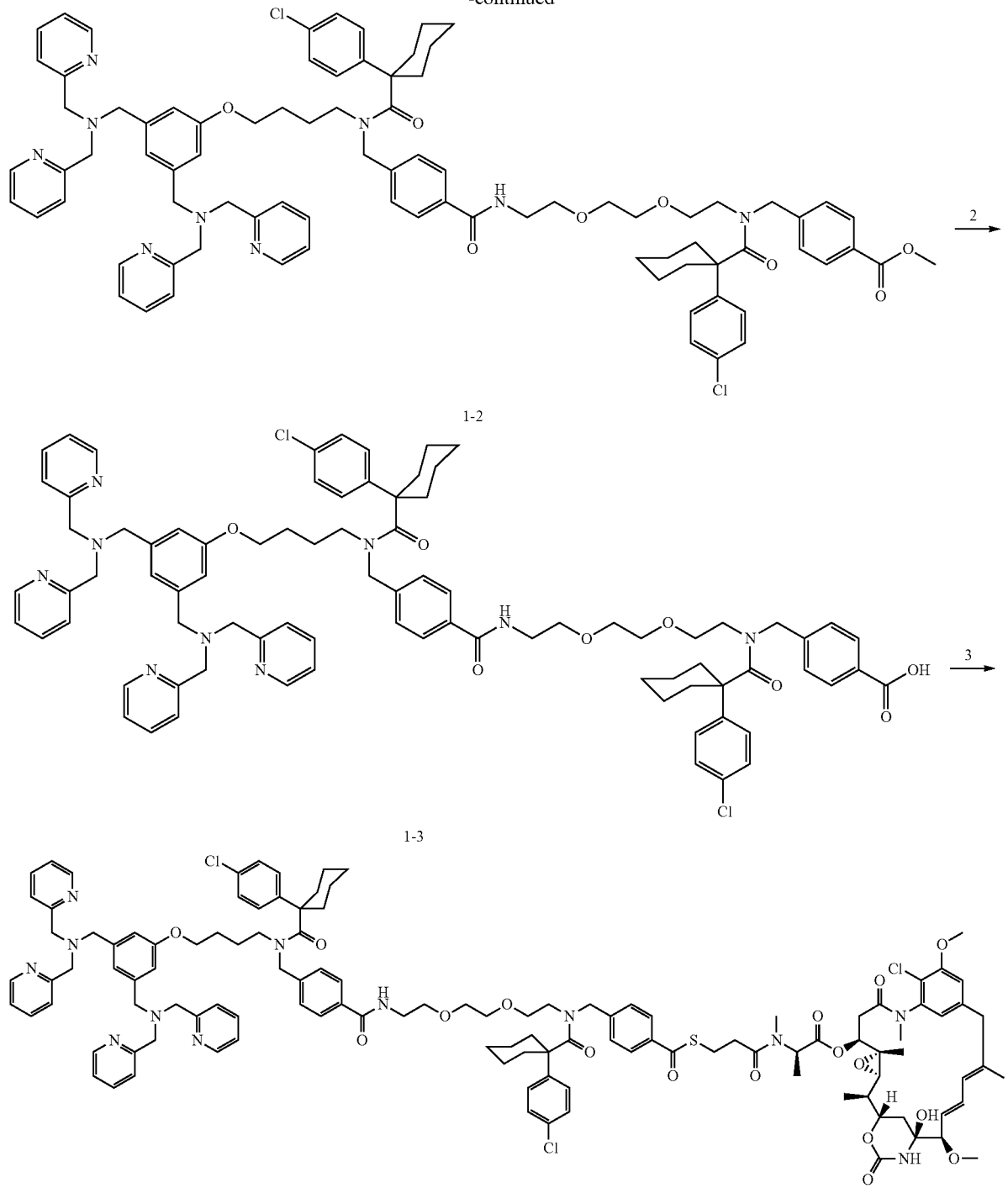

Compound 1

Scheme 11. Reagents and condition for preparing compound 1:
(1) 4-({{2-[2-(2-Amino-ethoxy)-ethoxy]-ethyl}-[1-(4-chloro-phenyl)-cyclohexanecarbonyl]-amino}-methyl}-methyl)-benzoic acid methyl ester, HOBt, EDCI, DCM.
(2) LiOH, MeOH.
(3) DM-1, DMAP, EDCI, DMF.

To a solution of compound 1-1 (200 mg, 0.20 mmol) in CH$_2$Cl$_2$ was added 1-Ethyl-3-(3-dimethylaminopropyl)carbodiimide (EDCI, 60 mg, 0.38 mmol), hydroxybenzotriazole (HOBt, 60 mg, 0.44 mmol), and 4-({12-[2-(2-Amino-ethoxy)-ethoxy]-ethyl-[1-(4-chloro-phenyl)-cyclohexane-carbonyl]-amino}-methyl)-benzoic acid methyl ester (100 mg, 0.19 mmol). The reaction solution was stirred at room temperature for 1 hour and quenched with 1 M HCl (aq.). The organic and aqueous phases were separated. The aqueous solution was neutralized and the product was extracted with CH$_2$Cl$_2$. The extract was concentrated and the resultant crude product was purified by flash chromatography to give compound 1-2 (100 mg, 0.07 mmol, 35%).

A mixture of compound 1-2 (100 mg, 0.07 mmol) and 0.5 M LiOH (aq.) in MeOH was stirred at room temperature for 15 hours. MeOH was removed. To the resultant residue, CH$_2$Cl$_2$ was added to give a precipitate. The precipitate was filtered off and the filtrate was dried over Na$_2$SO$_4$ and condensed under vacuum to give compound 1-3 as a yellowish powder (80 mg, 0.05 mmol, 71%).

Compound 1-3 (80 mg, 0.05 mmol) was added to a solution of DM-1 (45 mg, 0.06 mmol), DMAP (30 mg, 0.24 mmol), and EDCI (40 mg, 0.21 mmol) in 3 mL DMF. The reaction solution was stirred at room temperature for 1 hour, quenched with water, extracted with CH$_2$Cl$_2$. The extract was condensed to give a residue. The residue was purified by flash chromatography over silica gel to give compound 1 (48 mg, 0.02 mmol, 40%). $^1$H NMR (400 MHz, CDCl$_3$) δ 8.49 (d, J=4.6 Hz, 4H), 7.68 (d, J=7.8 Hz, 2H), 7.64-7.50 (m, 9H), 7.35-7.01 (m, 15H), 6.93 (d, J=33.5 Hz, 3H), 6.78 (d, J=8.9 Hz, 5H), 6.66 (s, 1H), 6.44 (dd, J=15.3, 11.2 Hz, 1H), 6.22 (s, 1H), 5.64 (dd, J=15.3, 9.0 Hz, 2H), 5.44 (dd, J=13.4, 6.5 Hz, 1H), 4.73 (dd, J=12.0, 2.8 Hz, 2H), 4.55 (s, 2H), 4.26 (dd, J=23.0, 12.1 Hz, 2H), 3.93 (d, J=16.5 Hz, 4H), 3.86-3.71 (m, 9H), 3.71-3.39 (m, 15H), 3.39-3.17 (m, 7H), 3.06 (dd, J=32.1, 18.9 Hz, 6H), 2.85-2.71 (m, 4H), 2.69-2.48 (m, 3H), 2.18 (tt, J=25.3, 23.2 Hz, 5H), 1.89-1.37 (m, 25H), 1.37-1.12 (m, 8H), 0.92-0.71 (m, 4H). ESI-MS C$_{119}$H$_{139}$Cl$_{13}$N$_{12}$O$_{17}$S$^{2+}$: 1074.94, found: 1074.41 (M+2H$^+$)

Synthesis of Compound 2

Scheme 12

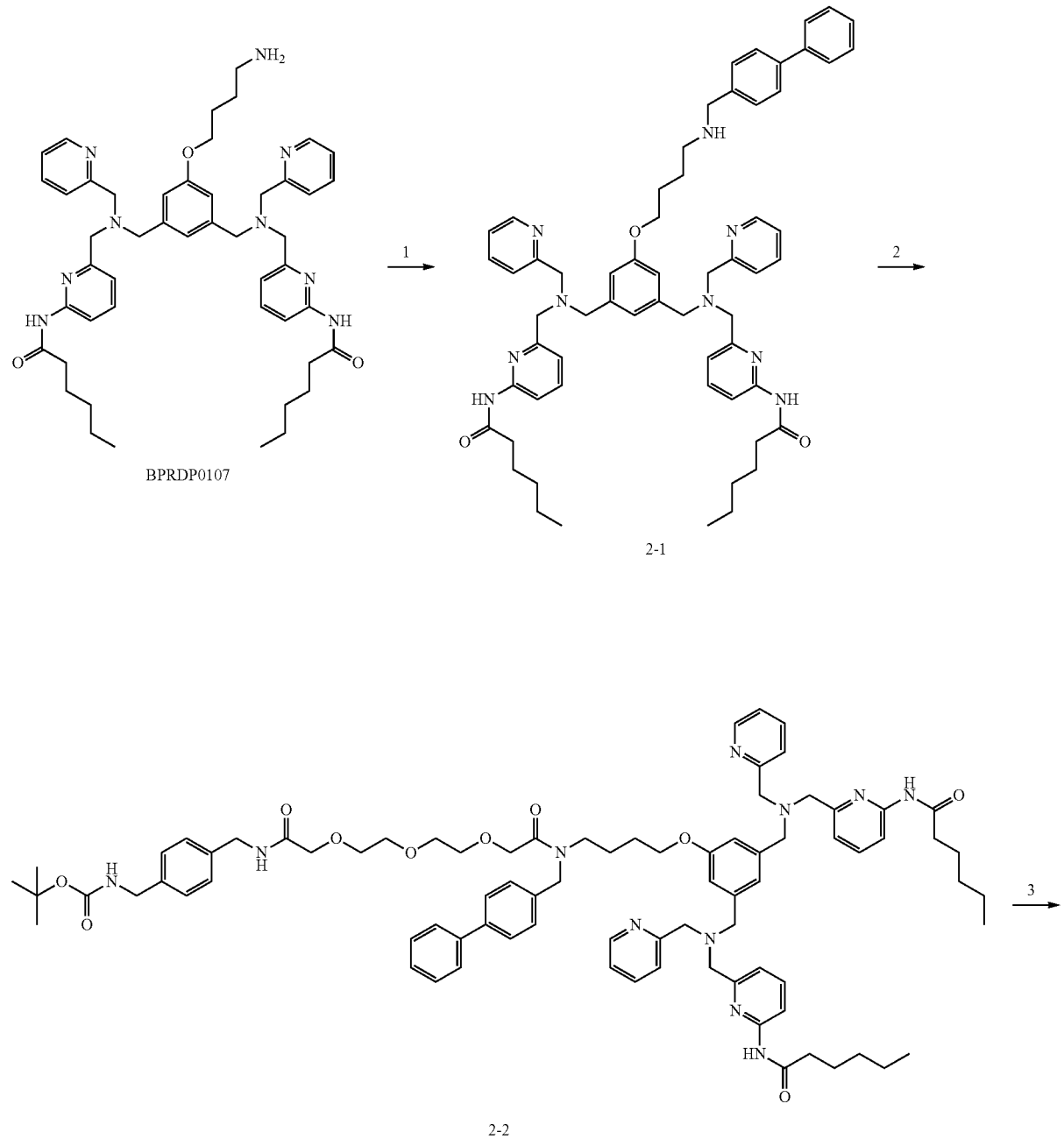

-continued

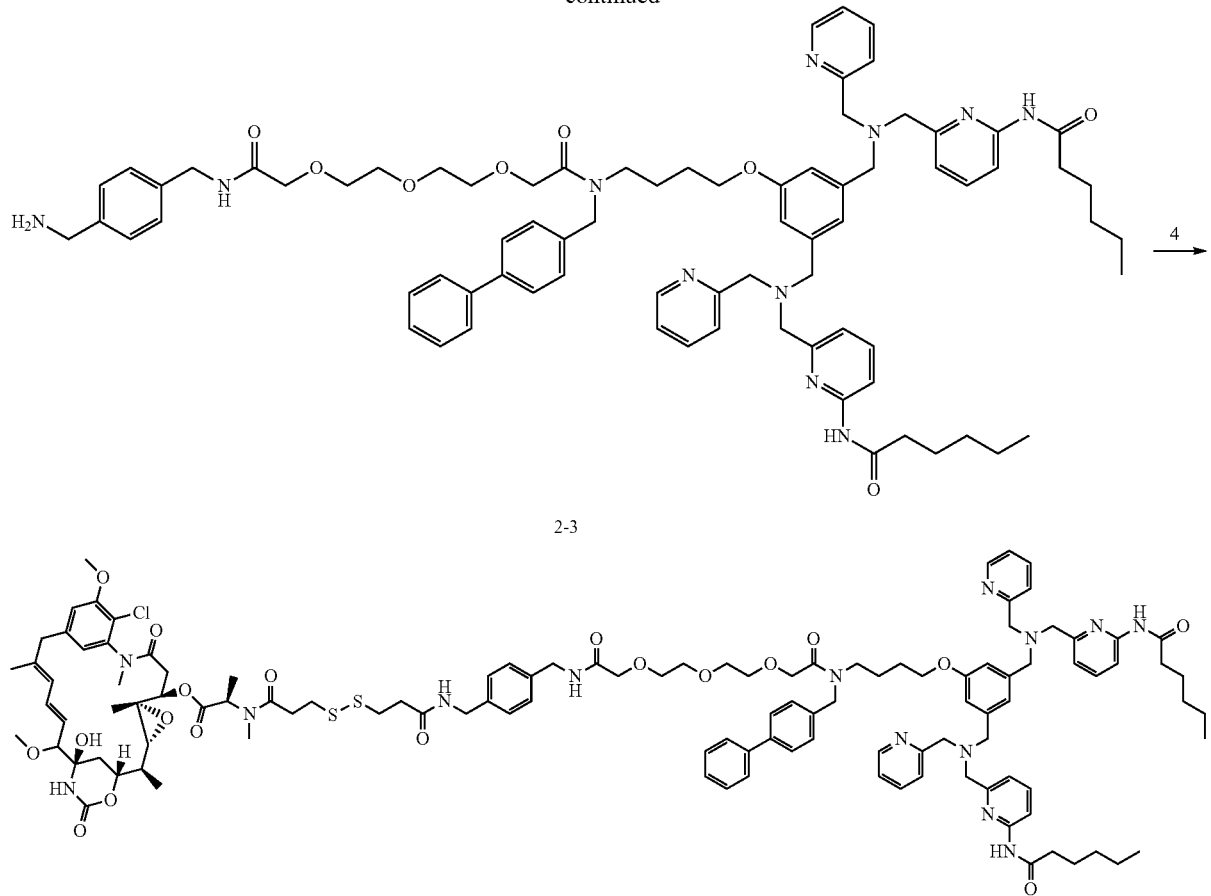

Compound 2

Scheme 12. Reagents and conditions for preparing compound 2: (1) biphenyl-4-carboxaldehyde, NaBH₄, MeOH, 70° C., 24 hr, 68%. (2) 1-(4-(((tert-butoxycarbonyl)amino)methyl)phenyl)-3-oxo-5,8,11-trioxa-2-azatridecan-13-oic acid, HBTU, HOBt, NMM, 18 hr, 70%. (3) TFA, DCM, 2 hr. (4) 3-[(3-{[(2R)-1-{[(1R,2S,3R,6R,16E,18E,20S,21R)-11-chloro-21-hydroxy-12,20-dimethoxy-2,5,9,16-tetramethyl-8,23-dioxo-4,24-dioxa-9,22-diazatetracyclo[19.3.1,1¹⁰,¹⁴.0³,⁵]hexacosa-10(26),11,13,16,18-pentaen-6-yl]oxy}-1-oxopropan-2-yl](methyl)amino}-3-oxopropyl)disulfanyl]propanoic acid, EDCI, HOBt, NMM, 19 hr, 45%.

N,N'-(6,6'-(((((5-(4-(([1,1'-biphenyl]-4-ylmethyl)amino)butoxy)-1,3-phenylene)bis(methylene))bis((pyridin-2-ylmethyl)azanediyl))bis(methylene))bis(pyridine-6,2-diyl))dihexanamide (compound 2-1): To a solution of BPRDP0107 (200 mg, 0.246 mmol) in MeOH (3 mL) at room temperature was added biphenyl-4-carboxaldehyde (90 mg, 0.491 mmol). The reaction solution was then slowly warmed to 70° C. and stirred overnight. The resultant solution was cooled down to 0° C. and sodium borohydride (37 mg, 0.983 mmol) was added. The solution was slowly warmed to room temperature, stirred for 2 hours, and poured into saturated NH₄Cl₍aq.₎. MeOH was removed and the residue was extracted with DCM three times. The combined organic extracts were dried over Na₂SO₄ and concentrated in vacuo. The resultant residue was purified by flash chromatography over silica gel with MeOH/DCM (5/95) to afford compound 2-1 (165 mg, 68%).

Tert-butyl 4-(14-([1,1'-biphenyl]-4-ylmethyl)-18-(3,5-bis(((((6-hexanamidopyridin-2-yl)methyl)(pyridin-2-ylmethyl)amino)methyl)phenoxy)-3,13-dioxo-5,8,11-trioxa-2,14-diazaoctadecyl)benzylcarbamate (compound 2-2): To a solution of 1-(4-(((tert-Butoxycarbonyl)amino)methyl)phenyl)-3-oxo-5,8,11-trioxa-2-azatridecan-13-oic acid (65 mg, 0.149 mmol) in DCM (1.5 mL) at room temperature was added O-(benzotriazol-1-yl)-N,N,N',N'-tetramethyluronium hexafluorophosphate (HBTU, 85 mg, 0.223 mmol) and hydroxybenzotriazole (HOBt, 30 mg, 0.223 mmol). The reaction solution was stirred for 30 mins. Compound 2-1 (73 mg, 0.074 mmol) and N-methylmorpholine (NMM, 0.07 mL, 0.594 mmol) was added subsequently. The resultant reaction solution was stirred for 18 hours, quenched with saturated NH₄Cl₍aq.₎, and extracted with DCM. The extracts were dried over Na₂SO₄ and concentrated in vacuo to give a residue. The residue was purified by flash chromatography over silica gel with MeOH/DCM (5/95) to afford compound 2-2 (73 mg, 70%).

N,N'-(6,6'-(((((5-((14-([1,1'-biphenyl]-4-ylmethyl)-1-(4-(aminomethyl)phenyl)-3,13-dioxo-5,8,11-trioxa-2,14-diazaoctadecan-18-yl)oxy)-1,3-phenylene)bis(methylene))bis((pyridin-2-ylmethyl)azanediyl))bis(methylene))bis(pyridine-6,2-diyl))dihexanamid (compound 2-3): To a solution of compound 2-2 (47 mg, 0.034 mmol) in DCM (0.5 mL) at room temperature was added TFA (0.5 mL) and the reaction solution was stirred for 2 hours. The excess of TFA was removed under reduced pressure to give crude compound 2-3, which was used in a next reaction without further purification.

To a solution of 3-[(3-{[(2R)-1-{[(1R,2S,3R,6R,16E,18E,20S,21R)-11-chloro-21-hydroxy-12,20-dimethoxy-2,5,9,16-tetramethyl-8,23-dioxo-4,24-dioxa-9,22-diazatetracyclo[19.3.1.1$^{10,14}$0$^{3,5}$]hexacosa-10(26),11,13,16,18-pentaen-6-yl]oxy}-1-oxopropan-2-yl](methyl)amino}-3-oxopropyl)disulfanyl]propanoic acid (194 mg, 0.230 mmol) in DCM (3 mL) at room temperature was added 1-(3-dimethylaminopropyl)-3-ethylcarbodiimide hydrochloride (EDCI, 44 mg, 0.230 mmol) and HOBt (31 mg, 0.230 mmol). The resultant reaction solution was stirred for 30 mins. Compound 2-3 (200 mg, 0.154 mmol) and NMM (1 mL, 0.921 mmol) were added consecutively. The reaction solution was stirred for 19 hours, quenched with saturated NH$_4$Cl$_{(aq.)}$, and then extracted with DCM. The organic extracts were dried over Na$_2$SO$_4$, filtered, and concentrated in vacuo. The resultant residue was purified by flash chromatography over silica gel with MeOH/DCM (7/93) to afford Compound 2 (146 mg, 45%). $^1$H NMR (400 MHz, CDCl$_3$): δ 8.93 (br, 2H), 8.41 (d, J=4.6 Hz, 2H), 8.06 (d, J=7.8 Hz, 2H), 7.60 (t, J=7.9 Hz, 2H), 7.51-7.24 (m, 13H), 7.22-7.11 (m, 8H), 7.09-7.04 (m, 2H), 6.78-6.69 (m, 2H), 6.64-6.54 (m, 4H), 6.34 (dd, J=15.3, 11.1 Hz, 1H), 6.23 (br, 1H), 5.58 (dd, J=15.3, 9.1 Hz, 1H), 5.25 (br, 1H), 4.75-4.69 (m, 1H), 4.50 (d, J=33.6 Hz, 2H), 4.39-4.34 (m, 2H), 4.34-4.29 (m, 2H), 4.22 (t, J=11.3 Hz, 1H), 4.07-3.93 (m, 4H), 3.90 (s, 3H), 3.86-3.81 (m, 2H), 3.70 (s, 4H), 3.62 (s, 4H), 3.59-3.46 (m, 10H), 3.45-3.33 (m, 5H), 3.25-3.21 (m, 3H), 3.21-3.17 (m, 1H), 3.16-3.13 (m, 3H), 3.04 (d, J=12.7 Hz, 1H), 2.94 (d, J=9.6 Hz, 1H), 2.91-2.84 (m, 1H), 2.79-2.74 (m, 5H), 2.62-2.44 (m, 5H), 2.10 (dd, J=14.3, 2.7 Hz, 1H), 2.01-1.93 (m, 4H), 1.71-1.61 (m, 4H), 1.56 (s, 3H), 1.54-1.51 (m, 1H), 1.50-1.42 (m, 4H), 1.23-1.18 (m, 8H), 1.17-1.03 (m, 10H), 0.78-0.72 (m, 9H). ESI-MS C$_{115}$H$_{145}$ClN$_{14}$O$_{19}$S$_2$: 2127.0, found: 709.8 (M+3H$^+$)$^{3+}$.

Synthesis of Compound 3

Scheme 13

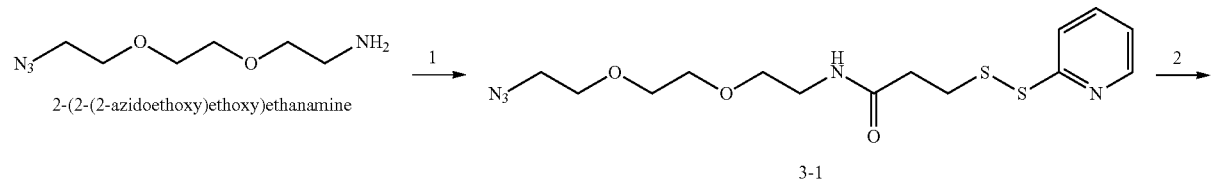

2-(2-(2-azidoethoxy)ethoxy)ethanamine 3-1

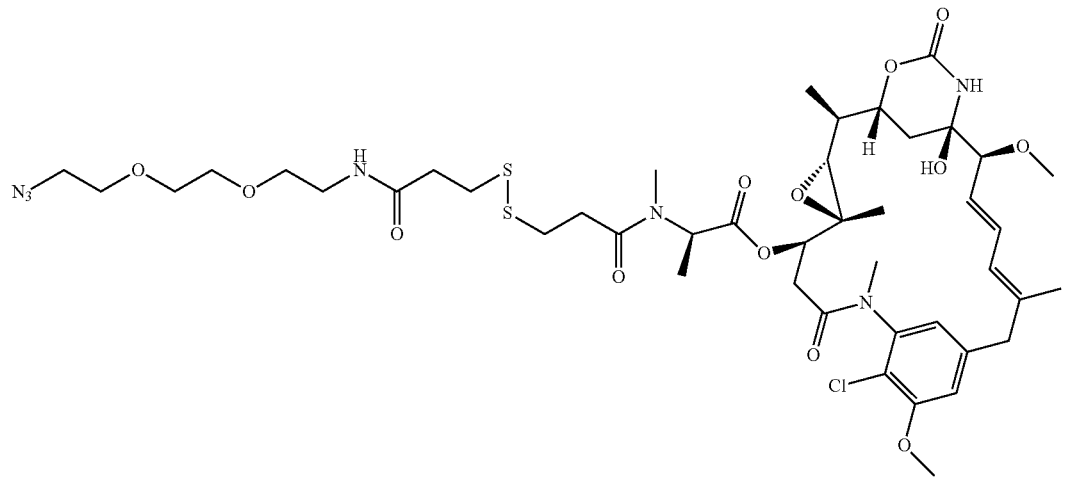

3-2

Scheme 13. Reagents and conditions for preparing compound b: (1) HOBt, EDCI, NMM, 3-(2-(pyridin-2-yl)disulfanyl) propanoic acid, DMF, rt, 15 hr, 75%. (2) DM-1, DCM, rt, 15 hr, 70%.

Scheme 14
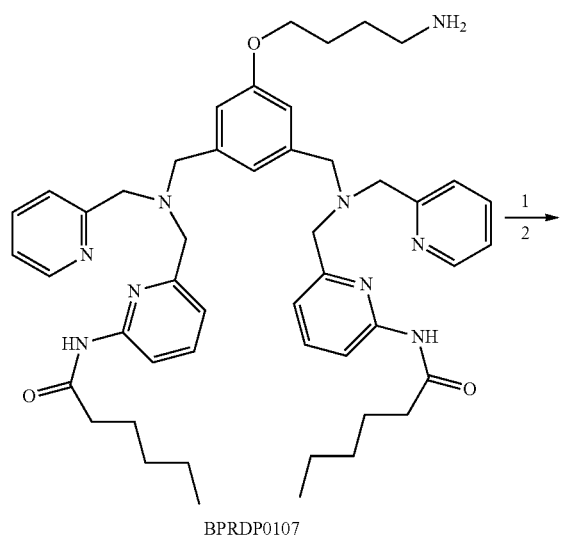
BPRDP0107
$\xrightarrow{\phantom{xx}1\phantom{xx}}_{2}$
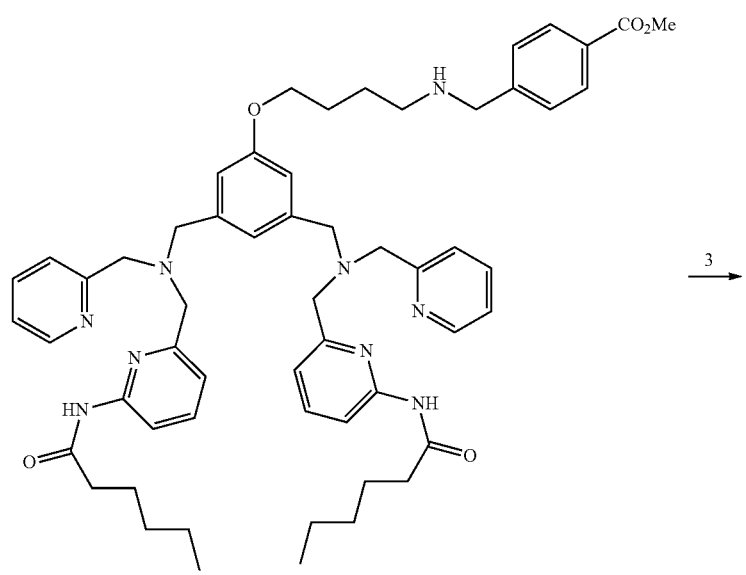
3-3
$\xrightarrow{\phantom{xx}3\phantom{xx}}$ -continued
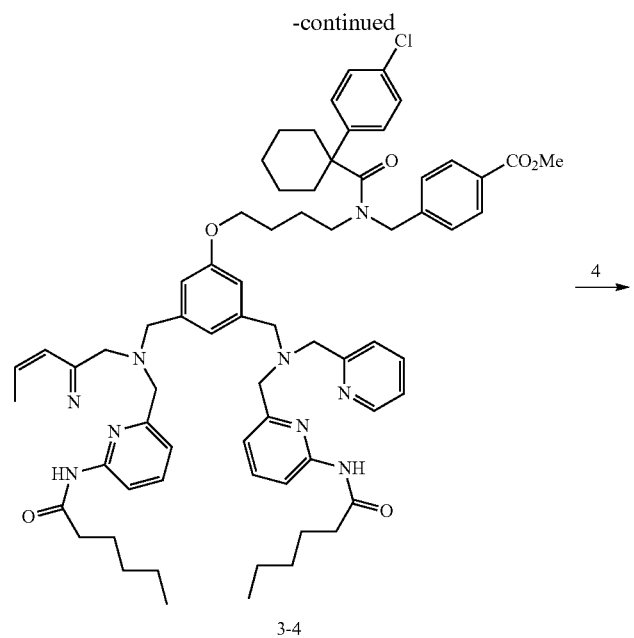
3-4
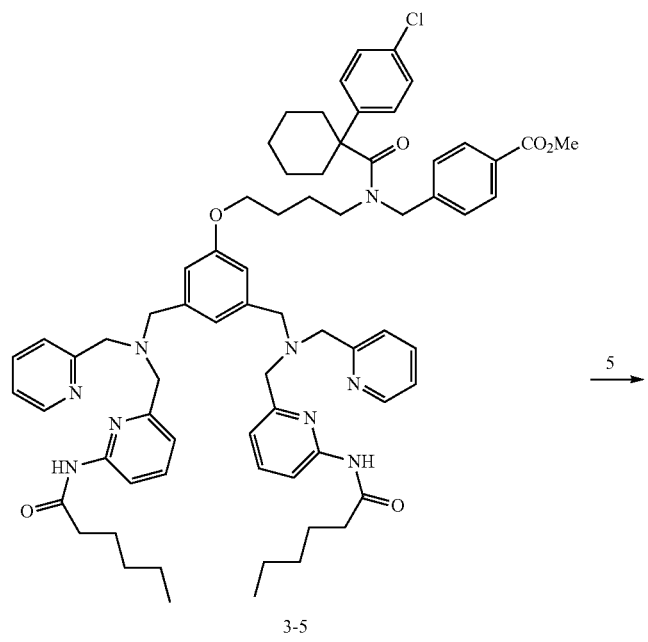
3-5

-continued
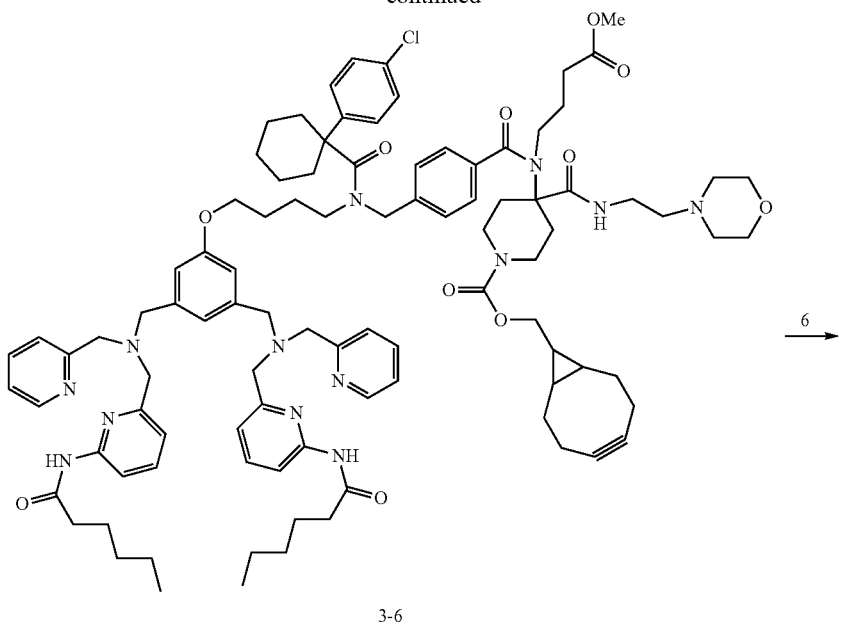
3-6
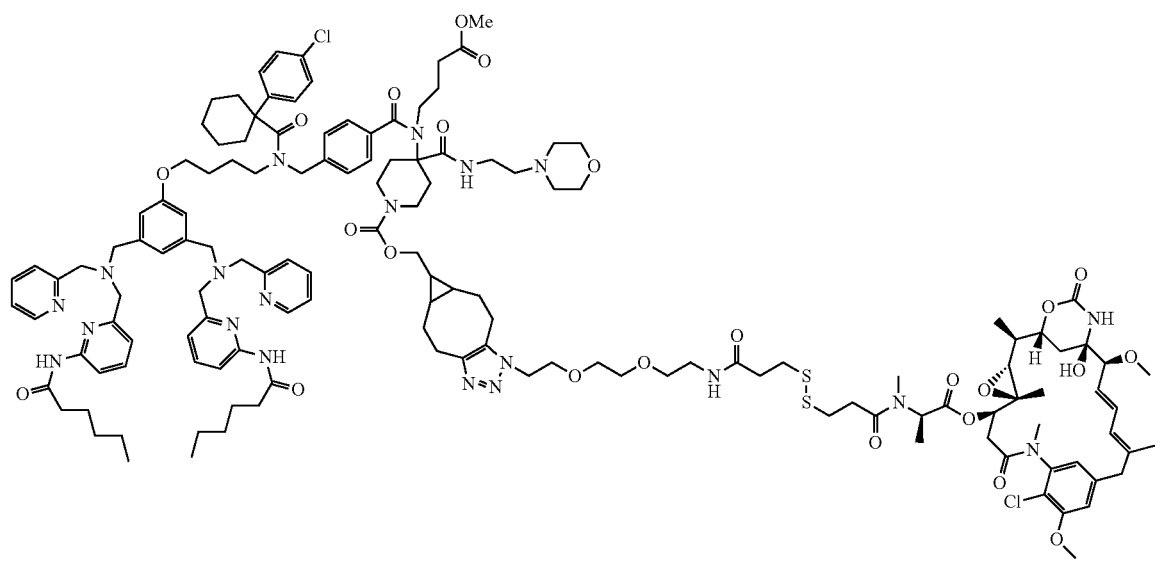
Compound 3
Scheme 14. Reagents and conditions for preparing compound 3:
(1) methyl 4-formylbenzoate, MeOH, rt, 15 hr.
(2) NaBH₄, 0° C., 1 hr, 55%.
(3) 1-(4-chlorophenyl)cyclohexanecarbonyl chloride, TEA, DCM, 0° C., 1 hr, 75%.
(4) LiOH (0.5N), MeOH, rt, 15 hr, 90%.
(5) Methyl 4-aminobutyrate hydrocloride, 2-Morpholinoethyl isocyanide, (bicyclo[6.1.0]non-4-yn-9-yl)methyl 4-oxopiperidine-1-carboxylate, MeOH, rt, 15 hr, 45%
(6) compound 3-2, DMF, rt, 3 hr, 70%.

To a stirred solution of 2-(2-(2-azidoethoxy)ethoxy)ethanamine (100 mg, 0.57 mmol, 1 eq.) in 5 mL of DMF at room temperature, 3-(2-(pyridin-2-yl)disulfanyl) propanoic acid (150 mg, 0.68 mmol, 1.2 eq.), HOBt (160 mg, 1.14 mmol, 2 eq.), EDCI (220 mg, 1.14 mmol, 2 eq.), and NMM (230 mg, 2.28 mmol, 4 eq.) were slowly added. The reaction solution was stirred at room temperature for 15 hours and then concentrated. The resultant residue was diluted with $CH_2Cl_2$ (200 mL). The $CH_2Cl_2$ solution was then washed with a saturated aqueous solution of $NaHCO_3$ (200 mL) and water (3×200 mL), dried over $MgSO_4$, and concentrated under reduced pressure to give a residue. The residue was purified by flash chromatography over silica gel with Ethyl acetate/Hexane (7/3) to yield compound 3-1 (160 mg, 75%).

To a stirred solution of compound 3-1 (50 mg, 0.135 mmol, 1 eq.) in 1 mL of dry DCM at room temperature, DM-1 (120 mg, 0.16 mmol, 1.2 eq.) was slowly added. The reaction solution was stirred for 15 hours. DCM was removed. The resultant residue was diluted with $CH_2Cl_2$ (200 mL). The $CH_2Cl_2$ solution was then washed with water (200 mL), dried over $MgSO_4$, and concentrated under reduced pressure to give a residue. The residue was purified by flash chromatography over silica gel with MeOH/Ethyl acetate (3/93) to yield compound 3-2 (94 mg, 70%). $^1$H NMR (400 MHz, $CDCl_3$): δ 6.80 (s, 1H), 6.67 (d, J=11.2 Hz, 1H), 6.59 (s, 1H), 6.43-6.36 (m, 1H), 6.30 (m, 1H), 5.63 (q, J=9.2 Hz, 1H), 5.37-5.32 (m, 1H), 4.74 (d, J=9.6 Hz, 1H), 4.24 (t, J=10.8 Hz, 1H), 3.94 (s, 3H), 3.69-3.60 (m, 5H), 3.53-3.50 (m, 2H), 3.47-3.45 (m, 1H), 3.42-3.39 (m, 2H), 3.37-3.34 (m, 2H), 3.32 (s, 3H), 3.19 (s, 3H), 3.10-3.06 (m, 1H), 2.99-2.91 (m, 3H), 2.82 (s, 3H), 2.79-2.74 (m, 2H), 2.65-2.54 (m, 2H), 2.48-2.44 (m, 2H), 2.15-2.11 (m, 1H), 1.60 (s, 3H), 1.54-1.51 (m, 1H), 1.46-1.39 (m, 1H), 1.28-1.22 (m, 7H), 0.86-0.82 (m, 2H), 0.77 (s, 3H). ESI-MS $C_{44}H_{64}ClN_7O_{13}S_2$: 997.3692, found 499 $(EM+2H^+)/2$.

To a stirred solution of BPRDP0107 (1 g, 1.22 mmol, 1 eq.) in 20 mL of methanol at room temperature, methyl 4-formylbenzoate (800 mg, 4.88 mmol, 4 eq.) was slowly added. The reaction solution was stirred at room temperature for 15 hours. The solution was then cooled to 0° C., and sodium borohydride (500 mg, 12.2 mmol, 10 eq.) was added. The resultant mixture was stirred at 0° C. for 1 hour. MeOH was removed and the resultant residue was diluted with $CH_2Cl_2$ (200 mL). The $CH_2Cl_2$ solution was then washed with a saturated ammonium chloride aqueous solution (200 ml), dried over $MgSO_4$, and concentrated under reduced pressure. The resultant residue was purified by flash chromatography over silica gel with MeOH/DCM (5/95) to yield compound 3-3 (650 mg, 55%).

To a stirred solution of compound 3-3 (800 mg, 0.83 mmol, 1 eq.) in 80 ml of dry DCM at 0° C., 1-(4-chlorophenyl)cyclohexanecarbonyl chloride (850 mg, 3.32 mmol, 4 eq.) and TEA (2 mL) were slowly added. The reaction solution was stirred for 1 hour. DCM was removed. The resultant residue was diluted with $CH_2Cl_2$ (200 mL). The $CH_2Cl_2$ solution was then washed with a saturated ammonium chloride aqueous solution (200 mL), dried over $MgSO_4$, and concentrated under reduced pressure. The resultant residue was purified by flash chromatography over silica gel with Ethyl acetate/Hexane (9/1) to yield compound 3-4 (737 mg, 75%).

To a stirred solution of compound 3-4 (500 mg, 0.42 mmol) in 20 mL of methanol at room temperature, LiOH aqueous solution (20 mL, 0.5 N) was slowly added. The reaction solution was stirred at room temperature for 15 hours. MeOH was removed and the resultant residue was extracted with $CH_2Cl_2$ (200 mL). The extract was then washed with a saturated ammonium chloride aqueous solution (200 mL), dried over $MgSO_4$, and concentrated under reduced pressure to yield compound 3-5 (445 mg, 90%).

To a stirred solution of compound e (100 mg, 0.086 mmol, 1 eq.) in 1 mL of methanol at room temperature, Methyl 4-aminobutyrate hydrochloride (70 mg, 0.43 mmol, 5 eq.), 2-Morpholinoethyl isocyanide (85 mg, 0.6 mmol, 7 eq.), and (bicyclo[6.1.0]non-4-yn-9-yl)methyl 4-oxopiperidine-1-carboxylate (50 mg, 0.17 mmol, 2 eq.) were slowly added. The reaction solution was stirred at room temperature for 15 hours. MeOH was removed and the resultant residue was extracted with $CH_2Cl_2$ (200 mL). The extract was washed with a saturated ammonium chloride aqueous solution (200 mL), dried over $MgSO_4$, and concentrated under reduced pressure. The resultant residue was purified by flash chromatography over silica gel with MeOH/DCM (5/95) to yield compound 3-6 (65 mg, 45%). $^1$H NMR (300 MHz, $CDCl_3$): δ 8.48 (d, J=5.7 Hz, 2H), 8.18 (m, 2H), 8.12 (d, J=8.1 Hz, 2H), 7.69-7.64 (m, 2H), 7.57-7.46 (m, 4H), 7.37-7.35 (m, 2H), 7.26-7.24 (m, 5H), 7.19-7.10 (m, 4H), 6.68 (s, 2H), 4.57 (s, 1H), 4.12 (s, 1H), 4.00 (m, 2H), 3.77 (s, 4H), 3.73-3.67 (m, 9H), 3.58 (s, 4H), 3.51 (s, 4H), 3.43-3.37 (m, 8H), 2.52-2.44 (m, 16H), 2.40-2.23 (m, 6H), 2.16-2.00 (m, 10H), 1.78-1.65 (m, 8H), 1.57-1.47 (m, 4H), 1.42-1.30 (m, 4H), 1.24-1.12 (m, 8H), 0.83-0.79 (m, 6H), 0.76-0.69 (m, 1H).

To a stirred solution of compound 3-6 (44 mg, 0.026 mmol, 1 eq.) in 7 mL of DMF at room temperature, compound 3-2 (30 mg, 0.029 mmol, 1.1 eq.) was slowly added. The reaction solution was stirred at room temperature for 3 hours. DMF was removed. The resultant residue was extracted with $CH_2Cl_2$ (200 mL). The $CH_2Cl_2$ extract was then washed with water (3×200 mL), dried over $MgSO_4$, and concentrated under reduced pressure. The resultant residue was purified by flash chromatography over silica gel with MeOH/DCM (8/92) to yield compound 3 (49 mg, 70%). $^1$H NMR (400 MHz, $CDCl_3$): δ 8.48 (d, J=5.6 Hz, 2H), 8.13-8.11 (m, 4H), 7.68-7.65 (m, 2H), 7.56-7.52 (m, 2H), 7.49-7.47 (m, 2H), 7.37-7.35 (m, 2H), 7.28-7.24 (m, 5H), 7.19-7.17 (m, 2H), 7.14-7.11 (m, 2H), 6.83 (s, 1H), 6.70-6.67 (m, 4H), 6.62 (s, 1H), 6.44-6.38 (m, 1H), 6.28 (m, 1H), 5.66 (q, J=9.2 Hz, 1H), 5.37-5.34 (m, 1H), 4.77 (d, J=9.2 Hz, 1H), 4.57 (s, 1H), 4.40-4.37 (m, 2H), 4.27 (t, J=10.4 Hz, 1H), 4.12 (s, 1H), 3.97 (s, 3H), 3.90 (m, 1H), 3.88-3.85 (m, 4H), 3.77 (s, 4H), 3.72-3.69 (m, 9H), 3.66-3.62 (m, 2H), 3.58 (s, 4H), 3.55-3.49 (m, 9H), 3.46-3.44 (m, 4H), 3.41-3.36 (m, 4H), 3.32 (s, 3H), 3.21 (s, 3H), 3.12-3.00 (m, 1H), 2.95-2.87 (m, 3H), 2.85 (s, 3H), 2.82-2.77 (m, 2H), 2.69-2.60 (m, 4H), 2.56-2.48 (m, 10H), 2.43-2.34 (m, 8H), 2.19-2.14 (m, 3H), 2.08-2.04 (m, 10H), 1.78-1.74 (m, 2H), 1.62-1.58 (m, 9H), 1.54-1.42 (m, 4H), 1.40-1.32 (m, 2H), 1.30-1.23 (m, 11H), 1.20-1.12 (m, 10H), 0.91-0.85 (m, 2H), 0.84-0.77 (m, 10H). ESI-MS $C_{54}H_{59}F_2N_{11}O_3$: 2679.2924, found 894 $(EM+3)/3$.

Synthesis of Compound 4
Scheme 15
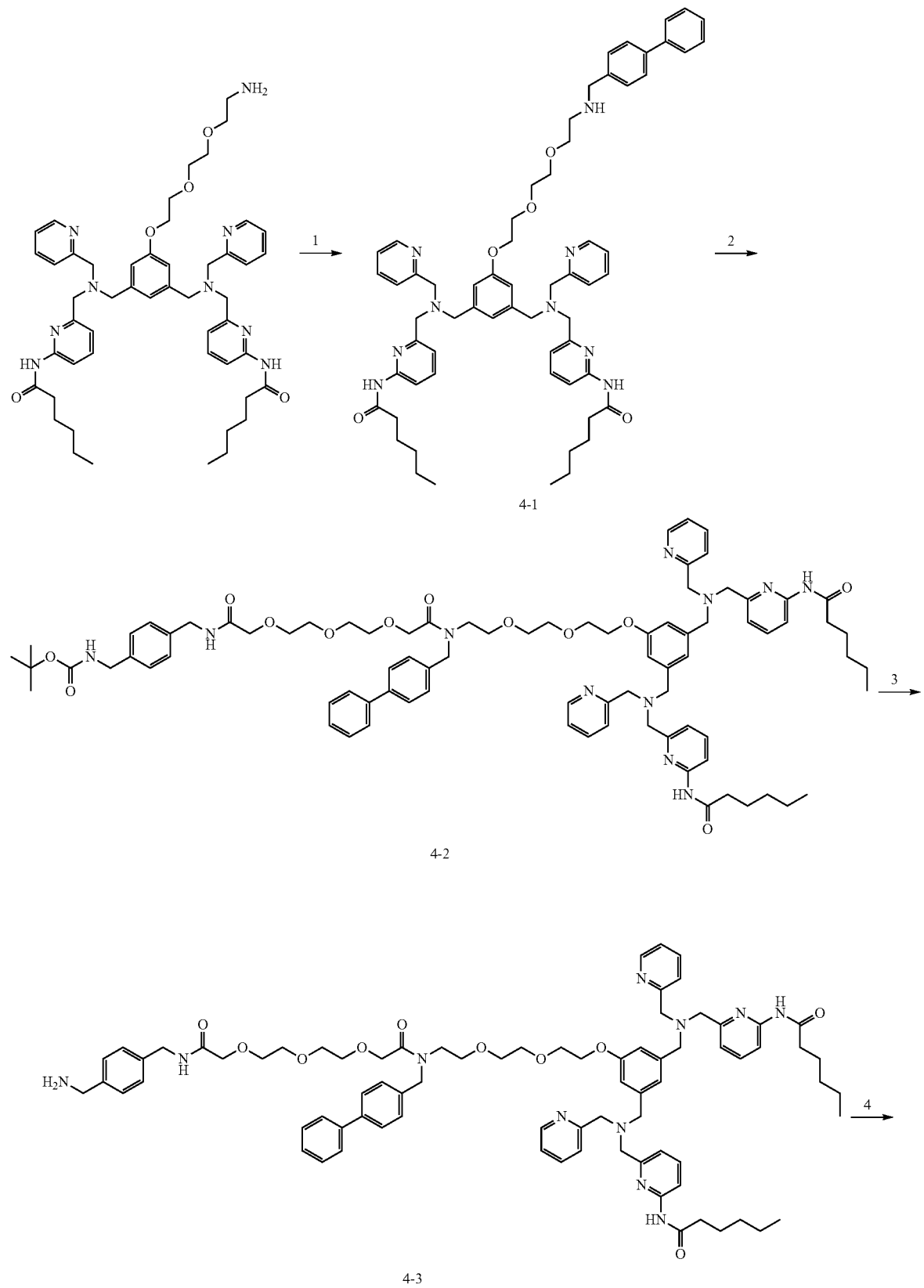

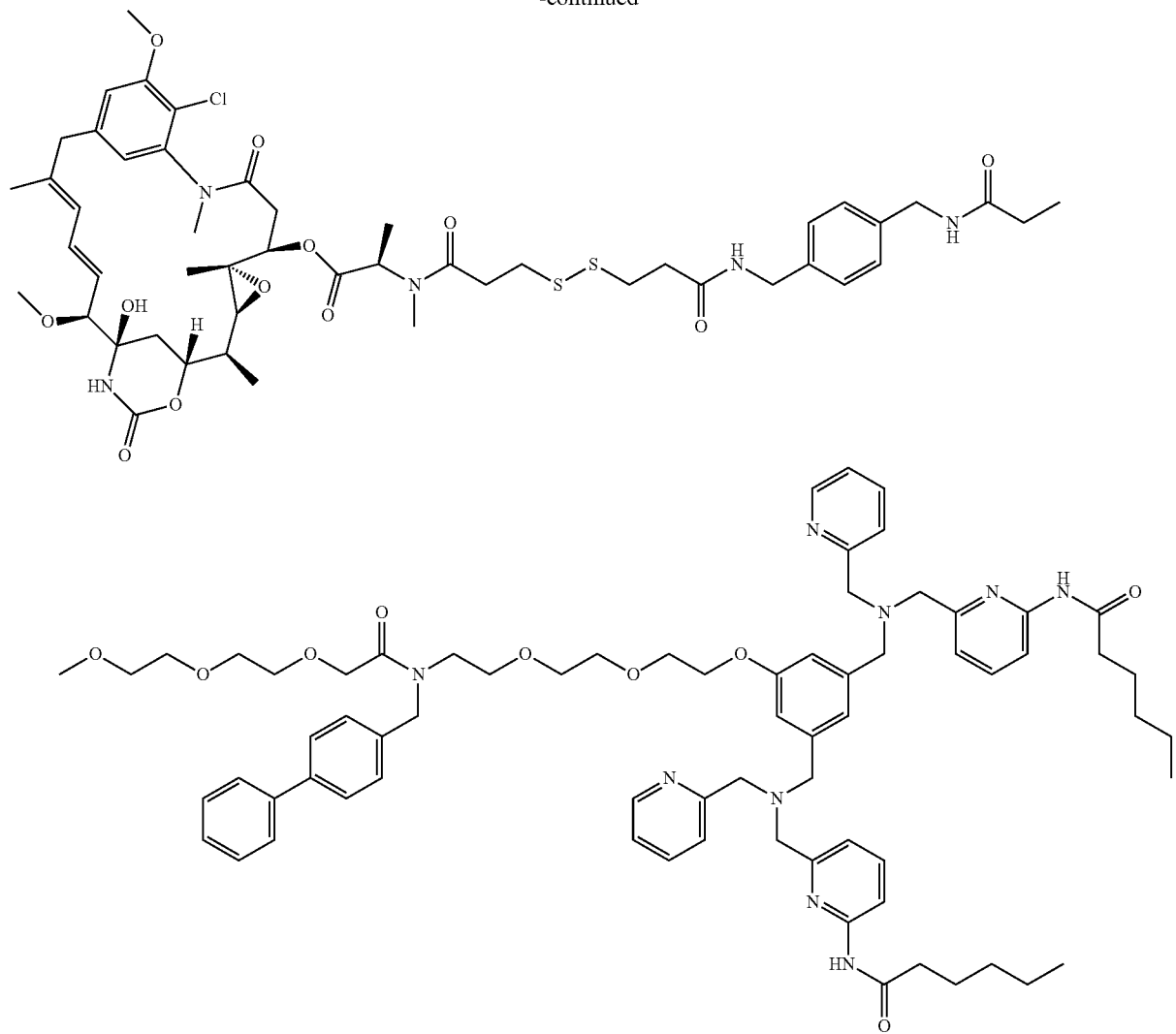

Compound 4

Scheme 15. Reagents and conditions for preparing compound 4:
(1) biphenyl-4-carboxaldehyde, NaBH₄, MeOH, 70° C., 22 hr, 76%.
(2) 1-(4-(((tert-butoxycarbonyl)amino)methyl)phenyl)-3-oxo-5,8,11-trioxa-2-azatridecane-13-oic acid, HBTU, HOBt, NMM, 19 h, 66%.
(3) TFA, DCM, 3 hr.
(4) 3-[(3-{[(2R)-1-{[1R,2S,3R,6R,16E,18E,20S,21R)-11-chloro-21-hydroxy-12,20-dimethoxy-2,5,9,16-tetramethyl-8,23-dioxo-4,24-dioxa-9,22-diazatetracyclo[19.3.1.1¹⁰,¹⁴.0³,⁵]hexacosa-10(26),11,13,16,18-pentaen-6-yl]oxy}-1-oxopropan-2-yl](methyl)amino}-3-oxopropyl)disulfanyl]propanoic acid, EDCI, HOBt, NMM, 20 hr, 49%.

To a solution of N,N'-(6,6'-(((((5-(2-(2-(2-aminoethoxy)ethoxy)ethoxy)-1,3-phenylene)bis(methylene))bis((pyridin-2-ylmethyl)azanediyl))bis(methylene))bis(pyridine-6,2-diyl))dihexanamide (240 mg, 0.275 mmol) in MeOH (6 mL) at room temperature was added biphenyl-4-carboxaldehyde (100 mg, 0.549 mmol). The reaction solution was then slowly warmed to 70° C. and stirred overnight. The solution was then cooled down to 0° C. and sodium borohydride (42 mg, 1.098 mmol) was added. The solution was slowly warmed to room temperature, stirred for 2 hours, and quenched with saturated NH₄Cl$_{(aq.)}$. MeOH was removed. The residue was extracted with DCM three times. The combined organic extracts were dried over Na₂SO₄, filtered, and concentrated in vacuo. The resultant residue was purified by flash chromatography over silica gel with MeOH/DCM (4/96) to afford compound 4-1 (217 mg, 76%).

To a solution of 1-(4-(((tert-butoxycarbonyl)amino)methyl)phenyl)-3-oxo-5,8,11-trioxa-2-azatridecan-13-oic acid (100 mg, 0.226 mmol) in DCM (4 mL) at room temperature was added O-(benzotriazol-1-yl)-N,N,N',N'-tetramethyluronium hexafluorophosphate (HBTU, 214 mg, 0.565 mmol) and hydroxybenzotriazole (HOBt, 76 mg, 0.565 mmol). The reaction solution was stirred for 30 mins. Compound 4-1 (196 mg, 0.188 mmol) and N-methylmorpholine (NMM, 0.06 mL, 0.565 mmol) were added to the solution consecutively. The resultant reaction solution was stirred for 19 hours, quenched with saturated NH₄Cl$_{(aq.)}$, and then extracted with DCM three times. The combined organic extracts were dried over Na₂SO₄, filtered, and concentrated in vacuo. The resultant residue was purified by reverse-phase chromatography with 80% MeOH in H₂O to afford compound 4-2 (182 mg, 66%).

TFA (1 mL) was added into a solution of compound 4-2 (120 mg, 0.082 mmol) in DCM (1 mL) at room temperature. The reaction solution was stirred for 3 hours. After reaction was completed, the excess amount of TFA was removed under reduced pressure to give compound 4-3 which was used without further purification.

To a solution of 3-[(3-{[(2R)-1-{[(1R,2S,3R,6R,16E,18E,20S,21R)-11-chloro-21-hydroxy-12,20-dimethoxy-2,5,9,16-tetramethyl-8,23-dioxo-4,24-dioxa-9,22-diazatetracyclo[19.3.1.1$^{10,14}$.0$^{3,5}$]hexacosa-10(26),11,13,16,18-pentaen-6-yl]oxy}-1-oxopropan-2-yl](methyl)amino}-3-oxopropyl)disulfanyl]propanoic acid (83 mg, 0.098 mmol) in DCM (2 mL) at room temperature was added 1-(3-Dimethylaminopropyl)-3-ethylcarbodiimide hydrochloride (EDC, 31 mg, 0.164 mmol) and HOBt (22 mg, 0.164 mmol). The reaction solution was stirred for 30 mins. Compound 4-3 (112 mg, 0.082 mmol) and NMM (0.07 mL, 0.655 mmol) were added consecutively. The reaction solution was stirred for 20 hours, quenched with saturated NH$_4$Cl$_{(aq.)}$, and then extracted with DCM three times. The extracts were dried over Na$_2$SO$_4$, filtered, and concentrated in vacuo. The resultant residue was purified by flash chromatography over silica gel with 4% MeOH in DCM to afford compound 4 (88 mg, 49%). $^1$H NMR (400 MHz, CDCl$_3$) δ 8.89 (d, J=10.3 Hz, 2H), 8.48 (d, J=4.6 Hz, 2H), 8.11 (d, J=8.3 Hz, 2H), 7.65 (t, J=7.9 Hz, 2H), 7.58-7.27 (m, 13H), 7.26-7.09 (m, 10H), 6.84-6.62 (m, 6H), 6.41 (dd, J=15.4, 11.0 Hz, 1H), 6.29 (br, 1H), 5.65 (dd, J=15.4, 9.1 Hz, 1H), 5.31 (br, 1H), 4.83-4.75 (m, 1H), 4.64 (d, J=16.5 Hz, 2H), 4.47-4.41 (m, 2H), 4.41-4.35 (m, 2H), 4.32-4.25 (m, 1H), 4.23-3.99 (m, 6H), 3.96 (s, 3H), 3.85-3.79 (m, 2H), 3.76 (s, 4H), 3.67 (s, 4H), 3.66-3.49 (m, 15H), 3.49-3.44 (m, 6H), 3.44-3.33 (m, 2H), 3.31 (s, 2H), 3.22 (d, J=8.0 Hz, 2H), 3.11 (d, J=13.1 Hz, 1H), 3.01 (d, J=9.6 Hz, 1H), 2.96-2.89 (m, 1H), 2.86-2.79 (m, 5H), 2.69-2.50 (m, 5H), 2.20-2.14 (m, 1H), 2.07 (dd, J=13.5, 5.8 Hz, 4H), 1.94-1.76 (m, 4H), 1.63 (s, 3H), 1.60-1.48 (m, 3H), 1.30-1.24 (m, 8H), 1.24-1.12 (m, 8H), 0.86-0.78 (m, 10H). ESI-MS C$_{117}$H$_{149}$ClN$_{14}$O$_{21}$S$_2$: 2187.1, found: 1094.2 (M+2H$^+$)$^{2+}$ Synthesis of Compound 5

Scheme 16

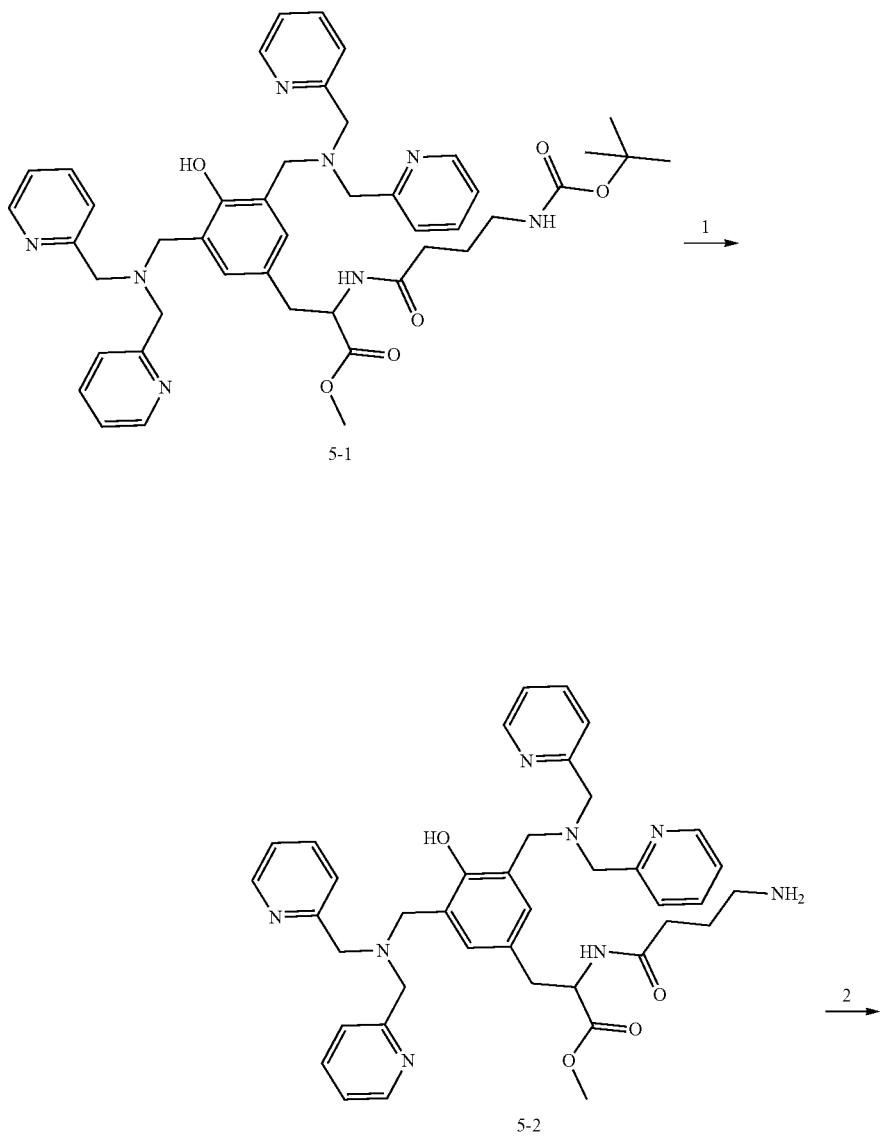

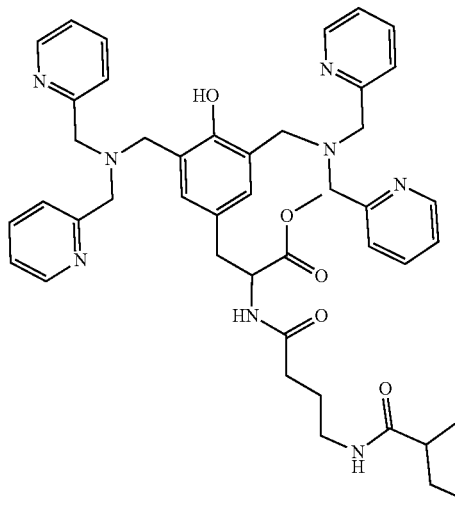

Compound 5

Scheme 16. Reagents and conditions for preparing compound 5:
(1) 10% TFA, DCM, 4 hr, 90%.
(2) 4-(2,5-Dioxo-2,5-dihydro-pyrrol-1-ylmethyl)-cyclohexanecarboxylic acid 2,5-dioxo-pyrrolidin-1-yl ester, DM-1, TEA, DMF, rt, 15 hr, 38%.

To a solution of compound 5-1 (7.04 mmol, 5.44 g) in $CH_2Cl_2$ (2 mL) was added TFA (20 mL). The reaction solution was stirred at room temperature for 12 hours and concentrated under reduced pressure to give compound 5-2 as a pale yellow oil (4.45 g, 90%).

To a solution of compound 5-2 (0.09 nmol, 64.60 mg) in DMF (2 mL) was added 4-(2,5-Dioxo-2,5-dihydro-pyrrol-1-ylmethyl)-cyclohexanecarboxylic acid 2,5-dioxo-pyrrolidin-1-yl ester (0.09 mmol, 30.70 mg) and triethylamine (TEA) (0.18 nmol, 23.80 mg). The reaction solution was stirred at room temperature for 4 hours. DM-1 (0.09 mmol, 67.9 mg) was added. The resultant reaction solution was stirred at room temperature for 11 hours and then poured into saturated $NH_4Cl_{(aq.)}$ (25 mL). DMF was removed under reduced pressure and the residue was extracted with $Cl_2C_2$ (2×25 mL). The combined organic extracts were dried over $Na_2SO_4$, filtered, and concentrated in vacuo. The residue was purified by chromatography over silica gel with Methanol/$CH_2Cl_2$ (3/97) to give compound 5 as a pale yellow oil (58 mg, 38%). $^1$H NMR (400 MHz, $CDCl_3$): δ 8.52 (d, J=4.8 Hz, 4H), 7.61 (td, J=7.6, 1.6 Hz, 4H), 7.45 (d, J=8 Hz, 4H), 7.14 (td, J=5.6, 1.6 Hz 4H), 7.05 (dd, J=18.4, 7.6 Hz 1H), 6.96 (d, J=2.0 Hz 2H), 6.82 (t, J=2.4 Hz 1H), 6.73-6.68 (m, 1H), 6.66 (dd, J=6.4, 1.6 Hz 1H), 6.54-6.46 (m, 1H), 6.45-6.38 (m, 1H), 6.27 (d, J=9.2 Hz, 1H), 5.70-5.63 (m, 1H), 5.37 (br, 1H), 4.80-4.73 (m, 2H), 4.32-4.26 (m, 1H), 4.15-4.14 (m, 1H), 3.98 (d, J=2.4 Hz, 3H), 3.84 (s, 9H), 3.76 (s, 3H), 3.67 (s, 3H), 3.65-3.61 (m, 2H), 3.49-3.46 (m, 2H), 3.32 (d, J=6.8 Hz, 3H), 3.30-3.26 (m, 2H), 3.21 (d, J=2.8 Hz, 3H), 3.18-2.92 (m, 6H), 2.89 (s, 3H), 2.84-2.72 (m, 1H), 2.64-2.48 (m, 3H), 2.47-2.35 (m, 1H), 2.35-2.22 (m, 1H), 2.18 (dd, J=13.6, 2.4 Hz, 1H), 2.12 (t, J=7.2 Hz 2H), 2.08-2.04 (m, 1H), 1.95-1.88 (m, 1H), 1.70-1.56 (m, 9H), 1.51-1.43 (m, 2H), 1.39-1.20 (m, 18H), 0.80 (s, 3H). ESI-MS $C_{87}H_{107}ClN_{12}O_{17}S$: 1658.73, found: 851.9 $(M+2H^+)^{2+}+Na^+$.

Synthesis of Compound 6

Scheme 17

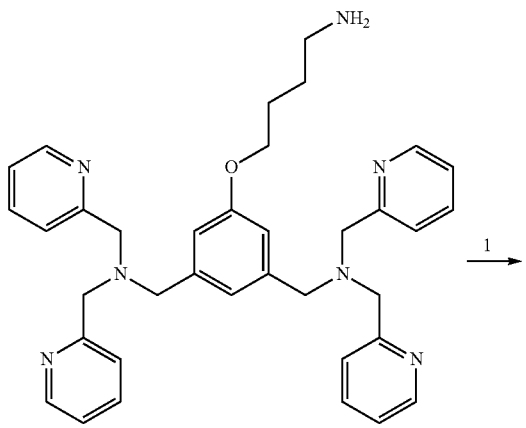

6-1

-continued

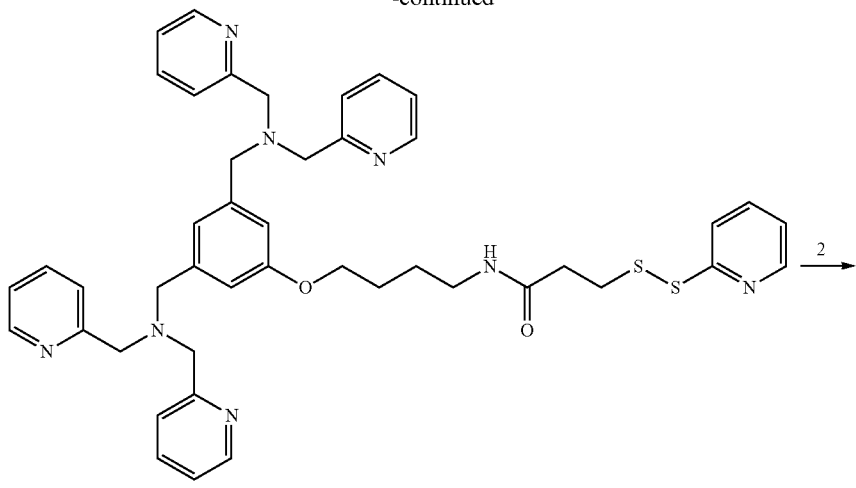

6-2

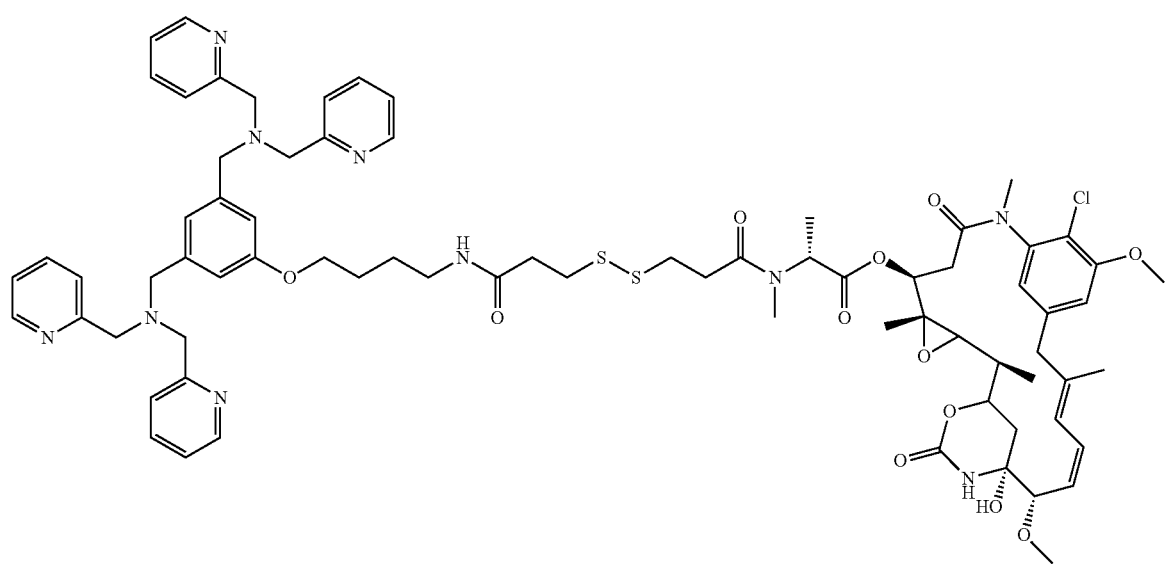

Compound 6

Scheme 17. Reagents and conditions for preparing compound 6:
(1) 3-(pyridin-2-yldisulfanyl)propanoic acid, EDCl, HOBt, N-Methylmorpholine, DCM, 15 hr, 52%.
(2) DM-1, DCM, overnight, 92%.

A mixture of 3-(pyridin-2-yldisulfanyl)propanoic acid (250.0 mg, 1.2 mmol, 1.1 eq.), EDCI (333.0 mg, 1.7 mmol, 1.5 eq.), and HOBt (235.4 mg, 1.7 mmol, 1.5 eq.) were stirred in $CH_2CO_2$ (10.6 mL) for 1 hour at room temperature. To the reaction solution was added a solution of compound 6-1 (620.5 mg, 1.1 mmol, 1.0 eq.) and N-Methylmorpholine (352.4 mg, 3.5 mmol, 3.0 eq.) in $CH_2Cl_2$ (1.0 mL). The resultant reaction solution was stirred at room temperature for 15 hours, quenched with saturated $NH_4Cl_{(aq.)}$, dried over $Na_2SO_4$, and concentrated in vacuo. The residue was purified by flash chromatography over silica gel to give compound 6-2 (434.0 mg, 52%).

To a solution of compound 6-2 (150.0 mg, 0.2 mmol, 1.1 eq.) in $CH_2Cl_2$ (3.6 mL) was added DM-1 (170.0 mg, 0.2 nmol, 1.0 eq.). The reaction solution was stirred at room temperature overnight and then concentrated in vacuo. The residue was purified by flash chromatography over silica gel to give compound 6 (235.2 mg, 92%). $^1$H NMR (400 MHz, CDCl$_3$): δ 8.50 (d, J=4.8 Hz, 4H), 7.68-7.53 (m, 8H), 7.14 (t, J=5.8 Hz, 4H), 7.08 (s, 1H), 6.85-6.80 (m, 3H), 6.67 (d, J=11.3 Hz, 1H), 6.64 (d, J=1.6 Hz, 1H), 6.42 (dd, J=15.4, 11.3 Hz, 1H), 6.24 (br, 1H), 6.00 (br, 1H), 5.67 (dd, J=15.4, 9.1 Hz, 1H), 5.32 (br, 1H), 4.80 (dd, J=11.2, 2.6 Hz, 1H), 4.30 (t, J=11.2 Hz, 1H), 4.05-3.92 (m, 5H), 3.80 (s, 8H), 3.68-3.60 (m, 5H), 3.48 (d, J=9.1 Hz, 1H), 3.37-3.27 (m, 4H), 3.22 (s, 3H), 3.12 (d, J=12.8 Hz, 1H), 3.02 (d, J=9.6 Hz, 1H), 2.99-2.92 (m, 1H), 2.87 (s, 3H), 2.86-2.78 (m, 3H), 2.70-2.57 (m, 3H), 2.49 (t, J=7.0 Hz, 2H), 2.22-2.15 (m, 1H), 1.88-1.75 (m, 2H), 1.64-1.62 (m, 3H), 1.52-1.39 (m, 1H), 1.35-1.24 (m, 9H), 0.91-0.86 (m, 3H), 0.81 (s, 3H). ESI-MS $C_{74}H_{91}ClN_{10}O_{12}S_2$: 1410.5948, found: 1412.7 $(M+2H^+)^{2+}$ Synthesis of Compound 7
Scheme 18
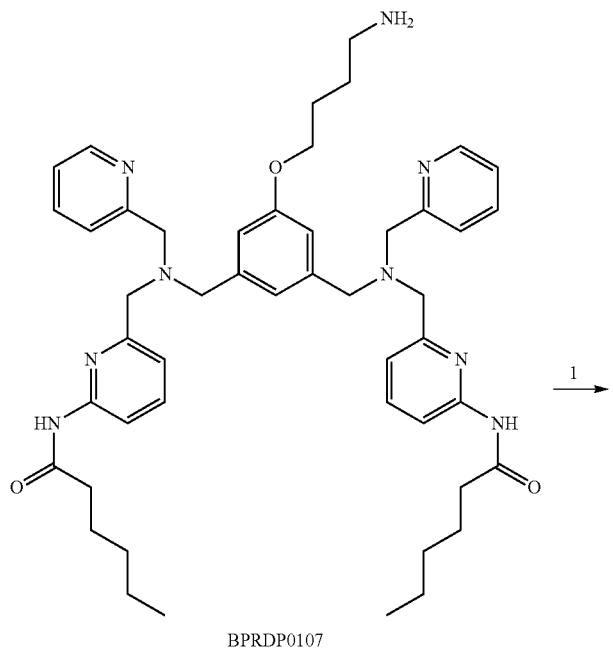
BPRDP0107
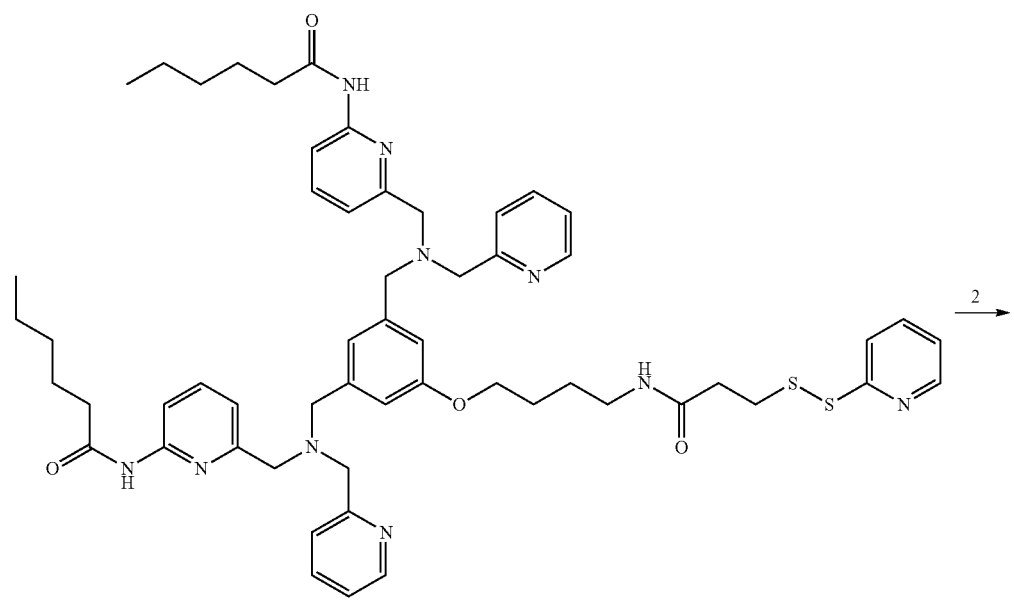
7-1

-continued

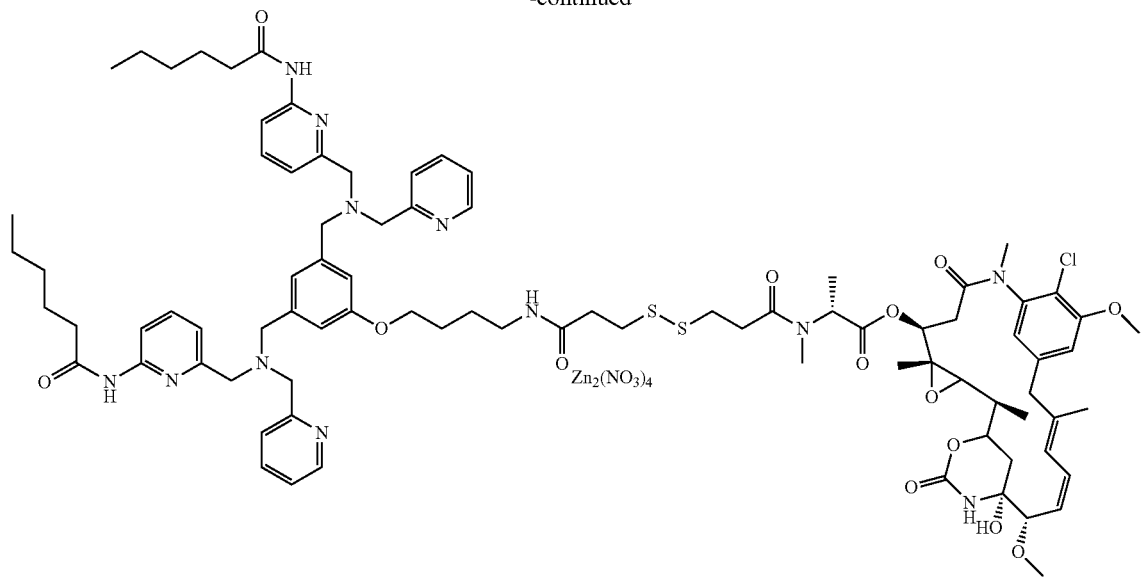

Compound 7

Scheme 18. Reagents and conditions for preparing compound 7:
(1) 3-(pyridin-2-yldisulfanyl)propanoic acid, EDCI, HOBt, N-Methylmorpholine, DCM, 15 hr, 52%.
(2) DM-1, DCM, overnight, 74%.

A mixture of 3-(pyridin-2-yldisulfanyl)propanoic acid (145.5 mg, 0.7 mmol, 1.1 eq.), EDCI (193.8 mg, 1.0 mmol, 1.5 eq.), and HOBt (137.0 mg, 1.0 mmol, 1.5 eq.) were stirred in $CH_2Cl$ (6.0 mL) for 1 hour at room temperature. To the reaction solution was added a solution of BPRDP0107 (500.2 mg, 0.6 mmol, 1.0 eq.) and N-Methylmorpholine (205.1 mg, 2.0 mmol, 3.0 eq.) in $CH_2C_2$ (1.0 mL). The resultant solution was stirred at room temperature for 15 hours, quenched with saturated $NH_4Cl_{(aq.)}$ dried over $Na_2SO_4$, and concentrated in vacuo. The residue was purified by flash chromatography over silica gel to give compound 7-1 (320.3 mg, 52%).

To a solution of compound 7-1 (160.2 mg, 0.2 mmol, 1.0 eq.) in $CH_2Cl_2$ (4.8 mL) was added DM-1 (175.4 mg, 0.2 mmol, 1.5 eq.). The reaction solution was stirred at room temperature overnight and then concentrated in vacuo. The residue was purified by flash chromatography over silica gel to give compound 7 (192.6 mg, 74%). $^1H$ NMR (400 MHz, $CDCl_3$): δ 8.90 (br, 2H), 8.49 (d, J=4.0 Hz, 2H), 8.13 (d, J=8.4 Hz, 2H), 7.68 (t, J=7.8 Hz, 2H), 7.58 (t, J=7.8 Hz, 2H), 7.51 (d, J=7.6 Hz, 2H), 7.33-7.28 (m, 2H), 7.25-7.22 (m, 1H), 7.18-7.12 (m, 2H), 6.83 (s, 1H), 6.71 (s, 2H), 6.69-6.57 (m, 2H), 6.46-6.38 (m, 1H), 6.30 (br, 1H), 5.96 (br, 1H), 5.70-5.62 (m, 1H), 5.31 (br, 1H), 4.81 (d, J=11.6 Hz, 1H), 4.34-4.26 (m, 1H), 3.98 (s, 3H), 3.96-3.90 (m, 2H), 3.79 (s, 4H), 3.70 (s, 4H), 3.64 (d, J=12.2 Hz, 1H), 3.59 (s, 4H), 3.48 (d, J=9.2 Hz, 1H), 3.35-3.26 (m, 4H), 3.22 (s, 3H), 3.12 (d, J=12.2 Hz, 1H), 3.01 (d, J=10.4 Hz, 1H), 2.98-2.92 (m, 1H), 2.87 (s, 3H), 2.85-2.78 (m, 3H), 2.72-2.56 (m, 3H), 2.50 (t, J=7.0 Hz, 2H), 2.21-2.16 (m, 1H), 2.12-2.01 (m, 4H), 1.83-1.75 (m, 2H), 1.74-1.44 (m, 10H), 1.38-1.12 (m, 18H), 0.88-0.74 (m, 9H). ESI-MS $C_{86}H_{113}ClN_{12}O_{14}S_2$: 1636.7629, found: 820.0 $(M+2H^+)^{2+}$ Synthesis of Compound 8

Scheme 19

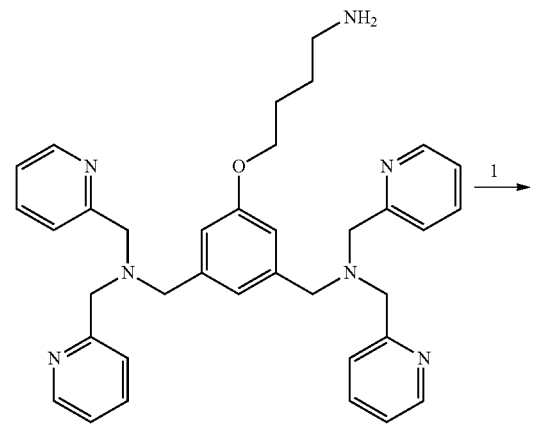

8-1

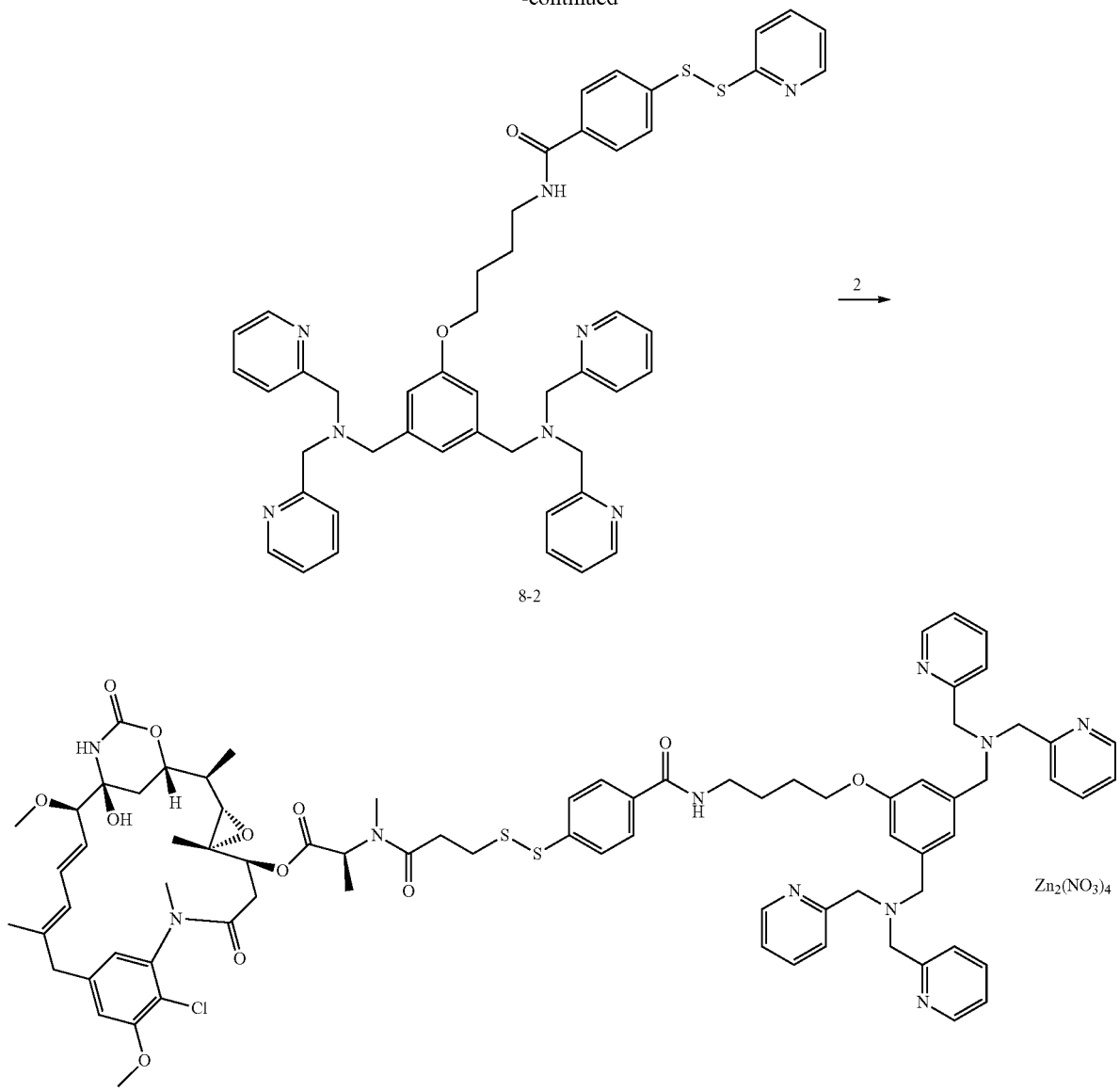

Compound 8

Scheme 19. Reagents and conditions for preparing compound 8:
(1) 2,2'-dipyridyl disulfide, 4-mercaptobenzoic acid, EDCI, HOBt, DIPEA, DCM, rt, 2 hr, 84%.
(2) DM-1, DMF, rt, 18 hr, 27%.

To a solution of 2,2'-dipyridyl disulfide, 4-mercaptobenzoic acid (136 mg, 0.517 mmol) in DCM (9 mL) at room temperature was added 1-(3-dimethylaminopropyl)-3-ethylcarbodiimide hydrochloride (EDCI, 135 mg, 0.704 mmol) and hydroxybenzotriazole (HOBt, 95 mg, 0.704 mmol). The reaction solution was stirred for 1 hour. Compound 8-1 (276 mg, 0.470 mmol) and N,N'-diisopropylethylamine (DIPEA, 0.25 mL, 1.409 mmol) were added consecutively. The resultant reaction solution was stirred for 1 hour and quenched with 2 N $HCl_{(aq.)}$. The organic and aqueous phases were separated. The aqueous solution was neutralized with saturated $NaHCO_{3(aq.)}$ and extracted with DCM three times. The combined organic extracts were dried over $Na_2SO_4$, filtered, and concentrated in vacuo. The residue was purified by flash chromatography over silica gel with 3% MeOH in DCM to afford compound 8-2 (147 mg, 84%).

To a solution of compound 8-2 (32 mg, 0.039 mmol) in anhydrous DMF (0.77 mL) at room temperature was added DM-1 (30 mg, 0.040 mmol). The reaction solution was stirred for 18 hours. DMF was removed. The residue was purified by flash chromatography over silica gel with 9% MeOH in DCM to give compound 8 (15 mg, 27%). $^1$H NMR (400 MHz, $CDCl_3$): δ 8.50 (d, J=4.2 Hz, 4H), 7.64-7.56 (m, 10H), 7.37 (d, J=8.6 Hz, 2H), 7.15-7.10 (m, 4H), 7.08 (s, 1H), 6.85 (s, 2H), 6.75 (d, J=1.8 Hz, 1H), 6.66 (d, J=10.7 Hz, 1H), 6.56 (d, J=1.6 Hz, 1H), 6.47 (br, 1H), 6.44-6.36 (m, 1H), 6.21 (s, 1H), 5.66 (dd, J=15.6, 9.2 Hz, 1H), 5.30 (br, 1H), 4.79 (dd, J=11.9, 2.9 Hz, 1H), 4.25 (t, J=11.1 Hz, 1H), 4.04-4.00 (m, 2H), 3.97 (s, 3H), 3.79 (s, 8H), 3.65 (s, 4H), 3.56-3.51 (m, 3H), 3.47 (d, J=9.0 Hz, 1H), 3.32 (s, 3H), 3.19 (s, 3H), 3.04-2.91 (m, 4H), 2.79 (s, 3H), 2.76-2.67 (m, 2H), 2.62-2.52 (m, 2H), 2.16 (dd, J=14.4, 2.9 Hz, 1H), 1.90-1.83 (m, 4H), 1.61 (s, 3H), 1.44 (d, J=6.8 Hz, 1H), 1.32-1.24 (m, 8H), 0.78 (s, 3H). ESI-MS $C_{78}H_{91}ClN_{10}O_{12}S_2$: 1460.2, found: 731.3 $(M+2H^+)^{2+}$ Synthesis of Compound 9
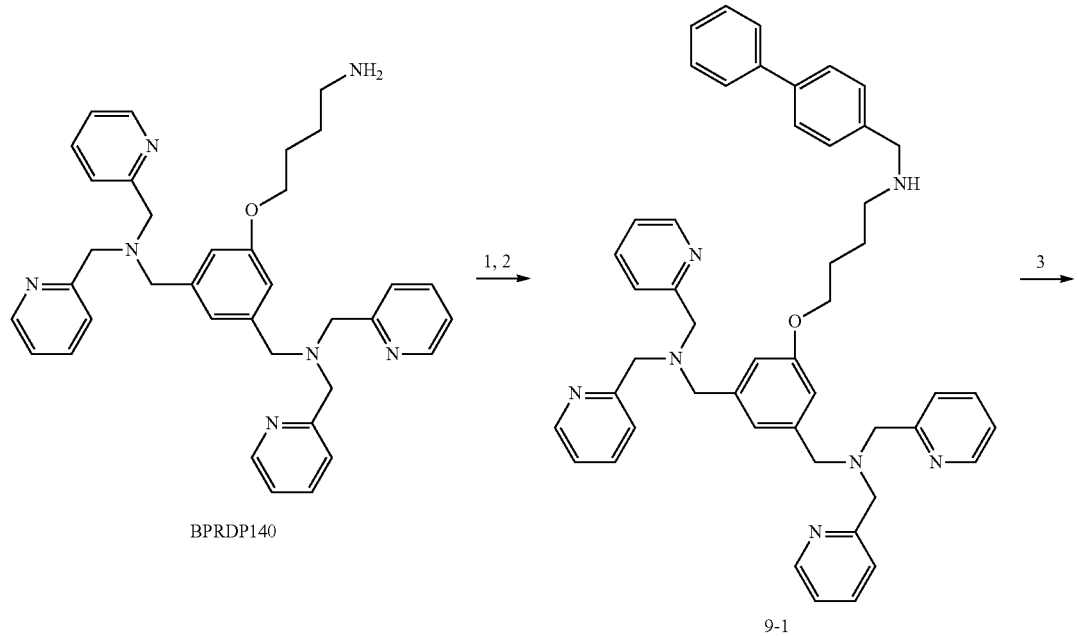
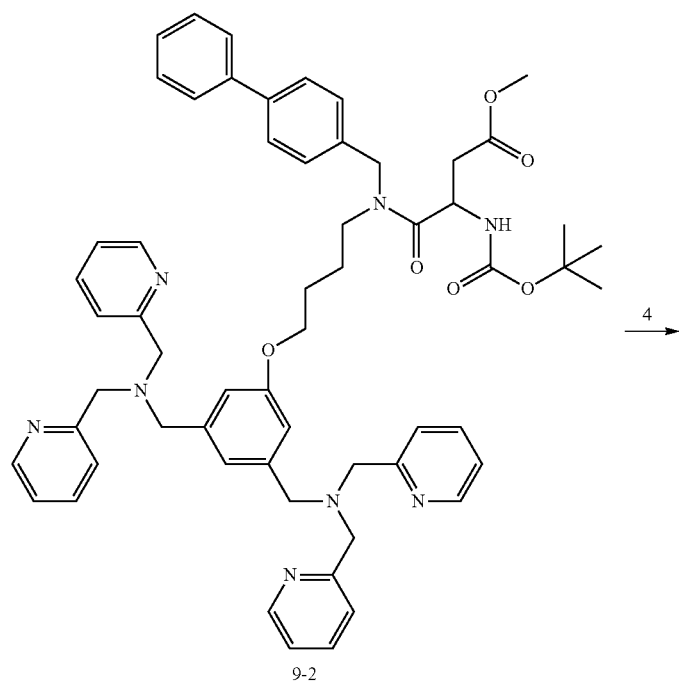

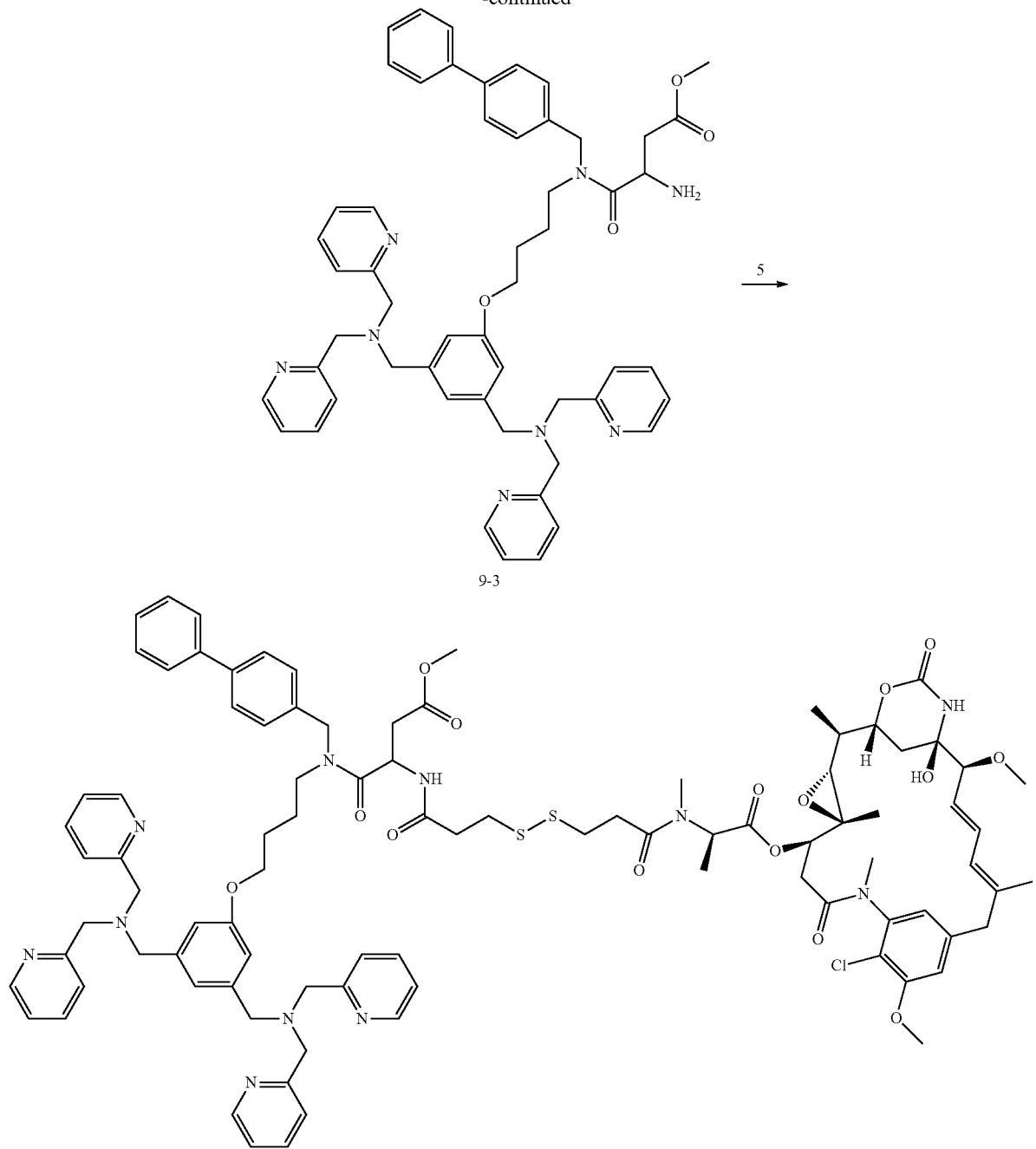

Compound 9

Scheme 20. Reagents and conditions for preparing compound 9: (1) Biphenyl-4-carboxaldehyde, MeOH, 70° C., 20 hr. (2) NaBH₄, MeOH, 4 hr, rt, 69%. (3) HBTU, HOBt, DIPEA, DCM, rt, 15 hr, 77%. (4) 2M HCl in ether, DCM, rt, 12 hr, 99%. (5) EDCl, 1-Hydroxy-pyrrolidine-2,5-dione, DM-1, DIPEA, DCM, 12 hr, rt, 61%.

To a solution of BPRDP140 (3.40 mmol, 2 g) in methanol (30 mL) was added a solution of Biphenyl-4-carboxaldehyde (6.81 mmol, 1.24 g) in methanol (4 mL). The reaction solution was stirred at 70° C. for 20 hours. Sodium borohydride (13.61 mmol, 0.52 g) was then added. The resultant reaction mixture was stirred at room temperature for 4 hours, and then poured onto saturated NH₄Cl$_{(aq.)}$. Methanol was removed in vacuo and the residue was extracted twice with CH₂Cl₂. The combined organic extracts were dried over Na₂SO₄, filtered, and concentrated in vacuo. The crude product was purified by flash chromatography over silica gel with Methanol/CH₂Cl₂ (5/95) to give compound 9-1 as a pale yellow oil (1.78 g. 69%).

To a solution of compound 9-1 (0.40 mmol, 0.30 g) in CH₂Cl₂ (8 mL) were added N,N,N',N'-Tetramethyl-O-(1H-benzotriazol-1-yl)uronium hexafluorophosphate (HBTU, 0.80 mmol, 0.30 g), 1-Hydroxybenzotriazole (HOBT; 0.80 mmol, 0.11 g), N,N-diisopropylethylamine (DIPEA, 3.18 mmol, 0.55 mL), and Boc-L-Aspartic acid 4-methyl ester (0.8 mmol, 0.20 g). The reaction mixture was stirred at room temperature for 15 hours and then poured onto saturated NH$_4$Cl$_{(aq.)}$. Methanol was then removed in vacuo and the residue was extracted twice with CH$_2$Cl$_2$. The combined organic extracts were dried over Na$_2$SO$_4$, filtered, and concentrated in vacuo. The crude product was purified by flash chromatography over silica gel with Methanol/CH$_2$Cl$_2$ (3197) to compound 9-2 as a pale yellow oil (0.30 g, 77%).

To a solution of compound 9-2 (0.31 mmol, 0.3 g) in CH$_2$C$_2$ (3 mL) was added a 2 M solution of HCl in ether (2.14 mmol, 1.07 mL) and the reaction mixture was stirred at room temperature for 12 hours. The solution was then concentrated to give compound 9-3 as a pale yellow oil (0.27 g, 99%).

To a solution of compound 9-3 (0.10 mmol, 85.00 mg) in CH$_2$Cl$_2$ (5 mL) were added N-Ethyl-N'-(3-dimethylaminopropyl)carbodiimide hydrochloride (EDCI, 0.14 nmol, 27.60 mg), 1-Hydroxybenzotriazole (HOBt, 0.14 mmol, 19.50 mg), N,N-diisopropylethylamine (DIPEA, 0.58 mmol, 0.10 mL), and DM-1 (0.14 mmol, 117.38 mg). The reaction solution was stirred at room temperature for 15 hours, poured onto saturated NH$_4$Cl$_{(aq.)}$ and extracted twice with CH$_2$Cl$_2$. The combined organic extracts were dried over Na$_2$SO$_4$, filtered, and concentrated in vacuo. The crude product was purified by flash chromatography over silica gel with Methanol/CH$_2$Cl$_2$ (5/95) to give compound 9 a pale yellow oil (0.100 g, 61%). $^1$H NMR (400 MHz, CDCl$_3$): δ 8.49 (d, J=4.8 Hz, 4H), 7.65-7.48 (m, 12H), 7.48-7.29 (m, 4H), 7.26 (s, 1H), 7.18-7.08 (m, 5H), 6.76-6.69 (m, 3H), 6.69-6.60 (m, 2H), 6.41 (dd, J=15.2, 11.2 Hz, 1H), 6.26 (d, J=7.6, 1H), 5.73-5.61 (m, 1H), 5.42-5.27 (m, 2H), 4.86-4.62 (m, 2H), 4.45 (d, J=14.8 Hz, 1H), 4.34-4.22 (m, 1H), 3.96 (s, 3H), 3.94-3.89 (m, 2H), 3.79 (s, 8H), 3.69-3.56 (m, 9H), 3.51-3.42 (m, 2H), 3.29 (d, J=12.8 Hz, 3H), 3.20 (d, J=2.8 Hz, 3H), 3.14-3.06 (m, 1H), 3.02 (d, J=9.2 Hz, 1H), 2.95-2.51 (m, 12H), 2.48-2.40 (m, 1H), 2.34-2.24 (m, 1H), 2.17 (d, J=14 Hz, 1H), 1.88-1.81 (m, 1H), 1.63 (s, 3H), 1.61-1.41 (m, 2H), 1.33-1.17 (m, 9H), 0.92-0.83 (m, 3H), 0.79 (s, 3H). ESI-MS C$_{92}$H$_{108}$ClN$_{11}$O$_{15}$S$_2$: 1705.72, found: 854.4 (M+2H$^+$)$^{2+}$ Synthesis of Compound 10

Scheme 21

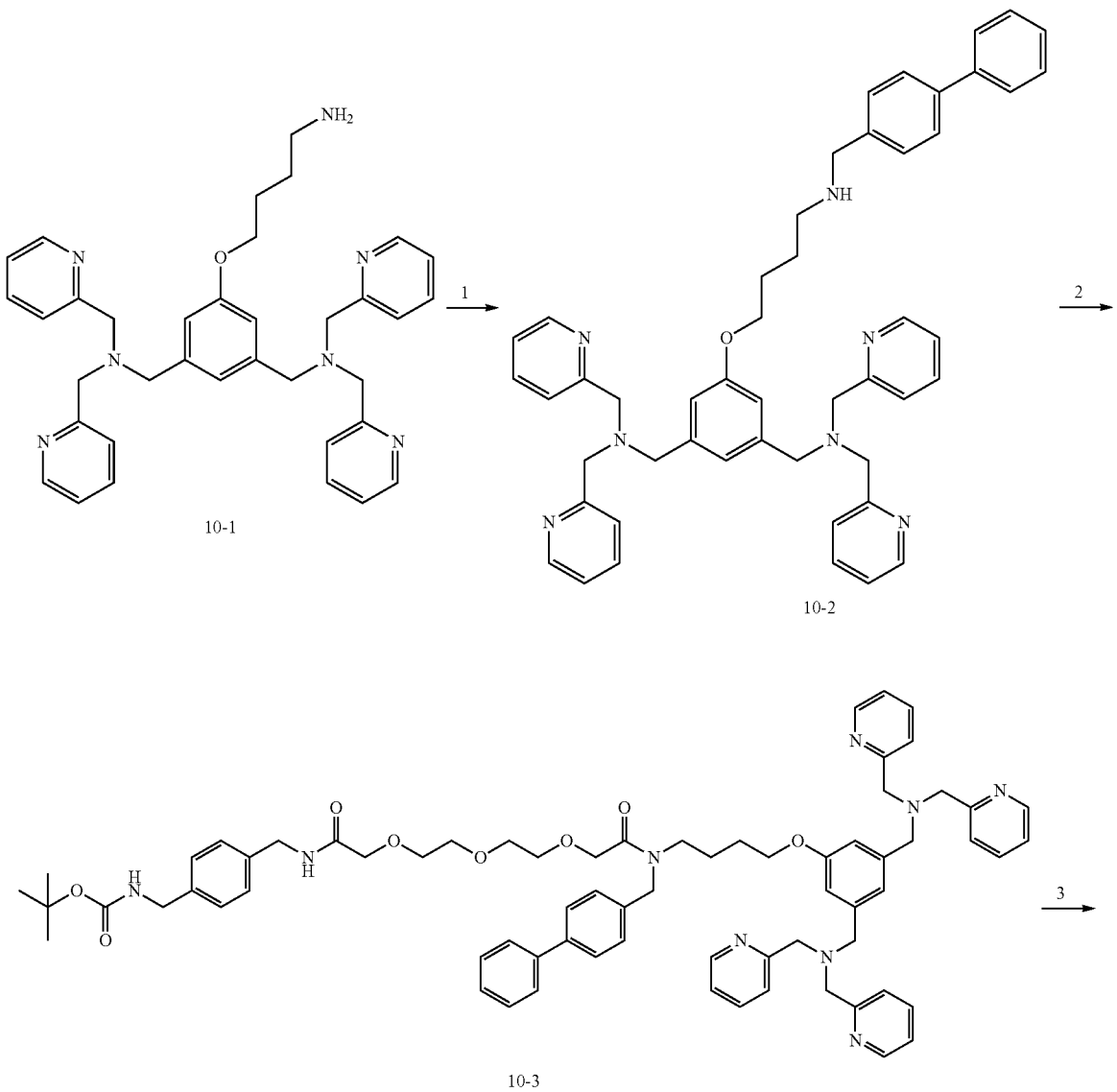

-continued

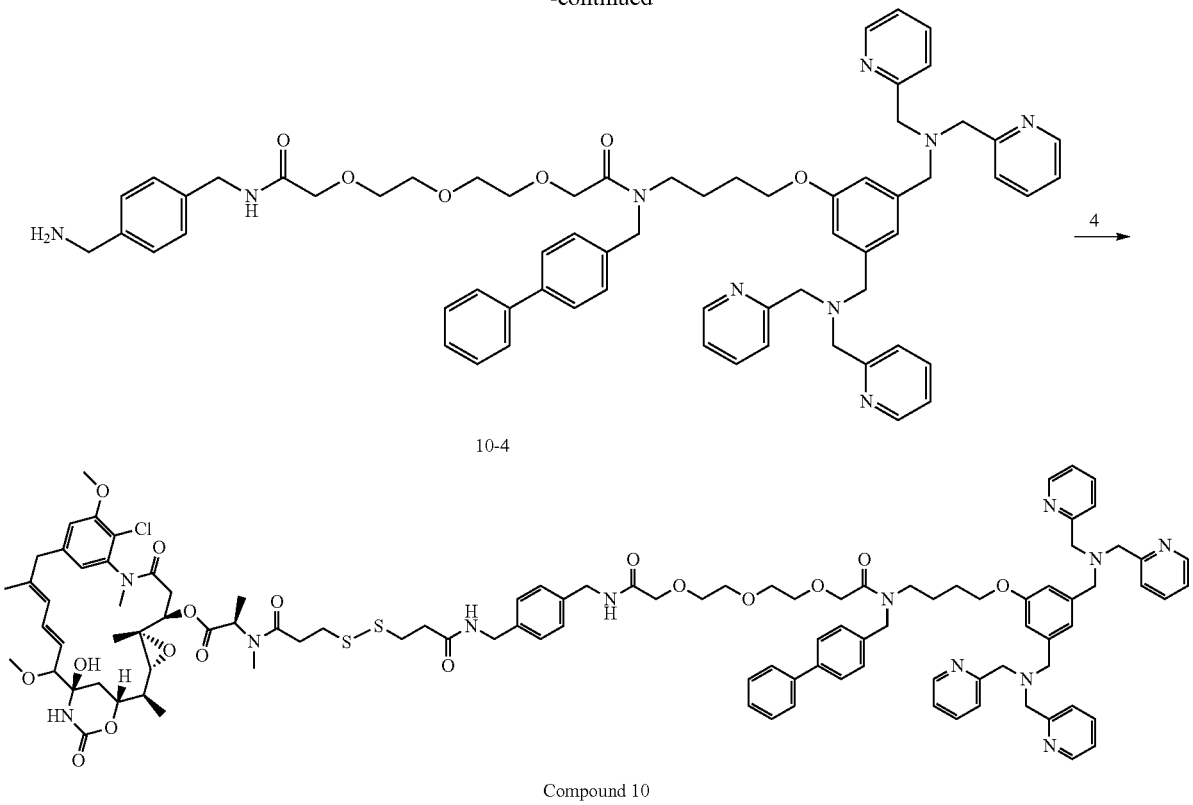

Compound 10

Scheme 21. Reagents and conditions for preparing compound 10:
(1) biphenyl-4-carboxaldehyde, NaBH$_4$, MeOH, 70° C., 24 hr, 69%.
(2) 1-(4-(((tert-butoxycarbonyl)amino)methyl)phenyl)-3-oxo-5,8,11-trioxa-2-azatridecan-13-oic acid, HBTU, HOBt, NMM, 18 hr, 64%.
(3) TFA, DCM, 2 hr.
(4) 3-[(3-{[(2R)-1-{[(1R,2S,3R.6R,16E,18E,20S,21R)-11-chloro-21-hydroxy-12,20-dimethoxy-2,5,9,16-tetramethyl-8,23-dioxo-4,24-dioxa-9,22-diazatetracyclo[19.3.1.1$^{10,14}$.0$^{3,5}$]hexacosa-10(26),11,13,16,18-pentaen-6-yl]oxy}-1-oxopropan-2-yl](methyl)amino}-3-oxopropyl)disulfanyl]propanoic acid, EDCI, HOBt, NMM, 19 hr, 47%.

To a solution of compound 10-1 (2000 mg, 3.403 mmol) in MeOH (34 mL) at room temperature was added biphenyl-4-carboxaldehyde (1240 mg, 6.806 mmol). The reaction solution was then slowly warmed to 70° C. and stirred overnight. The solution was cooled down to 0° C. Sodium borohydride (515 mg, 13.611 mmol) was added. The resultant solution was slowly warmed to room temperature and stirred for 4 hours, and then was poured into saturated NH$_4$Cl$_{(aq.)}$. MeOH was removed and the residue was extracted with DCM twice. The combined organic extracts were dried over Na$_2$SO$_4$, filtered, and concentrated in vacuo. The residue was purified by flash chromatography over silica gel with 5% MeOH in DCM to afford compound 10-2 (1780 mg, 69%).

To solution of 1-(4-(((tert-butoxycarbonyl)amino)methyl)phenyl)-3-oxo-5,8,11-trioxa-2-azatridecan-13-oic acid (159 mg, 0.360 mmol) in DCM (5 mL) at room temperature was added O-(benzotriazol-1-yl)-N,N,N',N'-tetramethyluronium hexafluorophosphate (HBTU, 273 mg, 0.721 mmol) and hydroxybenzotriazole (HOBt, 97 mg, 0.721 mmol). The reaction solution was stirred for 30 mins. Compound 10-2 and N-methylmorpholine (NMM, 0.16 mL, 1.441 mmol) were added consecutively. The resultant reaction solution was stirred for 18 hours, quenched with saturated NH$_4$Cl$_{(aq.)}$, and extracted with DCM twice. The organic extracts were dried over Na$_2$SO$_4$, filtered, and concentrated in vacuo. The residue was purified by flash chromatography over silica gel with 5% MeOH in DCM to afford compound 10-3 (181 mg, 64%).

To a solution of compound 10-3 (181 mg, 0.154 mmol) in DCM (1.5 mL) at room temperature was added TFA (1.5 mL) and the reaction solution was stirred for 2 hours. The excess amount of TFA was removed under reduced pressure to give compound 10-4, which was used without further purification.

A solution of 3-[(3-{[(2R)-1-{[(1R,2S,3R,6R,16E,18E,20S,21R)-11-chloro-21-hydroxy-12,20-dimethoxy-2,5,9,16-tetramethyl-8,23-dioxo-4,24-dioxa-9,22-diazatetracyclo[19.3.1.1$^{10,14}$.0$^{3,5}$]hexacosa-10(26),11,13,16,18-pentaen-6-yl]oxy}-1-oxopropan-2-yl](methyl)amino}-3-oxopropyl)disulfanyl]propanoic acid (90 mg, 0.107 mmol) in DCM (2 mL) at room temperature was added 1-(3-dimethylaminopropyl)-3-ethylcarbodiimide hydrochloride (EDCI, 31 mg, 0.160 mmol) and HOBt (22 mg, 0.160 mmol). The reaction solution was stirred for 30 mins. Compound 10-3 (100 mg, 0.093 mmol) and NMM (0.14 mL, 1.282 mmol) were added consecutively. The resultant reaction solution was stirred for 19 hours, quenched with saturated NH$_4$Cl$_{(aq.)}$, and extracted with DCM twice. The organic extracts were dried over Na$_2$SO$_4$, filtered, and concentrated in vacuo. The residue was purified by flash chromatography over silica gel with 9% MeOH in DCM to give compound 10 (84 mg, 47%). $^1$H NMR (400 MHz, CDCl$_3$): δ 8.49 (d, J=4.7 Hz, 4H), 7.63-7.49 (m, 12H), 7.48-7.38 (m, 4H), 7.38-7.27 (m, 4H), 7.23-7.19 (m, 4H), 7.15-7.10 (m, 4H), 6.83-6.78 (m, 3H), 6.67 (d, J=11.0 Hz, 1H), 6.63-6.61 (m, 1H), 6.45-6.36 (m, 1H), 6.23 (br, 1H), 5.69-5.61 (m, 1H), 5.31 (br, 1H), 4.82-4.76 (m, 1H), 4.58 (d, J=33.4 Hz, 2H), 4.46-4.42 (m, 2H), 4.41-4.37 (m, 2H), 4.33-4.25 (m, 1H), 4.12-3.99 (m, 4H), 3.96 (s, 3H), 3.94-3.90 (m, 2H), 3.79 (s, 8H), 3.66-3.58 (m, 8H), 3.57-3.52 (m, 1H), 3.50-3.41 (m, 6H), 3.30 (d, J=4.8 Hz, 1H), 3.21 (s, 3H), 3.10 (d, J=13.7 Hz, 1H), 3.01 (d, J=9.2 Hz, 1H), 2.96-2.91 (m, 1H), 2.87-2.76 (m, 8H), 2.64-2.51 (m, 5H), 2.20-2.14 (m, 1H), 1.76-1.70 (m, 4H), 1.63 (s, 3H), 1.48-1.42 (m, 1H), 1.29 (s, 10H), 0.80 (s, 3H). ESI-MS $C_{103}H_{123}ClN_{12}O_{17}S_2$: 1900.7, found: 951.5 $(M+2H^+)^{2+}$.
Synthesis of Compound 11
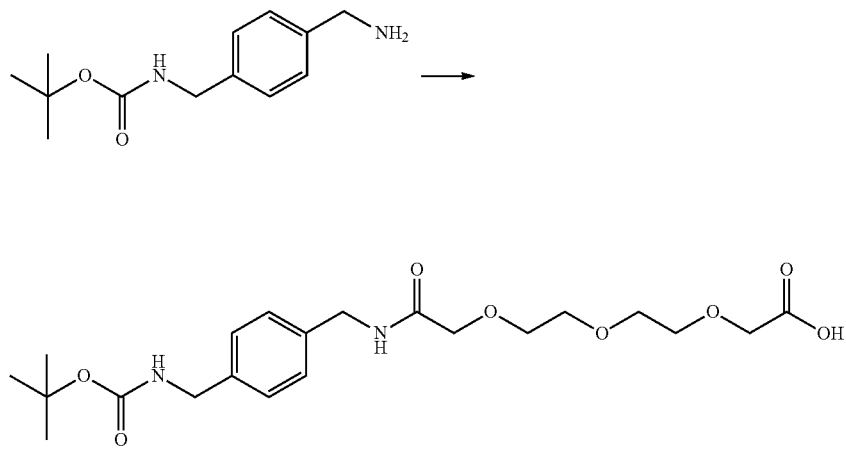
Linker a
Scheme 22. Reagents and conditions for preparing linker a: 2,2′-((Oxybis(ethane-2,1-diyl))bis(oxy))diethanol, EDCI, DCM, 0° C. to rt, 18 hr, 85%.
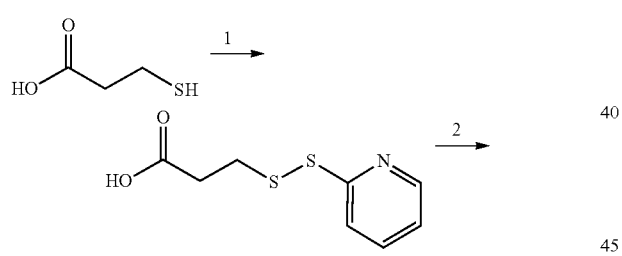
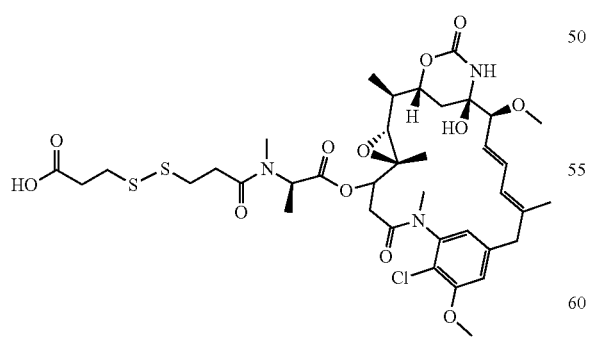
Linker b
Scheme 23. Reagents and conditions for preparing linker b:
(1) 2,2′-Dipyridyl disulfide, MeOH, 15 hr, 74%.
(2) DM-1, DCM, 35° C., 15 hr, 86 %.

Scheme 24
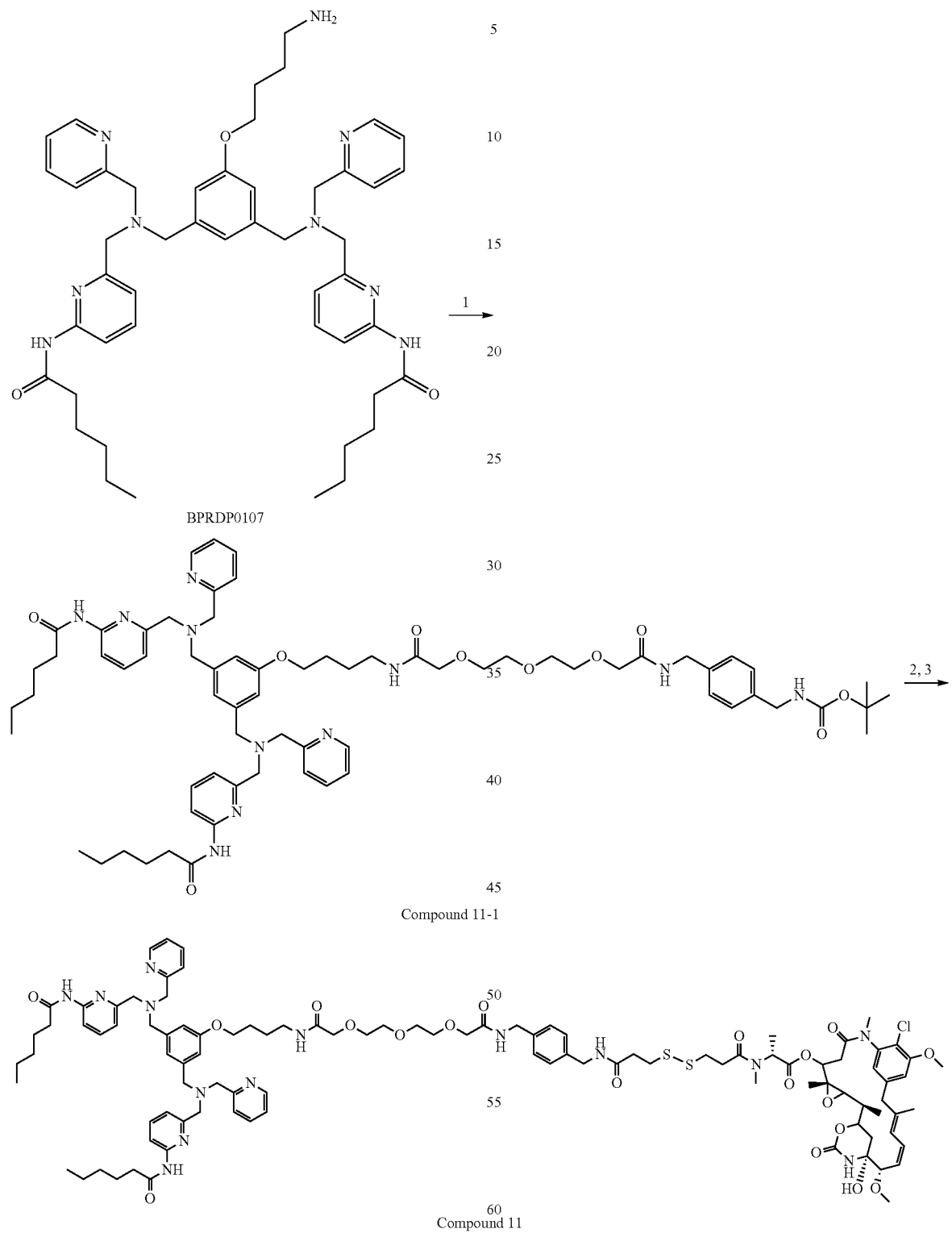
Scheme 24. Reagents and conditions for preparing compound 11:
(1) linker a, 1-(4-{[tert-butoxycarbonyl)amino]methyl}phenyl)-3-oxo-5,8,11-trioxa-2-azatridecan-13-oic acid, EDCl, HOBt, N-Methylmorpholine, DCM, 15 hr, 77%.
(2) TFA, DCM.
(3) linker b, EDCl, HOBt, N-Methylmorpholine, DCM, overnight, 74%.

1-(4-(((Tert-butoxycarbonyl)amino)methyl)phenyl)-3-oxo-5,8,11-trioxa-2-azatridecan-13-oic acid (linker a): To a solution of 2,2'-((Oxybis(ethane-2,1-diyl))bis(oxy))diethanol (2.82 g, 12.695 mmol) in DCM (42 mL) at room temperature was added 1-(3-dimethylaminopropyl)-3-ethylcarbodiimide hydrochloride (EDCI, 1.21 g, 6.35 mmol). The reaction solution was stirred for 30 mins and tert-Butyl 4-(aminomethyl)benzylcarbamate (1 g, 4.231 mmol) was added. The resultant reaction was stirred for 18 hours, quenched with saturated $NH_4Cl_{(aq.)}$, and extracted with DCM. The organic extracts were washed with saturated $NaHCO_{3(aq.)}$ and extracted with Ethyl acetate. The aqueous extracts were neutralized by 2 N $HCl_{(aq.)}$. The combined organic extracts were dried over $Na_2SO_4$, filtered, and concentrated in vacuo to afford linker a (1.59 g, 85%). $^1$H NMR (400 MHz, $CD_3OD$): δ 7.29-7.20 (m, 4H), 4.43 (s, 2H), 4.20 (s, 2H), 4.07-4.00 (m, 4H), 3.72-3.59 (m, 8H), 1.45 (s, 9H). ESI-MS $C_{21}H_{32}N_2O_8$: 440.5, found: 440.1. Purity: 96%.

To a solution 3-mercaptopropionic acid (18.84 mmol, 2 g) in methanol (13 mL) was added 2,Dipyridyl disulfide (2826 mmol, 6323 g) and the reaction mixture was stirred at room temperature for 15 hours. The solvent was then removed in vacuo. The crude product was purified by flash chromatography over silica gel with Ethyl acetate/Hexane (1/1) to give 3-(pyridin-2-yldisulfaneyl)propanoic acid as a white solid (3.00 g, 74%).

To a solution 3-(pyridin-2-yldisulfanyl)-propionic acid (0.28 mmol, 61.20 mg) in $CH_2Cl_2$ (5 mL) was added DM-1 (0.27 mmol, 0.20 g) and the reaction mixture was stirred at 35° C. for 15 hours. The solvent was then removed in vacuo. The product was purified by flash chromatography over silica gel with Methanol/$CH_2Cl_2$ (3/97) to give linker b as a white solid (0.20 g, 86%). $^1$H NMR (400 MHz, $CDCl_3$): δ 6.83 (s, 1H), 6.66 (s, 1H), 6.64 (d, J=12.4 Hz, 1H), 6.56 (s, 1H), 6.43 (dd, J=15.2, 11.2 Hz, 1H), 5.65 (dd, J=15.2, 8.8 Hz, 1H), 5.28 (br, 1H), 4.79 (dd, J=12.0, 2.4 Hz 1H), 4.30 (t, J=11.2 Hz, 1H), 3.99 (s, 3H), 3.65 (d, J=12.8 Hz, 1H), 3.49 (d, J=9.2 Hz, 1H), 3.36 (s, 3H), 3.23 (s, 3H), 3.13 (d, J=12.4 Hz, 1H), 3.00 (d, J=9.6 Hz, 1H), 2.94 (dd, J=14.8, 7.2 Hz, 1H), 2.89 (s, 3H), 2.87-2.77 (m, 1H), 2.76-2.64 (m, 2H), 2.61 (d, J=12.4 Hz, 1H), 2.20 (dd, J=18.8, 4.0 Hz, 1H), 1.65 (s, 3H), 1.60 (d, J=13.2 Hz, 1H), 1.53-1.38 (m, 1H), 1.36-1.20 (m, 9H), 0.88 (t, J=6.8 Hz, 3H), 0.81 (s, 3H). ESI-MS $C_{38}H_{52}ClN_3O_{12}S_2$: 841.27, found: 840.2 $(M-H^+)^-$. Purity: 95%.

A mixture of Linker a, 1-(4-{[(tert-butoxycarbonyl) amino]methyl}phenyl)-3-oxo-5,8,11-trioxa-2-azatridecan-13-oic acid (1217 mg, 0.3 nmol, 1.5 eq.), EDCI (79.3 mg, 0.4 mmol, 1.5 eq.) and HOBt (56.0 mg, 0.4 mmol, 1.5 eq.) were stirred in DCM (2.7 mL) for 1 hour at room temperature. A solution of BPRDP0107 (150.0 mg, 0.2 mmol, 1.0 eq.) and N-Methylmorpholine (83.9 mg, 0.8 mmol, 3.0 eq.) in $CH_2Cl_2$ (1.0 mL) was added to the reaction mixture. The reaction solution was stirred at room temperature for 15 hours, quenched with saturated $NH_4Cl_{(aq.)}$, dried over $Na_2SO_4$, and concentrated in vacuo. The residue was purified by flash chromatography over silica gel to give compound 11-1 (176.5 mg, 77%).

To a solution of compound 11-1 (176.5 mg, 0.1 nmol) in $CH_2Cl_2$ (1.4 mL) was added TFA (1.4 mL). The reaction mixture was stirred at room temperature overnight. After the reaction was completed, the excess amount of TFA was removed under vacuum to give N-[4-(aminomethyl)benzyl]-16-(3,5-bis{[{[6-(hexanoylamino)pyridin-2-yl]methyl} (pyridin-2-ylmethyl)amino]methyl}phenoxy)-11-oxo-3,6,9-trioxa-12-azahexadecan-1-amide.

A mixture of linker b (148.6 mg, 0.2 mmol, 1.2 eq.), EDCI (101.2 mg, 0.5 mmol, 3.0 eq.), and HOBt (71.5 mg. 0.5 mmol. 3.0 eq.) were stirred in $CH_2C_2$ (2.5 mL) for 1 hour at room temperature. A solution of N-[4-(aminomethyl)benzyl]-16-(3,5-bis{[{[6-(hexanoylamino)pyridin-2-yl] methyl}(pyridin-2-ylmethyl)amino]methyl}phenoxy)-11-oxo-3,6,9-trioxa-12-azahexadecan-1-amide (181.8 mg, 0.1 mmol, 1.0 eq.) and N-Methylmorpholine (214.1 mg, 2.1 mmol, 12.0 eq.) in $CH_2Cl_2$ (1.0 mL) was added to the reaction mixture and was stirred at room temperature overnight. The reaction mixture was washed with saturated $NH_4Cl_{(aq.)}$ dried over $Na_2SO_4$, and concentrated in vacuo. The product was purified by flash chromatography over silica gel to give compound 11 (213.4 mg, 74%). $^1$H NMR (400 MHz, $CDCl_3$): δ 8.94 (br, 2H), 8.49 (d, J=4.4 Hz, 2H), 8.12 (d, J=8.4 Hz, 2H), 7.67 (t, J=7.8 Hz, 2H), 7.57 (t, J=7.4 Hz, 2H), 7.50 (d, J=7.2 Hz, 2H), 7.34-7.28 (m, 2H), 7.25-7.17 (m, 6H), 7.16-7.12 (m, 2H), 7.02 (br, 1H), 6.89 (br, 1H), 6.83 (s, 1H), 6.72 (s, 2H), 6.68 (d, J=10.8 Hz, 1H), 6.63 (s, 1H), 6.45-6.38 (m, 1H), 6.29 (br, 1H), 5.66 (dd, J=15.2, 9.2 Hz, 1H), 5.39-5.30 (m, 1H), 4.88-4.69 (m, 1H), 4.46 (d, J=6.0 Hz, 2H), 4.38 (d, J=5.6 Hz, 2H), 4.33-4.26 (m, 1H), 4.05 (s, 2H), 3.98 (s, 3H), 3.95-3.90 (m, 2H), 3.77 (s, 4H), 3.71-3.55 (m, 17H), 3.50-3.43 (m, 3H), 3.30 (s, 3H), 3.23-3.19 (m, 4H), 3.12 (d, J=13.2 Hz, 1H), 3.01 (d, J=9.2 Hz, 1H), 3.00-2.92 (m, 1H), 2.89-2.82 (m, 6H), 2.70-2.56 (m, 5H), 2.20-2.15 (m, 1H), 2.11-2.04 (m, 4H), 1.79-1.73 (m, 1H), 1.61-1.50 (m, 7H), 1.31-1.16 (m, 19H), 0.87-0.76 (in, 12H). ESI-MS $C_{102}H_{135}ClN_{14}O_{19}S_2$: 1958.9158, found: 981.0 $(M+2H^+)^{2+}$.

Synthesis of Compound 12

Scheme 25
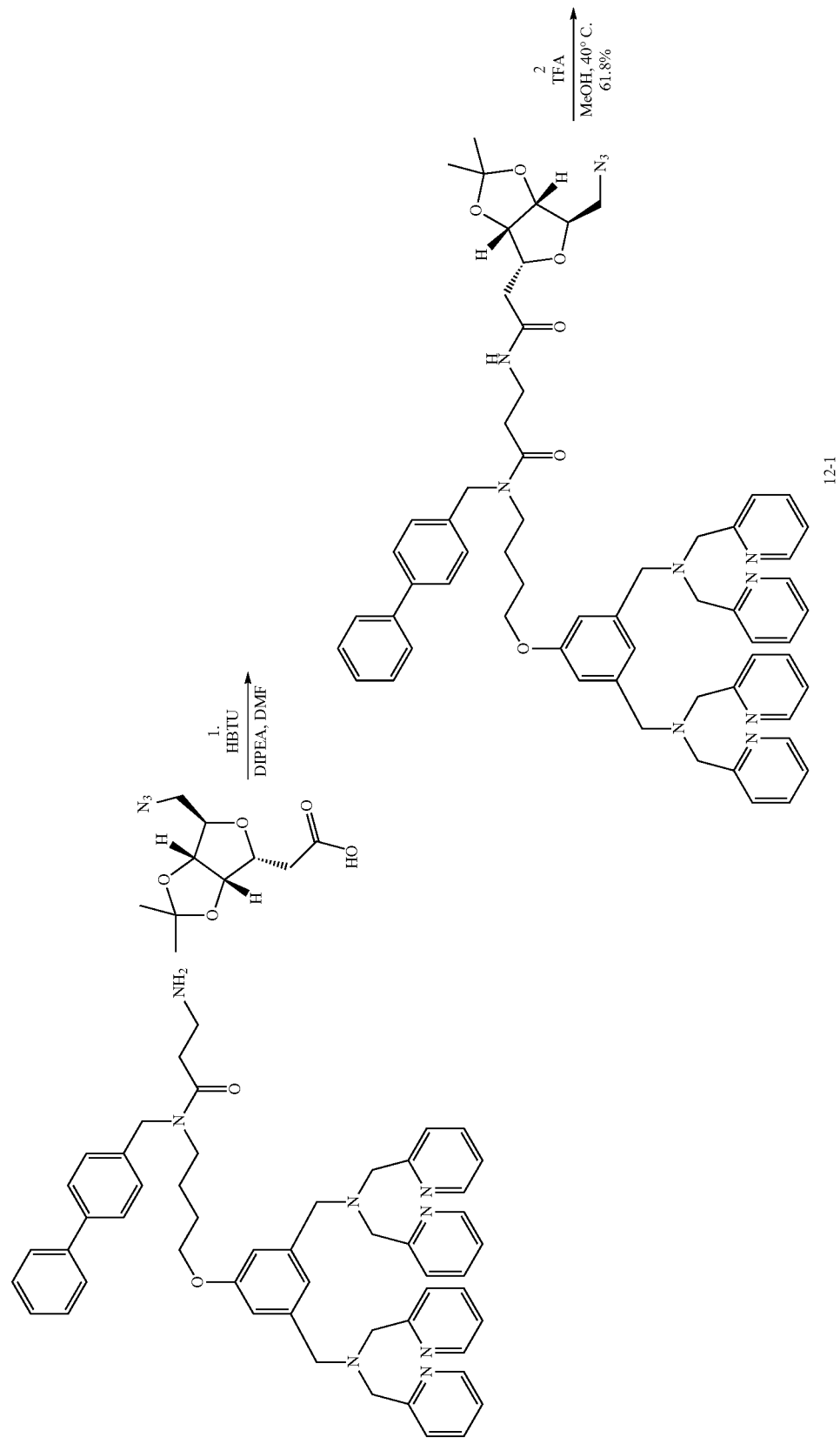

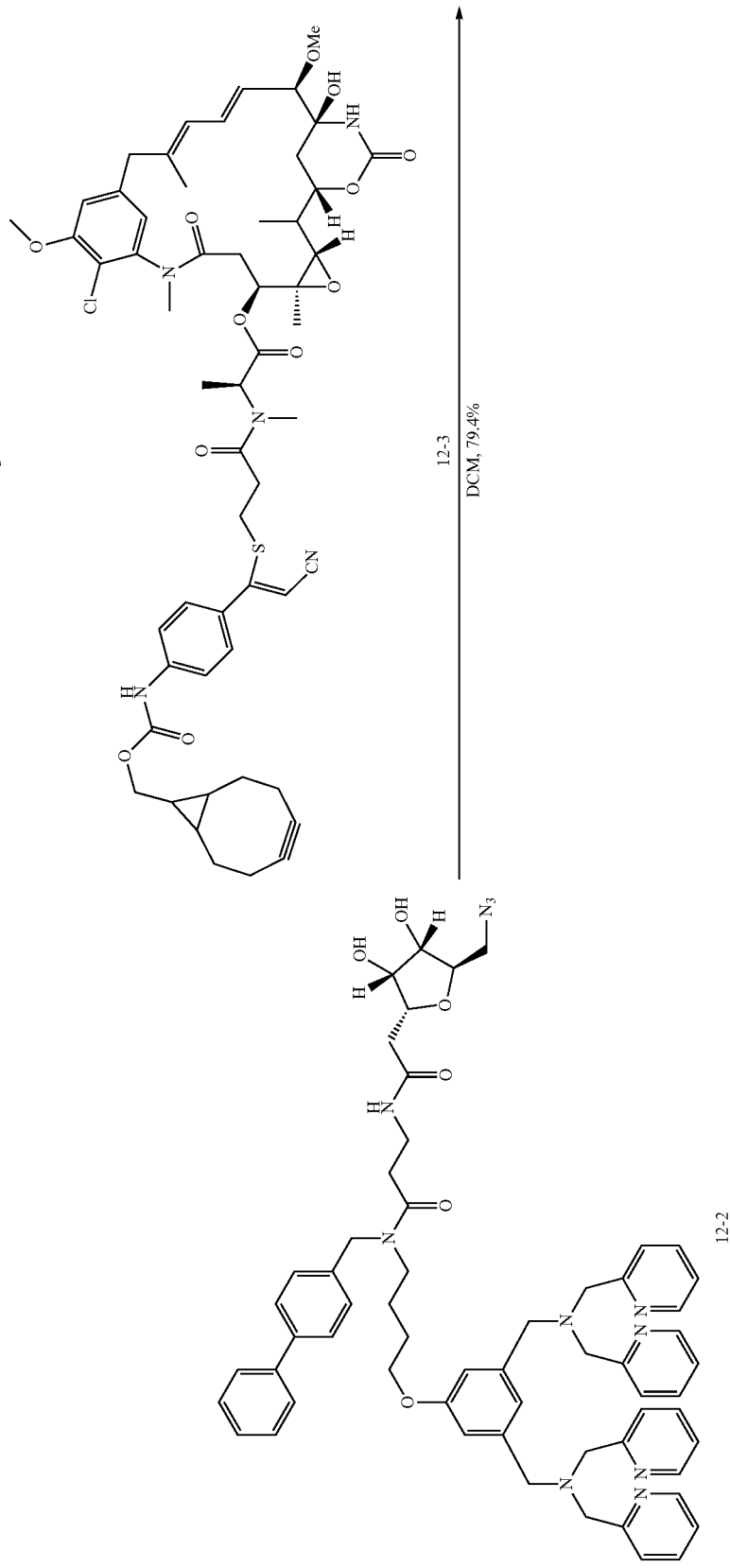

-continued
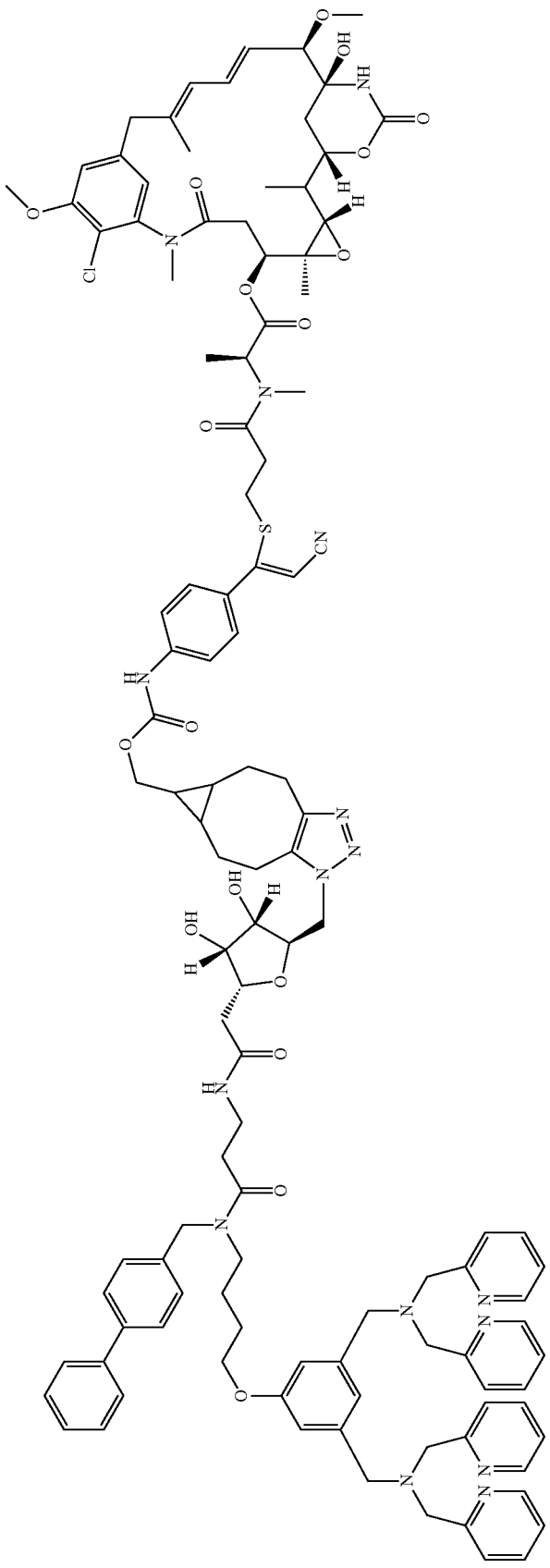
Compound 12
Scheme 25. Reagents and conditions for preparing compound 12: (1) HBTU, DIPEA, DMF. (2) TFA, MeOH, 40° C. 61.8%. (3) compound 12-3, DCM, 1 hr, 79.4%.

A mixture of N-([1,1'-biphenyl]-4-ylmethyl)-3amino-N-(4-(3,5-bis((bis(pyridin-2-ylmethyl)amino)methyl)phenoxy)butyl)propenamide (282.2 mg, 0.342 mmol) and 2-((3aS,4R,6R,6aR)-6-(azidomethyl)-2,2,3a,6a-tetramethyltetrahydrofuro[3,4-d][1,3]dioxol-4-yl)acetic acid (80 mg, 0.311 mmol) was dissolved in DMF at 25° C. HBTU (176.9 mg, 0.311 mmol) and diisopropylethylamine (95 mg, 0.93 mmol) were added. The reaction solution was stirred at room temperature for 15 hours and diluted with $H_2O$. The aqueous and organic phase solutions was separated. The organic solution was extracted three times with $CH_2Cl_2$. The combined extracts were washed with brine (3×50 mL), dried over $Na_2SO_{4(s)}$, filtered, and concentrated. The residue was purified by flash chromatography over silica gel with $MeOH/CH_2Cl_2$ (5/95) to give compound 12-1 (96.8 mg).

To a solution of compound 12-1 (80.0 mg, 0.075 mmol) in MeOH (0.2M) was added TFA (0.2 mL). The reaction solution was stirred at 40° C. for 15 hours and then concentrated. The residue was purified by flash chromatography over silica gel with $MeOH/CH_2Cl_2$ (10/90) to give compound 12-2 (47.7 mg, 0.046 mmol, 61.8%). $^1$H NMR (400 MHz, Chloroform-d) δ 8.54 (d, J=4.7 Hz, 4H), 7.69-7.60 (m, 4H), 7.57-7.50 (m, 10H), 7.44-7.37 (m, 3H), 7.33 (d, J=7.0 Hz, 2H), 7.26 (d, J=1.3 Hz, 6H), 7.21-7.14 (m, 5H), 7.02-6.97 (m, 2H), 6.91 (s, 2H), 6.89 (s, 1H), 4.61 (s, 1H), 4.56 (s, 1H), 3.97 (d, J=10.3 Hz, 10H), 3.83 (s, 2H), 3.79 (s, 2H), 3.49 (s, 1H), 3.37-3.31 (m, 2H), 3.00 (s, 1H), 2.90 (s, 1H), 1.75 (s, 3H). ESI-MS $C_{59}H_{65}N_{11}NaO_6^+$: 1047.2292, found: 1047 $(M+Na^+)^+$.

A solution of compound 12-2 (10.0 mg, 0.01 mmol) and compound 12-3 (10.3 mg, 0.01 mmol) in DCM was stirred overnight. DCM was then removed. The crude residue was purified by flash chromatography over silica gel with $MeOH/CH_2Cl_2$ (8/92) to give compound 12 (16.5 mg, 0.0079 mmol, 79.4%). $^1$H NMR (400 MHz, Chloroform-d) δ 8.52 (s, 4H), 7.66 (brs, 4H), 7.57 (d, J=8.1 Hz, 4H), 7.51-7.42 (m, 8H), 7.39-7.17 (m, 12H), 6.93 (s, 2H), 6.77 (d, J=12.6 Hz, 4H), 6.65-6.56 (m, 5H), 5.64 (dt, J=14.7, 6.7 Hz, 3H), 5.41 (t, J=9.1 Hz, 3H), 4.73 (d, J=12.4 Hz, 3H), 4.18-3.97 (m, 6H), 3.81 (s, 8H), 3.72-3.59 (m, 8H), 3.57-3.30 (m, 4H), 3.06 (s, 3H), 2.97-2.58 (m, 8H), 2.27-2.15 (m, 6H), 1.76 (s, 5H), 1.48-1.42 (m, 9H), 1.41 (s, 3H), 1.37-1.21 (m, 8H), 1.09 (s, 3H), 0.85 (s, 2H), 0.79 (d, J=6.7 Hz, 6H). ESI-MS $C_{114}H_{133}ClN_{16}O_{18}S^{2+}$: 1040.9708, found: 1040 $(M+2H^+)^{2+}$. Purity: 97%.

Synthesis of Compound 13

Scheme 26
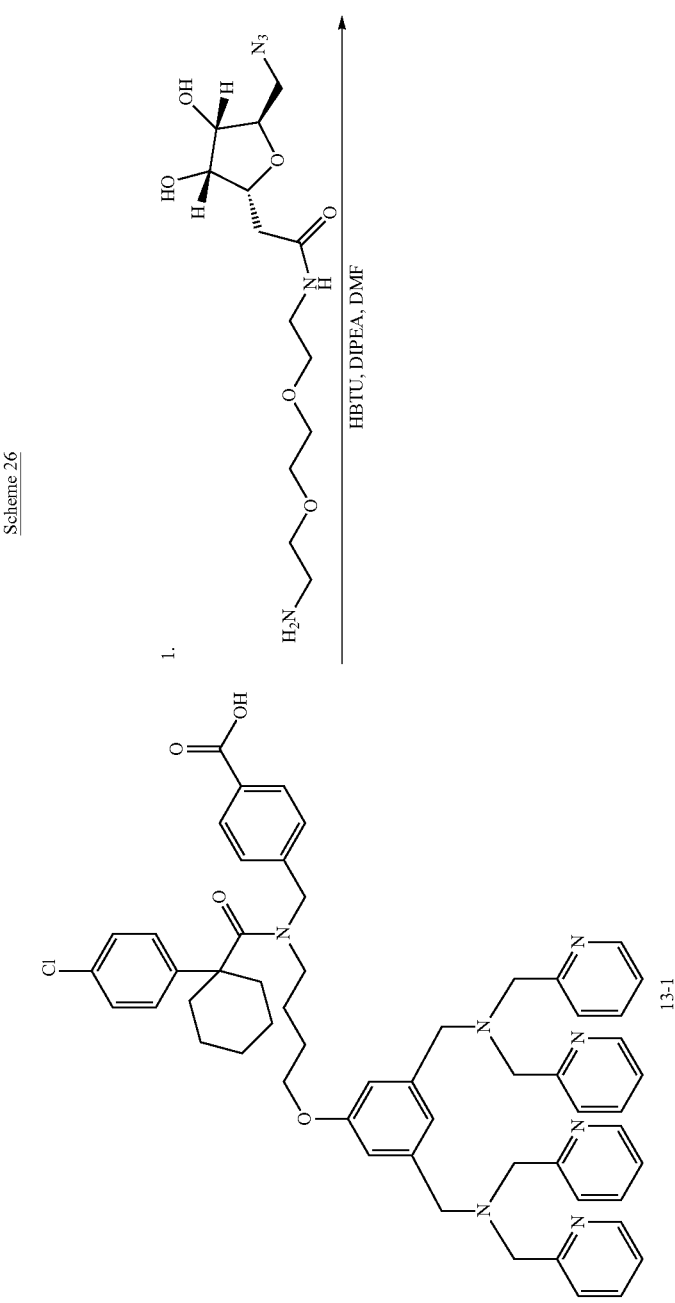

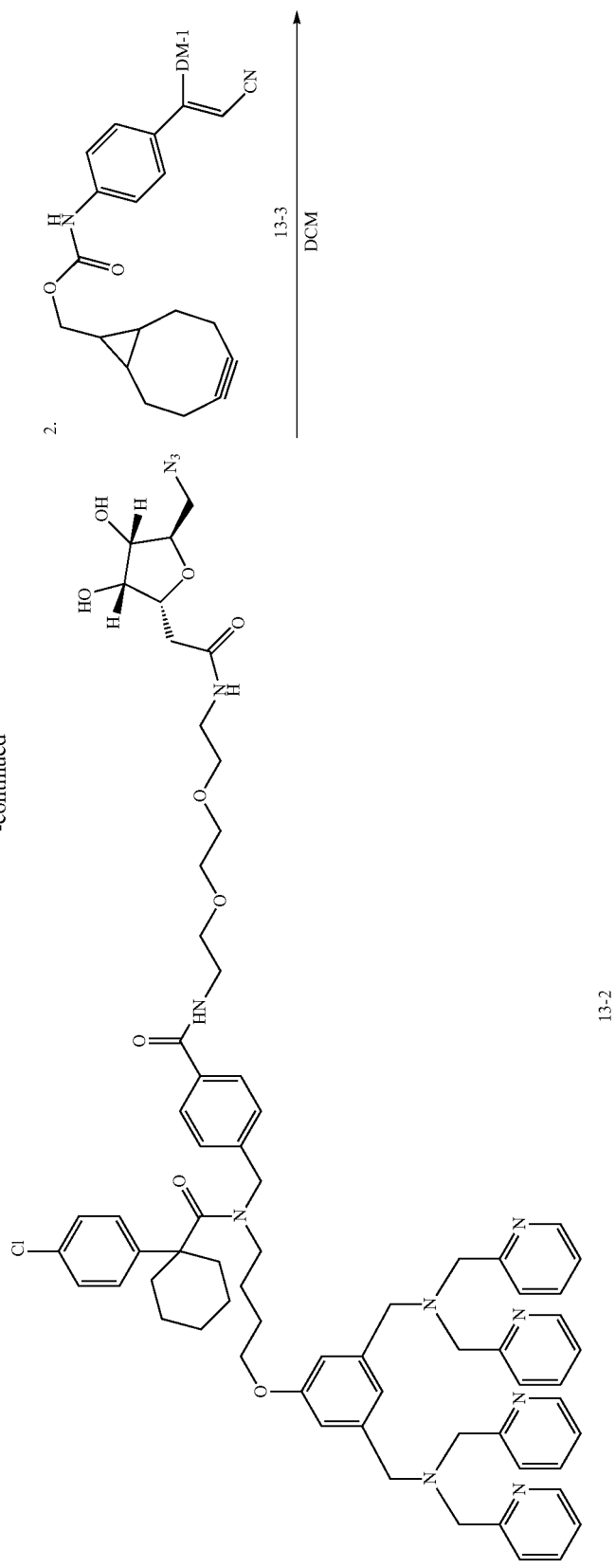

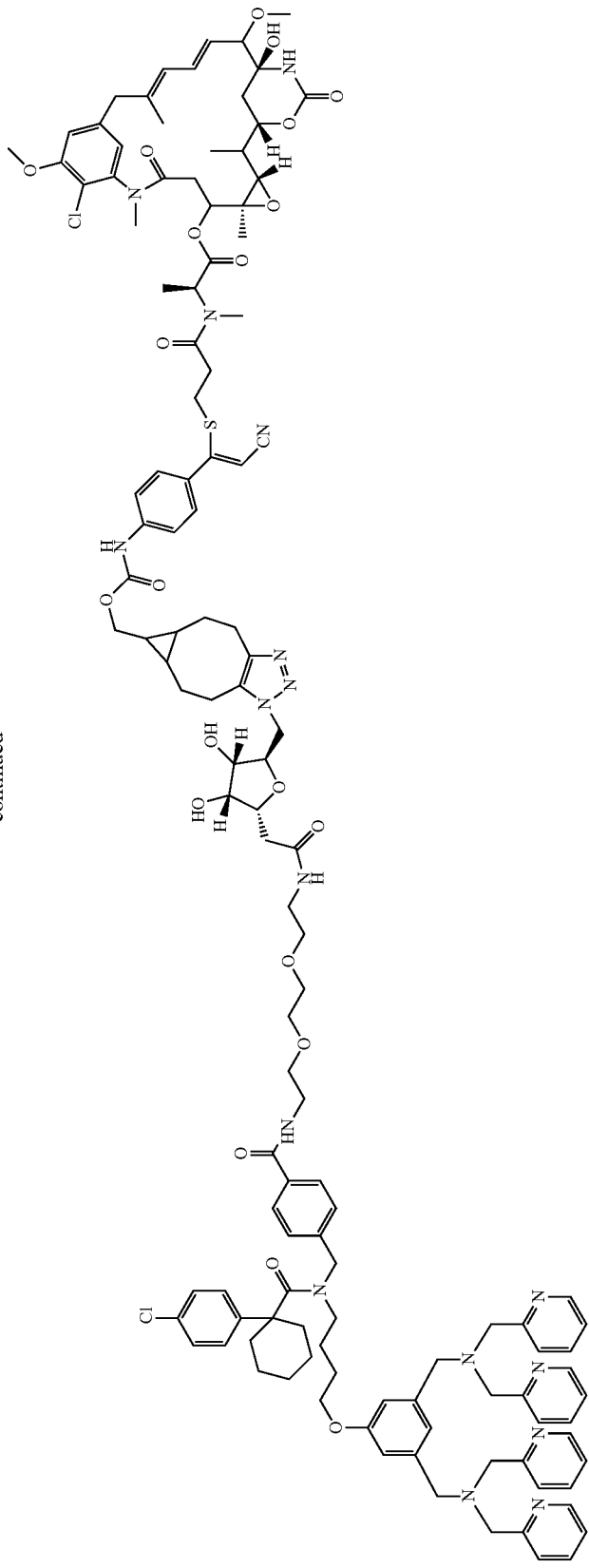
Scheme 26. Reagents and conditions for preparing compound 13: (1) HBTU, DIPEA, DMF. (2) DCM, 1 hr, 46.5%.
Compound 13

To a solution of compound 13-1 (140 mg, 0.15 mmol) and N-(2-2-(2-aminoethoxy)ethoxy)ethyl-2-((2R,3R,4S,5R)-5-(azidomethyl)-3,4-dihydroxytetrahydrofuran-2-yl)acetamide (56.75 mg, 0.16 mmol) in DMF were added HBTU (112.6 mg, 0.3 mmol) and diisopropylethylamine (45 mg, 0.45 mmol). The reaction solution was stirred at room temperature for 15 hours and quenched with $H_2O$. The aqueous solution was separated and extracted with $CH_2Cl_2$. The combined extracts were washed with brine (3×50 mL), dried over $Na_2SO_{4(s)}$, filtered, and evaporated. The crude residue was purified by flash chromatography over silica gel with $MeOH/CH_2Cl_2$ (12/88) to give compound 13-2 (67.1 mg).

$^1$H NMR (300 MHz, CDCl$_3$) δ 8.48 (d, J=4.8 Hz, 4H), 7.71 (d, J=7.9 Hz, 2H), 7.63-7.55 (m, 10H), 7.31-7.02 (m, 13H), 6.98 (s, 1H), 6.82-6.76 (m, 3H), 4.55 (s, 1H), 4.12-4.10 (m, 2H), 4.08-4.00 (m, 2H), 3.99 (s, 1H), 3.88 (s, 1H), 3.78 (s, 8H), 3.68-3.62 (m, 14H), 3.49 (dd, J=15.0, 3.8 Hz, 4H), 3.46-3.36 (m, 2H), 3.30-3.18 (m, 2H), 2.96-2.92 (m, 2H), 2.60-2.58 (m, 2H), 2.24 (brs, 1H), 1.48-1.23 (m, 6H). ESI-MS $C_{70}H_{83}ClN_{12}NaO_9^+$: 1294.9482, found: 1294 $(M+Na^+)^+$.

A mixture of compound 13-2 (26.0 mg, 0.02 mmol) and compound 13-3 (21.6 mg, 0.02 mmol) in DCM was stirred overnight. DCM was then removed and the crude residue was purified by flash chromatography over silica gel eluting with $MeOH/CH_2Cl_2$ (12/88) to give compound 13 (21.8 mg, 46.5%). $^1$H NMR (400 MHz, Chloroform-d) δ 8.55-8.41 (m, 4H), 7.79-7.67 (m, 2H), 7.67-7.45 (m, 10H), 7.34 (d, J=8.5 Hz, 3H), 7.29-7.01 (m, 13H), 6.95 (s, 2H), 6.91-6.70 (m, 4H), 6.63-6.53 (m, 2H), 6.46-6.27 (m, 3H), 5.62 (ddd, J=14.8, 9.2, 3.7 Hz, 1H), 5.23 (s, 1H), 4.76 (dt, J=12.1, 3.0 Hz, 1H), 4.21 (t, J=11.3 Hz, 8H), 4.17-3.92 (m, 8H), 3.78 (s, 8H), 3.73-3.50 (m, 16H), 3.43 (dd, J=18.7, 7.1 Hz, 4H), 3.31 (s, 3H), 3.15 (d, J=2.4 Hz, 3H), 3.08-2.94 (m, 8H), 2.74 (d, J=19.5 Hz, 4H), 2.58-2.50 (m, 4H), 2.42-2.36 (m, 4H), 2.20-2.00 (s, 11H), 1.43 (d, J=7.6 Hz, 4H), 1.35-1.19 (m, 11H), 0.78 (s, 3H). ESI-MS $C_{125}H_{151}Cl_2N_{17}O_{21}S^{2+}$: 1164.5195, found: 1164.32 $(M+2H^+)^{2+}$. Purity: 95%.

Synthesis of Compound 14

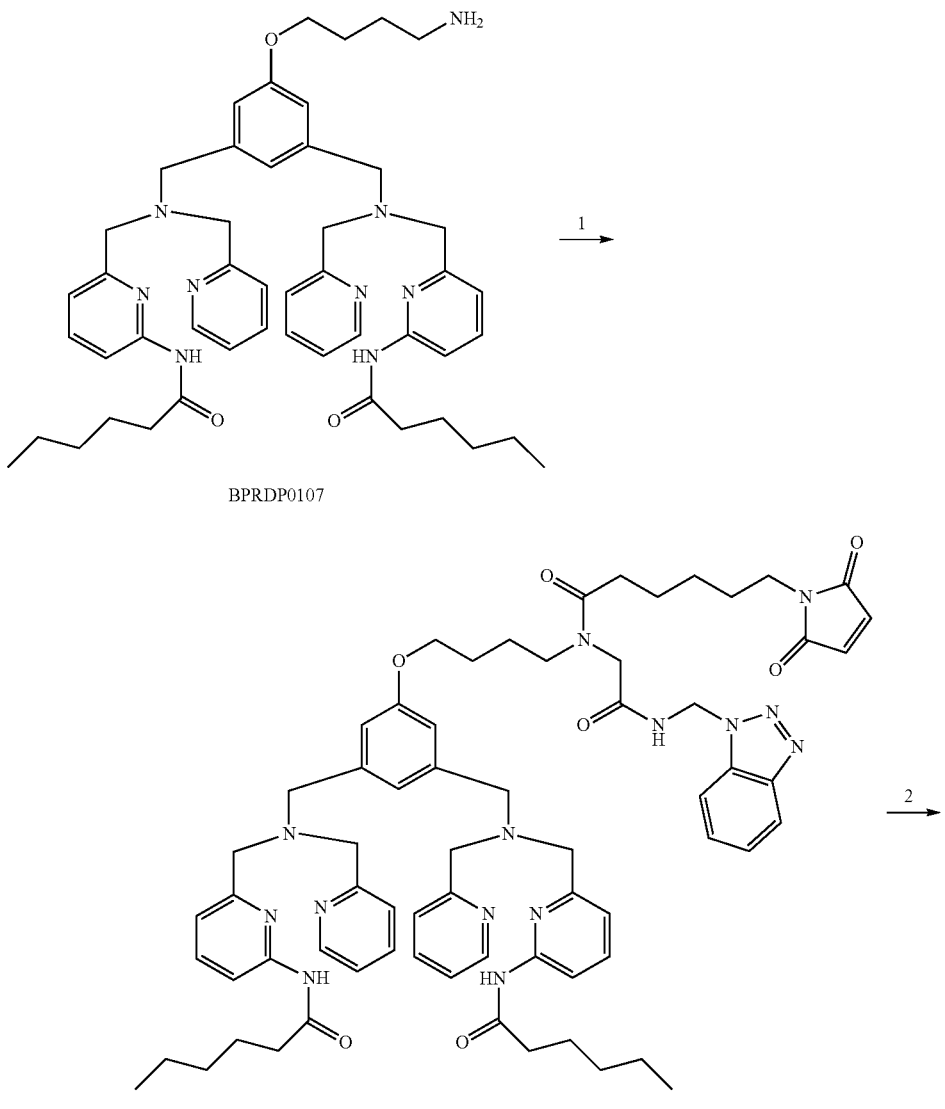

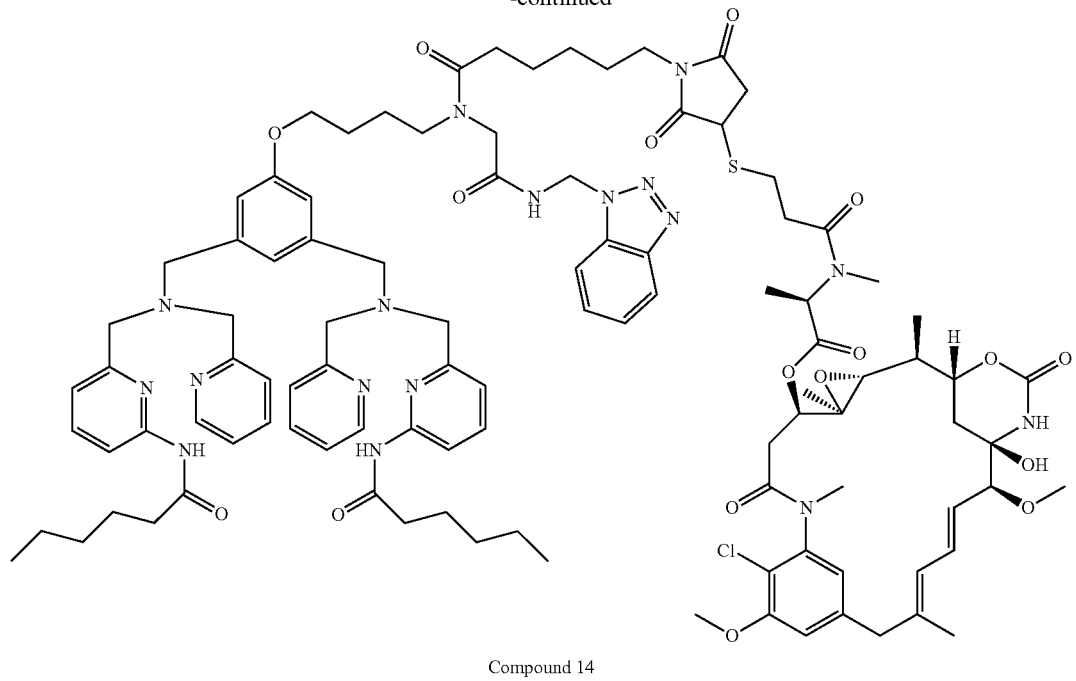

Compound 14

Scheme 27. Reagents and conditions for preparing compound 14: (1) Formaldehyde, 6-maleimidocaproic acid, 1-(isocyanomethyl)-1H-benzotriazole, MeOH, 16 hr, 39%. (2) DM-1, DCM, 1 hr, 43%.

A mixture of BPRDP0107 (200.0 mg, 0.25 mmol), 1-(isocyanomethyl)-1H-benzotriazole (39.5 mg, 0.25 mmol), 6-maleimidocaproic acid (52.8 mg, 0.25 mmol), and formaldehyde (0.02 mL, 0.25 mmol) in MeOH (2.5 mL) was stirred overnight at room temperature. MeOH was removed and the residue was purified by reverse phase column chromatography (dry loading; 70% to 90% MeOH in H$_2$O as gradient eluents) and normal phase column chromatography (DCM loading; 2.5% to 5.0% MeOH in DCM with 0.1% NH$_4$OH$_{(aq.)}$ as gradient eluents). Compound 14-1 was obtained as a yellow oil (115.9 mg, 39%).

A mixture of compound 14-1 (115.9 mg, 0.10 mmol) and DM-1 (73.8 mg, 0.10 mmol) was dissolved in 1 mL DCM and the reaction solution was stirred 1 hour at room temperature. DCM was removed and the residue was purified by reverse phase column chromatography (dry loading; 70% to 100% MeOH in H$_2$O as gradient eluents) to give compound 14 as a white solid (84.0 mg, 43%). $^1$H NMR (400 MHz, CDCl$_3$): δ 9.00 (s, 1H), 8.96 (s, 1H), 8.49 (d, J=4.0 Hz, 2H), 8.17 (dd, J=6.8, 5.2 Hz, 1H), 8.13 (d, J=8.4 Hz, 2H), 7.97 (d, J=8.0 Hz, 1H), 7.86 (d, J=8.0 Hz, 1H), 7.68 (t, J=8.0 Hz, 2H), 7.56 (td, J=8.0, 2.0 Hz, 2H), 7.50 (d, J=8.0 Hz, 2H), 7.44 (t, J=8.0 Hz, 1H), 7.33-7.25 (m, 3H), 7.14 (t, J=6.0 Hz, 2H), 6.83 (d, J=4.4 Hz, 1H), 6.67 (s, 2H), 6.65 (d, J=2.0 Hz, 1H), 6.43 (dd, J=14.0, 12.4 Hz, 1H), 6.37 (d, J=4.4 Hz, 1H), 6.05 (d, J=6.8 Hz, 2H), 5.66 (dd, J=14.0, 9.2 Hz, 1H), 5.36 (t, J=5.2 Hz, 1H), 4.78 (dd, J=12.4, 3.2 Hz, 1H), 4.29 (t, J=10.0 Hz, 1H), 4.18~3.63 (m, 5H), 3.98 (s, 3H), 3.98 (s, 2H), 3.78 (s, 4H), 3.70 (s, 4H), 3.59 (s, 4H), 3.48~2.84 (m, 11H), 3.29 (d, J=2.8 Hz, 3H), 3.20 (s, 3H), 2.85 (d, J=7.2 Hz, 3H), 2.61 (t, J=12.8 Hz, 2H), 2.39-2.27 (m, 3H), 2.19 (dd, J=14.8, 2.4 Hz, 1H), 2.06 (t, J=7.6 Hz, 4H), 2.06 (t, J=7.6 Hz, 2H), 1.99 (s, 3H), 1.65 (s, 3H), 1.61~1.47 (m, 12H), 1.32~1.14 (m, 15H), 0.82 (t, J=7.2 Hz, 6H), 0.81 (s, 3H). ESI-MS C$_{102}$H$_{130}$ClN$_{17}$O$_{17}$S: 1931.92, found: 1933.12 (M+H$^+$)$^+$, 1955.26 (M+Na$^+$)$^+$. Purity: 95%.

Synthesis of Compound 15
Scheme 28
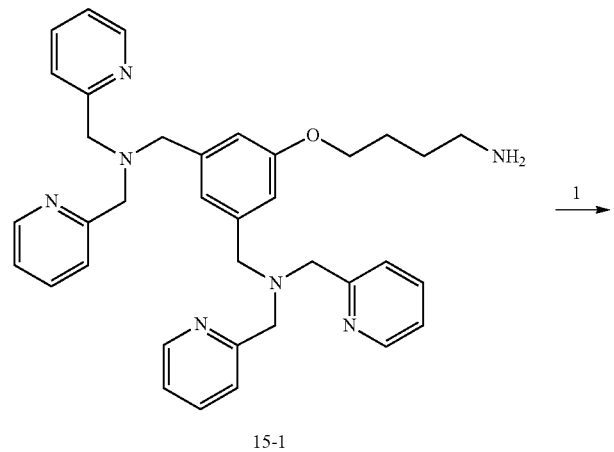
15-1
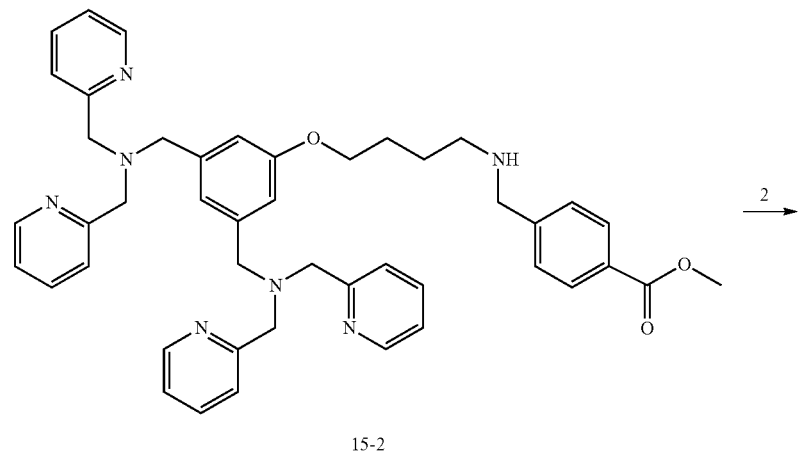
15-2
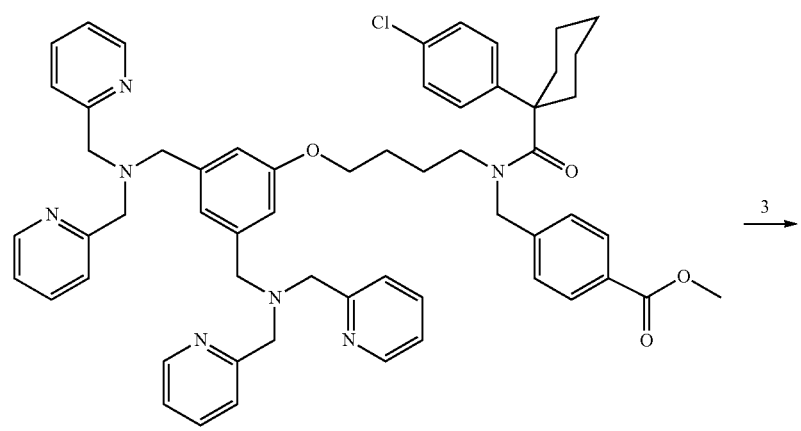
15-3

-continued
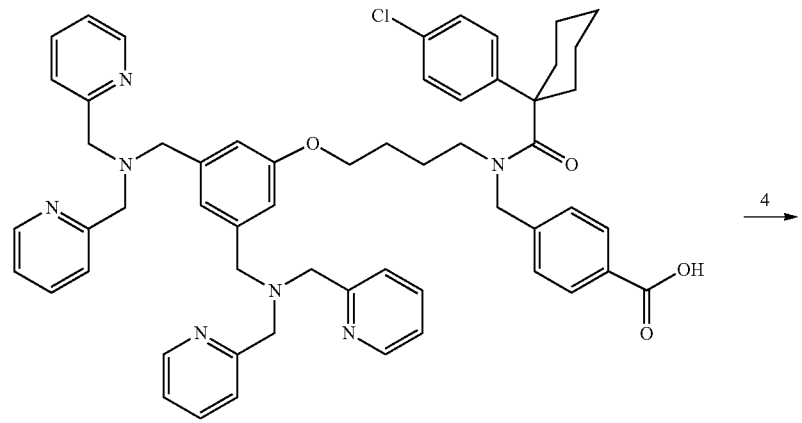
15-4
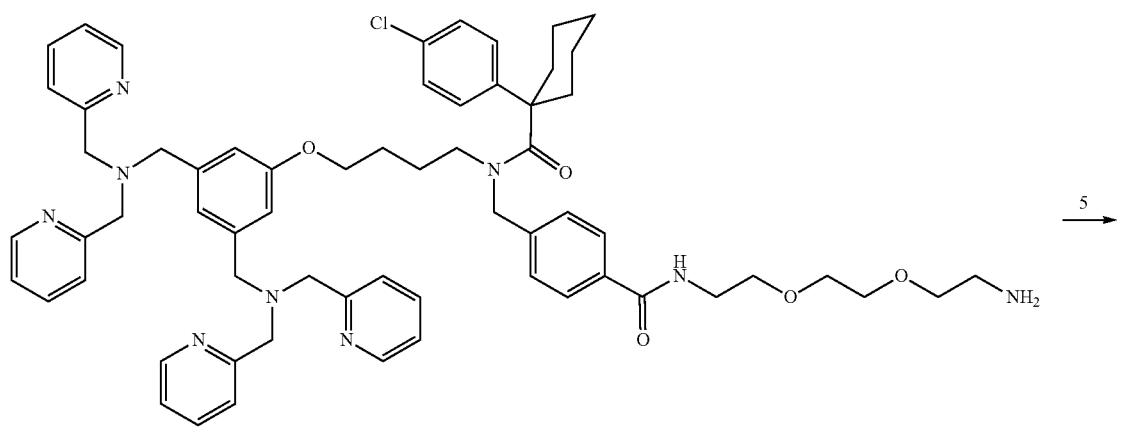
15-5

197
-continued
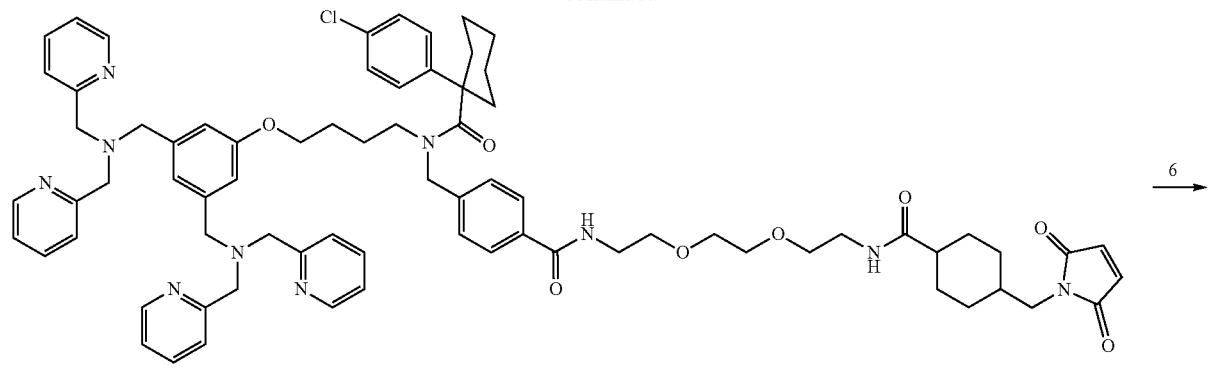
15-6
198
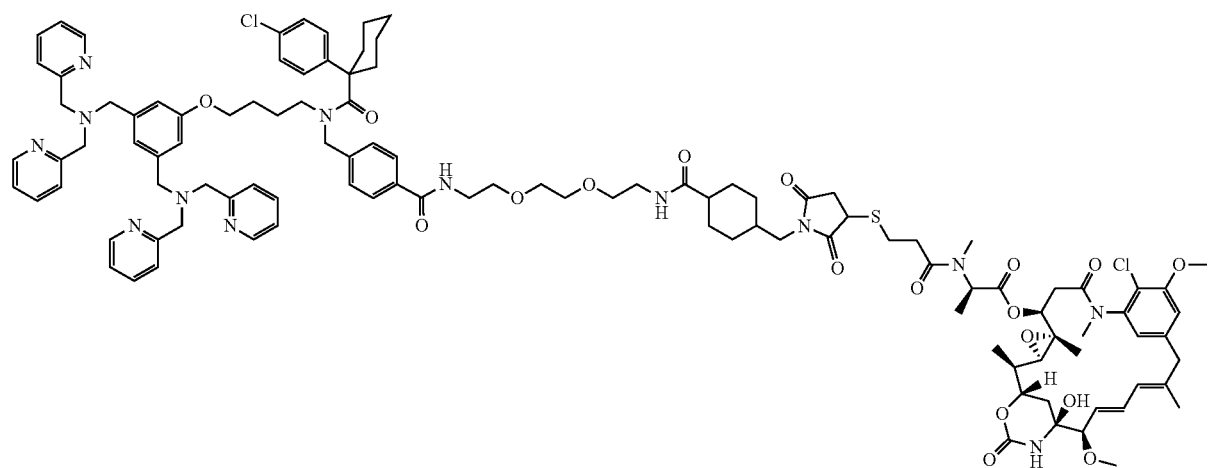
Compound 15
Scheme 28. Reagents and condition for preparimg compound 15: (1). Methyl 4-formylbenzoate, MeOH; NaBH₄, MeOH. (2). 1-(4-Chloro-phenyl)-cyclohexanecarbonyl chloride, Et₃N, DCM. (3). LiOH, MeOH. (4). {2-[2-(2-Amino-ethoxy)-ethoxy]-ethyl}-carbamic acid tert-butyl ester, HOBt, EDCI, DCM. (5). SMCC, DIPEA, DMF. (6). DM-1, DCM.

To methyl 4-formylbenzoate (5 g, 30.45 mmol, 1.8 eq.) in MeOH (200 mL) was added compound 15-1 (10 g, 17.01 mmol) and sodium borohydride (3.7 g, 97.80 mmol, 5.7 eq.) consecutively. The reaction solution was stirred at room temperature for 3 hours. MeOH was removed and the residue dissolved in 200 ml $CH_2Cl_2$. The protonated products were extracted from $CH_2Cl_2$ with 200 mL 1 M HCl (aq.). The aqueous layer was neutralized and the product extracted with 200 ml $CH_2Cl_2$. The organic extracts were combined, dried with $Na_2SO_4$, filtered, and concentrated to give compound 15-2 as a yellow oil (11.26 g, 15.30 mmol, 90%).

To a solution of 1-(4-chlorophenyl)cyclohexanecarbonyl chloride (7.71 g, 30.00 mmol, 2 eq.) and triethylamine (5 mL, 21.54 mmol) in 200 mL $CH_2Cl_2$ was added compound 15-2 (11.26 g, 15.30 mmol). The reaction solution was stirred for 2 hours at room temperature. The protonated product was extracted with a mixture of 200 mL $CH_2Cl_2$ and 200 mL 1 M HCl (aq.). The aqueous solution was neutralized and extracted with 200 mL $CH_2Cl_2$. The organic extract was dried with $Na_2SO_4$, filtered, and concentrated to give compound 15-3 as a yellow oil (13.17 g, 13.77 mmol, 90%).

To a solution of compound 15-3 (13.17 g, 13.77 mmol) in 300 mL MeOH was added 50 mL 0.5 M LiOH (aq.). The reaction mixture was stirred at room temperature for 15 hours. MeOH was removed and the residue was re-dissolved in $CH_2Cl_2$. The insoluble residue was filtered. The filtrate was washed with $CH_2Cl_2$, dried over $Na_2SO_4$, and concentrated under vacuum to give compound 15-4 as a yellowish powder (11.68 g, 12.39 mmol, 90%).

To a solution of compound 15-4 (300 mg, 0.31 mmol) in $CH_2Cl_2$ was added 1-Ethyl-3-(3-dimethylaminopropyl)carbodiimide (EDCI, 60 mg, 0.38 mmol), hydroxybenzotriazole (HOBt, 60 mg, 0.44 mmol) and {2-[2-(2-Aminoethoxy)-ethoxy]-ethyl}-carbamic acid tert-butyl ester (150 mg, 0.60 mmol). The reaction solution was stirred at room temperature for 2 hours. The protonated product was extracted with a mixture of 100 mL $CH_2Cl_2$ and 100 mL 1M HCl (aq.). The aqueous solution was neutralized and extracted with 100 mL $CH_2Cl_2$. The organic extract was washed with water, dried over $Na_2SO_4$, filtered, and concentrated. The crude product was purified by flash chromatography over silica gel to give compound 15-5 (230 mg, 0.21 mmol, 67%).

To a solution of 15-5 (90 mg, 0.08 mmol) in DMF was added N,N-Diisopropylethylamine (DIPEA, 4 drop) and succinimidyl 4-(N-maleimidomethyl)cyclohexane-1-carboxylate (SMCC, 35 mg, 0.10 mmol) at room temperature for 2 hours. The aqueous layer was neutralized and the product extracted into 100 ml $CH_2Cl_2$. The organic extract was dried with $Na_2SO_4$, filtered, and concentrated to give compound 15-6 (110 mg, 0.08 mmol, 100%). $^1$H NMR (400 MHz, $CDCl_3$) δ 8.47 (d, J=4.4 Hz, 4H), 7.71 (d, J=8.1 Hz, 2H), 7.65-7.47 (m, 8H), 7.24 (s, 2H), 7.17 (d, J=8.0 Hz, 2H), 7.14-7.06 (m, 5H), 6.96 (s, 2H), 6.76 (s, 2H), 6.68 (d, J=11.0 Hz, 2H), 3.77 (s, 8H), 3.71-3.54 (m, 12H), 3.54-3.43 (m, 2H), 3.37 (d, J=7.0 Hz, 2H), 3.32 (d, J=6.8 Hz, 2H), 2.28 (br, 10H), 2.00 (m, 2H), 1.84 (d, J=11.7 Hz, 2H), 1.65 (br, 10H), 1.39 (d, J=12.5 Hz, 2H), 1.24 (s, 2H).

To a solution of compound 15-6 (100 mg, 0.07 mmol) in $CH_2Cl_2$ was added DM-1 at room temperature during a 0.5-hour period. $CH_2Cl_2$ was removed. The crude residue was purified by flash chromatography over silica gel to give compound 15 (78 mg, 0.03 mmol, 50%) $^1$H NMR (400 MHz, $CDCl_3$) δ 8.48 (d, J=4.7 Hz, 4H), 7.71 (d, J=8.0 Hz, 2H), 7.59 (dt, J=17.1, 4.4 Hz, 8H), 7.30-7.04 (m, 11H), 6.95 (d, J=14.6 Hz, 2H), 6.82 (dd, J=7.3, 1.5 Hz, 1H), 6.77 (s, 2H), 6.68 (d, J=11.0 Hz, 1H), 6.65-6.59 (m, 1H), 6.41 (dd, J=15.2, 11.2 Hz, 2H), 6.27 (s, 1H), 6.12 (s, 1H), 5.65 (dd, J=14.6, 10.0 Hz, 2H), 5.35 (d, J=12.4 Hz, 1H), 4.76 (d, J=11.8 Hz, 1H), 4.56 (s, 1H), 4.27 (t, J=11.2 Hz, 2H), 4.10 (s, 1H), 3.97 (s, 4H), 3.78 (s, 8H), 3.74-3.55 (m, 14H), 3.51 (t, J=5.0 Hz, 2H), 3.49-3.43 (m, 2H), 3.39 (s, 2H), 3.31 (s, 3H), 3.18 (d, J=0.9 Hz, 4H), 3.10 (d, J=8.2 Hz, 2H), 3.00 (d, J=9.4 Hz, 2H), 2.84 (s, 4H), 2.61 (m, 3H), 2.37 (dd, J=6.1, 3.8 Hz, 1H), 2.33 (dd, J=6.1, 3.8 Hz, 2H), 2.19 (d, J=7.7 Hz, 1H), 2.15 (s, 1H), 2.03 (s, 8H), 1.83 (d, J=12.5 Hz, 2H), 1.66 (s, 4H), 1.53 (s, 1H), 1.45-1.37 (m, 4H), 1.31-1.26 (m, 8H), 1.24 (s, 3H), 0.93 (d, J=12.4 Hz, 2H), 0.86 (t, J=6.8 Hz, 1H), 0.79 (s, 3H). ESI-MS $C_{110}H_{135}Cl_2N_{13}O_{18}S^+$: 2027.91, found: 2029.00 (M+H$^+$). HPLC Purity: 97%.

Synthesis of Compound 16

Scheme 29

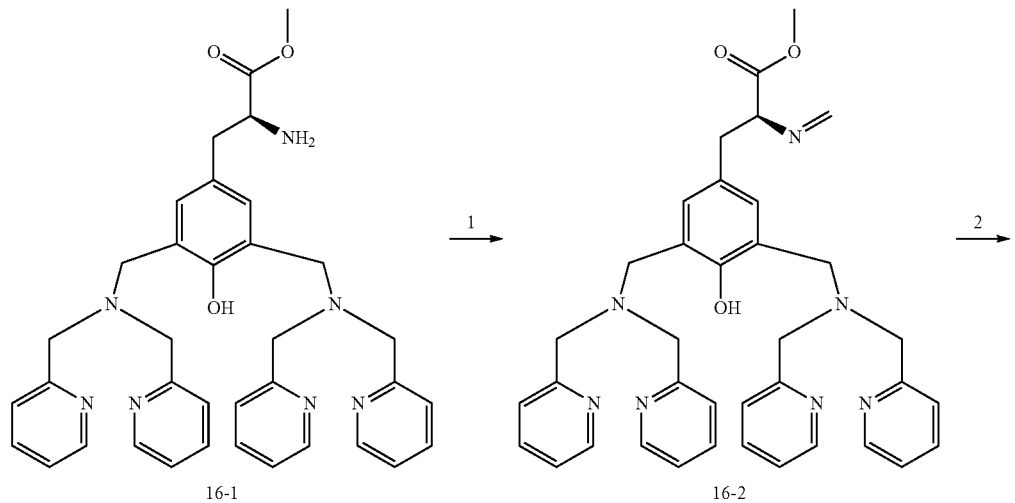

16-1         16-2

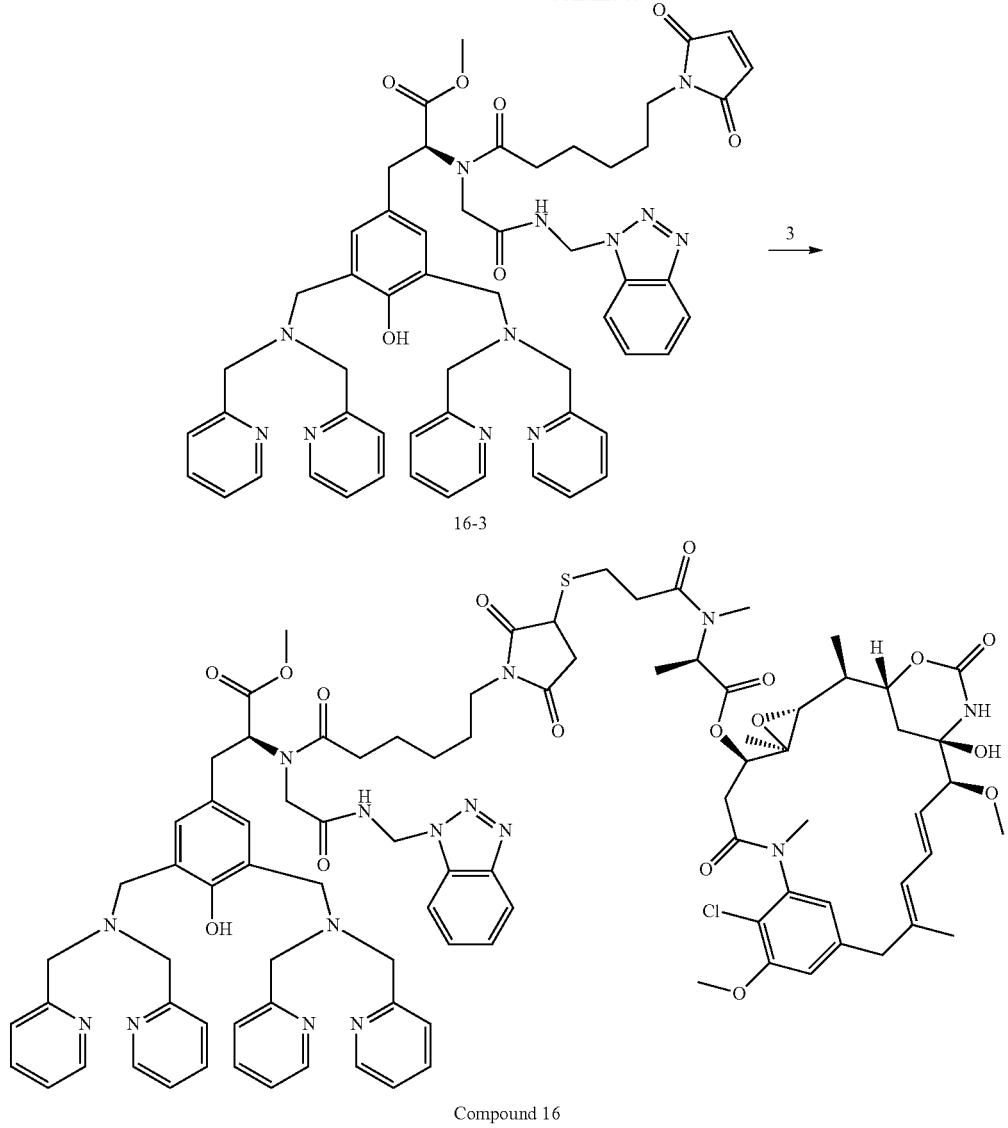

Compound 16

Scheme 29. Reagents and conditions for preparing compound 16: (1) formaldehyde, EtOH, 110° C., 16 hr. (2) 6-maleimidocaproic acid, 1-(isocyanomethyl)-1H-benzotriazole, TFE, 2 hr, 13%. (3) DM-1, DCM, 3 hr, 28%.

Compound 16-1 (533.6 mg, 0.86 mmol) was dissolved in 4.5 mL EtOH, and the formaldehyde (0.19 mL, 2.58 mmol) was added. The reaction solution was heated at 110° C. for 16 hours. EtOH was then removed. The residue was extracted with DCM and H$_2$O, the organic extracts were collected, dried with Na$_2$SO$_4$, filtered, and concentrated to give compound 16-2 (522.8 mg).

A mixture of compound 16-2 (522.8 mg, 0.83 mmol), 1-(isocyanomethyl)-1H-benzotriazole (131.3 mg, 0.83 mmol) and 6-maleimidocaproic acid (175.3 mg, 0.83 mmol) was dissolved in 8.0 mL TFE and stirred 2 hours at room temperature. TFE was removed and the residue was purified by reverse phase column chromatography (dry loading; 50% to 60% MeOH in H$_2$O as gradient eluents) to give compound 16-3 as a yellow oil (60.6 mg, 13% over 2 steps). $^1$H NMR (400 MHz, CDCl$_3$): δ 9.62 (t, J=6.4 Hz, 1H), 8.49 (dd, J=9.6, 4.8 Hz, 4H), 8.03 (d, J=8.0 Hz, 1H), 7.78 (d, J=8.4 Hz, 1H), 7.63-7.60 (m, 5H), 7.58-7.34 (m, 7H), 7.12-7.09 (m, 5H), 6.93 (s, 2H), 6.05 (d, J=6.8 Hz, 2H), 3.86-3.69 (m, 18H), 3.60-3.49 (m, 2H), 3.37 (t, J=7.2 Hz, 2H), 3.16 (d, J=4.8 Hz, 2H), 1.38-1.29 (m, 4H), 0.90-0.85 (m, 2H).

A mixture of compound 16-3 (111.2 mg, 0.11 mmol) and DM-1 (81.2 mg, 0.11 mmol) was dissolved in 1 mL DCM and stirred 3 hours at room temperature. DCM was removed, and the residue was purified by reverse phase column chromatography (dry loading; 70% to 100% MeOH in H$_2$O as gradient eluents) to give compound 16 as a white solid (52.9 mg, 28%). $^1$H NMR (400 MHz, CDCl$_3$): δ 9.59 (s, 1H), 8.48 (d, J=4.4 Hz, 4H), 8.01 (d, J=8.4 Hz, 1H), 7.78 (d, J=8.4 Hz, 1H), 7.59 (t, J=7.6 Hz, 4H), 7.42 (d, J=7.6 Hz, 4H), 7.42 (t, J=7.6 Hz, 1H), 7.36 (t, J=7.6 Hz, 1H), 7.11 (t, J=6.0 Hz, 4H), 6.93 (s, 2H), 6.84 (d, J=8.0 Hz, 1H), 6.72 (t, J=4.8 Hz, 1H), 6.65 (d, J=4.8 Hz, 1H), 6.43 (dd, J=14.8, 11.6 Hz, 1H), 6.36 (s, 1H), 6.04 (s, 2H), 5.69 (dd, J=14.8, 8.8 Hz, 1H), 5.43 (d, J=6.8 Hz, 1H), 4.78 (d, J=11.6 Hz, 1H), 4.28 (t, J=11.2 Hz, 1H), 4.28 (t, J=11.2 Hz, 1H), 4.07 (s, 1H), 3.98 (s, 3H), 3.82~3.65 (m, 17H), 3.56~3.45 (m, 3H), 3.32~2.85 (m, 13H), 3.21 (s, 3H), 3.03 (d, J=9.6 Hz, 1H), 2.85 (s, 3H), 2.62 (t, J=14.0 Hz, 2H), 2.62 (t, J=12.4 Hz, 1H), 2.38-2.30 (m, 1H), 2.18 (d, J=14.0 Hz, 1H), 1.88~1.26 (m, 13H), 1.65 (s, 3H), 1.56 (d, J=12.8 Hz, 1H), 0.88~0.81 (m, 2H), 0.81 (s, 3H). ESI-MS C$_{90}$H$_{106}$ClN$_{15}$O$_{17}$S: 1735.73, found: 1737.37 (M+H$^+$)$^+$, 1759.20 (M+Na$^+$)$^+$. Purity: 95%.

Synthesis of Compound 17
Scheme 30
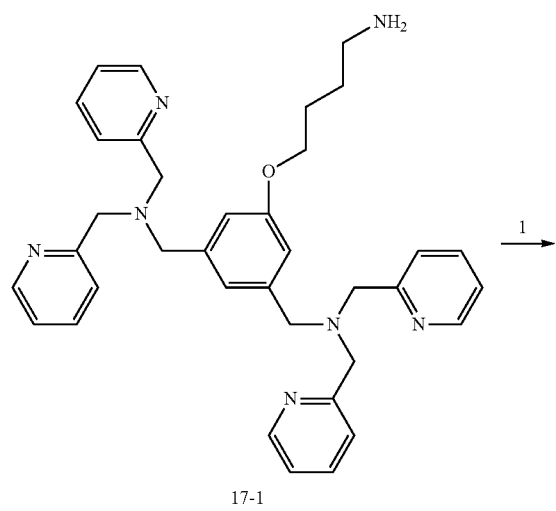
17-1
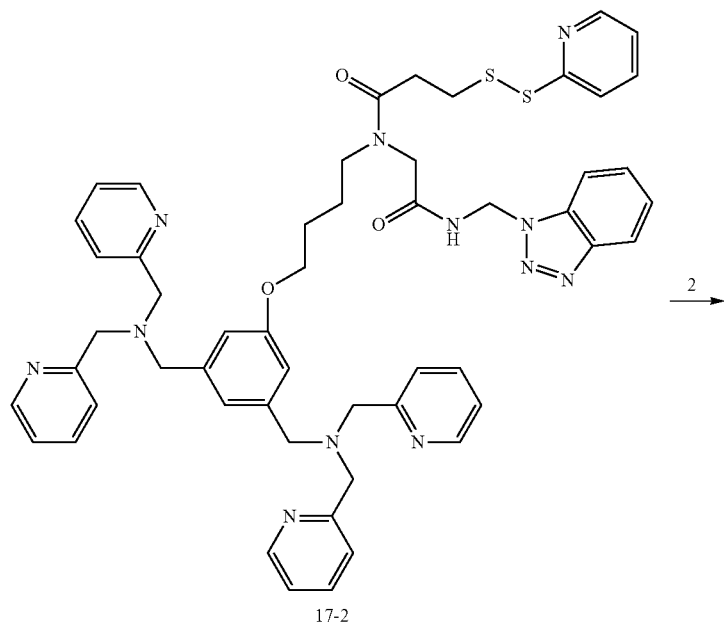
17-2

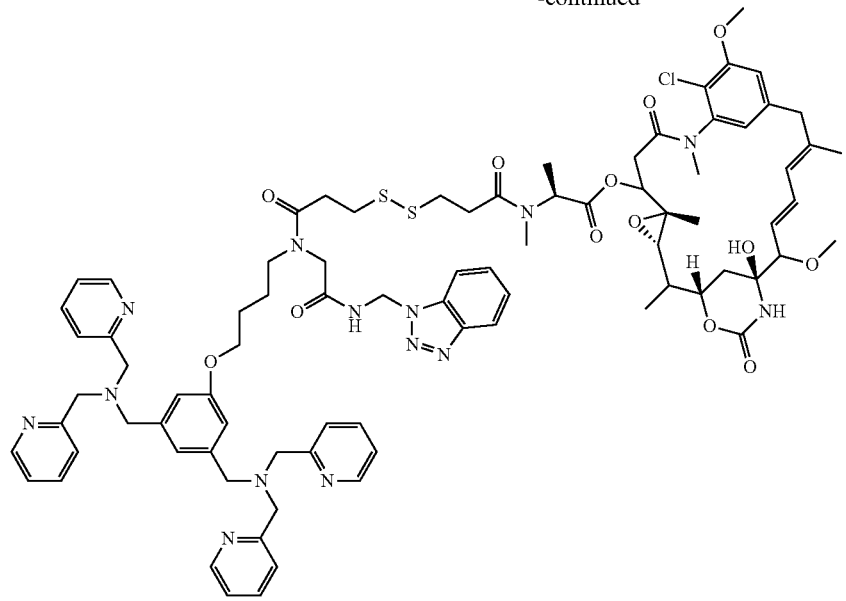

Compound 17

Scheme 30. Reagents and conditions for preparing compound 17: (1) formaldehyde, 3-(2-pyridyldithio) propanic acid, 1-(isocyanomethyl)-1H-benzotriazole, MeOH, 16 hr, 54%. (2) DM-1, DCM, 35° C., 15 hr.

A mixture of compound 17-1 (146.3 mg, 0.25 mmol), 1-(isocyanomethyl)-1H-benzotriazole (39.5 mg, 0.25 mmol), 3-(2-pyridyldithio) propanic acid (53.8 mg, 0.25 mmol) and formaldehyde (0.02 mL, 0.25 mmol) was dissolved in 2.5 mL MeOH and stirred overnight at room temperature. MeOH was removed and the residue was purified by reverse phase column chromatography (dry loading; 50% to 90% MeOH in H$_2$O as gradient eluents) to give compound 17-2 as a yellow oil (131.9 mg, 54%). $^1$H NMR (300 MHz, CDCl$_3$): δ 8.48 (d, J=4.5 Hz, 4H), 8.44-8.39 (m, 2H), 7.98 (t, J=7.2 Hz, 1H), 7.88 (t, J=8.4 Hz, 1H), 7.66-7.58 (m, 10H), 7.46 (d, J=6.9 Hz, 1H), 7.33 (d, J=6.9 Hz, 1H), 7.14 (t, J=6.3 Hz, 4H), 7.08 (s, 1H), 6.80 (s, 2H), 6.06 (d, J=6.9 Hz, 2H), 4.01 (s, 2H), 3.85-3.30 (m, 8H), 3.79 (s, 8H), 3.65 (s, 4H), 3.03 (t, J=6.9 Hz, 2H), 2.82 (t, J=6.9 Hz, 2H).

To a solution compound 17-2 (0.06 mmol, 53.7 mg) in CH$_2$Cl$_2$ (1.0 mL) was added DM-1 (0.06 mmol, 46.8 mg) and the reaction mixture was stirred at 35° C. for 15 hours. The solvent was removed in vacuo. The residue was purified by flash chromatography over silica gel with Methanol/CH$_2$Cl$_2$ (7/93) to give compound 17 as a pale yellow oil (49.7 mg, 56%). $^1$H NMR (400 MHz, CDCl$_3$): δ 8.50 (s, 4H), 8.01-7.96 (m, 2H), 7.86 (d, J=7.6 Hz, 1H), 7.68-7.52 (m, 8H), 7.45 (t, J=3.4 Hz, 1H), 7.31 (t, J=7.8 Hz, 1H), 7.14 (s, 5H), 6.84 (s, 1H), 6.78 (s, 2H), 6.65 (s, 1H), 6.42 (dd, J=15.2, 11.6 Hz, 1H), 6.26 (s, 1H), 6.05 (d, J=5.2 Hz, 2H), 5.64 (dd, J=20, 12.4 Hz, 1H), 5.30 (br, 1H), 4.84 (d, J=12.4 Hz, 1H), 4.32 (t, J=12.4 Hz, 1H), 4.01 (s, 2H), 3.97 (s, 3H), 3.83 (s, 2H), 3.80 (s, 8H), 3.69-3.58 (m, 5H), 3.46 (d, J=12.0 Hz, 1H), 3.37 (s, 2H), 3.29 (s, 1H), 3.26 (s, 3H), 3.23 (s, 3H), 3.12 (d, J=13.2 Hz, 1H), 3.01 (d, J=8.8 Hz, 1H), 2.99-2.90 (m, 1H), 2.87 (s, 3H), 2.84-2.55 (m, 7H), 2.19 (d, J=14.0 Hz, 1H), 1.76-1.17 (m, 15H), 0.91-0.83 (m, 3H), 0.82 (s, 3H). ESI-MS C$_{83}$H$_{99}$ClN$_{14}$O$_{13}$S$_2$: 1598.66, found: 800.8 (M+2H$^+$)$^{2+}$. Purity: 95%.

Synthesis of Compound 18

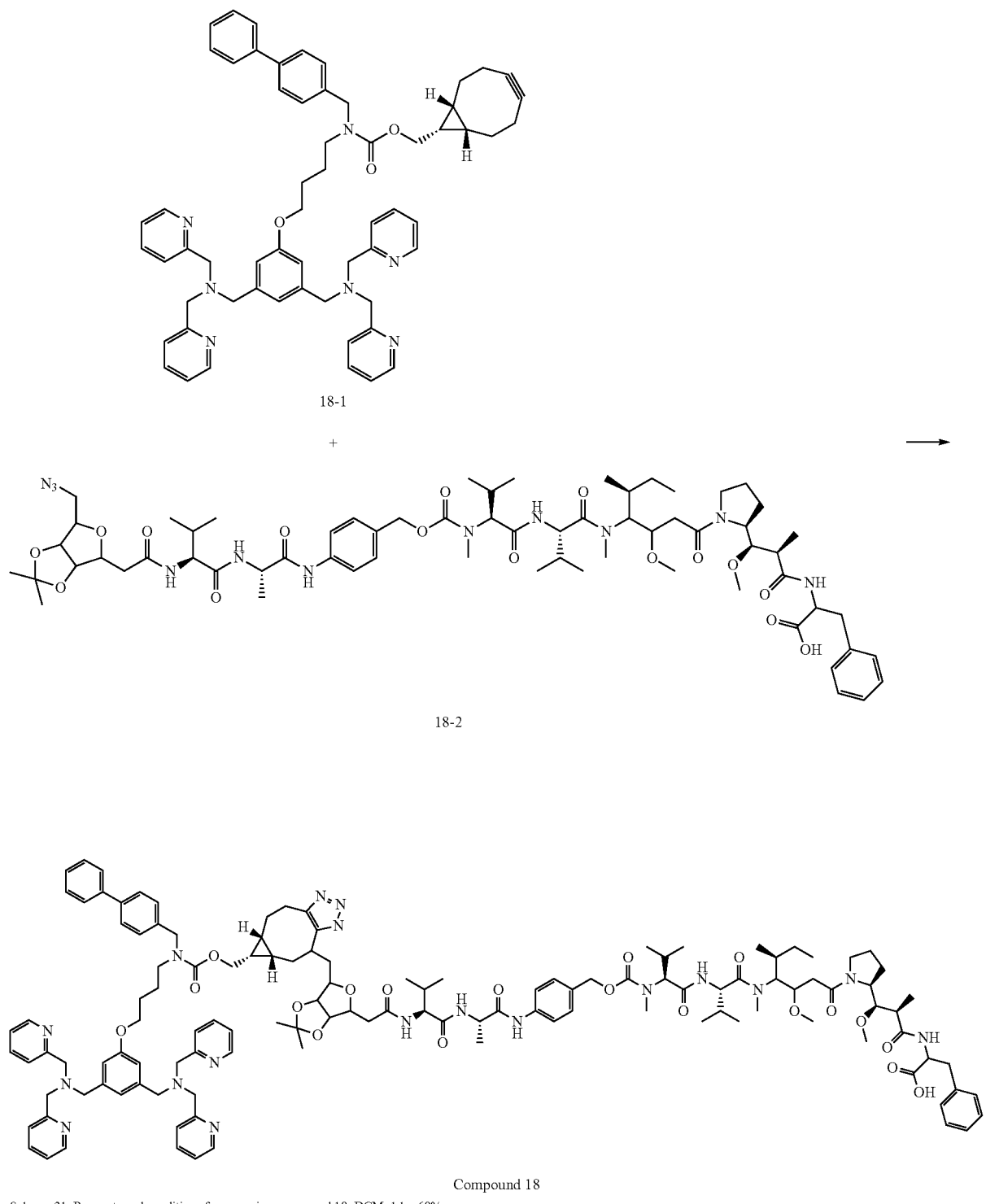

Scheme 31. Reagents and conditions for preparing compound 18: DCM, 1 hr, 68%.

A mixture of compound 18-1 (55.5 mg, 0.043 mmol) and compound 18-2 (40.0 mg, 0.043 mmol) was dissolved in DCM and stirred overnight. DCM was then removed. The residue was purified by flash chromatography over silica gel eluting with MeOH/CH$_2$Cl$_2$ (12/88) to give compound 18 (64.91 mg, 68.0%). ESI-MS C$_{125}$H$_{164}$N$_{18}$O$_{19}$$^{2+}$: 1111.1221, found: 1111.15 (M+2H$^+$)$^{2+}$.

Synthesis of Compound 19

Scheme 32
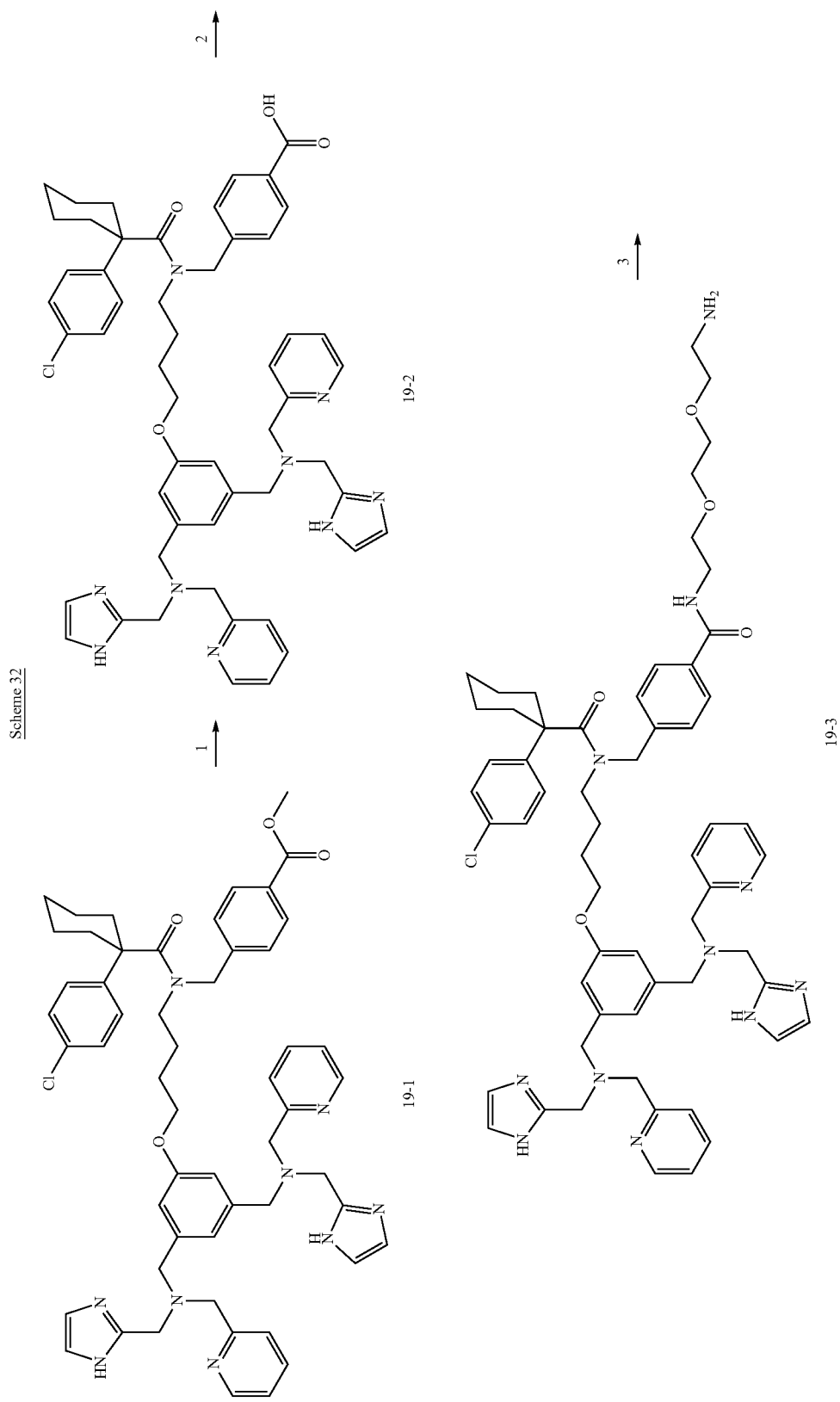

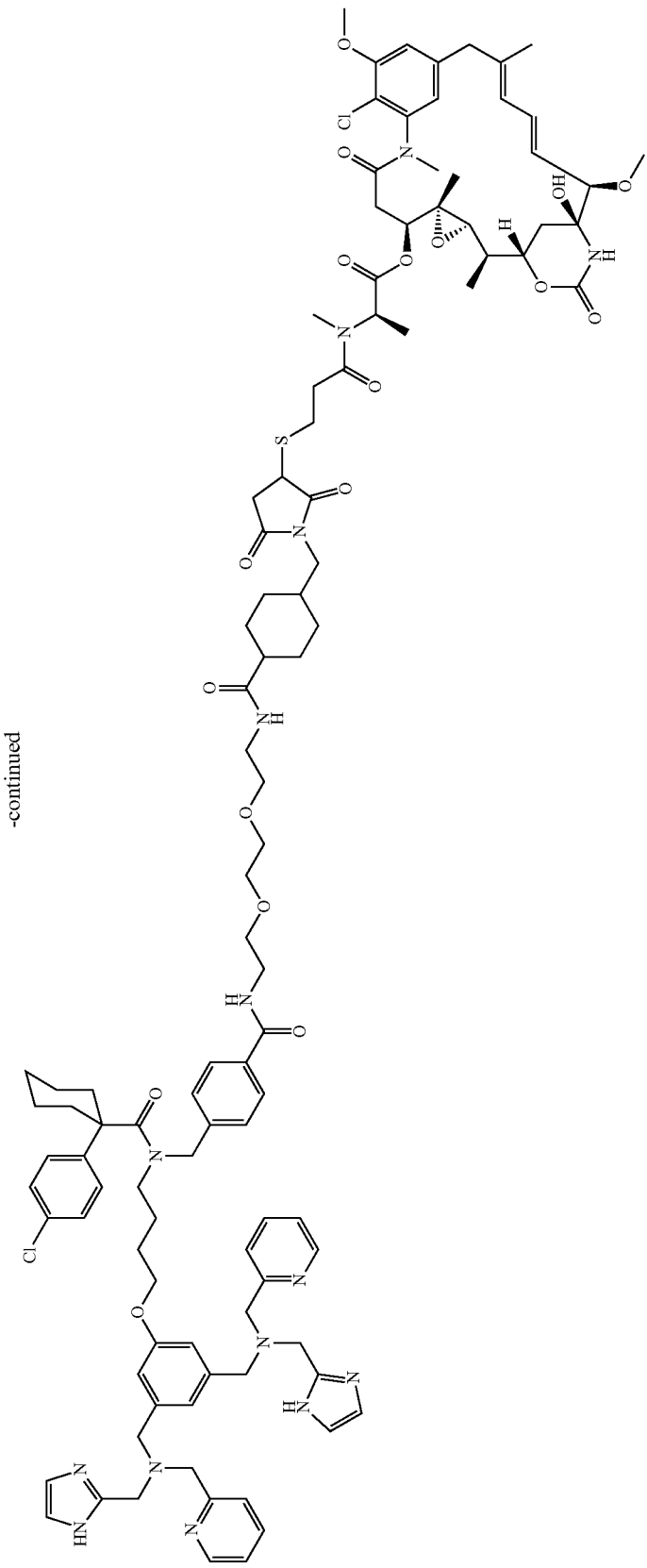
Compound 19
Scheme 32. Reagents and condition for preparing compound 19: (1). LiOH, MeOH. (2). {2-[2-(2-Amino-ethoxy)-ethoxy]-ethyl}-carbamic acid tert-butyl ester, HOBt, EDCI, DCM; SMCC, DIPEA, DMF. (3). DM-1, DCM.

To a solution of compound 19-1 (500 mg, 0.53 mmol) in 100 mL MeOH was added 0.5 M LiOH (aq.). The reaction mixture was stirred at room temperature for 15 hours. MeOH and water were removed to give compound 19-2 as a yellowish powder (400 mg, 0.43 mmol, 81%).

Compound 19-2 (250 mg, 0.27 mmol) was dissolved in DMF at room temperature. 1-Ethyl-3-(3-dimethylaminopropyl)carbodiimide (EDCI, 80 mg, 0.51 mmol), hydroxybenzotriazole (HOBt, 80 mg, 0.59 mmol), and {2-[2-(2-Aminoethoxy)-ethoxy]-ethyl}-carbamic acid tert-butyl ester (150 mg, 0.60 mmol) were added and the reaction solution was stirred at 50° C. for 15 hours. The solution was quenched with HCl (1 M, 100 ml, aq.). The protonated product was extracted with 100 mL $CH_2Cl_2$. The aqueous layer was neutralized and extracted with 100 mL $CH_2Cl_2$. The organic extracts were collected, dried with $Na_2SO_4$, filtered, and concentrated. Purification of the crude residue by flash chromatography over silica gel gave compound 19-3 (78 mg, 0.07 mmol, 25%).

To a solution of compound 19-3 (78 mg, 0.07 mmol) in DMF was added N,N-Diisopropylethylamine (DIPEA, 4 drop) and succinimidyl 4-(N-maleimidomethyl)cyclohexane-1-carboxylate (SMCC, 35 mg, 0.10 mmol). The reaction solution was stirred at room temperature for 2 hours. The aqueous layer was neutralized and extracted with 100 mL $CH_2Cl_2$. The organic extract was dried with $Na_2SO_4$, filtered, and concentrated. The residue was dissolved in $CH_2Cl_2$. To the resultant solution was added DM-1 at room temperature. The reaction solution was stirred at room temperature for 1 hour. $CH_2Cl_2$ was removed and the crude product was purified by flash chromatography over silica gel to give compound 19 (115 mg, 0.05 mmol, 71%).
$^1$H NMR (400 MHz, $CDCl_3$) δ 8.55 (d, J=4.0 Hz, 2H), 7.73 (d, J=8.0 Hz, 2H), 7.66 (dd, J=7.6, 6.1 Hz, 2H), 7.52 (d, J=7.6 Hz, 2H), 7.20 (dd, J=12.1, 8.0 Hz, 6H), 6.99 (s, 5H), 6.82 (d, J=7.3 Hz, 1H), 6.69 (d, J=11.5 Hz, 1H), 6.63 (d, J=6.1 Hz, 1H), 6.59 (s, 2H), 6.41 (dd, J=15.1, 11.3 Hz, 2H), 6.30 (s, 1H), 6.25 (d, J=5.6 Hz, 1H), 5.66 (dd, J=15.1, 6.4 Hz, 1H), 5.38 (d, J=6.5 Hz, 1H), 4.76 (d, J=9.5 Hz, 1H), 4.56 (s, 1H), 4.32-4.22 (m, 1H), 3.98 (s, 3H), 3.88 (s, 2H), 3.77 (s, 4H), 3.71-3.48 (m, 20H), 3.46 (d, J=8.9 Hz, 1H), 3.39 (s, 3H), 3.34 (s, 1H), 3.30 (s, 3H), 3.18 (s, 3H), 3.13-3.03 (m, 3H), 3.00 (d, J=9.8 Hz, 2H), 2.84 (s, 4H), 2.66-2.54 (m, 4H), 2.41-2.13 (m, 8H), 1.83 (d, J=11.7 Hz, 3H), 1.60 (br, 16H), 1.35-1.17 (m, 16H), 0.79 (s, 3H). ESI-MS $C_{106}H_{133}Cl_2N_{15}O_{18}S^+$: 2005.91, found: 2007.45 (M+H$^+$). HPLC Purity: 96%.

Synthesis of Compound 20

Scheme 33

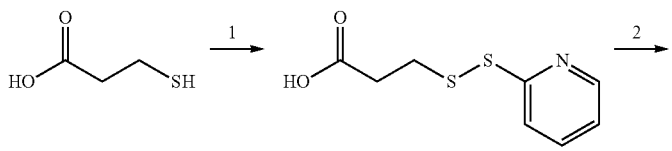

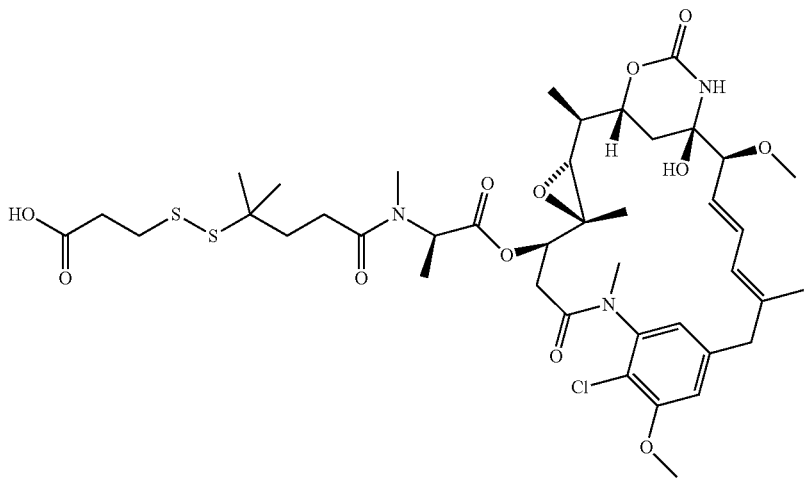

Linker d

Scheme 33. Reagents and conditions for preparing linker d: (1) 2,2'-Dipyridyl disulfide, MeOH, 15 hr, 74%.
(2) DM4, MeOH, 50 mM potassium phosphate buffer pH 7.5, rt, 15 hr, 71%.

Scheme 34
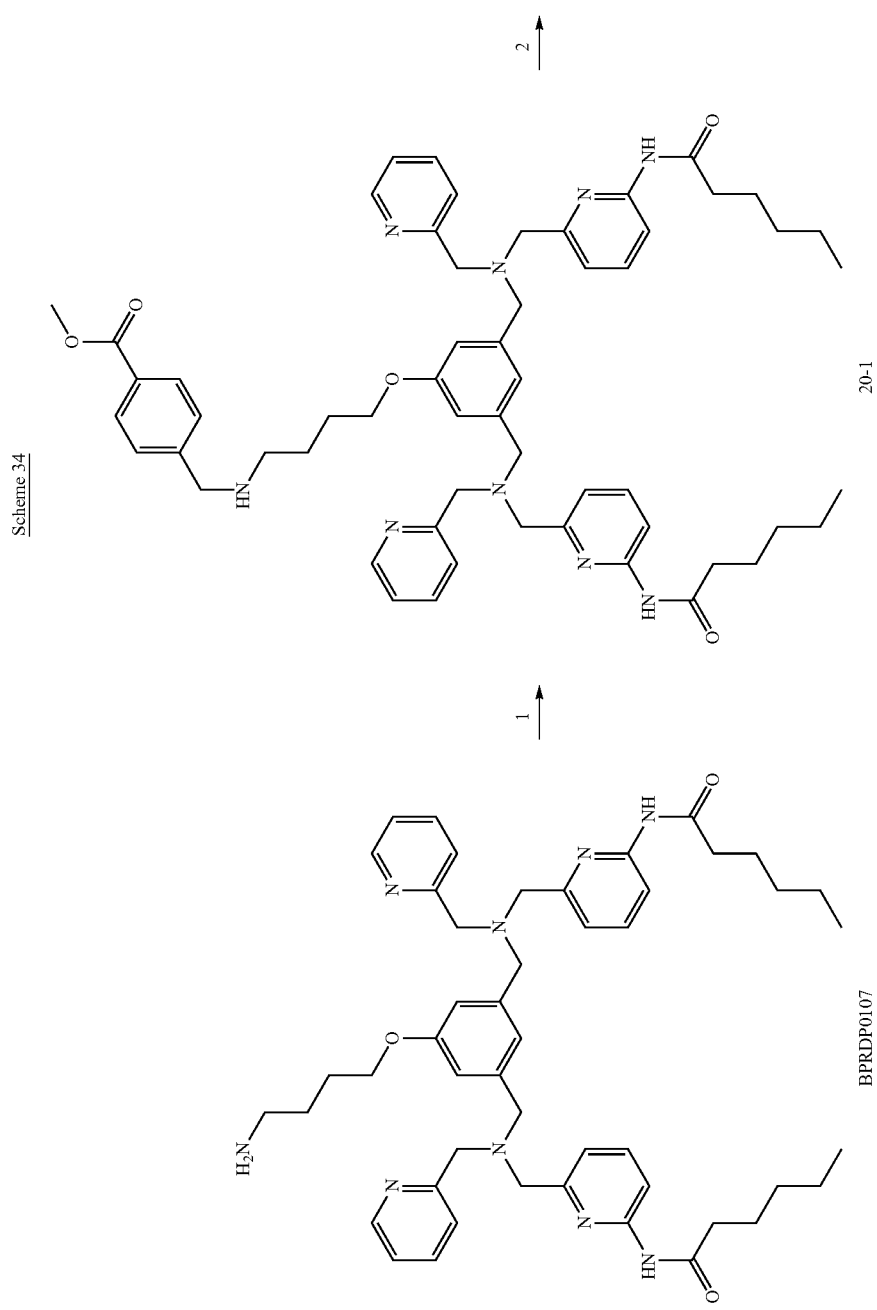

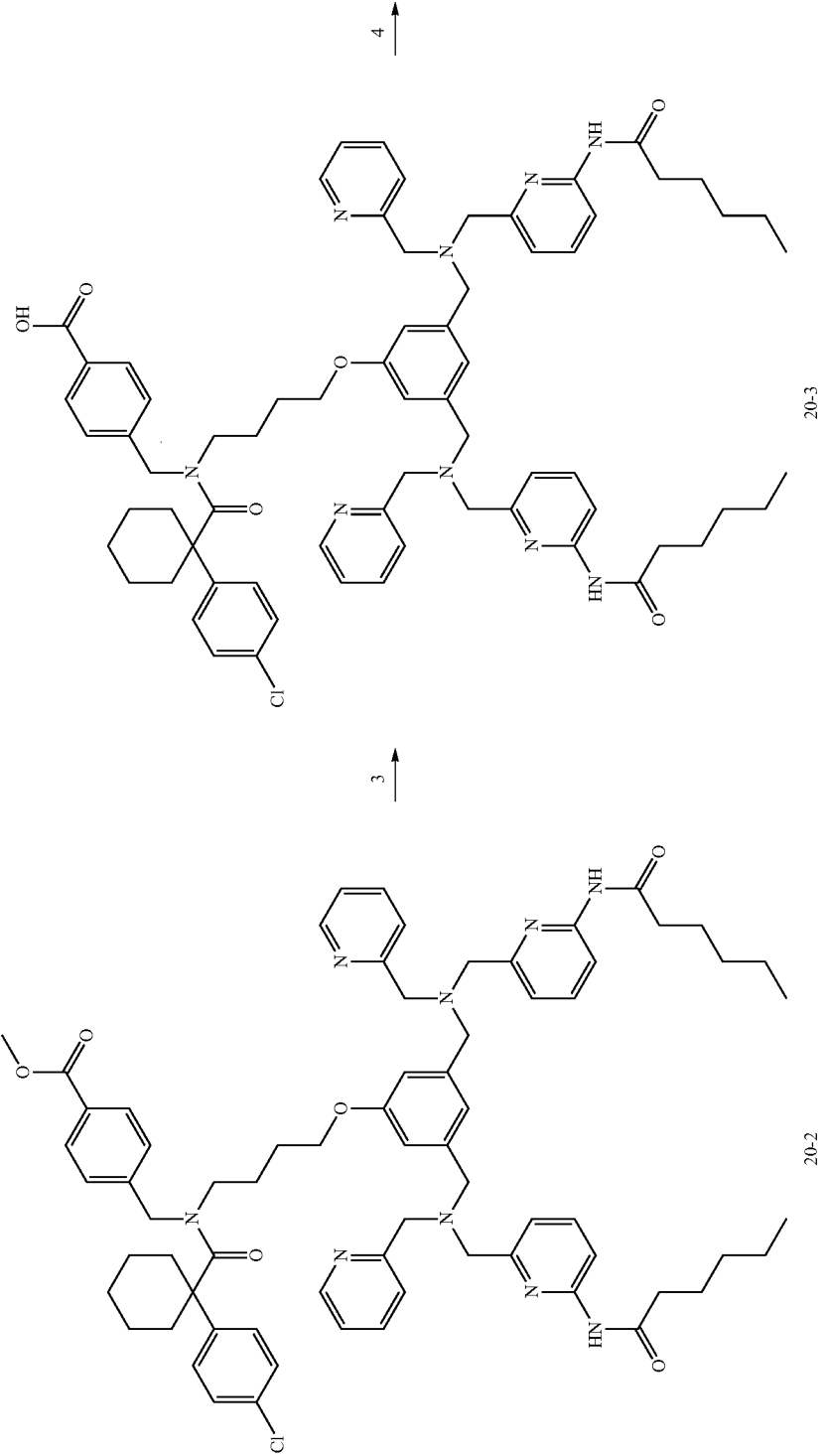

-continued
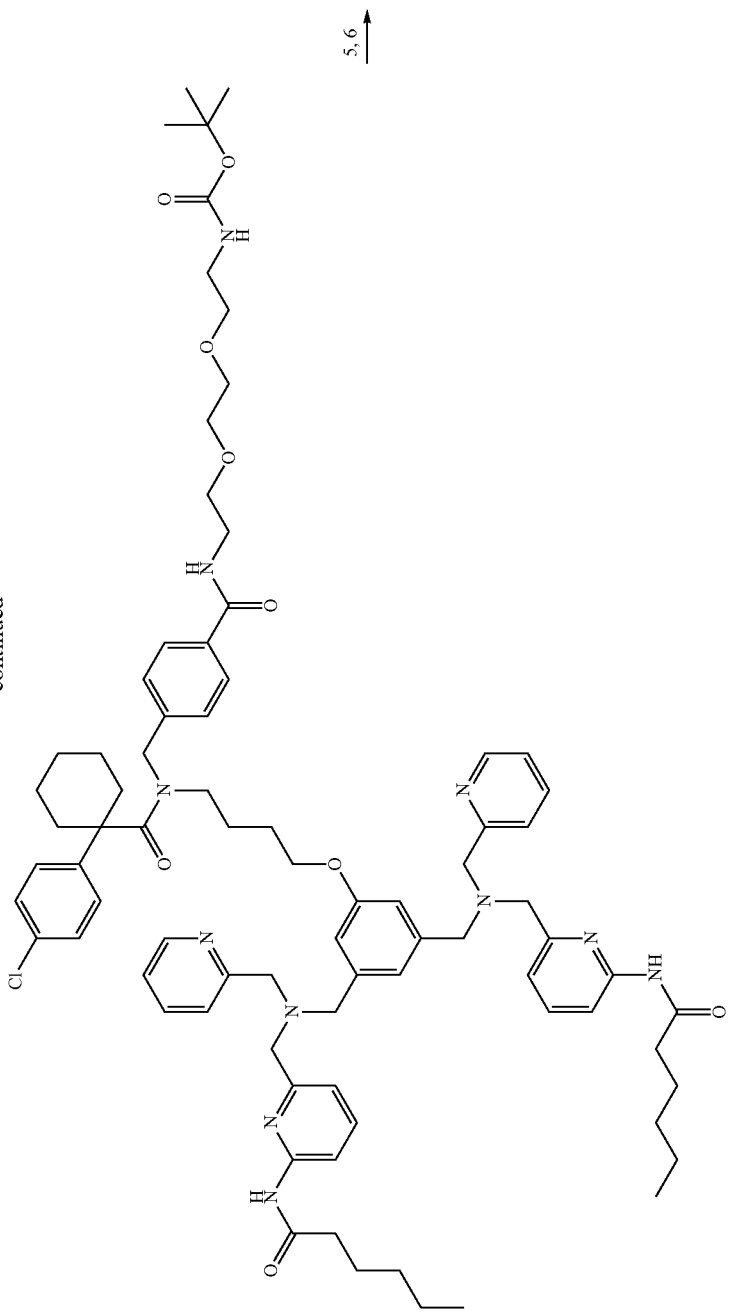
20-4

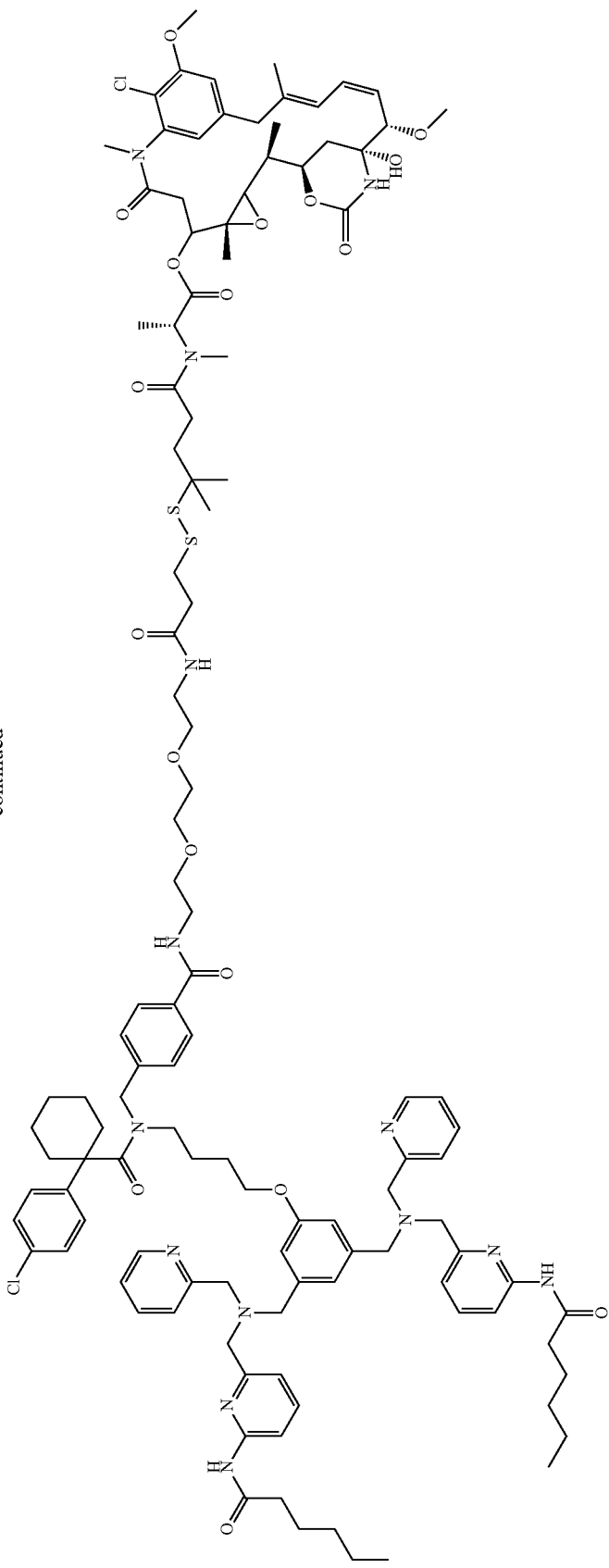
Compound 20
Scheme 34. Reagents and conditions for preparing compound 20: (1) Methyl 4-formylbenzoate, MeOH, 80° C.; NaBH4, 0° C., 66%. (2) 1-(4-Chlorophenyl)cyclohexanecarbonyl chloride, N,N,-diethylethanamine, DCM, 60%. (3) LiOH(aq), MeOH, 85%. (4) Tert-butyl (2-[2-(2-aminoethoxy)ethoxy]ethyl)carbamate, EDCI, HOBt, N-Methylmorpholine, DCM, 15 hr, 73%. (5) TFA, DCM. (6) Linker d, EDCI, HOBt, N-Methylmorpholine, DCM, overnight, 47%.

To a solution 3-mercaptopropionic acid (18.84 mmol, 2 g) in methanol (13 mL) was added 2,2'Dipyridyl disulfide (28.26 mmol, 6.23 g) and the reaction mixture was stirred at room temperature for 15 hours. MeOH was then removed in vacuo. The residue was purified by flash chromatography over silica gel with Ethyl acetate/Hexane (1/1) to give 3-(pyridin-2-yldisulfaneyl)propanoic acid a white solid (3.00 g, 74%).

To a solution 3-(pyridin-2-yldisulfanyl)-propionic acid (27.60 mg, 0.12 mmol) in MeOH (5 mL) and potassium phosphate buffer (50 mM, pH 7.5, 3.56 mL), DM4 (0.05 g, 0.06 mmol) was added. The reaction mixture was stirred at room temperature for 15 hours. The solvent was then removed in vacuo. The product was purified by flash chromatography over silica gel with Methanol/CH$_2$Cl$_2$ (3/97) to give Linker d as a white solid (0.04 g, 71%). $^1$H NMR (400 MHz, CDCl$_3$): δ 6.83 (d, J=1.2 Hz, 1H), 6.67 (d, J=10.8 Hz, 1H), 6.64 (d, J=1.2 Hz, 1H), 6.48 (s, 1H), 6.42 (dd, J=15.6, 9.2 Hz, 1H), 5.67 (dd, J=15.2, 9.2 Hz, 1H), 5.31 (br, 1H), 4.80 (dd, J=12.0, 3.2 Hz, 1H), 4.29 (t, J=12.0 Hz, 1H), 3.99 (s, 3H), 3.64 (d, J=12.8 Hz, 1H), 3.49 (d, J=9.2 Hz, 1H), 3.36 (s, 3H), 3.22 (s, 3H), 3.12 (d, J=12.8 Hz, 1H), 3.01 (d, J=9.6 Hz, 1H), 2.87 (s, 3H), 2.86 (t, J=7.2 Hz, 2H), 2.71-2.57 (m, 3H), 2.53-2.42 (m, 1H), 2.40-2.29 (m, 1H), 2.19 (dd, J=14.4, 2.8 Hz, 1H), 2.09-1.81 (m, 2H), 1.64 (s, 3H), 1.60 (d, J=13.6 Hz, 1H), 1.53-1.39 (m, 1H), 1.3 (t, J=7.2 Hz, 6H), 1.25 (s, 6H) 1.23-1.20 (m, 1H), 0.88 (t, J=6.8 Hz, 1H), 0.81 (s, 3H). ESI-MS C$_{41}$H$_{58}$ClN$_3$O$_{12}$S$_2$: 883.3, found: 882.3 (M–H$^+$)$^-$. Purity: 95%.

BPRDP0107 (2.2 g, 2.7 mmol, 1.0 eq.) and methyl 4-formylbenzoate (891.5 mg, 5.4 mmol, 2.0 eq.) were dissolved in MeOH (27.2 mL) and the reaction solution was stirred at 80° C. overnight. Sodium borohydride (410.9 mg, 10.9 mmol, 4.0 eq.) was added into the solution at 0° C. After the reaction was completed, the solvent was removed. The residue was dissolved in CH$_2$Cl$_2$ and extracted with saturated NH$_4$Cl$_{(aq.)}$. The combined organic extracts were dried over Na$_2$SO$_4$ and concentrated in vacuo. The residue was purified by flash chromatography over silica gel to give compound 20-1 (1.73 g, 66%).

To compound 20-1 (192.9 mg, 0.2 mmol, 1.0 eq.) in CH$_2$Cl$_2$ was added triethylamine (5.9 mL, 42.1 mmol, 6.0 eq.) and 1-(4-chlorophenyl)cyclohexanecarbonyl chloride (500 mg, 1.94 mmol, 5.0 eq.). The reaction solution was stirred at room temperature for 15 hours. The reaction mixture was washed with saturated NH$_4$Cl$_{(aq.)}$, dried over Na$_2$SO$_4$, and concentrated in vacuo. The residue was purified by flash chromatography over silica gel to give compound 20-2 (141.4 mg, 60%).

To compound 20-2 (948.2 mg, 0.8 mmol) in MeOH (16 mL) was added 0.5 N LiOH$_{(aq.)}$. The reaction mixture was stirred at room temperature overnight. After the reaction was completed, the solvent was removed. The residue was re-dissolved in CH$_2$Cl$_2$ and extracted with 2 N HCl$_{(aq.)}$. The combined organic extracts were dried over Na$_2$SO$_4$ and concentrated in vacuo. The residue was purified by flash chromatography over silica gel to give compound 20-3 (795.2 mg, 85%).

A mixture of compound 20-3 (795.2 mg, 0.7 mmol, 1.1 eq.), EDCI (195.1 mg, 1.0 mmol, 1.5 eq.) and HOBt (137.9 mg, 1.0 mmol, 1.5 eq.) in CH$_2$Cl$_2$ (13.7 mL) was stirred for 1 hour at room temperature. A solution of {2-[2-(2-Aminoethoxy)-ethoxy]-ethyl}-carbamic acid tert-butyl ester (253.4.0 mg, 1.0 mmol, 1.5 eq.) and N-Methylmorpholine (206.4 mg, 2.0 mmol, 3.0 eq.) in CH$_2$Cl$_2$ (2.0 mL) was added to the reaction mixture and the resultant reaction solution was stirred at room temperature for 15 hours. The reaction mixture was then washed with saturated NH$_4$Cl$_{(aq.)}$, dried over Na$_2$SO$_4$, and concentrated in vacuo. The residue was purified by flash chromatography over silica gel to give compound 20-4 (690.8 mg, 73%).

To a solution of compound 20-4 in CH$_2$Cl$_2$ (1.0 mL) was added TFA (1.0 mL). The reaction mixture was stirred at room temperature overnight. After the reaction was completed, the excess amount of TFA was removed under vacuum to give N-{2-[2-(2-aminoethoxy)ethoxy]ethyl]-4-[([4-(3,5-bis{[[{6-(hexanoylamino)pyridin-2-yl]methyl}(pyridin-2-ylmethyl)amino]methyl}phenoxy)butyl]{[1-(4-chlorophenyl)cyclohexyl]carbonyl}amino)methyl]benzamide.

A mixture of Linker d (92.6 mg, 0.1 mmol, 1.2 eq.). EDCI (42.0 mg, 0.2 mmol, 2.0 eq.) and H-OBt (29.6 mg, 0.2 mmol, 2.0 eq.) in CH$_2$Cl$_2$ was stirred (1.2 mL) for 1 hour at room temperature. A solution of N-{2-[2-(2-aminoethoxy)ethoxy]ethyl]-4-[([4-(3,5-bis{[{6-(hexanoylamino)pyridin-2-yl]methyl}(pyridin-2-ylmethyl)amino]methyl} phenoxy)butyl]{[1-(4-chlorophenyl)cyclohexyl]carbonyl}amino)methyl]benzamide (0.1 mmol, 1.0 eq.) and N-Methylmorpholine (66.6 mg, 0.7 mmol, 6.0 eq.) in CH$_2$Cl$_2$ (1.0 mL) was added to the reaction mixture. The resultant reaction solution was stirred at room temperature overnight, washed with saturated NH$_4$Cl$_{(aq.)}$, dried over Na$_2$SO$_4$, and concentrated in vacuo. The residue was purified by flash chromatography over silica gel to give compound 20 (97.3 mg, 47%). $^1$H NMR (400 MHz, CDCl$_3$): δ 8.96 (br, 2H), 8.49 (d, J=4.4 Hz, 2H), 8.13 (d, J=8.0 Hz, 2H), 7.75-7.63 (m, 4H), 7.56 (t, J=7.2 Hz, 2H), 7.49 (d, J=7.6 Hz, 2H), 7.27-7.20 (m, 6H), 7.20-7.11 (m, 4H), 6.98 (br, 1H), 6.88-6.81 (m, 2H), 6.74-6.62 (m, 4H), 6.42 (dd, J=15.1, 11.2 Hz, 1H), 6.35-6.24 (m, 2H), 5.68 (dd, J=15.1, 9.0 Hz, 1H), 5.38 (br, 1H), 4.85-4.72 (m, 1H), 4.62-4.50 (m, 1H), 4.28 (t, J=10.8 Hz, 1H), 4.19-4.04 (m, 1H), 3.98 (s, 3H), 3.92-3.83 (m, 1H), 3.78 (s, 4H), 3.73-3.68 (m, 5H), 3.68-3.60 (m, 11H), 3.58 (s, 4H), 3.54-3.39 (m, 6H), 3.32 (s, 3H), 3.21 (s, 3H), 3.12 (d, J=12.4 Hz, 1H), 3.02 (d, J=9.6 Hz, 1H), 2.89-2.83 (m, 5H), 2.66-2.56 (m, 1H), 2.52-2.44 (m, 3H), 2.36-2.26 (m, 2H), 2.20-2.15 (m, 1H), 2.08-1.98 (m, 7H), 1.88-1.81 (m, 1H), 1.64 (s, 3H), 1.58-1.45 (m, 8H), 1.32-1.20 (m, 30H), 0.84-0.80 (m, 9H). ESI-MS C$_{116}$H$_{152}$Cl$_2$N$_{14}$O$_{18}$S$_2$: 2163.0228, found: 716.5 (M+3H$^{3+}$)$^{3+}$. Purity: 95%.

Synthesis of Compound 21

Scheme 35
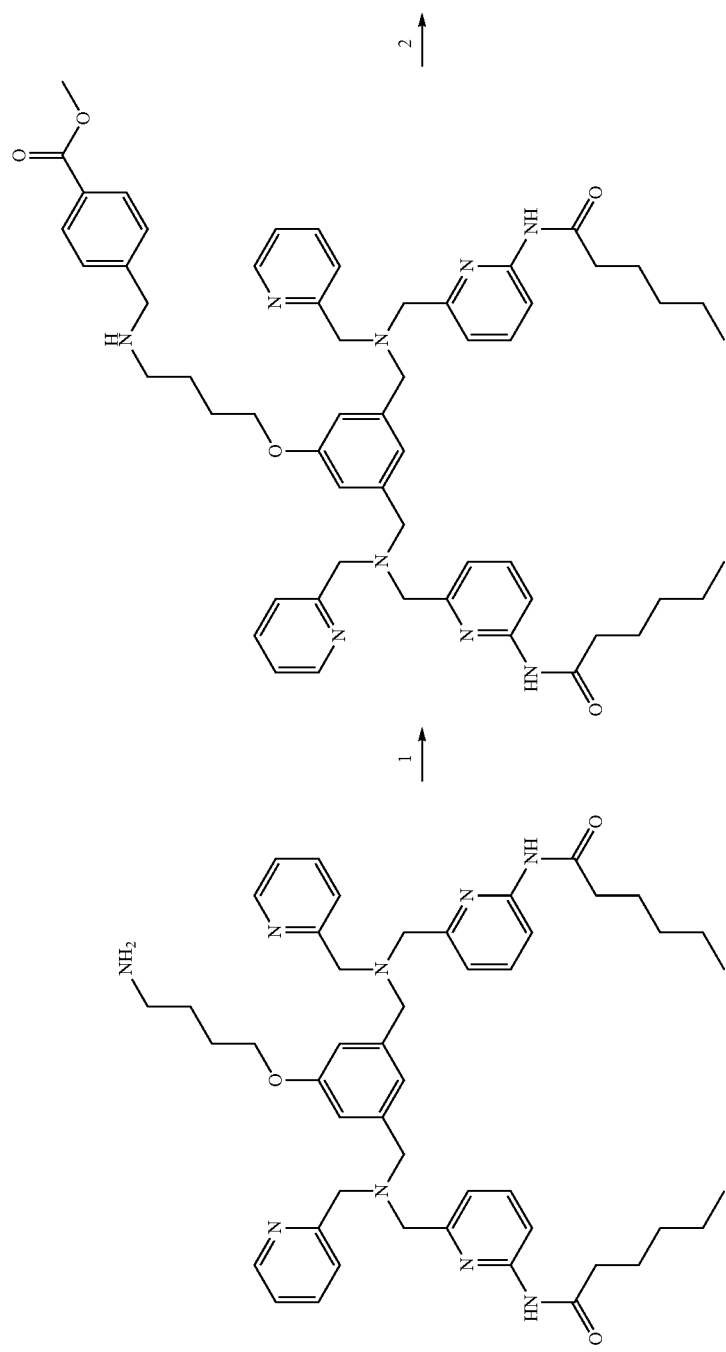

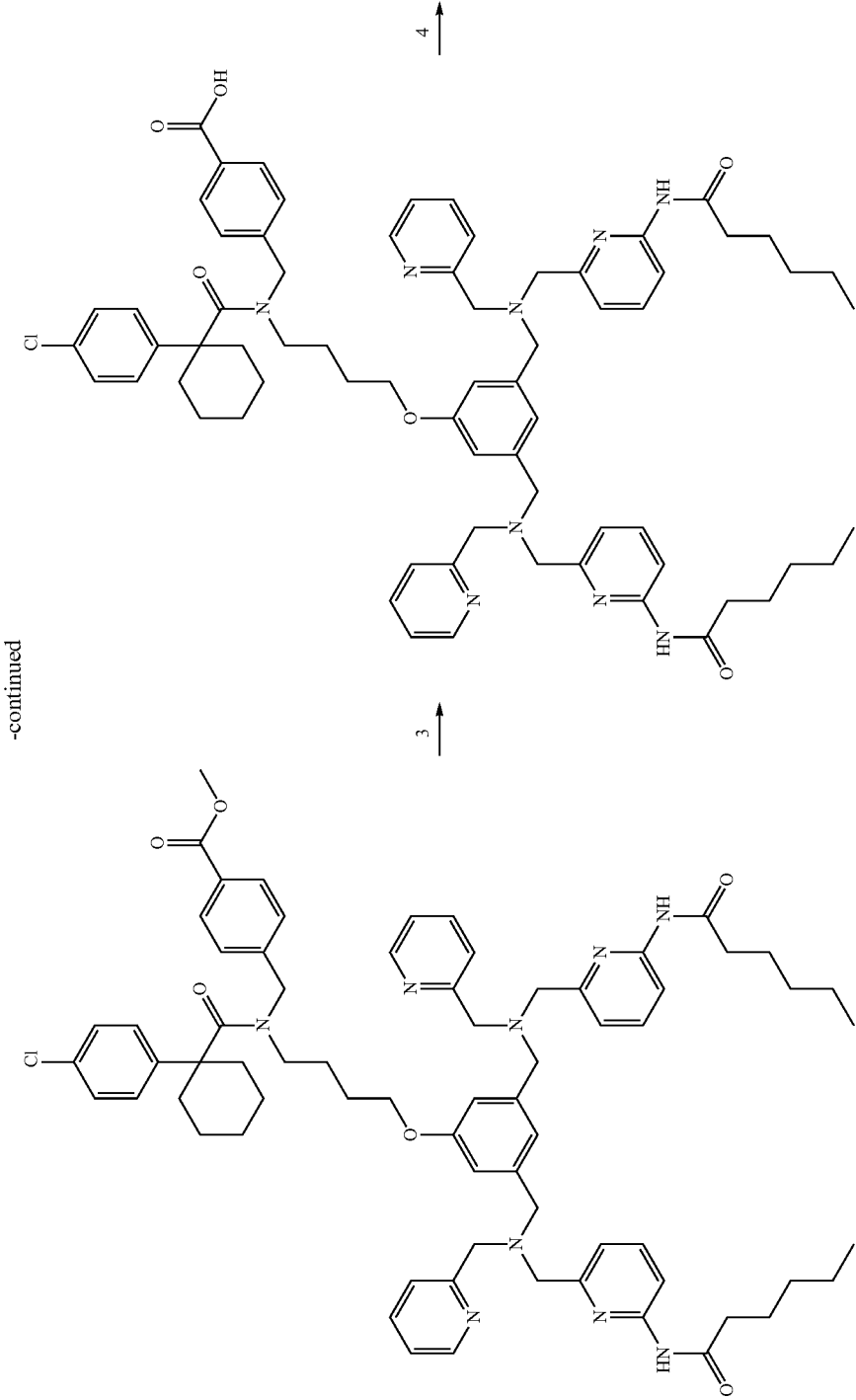

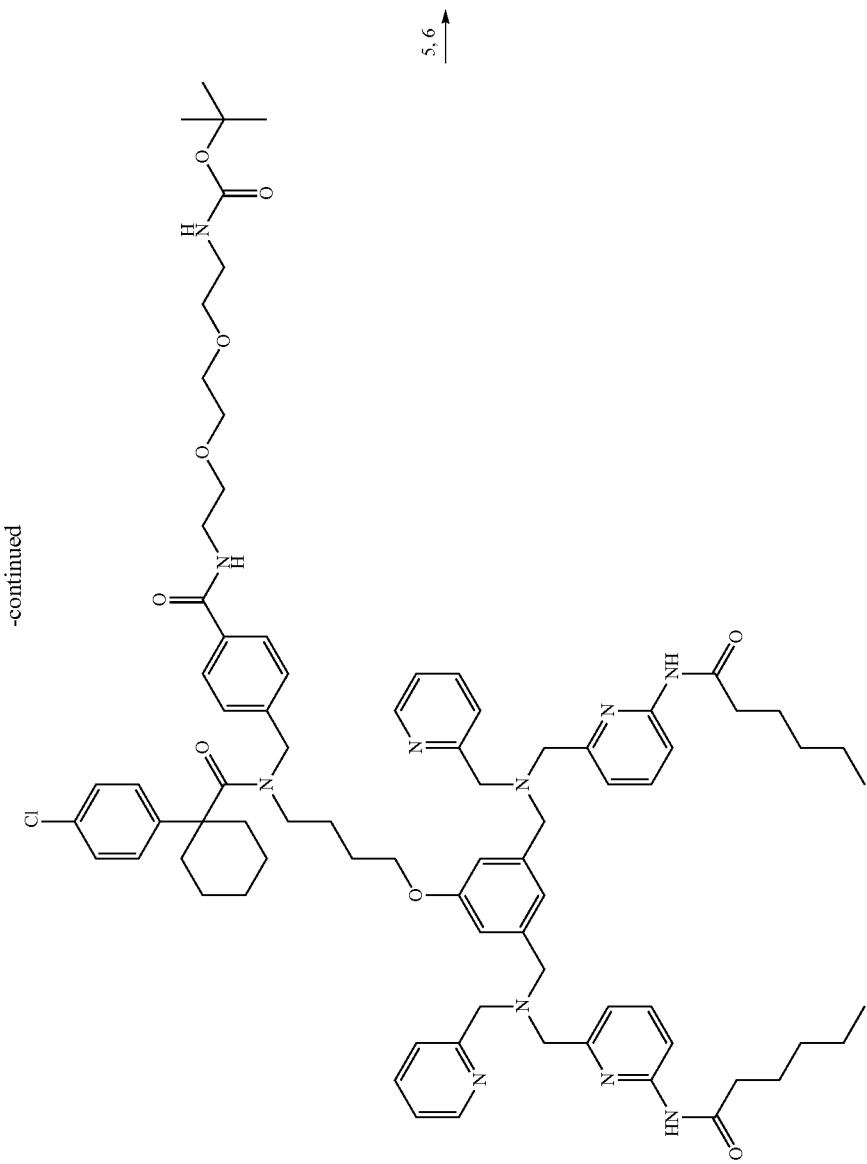

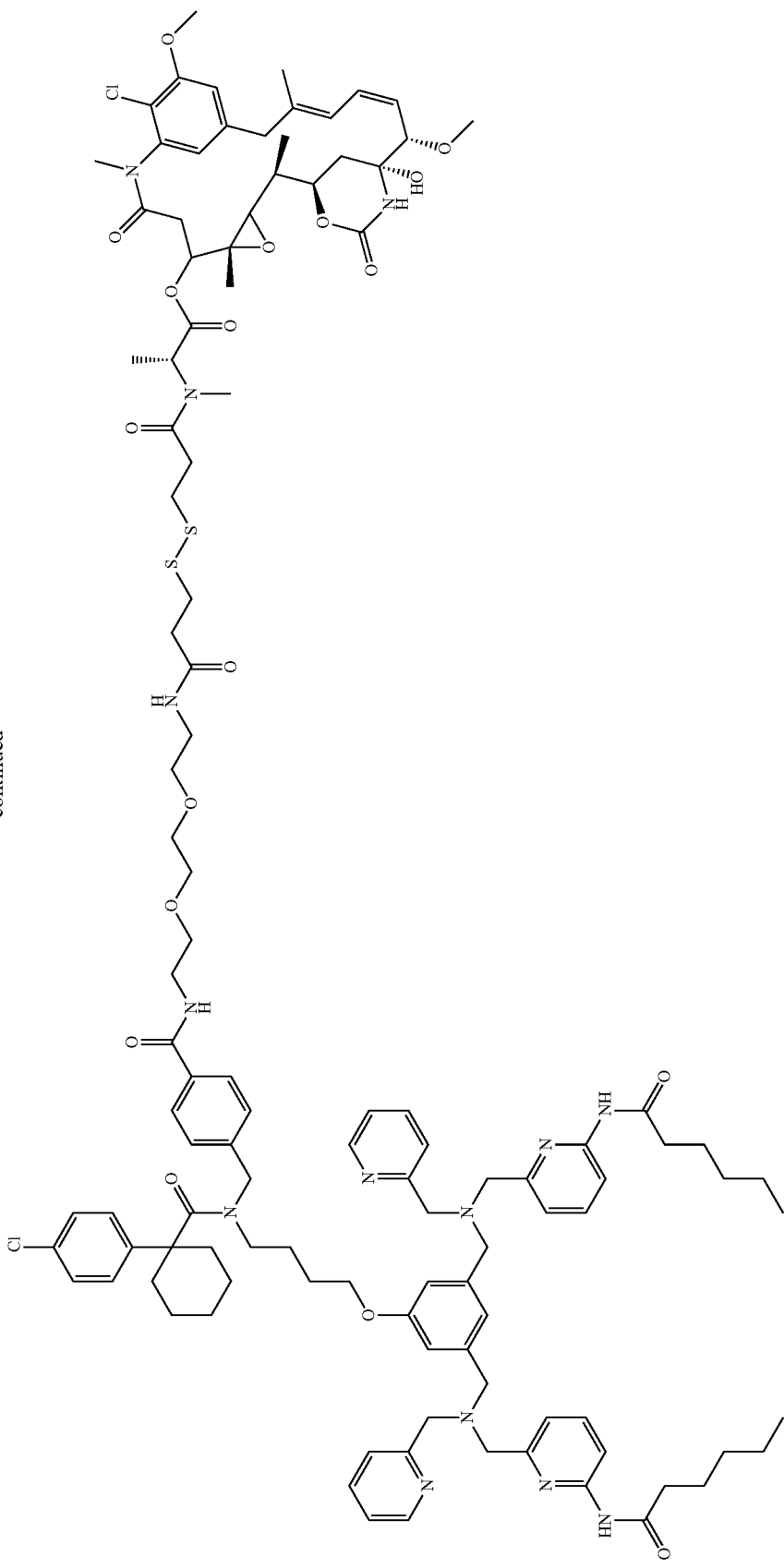
Compound 21
Scheme 35. Reagents and conditions for preparing compound 21: (1) Methyl 4-formylbenzoate, MeOH, 80° C.; NaBH₄, 0° C., 66%. (2) 1-(4-chlorophenyl)cyclohexanecarbonyl chloride, N,N-diethylethanamine, DCM, 60%. (3) LiOH(aq.), MeOH. (4) Tert-butyl {2-[2-(2-aminoethoxy)ethoxy]ethyl}carbamate, EDCI, HOBt, N-Methylmorpholine, DCM, overnight, 47%. (5) TFA, DCM, 15 hr, 73%. (6) Linker b, EDCI, HOBt, N-Methylmorpholine, DCM.

Compound 21 was prepared in a manner similar to compound 20. $^1$H NMR (400 MHz, CDCl$_3$): δ 8.95 (br, 2H), 8.49 (d, J=4.8 Hz, 2H), 8.13 (d, J=8.4 Hz, 2H), 7.74-7.64 (m, 4H), 7.56 (t, J=8 Hz, 2H), 7.49 (d, J=7.6 Hz, 2H), 7.26-7.23 (m, 6H), 7.21-7.11 (m, 4H), 6.98 (br, 1H), 6.85-6.80 (m, 2H), 6.72-6.65 (m, 3H), 6.63 (s, 1H), 6.42 (dd, J=15.1, 11.0 Hz, 1H), 6.33-6.24 (m, 2H), 5.66 (dd, J=15.1, 9.2 Hz, 1H), 5.34 (br, 1H), 4.83-4.76 (m, 1H), 4.59-4.50 (m, 1H), 4.29 (t, J=11 Hz, 1H), 4.17-4.05 (m, 1H), 3.98 (s, 3H), 3.94-3.82 (m, 1H), 3.78 (s, 4H), 3.74-3.33 (m, 22H), 3.32 (s, 3H), 3.22 (s, 3H), 3.12 (d, J=12.4 Hz, 1H), 3.02 (d, J=9.6 Hz, 1H), 2.99-2.92 (m, 1H), 2.89-2.77 (m, 8H), 2.71-2.48 (m, 5H), 2.36-2.21 (m, 2H), 2.21-2.15 (m, 1H), 2.09-1.98 (m, 4H), 1.64-1.37 (m, 18H), 1.36-1.08 (m, 20H), 0.87-0.77 (m, 9H). ESI-MS C$_{113}$H$_{146}$Cl$_2$N$_{14}$O$_{18}$S$_2$: 2120.9758, found: 708.96 (M+3H$^+$)$^{3+}$. Purity: 95%.
Synthesis of Compound 22
Scheme 36
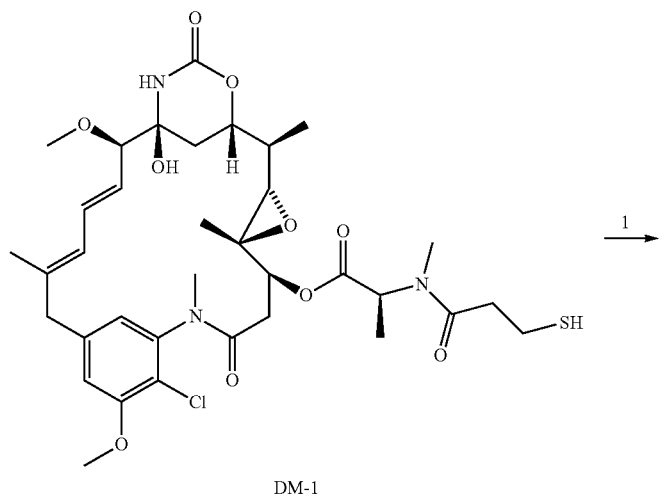
DM-1
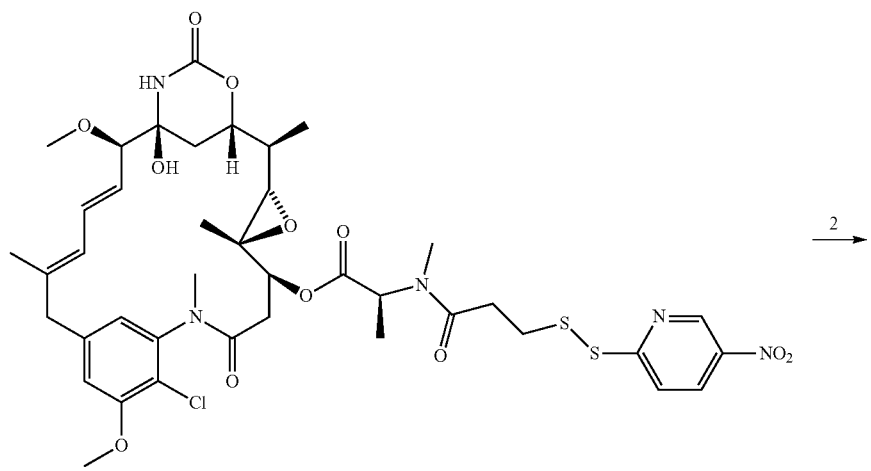

-continued
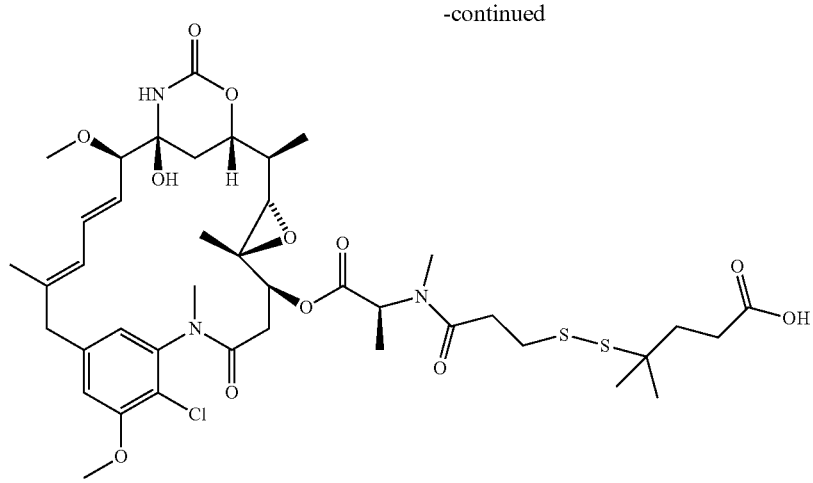
Linker c
Scheme 36. Reagents and conditions for preparing linker c: (1) 2,2'-Dithiobis(5-nitropyridine), NMM, DMF, THF, 15 hr, 83%. (2) 4-Mercapto-4-methylpentanoic acid, DMF, THF, 50 mM potassium phosphate buffer pH 7.5, rt, 15 hr, 29%.

Scheme 37
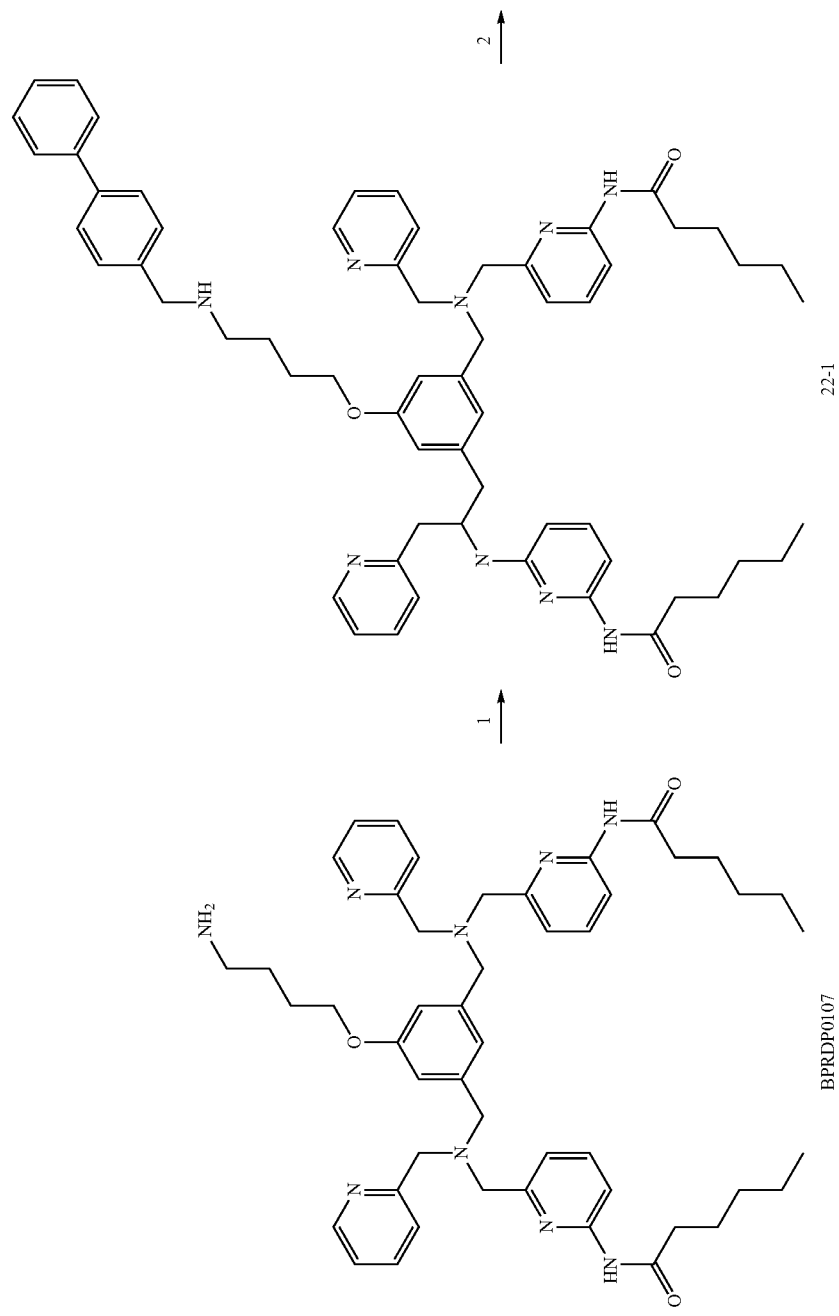

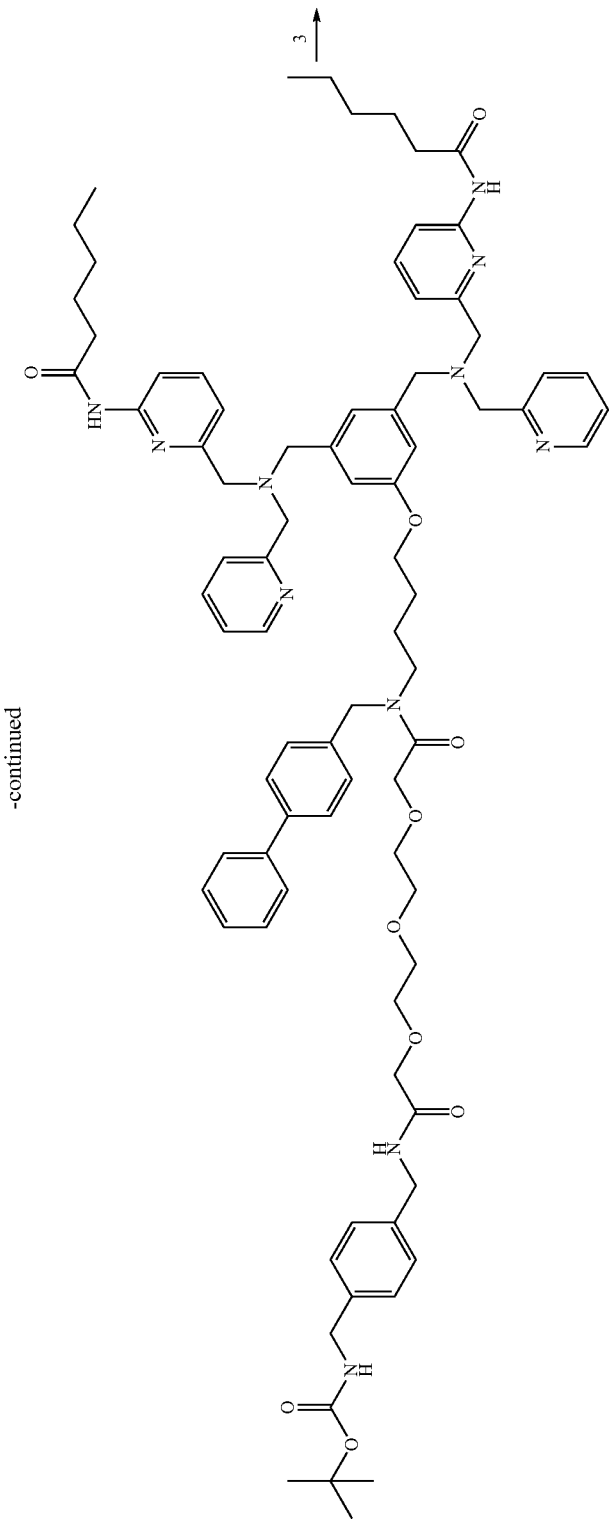
22-2

-continued
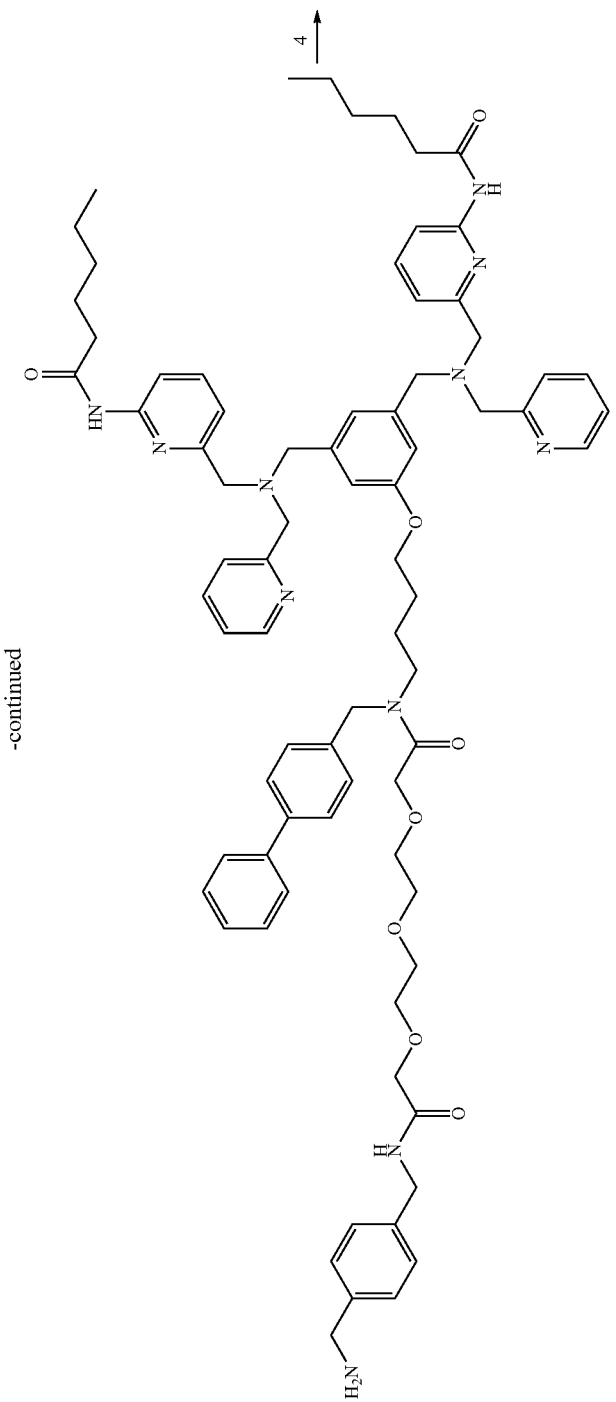
22-3

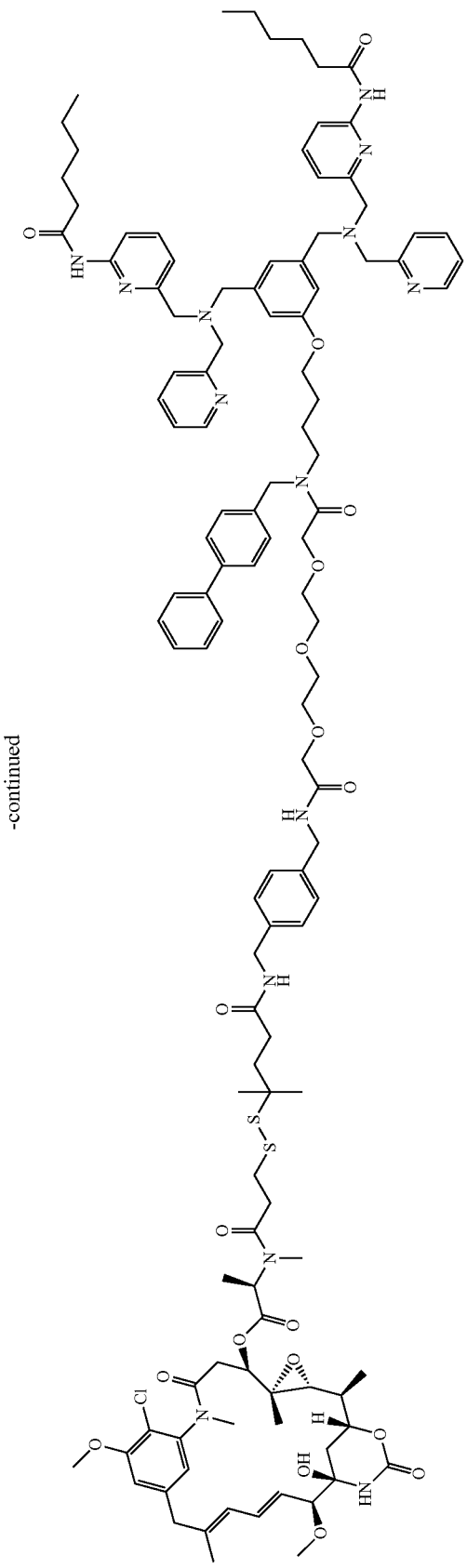
Compound 22
Scheme 37. Reagents and conditions for preparing compound 22: (1) biphenyl-4-carboxaldehyde, NaBH₄, MeOH, 70° C., 24 hr, 68%. (2) 1-(4-(((Tert-butoxycarbonyl)amino)methyl)phenyl)-3-oxo-5,8,11-trioxa-2-azatridecan-13-oic acid, HBTU, HOBt, NMM, 18 hr, 70%. (3) TFA, DCM, 2 hr. (4) Linker c, EDCI, HOBt, NMM, 18 hr, 36%.

To a solution DM-1 (0.2 g, 0.27 nmol) in DMF (9 mL) was added a solution of 2,2'-Dithiobis(5-nitropyridine) (0.19 g, 0.62 mmol) in THF (19 mL). N-Methylmorpholine (NMM, 1.43 mmol, 0.16 mL) was then added to the stirred solution. The resultant reaction solution was stirred at room temperature for 15 hours, poured onto saturated NaHCO$_3$ $_{(aq.)}$, and extracted twice with Ethyl acetate. The combined organic extracts were dried over Na$_2$SO$_4$, filtered, and concentrated in vacuo. The product was purified by flash chromatography over silica gel with methanol/dichloromethane (3/97) to give (14S,16S,32S,33S,2R,4S,10E,12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzenacyclotetradecaphane-10,12-dien-4-yl N-methyl-N-(3-((5-nitropyridin-2-yl)disulfaneyl)propanoyl)-L-alaninate as a white solid (0.20 g, 83%).

To a solution 4-Mercapto-4-methylpentanoic acid (49.80 mg, 0.34 mmol) in THF (0.75 mL) and potassium phosphate buffer (50 mM, pH 7.5, 2.80 mL) was added (14S,16S,32S,33S,2R,4S,10E,12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzenacyclotetradecaphane-10,12-dien-4-yl N-methyl-N-(3-((5-nitropyridin-2-yl)disulfaneyl)propanoyl)-L-alaninate (0.20 g, 0.22 mmol) in DMF (3.36 mL) and the reaction solution was stirred at room temperature for 15 hours. The solvent was then removed in vacuo. The product was purified by flash chromatography over silica gel with Methanol/CH$_2$Cl$_2$ (3/97) to give linker c as a white solid (57.00 mg, 29%). $^1$H NMR (400 MHz, CDCl$_3$): δ 6.83 (s, 1H), 6.68-6.61 (m, 2H), 6.46-6.38 (m, 2H), 6.466.38 (m, 2H), 5.64 (dd, J=15.6, 8.8 Hz, 1H), 5.27 (br, 1H), 4.81 (dd, J=12.4, 3.2 Hz, 1H), 4.30 (t, J=12.0 Hz, 1H), 3.98 (s, 3H), 3.65 (d, J=12.8 Hz, 1H), 3.49 (d, J=9.2 Hz, 1H), 3.36 (s, 3H), 3.24 (s, 3H), 3.11 (d, J=13.2 Hz, 1H), 3.00 (d, J=9.2 Hz, 1H), 2.97-2.9 (m, 1H), 2.89 (s, 3H), 2.88-2.73 (m, 2H), 2.70-2.57 (m, 3H), 2.40-2.32 (m, 2H), 2.19 (dd, J=14.4, 3.2 Hz, 1H), 1.92-1.82 (m, 2H), 1.65 (s, 3H), 1.60 (d, J=13.6 Hz, 1H), 1.51-1.40 (m, 1H), 1.36-1.24 (m, 6H), 1.21 (d, J=2.8 Hz, 6H), 0.91-0.82 (m, 1H), 0.81 (s, 3H). ESI-MS C$_{41}$H$_{58}$ClN$_3$O$_{12}$S$_2$: 883.3, found: 882.1 (M−H$^+$)$^-$. Purity: 95%.

To a solution of BPRDP0107 (200 mg, 0.246 mmol) in MeOH (3 mL) at room temperature was added biphenyl-4-carboxaldehyde (90 mg, 0.491 mmol). The reaction solution was then slowly warmed to 70° C. and stirred overnight. After reaction was completed, the resultant solution was cooled down to 0° C. and sodium borohydride (37 mg, 0.983 mmol) was added. The solution was slowly warmed to room temperature and stirred for 2 hours, poured into saturated NH$_4$Cl$_{(aq.)}$, concentrated, and extracted twice with DCM. The combined organic extracts were dried over Na$_2$SO$_4$, filtered, and concentrated in vacuo. The residue was purified by flash chromatography over silica gel with 5% MeOH in DCM to afford compound 22-1 (165 mg, 68%).

To a solution of 1-(4-(((tert-butoxycarbonyl)amino) methyl)phenyl)-3-oxo-5,8,11-trioxa-2-azatridecan-13-oic acid (65 mg, 0.149 mmol) in DCM (1.5 mL) at room temperature was added O-(benzotriazol-1-yl)-N,N,N',N'-tetramethyluronium hexafluorophosphate (HBTU, 85 mg, 0.223 mmol) and hydroxybenzotriazole (HOBt, 30 mg, 0.223 mmol). The reaction solution was stirred for 30 mins. Compound 22-1 (73 mg, 0.074 mmol) and N-methylmorpholine (NMM, 0.07 mL, 0.594 mmol) were added consecutively. The resultant reaction solution was stirred for 18 hours, quenched with saturated NH$_4$Cl$_{(aq.)}$, and extracted twice with DCM. The combined organic extracts were dried over Na$_2$SO$_4$, filtered, and concentrated in vacuo. The residue was purified by flash chromatography over silica gel with 5% MeOH in DCM to afford compound 22-2 (73 mg, 70%).

To a solution of compound 22-2 (47 mg, 0.034 mmol) in DCM (0.5 mL) at room temperature was added TFA (0.5 mL) and the reaction solution was stirred for 2 hours. After the reaction was completed, the excess amount of TFA was removed under reduced pressure to give compound 22-3.

To a solution of linker c (85 mg, 0.096 mmol) in DCM (1 mL) at room temperature was added 1-(3-Dimethylaminopropyl)-3-ethylcarbodiimide hydrochloride (EDCI, 27 mg, 0.143 mmol) and HOBt (19 mg, 0.143 mmol), then the reaction allowed to stir for 30 mins. Compound 22-3 (83 mg, 0.064 mmol) and NMM (0.04 mL, 0.382 mmol) were added consecutively. The resultant reaction solution was stirred for 18 hours, quenched with saturated NH$_4$Cl$_{(aq.)}$, and extracted twice with DCM. The combined organic extracts were dried over Na$_2$SO$_4$, filtered, and concentrated in vacuo. The residue was purified by flash chromatography over silica gel with 5% MeOH in DCM to afford compound 22 (50 mg, 36%).

$^1$H NMR (400 MHz, CDCl$_3$): δ 8.99 (br, 2H), 8.48 (d, J=5.1 Hz, 2H), 8.13 (dd, J=8.2, 2.7 Hz, 2H), 7.67 (t, J=7.9 Hz, 2H), 7.58-7.28 (m, 12H), 7.27-7.18 (m, 8H), 7.16-7.11 (m, 2H), 6.97 (br, 1H), 6.87 (br, 1H), 6.83-6.81 (m, 1H), 6.72-6.59 (m, 4H), 6.43-6.33 (m, 2H), 5.57 (dd, J=15.2, 9.2 Hz, 1H), 5.31 (br, 1H), 4.78-4.68 (m, 1H), 4.65-4.35 (m, 5H), 4.33-4.24 (m, 2H), 4.24-3.99 (m, 4H), 3.97 (s, 3H), 3.94-3.87 (m, 2H), 3.79-3.48 (m, 19H), 3.47-3.33 (m, 3H), 3.30-3.15 (m, 7H), 3.08 (d, J=13.2 Hz, 1H), 3.02 (d, J=9.7 Hz, 1H), 2.97-2.88 (m, 1H), 2.87-2.66 (m, 6H), 2.66-2.52 (m, 3H), 2.29-2.12 (m, 3H), 2.10-1.98 (m, 4H), 1.93-1.82 (m, 2H), 1.80-1.69 (m, 2H), 1.62 (s, 3H), 1.55-1.48 (m, 5H), 1.29-1.11 (m, 24H), 0.84-0.77 (m, 9H). ESI-MS C$_{118}$H$_{151}$ClN$_{14}$O$_{19}$S$_2$: 2169.13, found: 724.46 (M+3H$^+$)$^{3+}$. Purity: 95%.

Synthesis of Compound 23

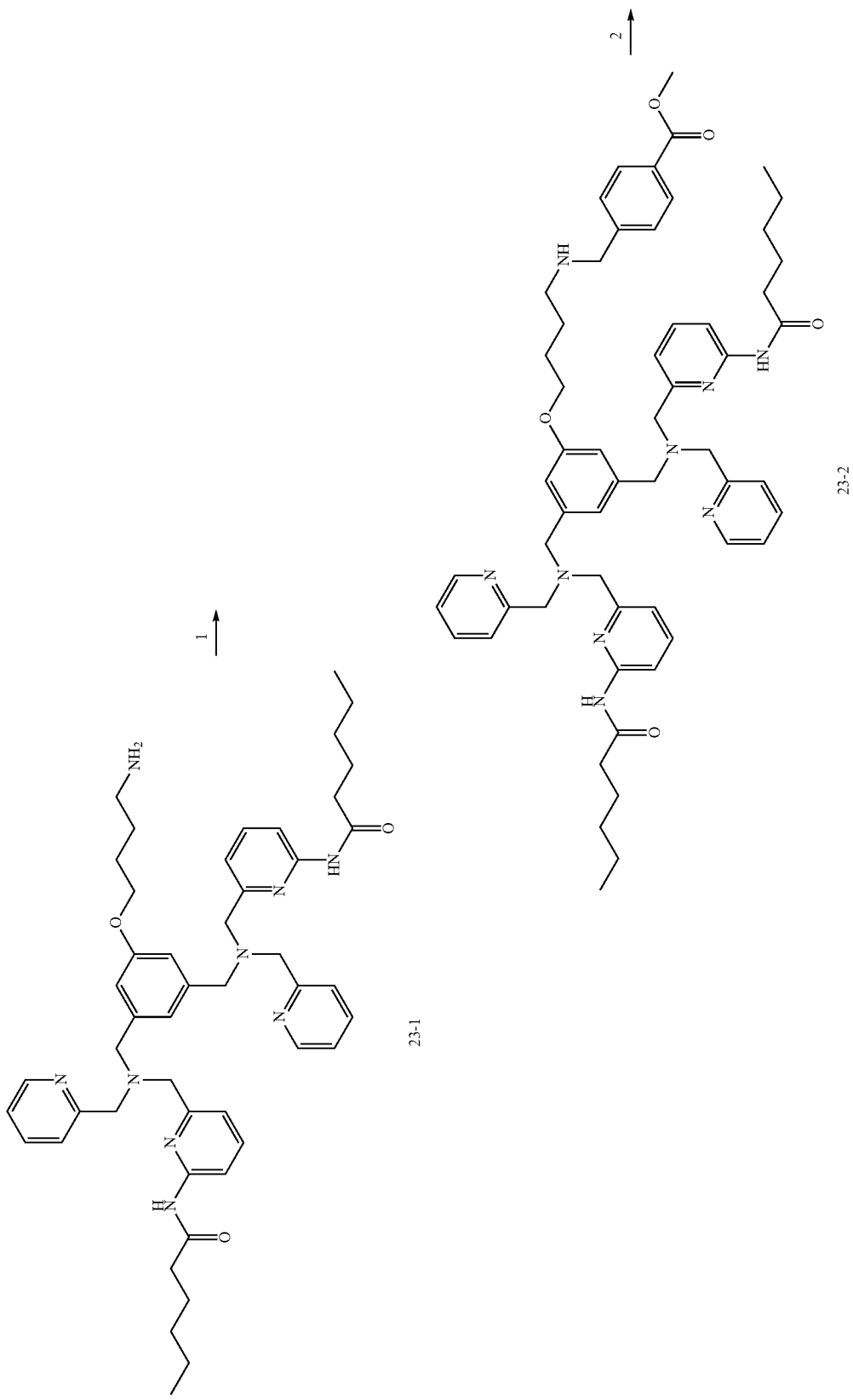
Scheme 38

-continued
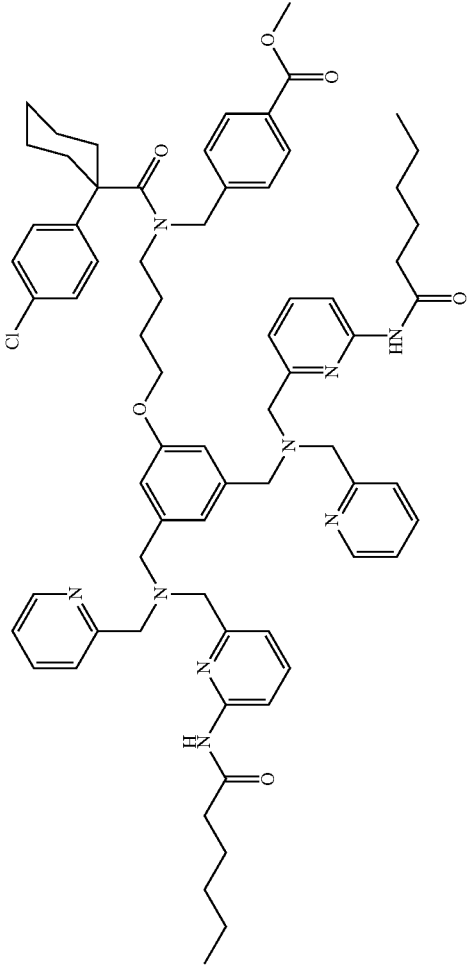
23-3
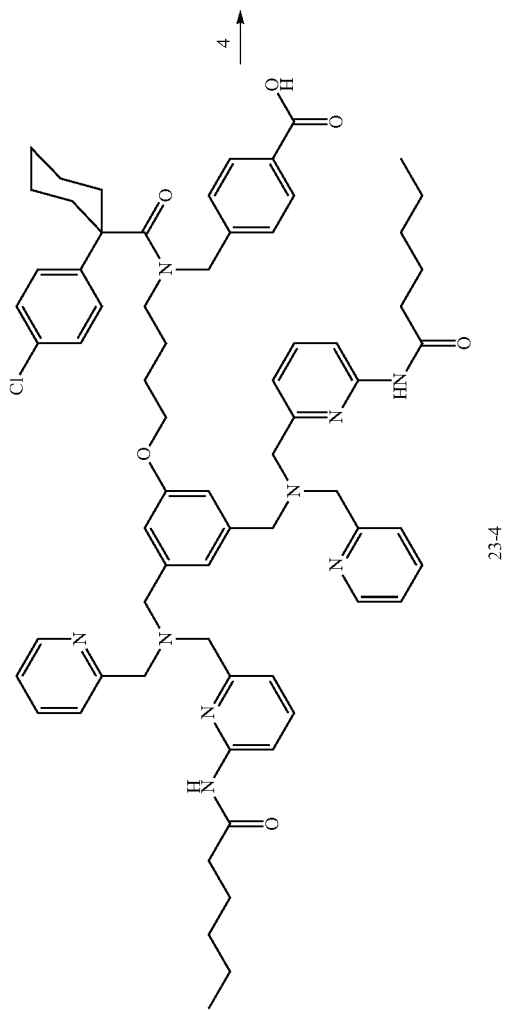
23-4

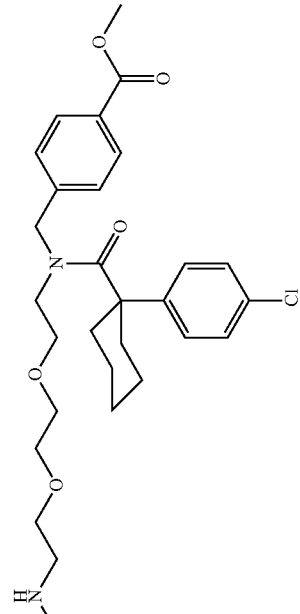
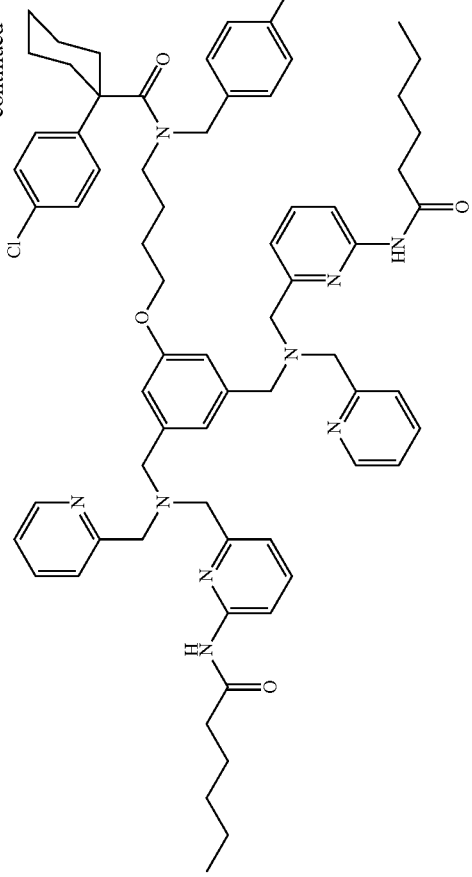
23-5
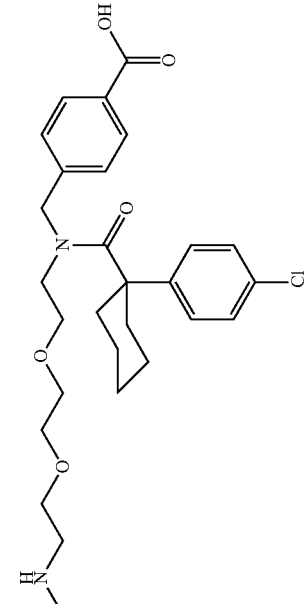
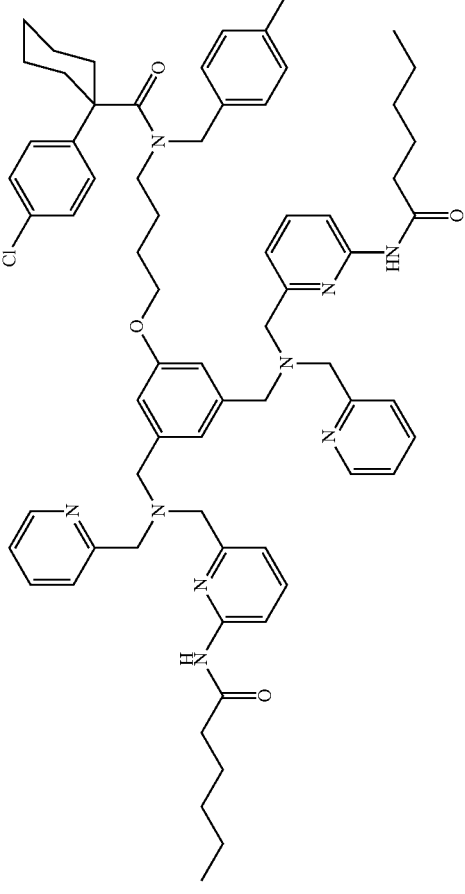
23-6

-continued
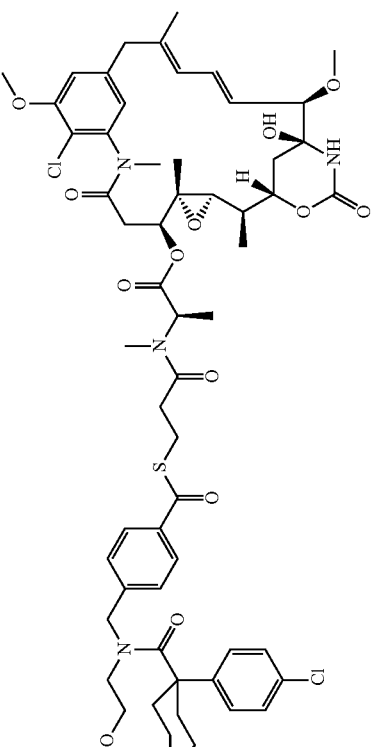
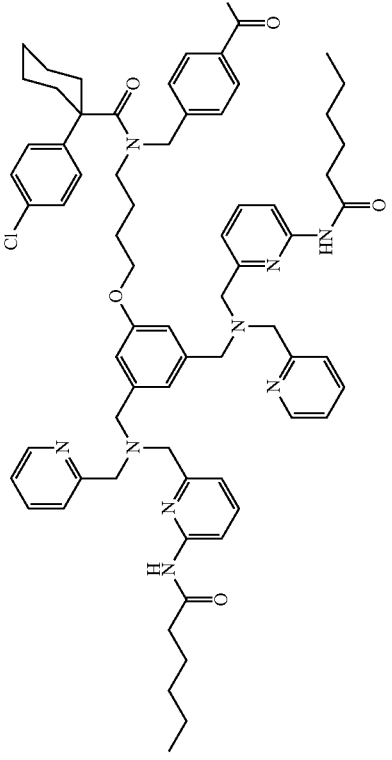
Compound 23
Scheme 38. Reagents and condition for preparing compound 23: (1). Methyl 4-formylbenzoate, MeOH; NaBH$_4$, MeOH. (2). 1-(4-Chloro-phenyl)-cyclohexanecarbonyl chloride, Et$_3$N, DCM. (3). LiOH, MeOH. (4). 4-(({2-[2-(2-Amino-ethoxy)-ethoxy]-ethyl}-[1-(4-chloro-phenyl)-cyclohexanecarbonyl]-amino)-methyl)-benzoic acid methyl ester, HOBt, EDCI, DCM. (5). LiOH, MeOH. (6). DM-1, DMAP, EDCI, DMF.

Compound 23-1 (500 mg, 0.61 mmol) was added to a solution of methyl 4-formylbenzoate (200 mg, 1.21 mmol) in MeOH. Sodium borohydride was then added. The reaction solution was stirred at room temperature for 1 hour. MeOH was removed and the residue was dissolved in $CH_2Cl_2$. The product was protonated with 1 M HCl(aq.). The aqueous solution was neutralized and extracted three times with $CH_2Cl_2$. The organic extracts were combined, dried with $Na_2SO_4$, filtered, and concentrated to give compound 23-2 as a yellow oil (500 mg, 0.52 mmol, 86%).

Compound 23-2 (500 mg, 0.52 mmol) was added into a solution of 1-(4-Chlorophenyl)cyclohexanecarbonyl chloride and triethylamine in $CH_2Cl_2$. The reaction solution was stirred for 1 hour at room temperature. The product was protonated with 1 M HCl(aq.). The aqueous solution was neutralized and extracted with $CH_2Cl_2$. The organic extract was dried with $Na_2SO_4$, filtered, and concentrated to give compound 23-3 as a yellow oil (440 mg, 0.37 mmol, 71%).

To a solution of compound 23-3 (440 mg, 0.37 mmol) in MeOH was added 0.5 M LiOH(aq.). The reaction mixture was stirred at room temperature for 15 hours. The solvent removed and the residue was re-dissolved in $CH_2Cl_2$. The insoluble precipitate was filtered. The filtrate was washed with $CH_2Cl_2$, dried over $Na_2SO_4$, and concentrated under vacuum to give compound 23-4 as a yellow powder (330 mg, 0.28 mmol, 75%).

Compound 23-4 (200 mg, 0.17 mmol) was dissolved in $CH_2Cl_2$ at room temperature. 1-Ethyl-3-(3-dimethylaminopropyl)carbodiimide (EDCI, 60 mg, 0.38 mmol), hydroxybenzotriazole (HOBt, 60 mg, 0.44 mmol), and 4-({{2-[2-(2-Amino-ethoxy)-ethoxy]-ethyl}-[1-(4-chloro-phenyl)-cyclohexanecarbonyl]-amino}-methyl)-benzoic acid methyl ester (100 mg, 0.19 mmol) were added. The reaction solution was stirred at room temperature for 1 hour. The product was protonated with 1 M HCl(aq.). The aqueous solution was neutralized and extracted with $CH_2Cl_2$. The residue was purified by flash chromatography over silica gel to give compound 23-5 (100 mg, 0.06 mmol, 35%). $^1H$ NMR (400 MHz, $CDCl_3$) δ 8.95 (s, 2H), 8.47 (d, J=4.7 Hz, 2H), 8.12 (d, J=8.2 Hz, 2H), 7.92 (d, J=7.6 Hz, 2H), 7.66 (t, J=8.2 Hz, 4H), 7.53 (m, 2H), 7.48 (d, J=7.7 Hz, 2H), 7.19 (m, 11H), 6.96 (s, 2H), 6.67 (s, 2H), 3.88 (s, 4H), 3.76 (s, 4H), 3.72-3.44 (m, 18H), 2.23 (dd, J=23.1, 15.9 Hz, 7H), 2.10-1.93 (m, 5H), 1.81-1.44 (m, 21H), 1.37-1.02 (m, 18H), 0.83 (dt, J=20.6, 6.8 Hz, 6H).

To a solution of compound 23-5 (100 mg, 0.06 mmol) in MeOH was added 0.5 M LiOH(aq.). The reaction mixture was stirred at room temperature for 15 hours. The solvent was removed and the residue was dissolved in $CH_2Cl_2$. The insoluble precipitate was filtered. The filtrate was washed with $CH_2Cl_2$, dried over $Na_2SO_4$, and concentrated under vacuum to give compound 23-6 as yellow powder (100 mg, 0.06 mmol, 100%).

Compound 23-6 (100 mg, 0.06 mmol) was added a solution of DM-1 (40 mg, 0.05 mmol), DMAP (10 mg, 0.08 mmol), and EDCI (15 mg, 0.07 mmol) in 5 ml DMF. The reaction solution was stirred at room temperature for 1 hour, quenched with water, extracted with $CH_2Cl_2$. The extract was condensed to give a residue. The residue was purified by flash chromatography over silica gel to give compound 23 (25 mg, 0.01 mmol, 16%). $^1H$ NMR (400 MHz, $cdcl_3$) δ 8.94 (s, 2H), 8.48 (d, J=4.3 Hz, 2H), 8.12 (d, J=8.2 Hz, 2H), 7.66 (t, J=7.9 Hz, 4H), 7.58 (d, J=13.4 Hz, 2H), 7.53 (d, J=7.6 Hz, 2H), 7.48 (d, J=7.7 Hz, 2H), 7.28 (s, 1H), 7.25-7.08 (m, 14H), 6.92 (d, J=26.7 Hz, 3H), 6.77 (d, J=11.6 Hz, 3H), 6.67 (d, J=8.5 Hz, 4H), 6.43 (dd, J=15.3, 11.2 Hz, 1H), 6.27 (s, 1H), 5.63 (dd, J=15.3, 9.0 Hz, 1H), 5.44 (q, J=6.7 Hz, 1H), 4.73 (dd, J=12.0, 2.9 Hz, 1H), 4.54 (s, 1H), 4.26 (d, J=11.9 Hz, 1H), 4.09 (s, 1H), 3.94 (s, 3H), 3.76 (d, J=8.2 Hz, 6H), 3.68 (s, 6H), 3.59 (d, J=14.4 Hz, 13H), 3.49 (d, J=9.1 Hz, 3H), 3.35 (s, 5H), 3.28-3.18 (m, 3H), 3.13-3.00 (m, 7H), 2.80 (s, 4H), 2.66 (br, 1H), 2.61-2.51 (m, 1H), 2.15 (dd, J=14.3, 2.7 Hz, 3H), 2.05 (s, 5H), 1.84 (s, 11H), 1.56-1.42 (m, 10H), 1.34-1.09 (m, 25H), 0.81 (t, J=7.0 Hz, 6H), 0.79 (s, 3H). ESI-MS $C_{131}H_{161}Cl_3N_{14}O_{19}S^{2+}$: 1186.54, found: 1187.79 ($M^{2+}$). HPLC purity: 98%

Synthesis of Compound 24

Scheme 39

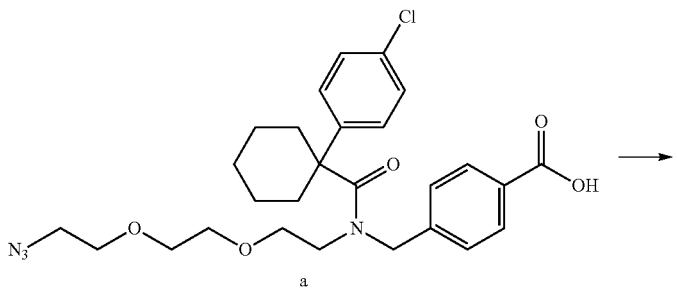

a 257 258
-continued
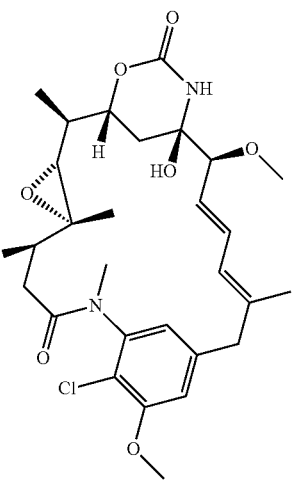
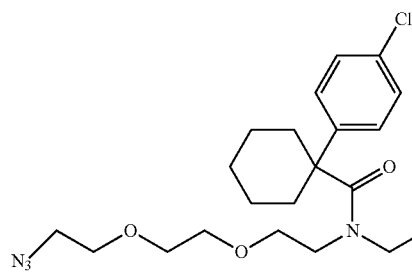
intermediate b
Scheme 39. Reagents and conditions for preparing intermediate b: DM-1, EDCI, DMAP, DMF, rt, 1 hr, 70%.
Scheme 40
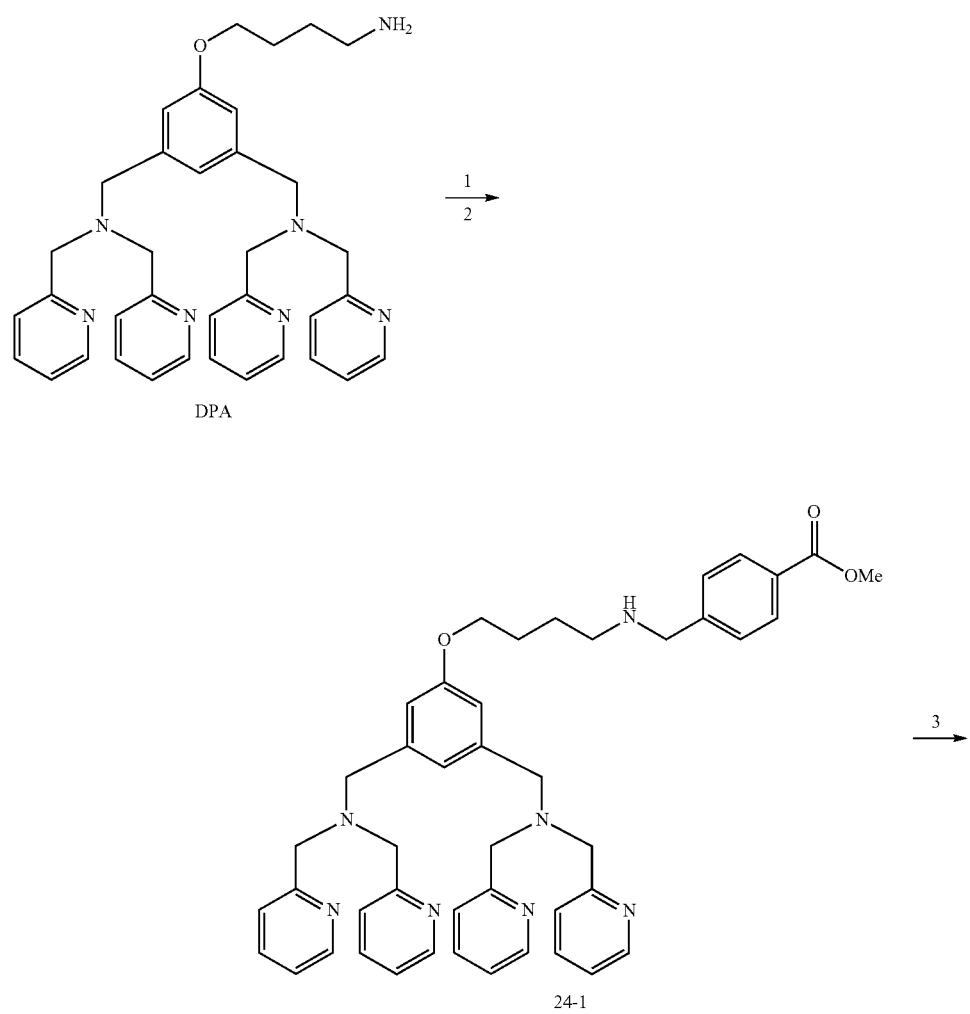

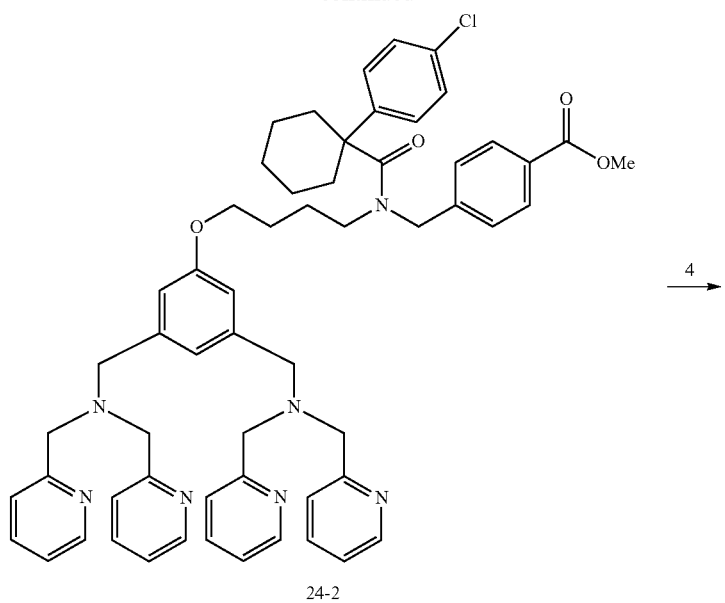
24-2
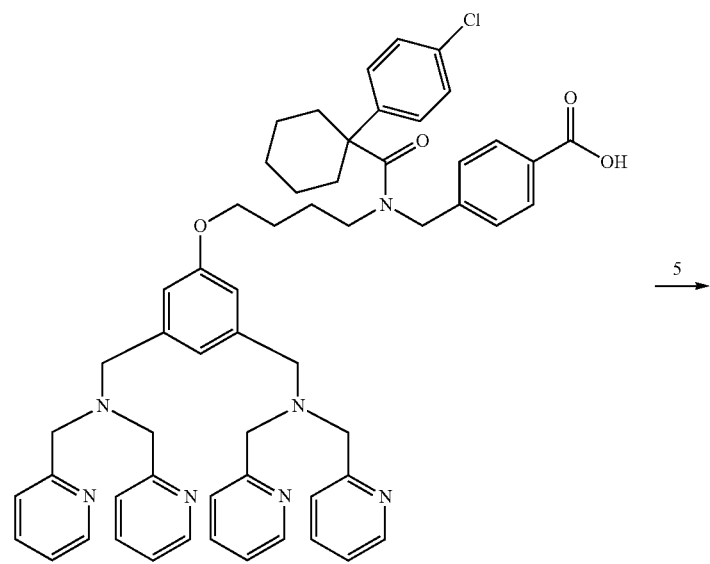
24-3

-continued

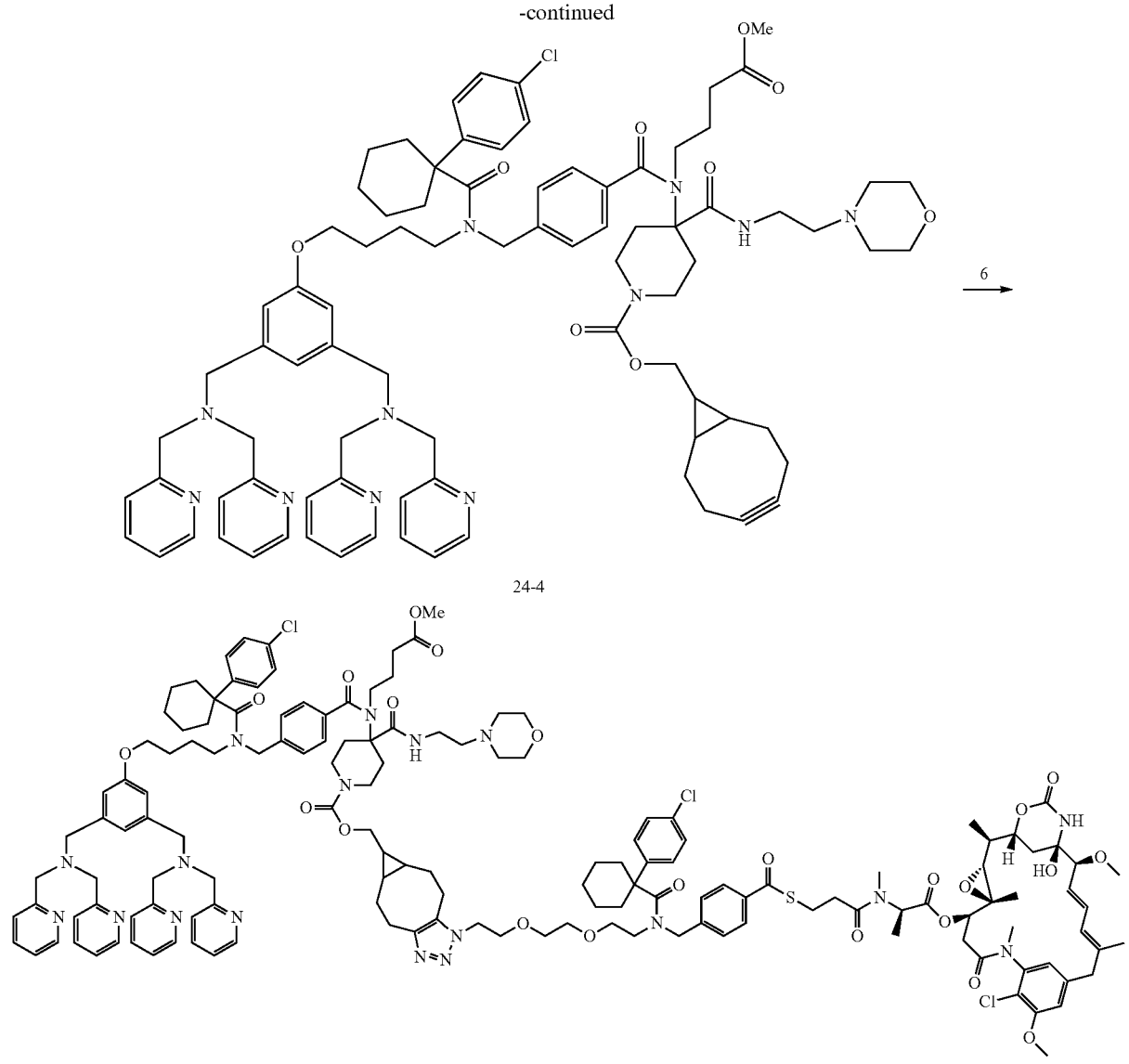

Compound 24

Scheme 40. Reagents and conditions for preparing compound 24: (1) Methyl 4-formylbenzoate, MeOH, rt, 15 hr. (2) NaBH₄, 0° C., 1 hr, 60%. (3) 1-(4-Chlorophenyl)cyclohexanecarbonyl chloride, TEA, DCM, 0° C., 1 hr, 70%. (4) LiOH (0.5N), MeOH, rt, 15 hr, 90%. (5) Methyl 4-aminobutyrate hydrochloride, 2-Morpholinoethyl isocyanide, (bicyclo[6.1.0]non-4-yn-9-yl)methyl 4-oxopiperidine-1-carboxylate, MeOH, rt, 15 hr, 60%. (6) intermediate b, DMF, rt, 1 hr, 80%.

To a stirred solution of compound a (50 mg, 0.095 mmol, 1 eq.) in 5 mL of DMF at room temperature, DM-1 (90 mg, 0.12 mmol, 1.3 eq.), EDCI (36 mg, 0.19 mmol, 2 eq.), and DMAP (23 mg, 0.19 mmol, 2 eq.) were slowly added consecutively. The resultant reaction mixture was stirred at room temperature for 1 hour. The solvent was removed and the residue was extracted with CH₂Cl₂ (200 mL). The CH₂Cl₂ solution was then washed with a saturated aqueous solution of NaHCO₃ (200 mL) and water (3×200 mL), dried over MgSO₄, and concentrated under reduced pressure. The crude product was purified by column chromatography over silica gel with Ethyl acetate/Hexane (9/1) to yield intermediate b (83 mg, 70%). ¹H NMR (300 MHz, CDCl₃): δ 7.60 (d, J=6.6 Hz, 2H), 7.30-7.26 (m, 2H), 7.21-7.19 (m, 3H), 6.92 (m, 1H), 6.82-6.76 (m, 2H), 6.65 (s, 1H), 6.48-6.40 (m, 1H), 6.34 (m, 1H), 5.63 (q, J=8.7 Hz, 1H), 5.48-5.41 (m, 1H), 4.76-4.71 (m, 1H), 4.31-4.24 (m, 2H), 3.97-3.95 (m, 4H), 3.78 (d, J=12.6 Hz, 1H), 3.68 (m, 1H), 3.62-3.49 (m, 6H), 3.39-3.26 (m, 7H), 3.17-3.01 (m, 7H), 2.85-2.77 (m, 4H), 2.70-2.52 (m, 3H), 2.18-2.12 (m, 3H), 1.64-1.56 (m, 8H), 1.31-1.23 (m, 9H), 0.89-0.78 (m, 6H).

To a stirred solution of DPA (1 g, 1.7 mmol, 1 eq.) in 50 mL of methanol at room temperature, methyl 4-formylbenzoate (560 mg, 3.4 mmol, 2 eq.) was slowly added. The resultant reaction mixture was stirred at room temperature for 15 hours. After the solution was cooled to 0° C., sodium borohydride (970 mg, 25.5 mmol, 15 eq.) was added. The mixture was stirred at 0° C. for 1 hour. After removal of MeOH, the resultant residue was extracted with CH₂Cl₂ (200 mL). The CH₂Cl₂ solution was then washed with a saturated ammonium chloride aqueous solution (200 ml), dried over MgSO₄, and concentrated under reduced pressure. The resultant residue was purified by column chromatography over silica gel with MeOH/DCM (1/9) to yield compound 24-1 (750 mg, 60%).

To a stirred solution of compound 24-1 (500 mg, 0.68 mmol, 1 eq.) in 50 mL of dry DCM at 0° C., 1-(4-chlorophenyl)cyclohexanecarbonyl chloride (700 mg, 2.72 mmol, 4 eq.) and TEA (2 mL) were slowly added consecutively. The resultant reaction mixture was stirred for 1 hour. The solvent was removed and the residue was extracted with $CH_2Cl_2$ (200 mL). The $CH_2Cl_2$ solution was then washed with a saturated ammonium chloride aqueous solution (200 mL), dried over $MgSO_4$, and concentrated under reduced pressure. The resultant residue was purified by column chromatography over silica gel with MeOH/DCM (7/93) to yield compound 24-2 (455 mg, 70%).

To a stirred solution of compound 24-2 (500 mg, 0.52 mmol) in 10 mL of methanol at room temperature, a LiOH aqueous solution (10 mL, 0.5 N) was slowly added. The resultant reaction mixture was stirred at room temperature for 15 hours. After removal of MeOH, the resultant residue was extracted with $CH_2Cl_2$ (200 mL). The $CH_2Cl_2$ solution was washed with a saturated ammonium chloride aqueous solution (200 mL), dried over $MgSO_4$, and concentrated under reduced pressure to yield compound 24-3 (440 mg, 90%).

To a stirred solution of compound 24-3 (100 mg, 0.107 mmol, 1 eq.) in 0.5 mL of methanol at room temperature, Methyl 4-aminobutyrate hydrochloride (80 mg, 0.535 mmol, 5 eq.), 2-Morpholinoethyl isocyanide (100 mg, 0.75 mmol, 7 eq.), and (bicyclo[6.1.0]non-4-yn-9-yl)methyl 4-oxopiperidine-1-carboxylate (60 mg, 0.21 mmol, 2 eq.) were slowly added consecutively. The resultant reaction mixture was stirred at room temperature for 15 hours. After removal of MeOH, the resultant residue was extracted with $CH_2Cl_2$ (200 mL). The $CH_2Cl_2$ solution was washed with a saturated ammonium chloride aqueous solution (200 mL), dried over $MgSO_4$, and concentrated under reduced pressure. The resultant residue was purified by column chromatography over silica gel with MeOH/DCM (1/9) to yield compound 24-4 (93 mg, 60%). $^1$H NMR (400 MHz, $CDCl_3$): δ 8.49 (d, J=8.49 Hz, 4H), 7.62-7.56 (m, 8H), 7.36 (d, J=6.8 Hz, 2H), 7.27-7.24 (m, 3H), 7.21-7.15 (m, 2H), 7.13-7.10 (m, 5H), 6.99 (s, 1H), 6.80 (s, 2H), 4.58 (s, 1H), 4.12 (s, 1H), 4.00-3.91 (m, 4H), 3.79 (s, 8H), 3.71-3.64 (m, 8H), 3.51 (s, 3H), 3.43-3.37 (m, 6H), 3.24 (m, 1H), 2.92 (m, 1H), 2.49 (m, 6H), 2.40-2.24 (m, 12H), 2.15-2.04 (m, 6H), 1.78-1.62 (m, 10H), 1.41-1.25 (m, 4H), 0.88-0.81 (m, 2H), 0.75-0.69 (m, 1H). ESI-MS $C_{85}H_{102}ClN_{11}O_9$: 1455.7551, found 729 $(EM+2H^+)/2$.

To a stirred solution of compound 24-4 (30 mg, 0.021 mmol, 1 eq.) in 3 mL of DMF at room temperature, intermediate b (26 mg, 0.021 mmol, 1 eq.) was slowly added. The resultant reaction mixture was stirred at room temperature for 1 hour. The solvent was removed and the resultant residue was extracted with $CH_2Cl_2$ (200 mL). The $CH_2Cl_2$ solution was washed with water (2×200 mL), dried over $MgSO_4$, and concentrated under reduced pressure. The resultant residue was purified by column chromatography over silica gel with MeOH/DCM (1/9) to yield compound 24 (45 mg, 80%). $^1$H NMR (300 MHz, $CDCl_3$): δ 8.50 (d, J=4.8 Hz, 4H), 7.63-7.57 (m, 10H), 7.36 (d, J=7.5 Hz, 2H), 7.29-7.10 (m, 15H), 7.01-6.91 (m, 2H), 6.80-6.76 (m, 4H), 6.65 (s, 1H), 6.48-6.39 (m, 1H), 6.23 (m, 1H), 5.67-5.59 (m, 1H), 5.46-5.43 (m, 1H), 4.73 (d, J=9.0 Hz, 1H), 4.58 (s, 1H), 4.36-4.26 (m, 2H), 4.12 (s, 1H), 3.94 (m, 8H), 3.79-3.75 (m, 9H), 3.73-3.65 (m, 9H), 3.51-3.34 (m, 20H), 3.29-3.22 (m, 3H), 3.07-3.00 (m, 7H), 2.92-2.86 (m, 1H), 2.81 (m, 4H), 2.69-2.61 (m, 3H), 2.56-2.48 (m, 6H), 2.34 (m, 12H), 2.17-2.04 (m, 7H), 1.92-1.85 (m, 2H), 1.76-1.58 (m, 18H), 1.34-1.25 (m, 13H), 0.89-0.79 (m, 9H). ESI-MS $C_{147}H_{181}Cl_3N_{18}O_{23}S$: 2703.23, found 903 $(EM+3H^+)/3$.

Synthesis of Compound 25

Scheme 41

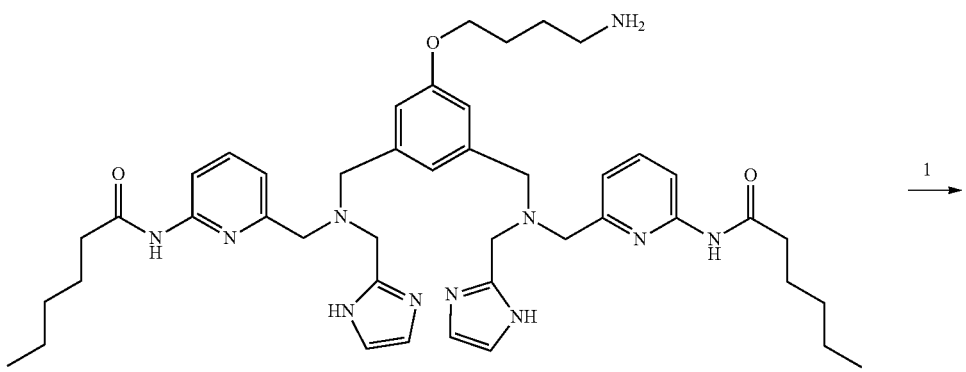

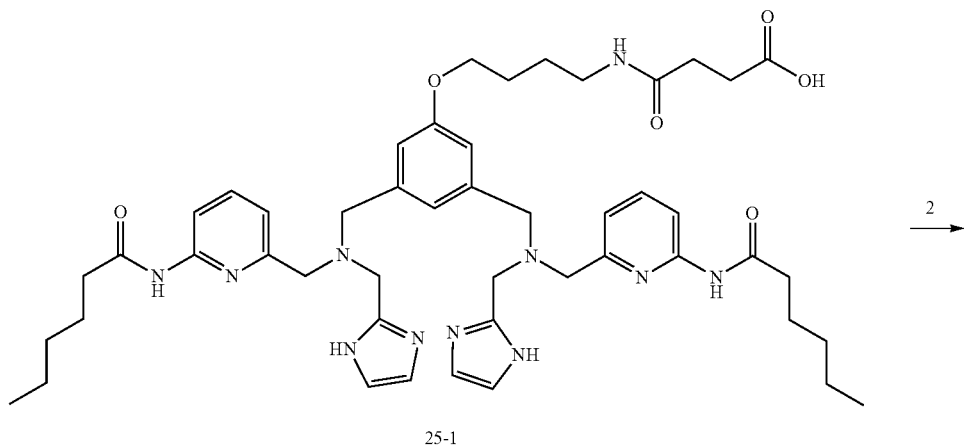
25-1
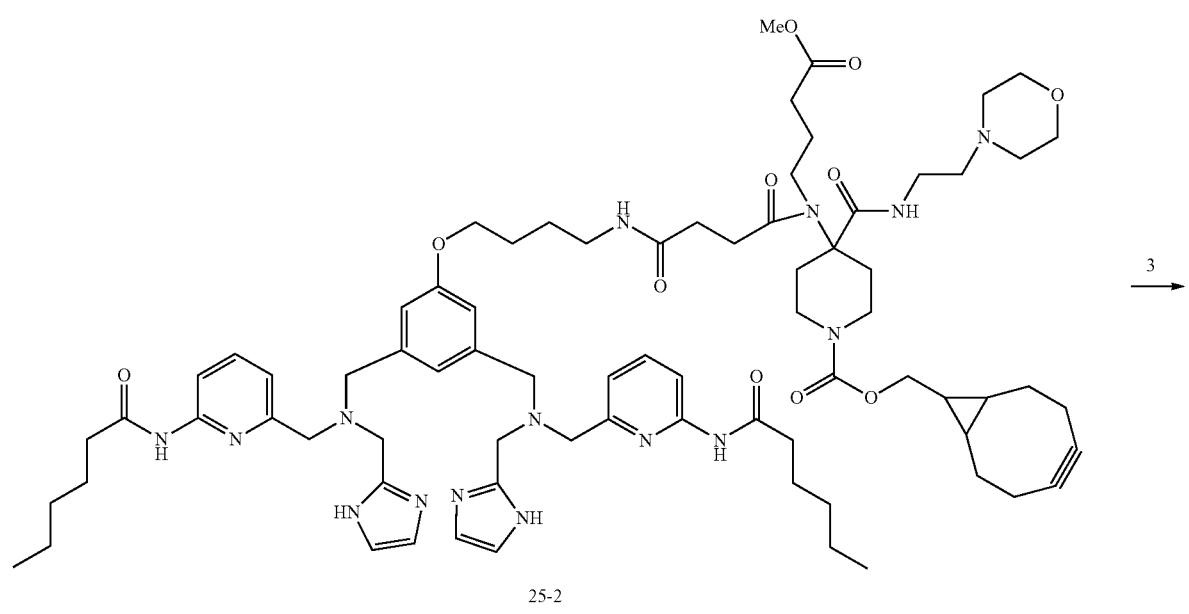
25-2

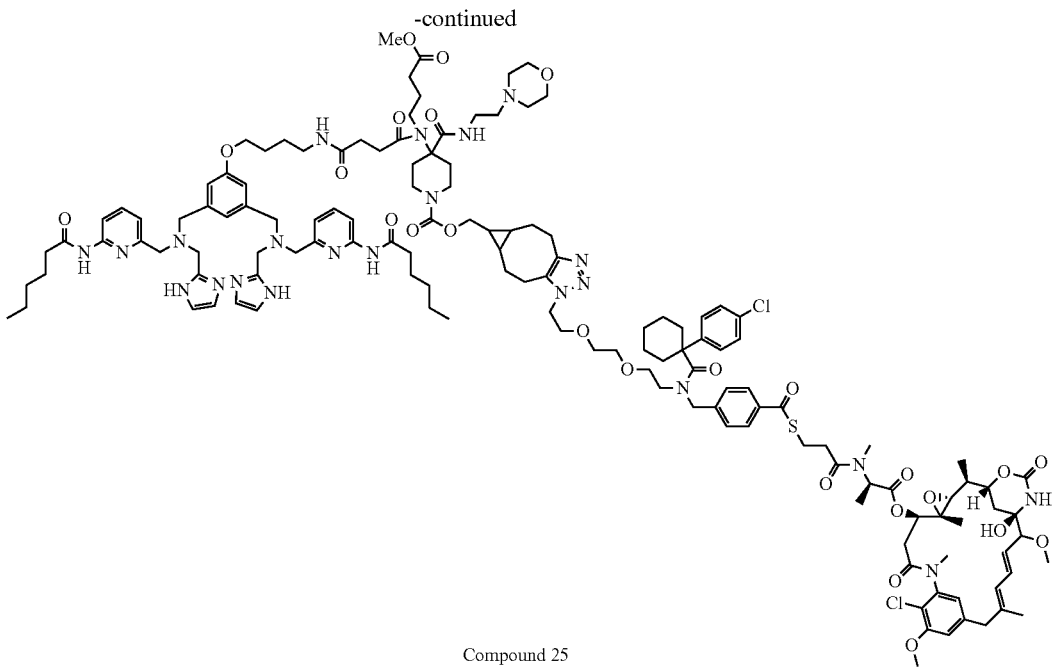

Compound 25

Scheme 41. Reagents and conditions for preparing compound 24:
(1) Succinic anhydride, DCM, rt, 15 hr, 90%. (2) Methyl 4-aminobutyrate hydrochloride, 2-Morpholinoethyl isocyanide,
(bicyclo[6.1.0]non-4-yn-9-yl)methyl 4-oxopiperidine-1-carboxylate, MeOH, rt, 15 hr, 50%. (3) intermediate b, DMF, rt, 1 hr, 75%.

To a stirred solution of BPRDP0157 (1 g, 1.26 mmol, 1 eq.) in 100 mL of dry DCM at room temperature, succinic anhydride (140 mg, 1.39 mmol, 1.1 eq.) was slowly added. The resultant reaction mixture was stirred for 15 hours. The resultant residue was extracted with $CH_2Cl_2$ (200 mL). The $CH_2Cl_2$ solution was washed with a saturated aqueous solution of $NaHCO_3$ (200 mL), dried over $MgSO_4$, and concentrated under reduced pressure to yield compound 25-1 (1 g, 90%). $^1$H NMR (400 MHz, $CD_3OD$): δ 7.84 (d, J=8.0 Hz, 2H), 7.68-7.64 (m, 2H), 7.19 (d, J=7.2 Hz, 2H), 7.05 (m, 4H), 6.94 (s, 1H), 6.79 (s, 2H), 3.95 (t, J=5.6 Hz, 2H), 3.80 (s, 4H), 3.63 (s, 4H), 3.61 (s, 4H), 3.23 (t, J=7.2 Hz, 2H), 2.54-2.52 (m, 2H), 2.46-2.38 (m, 6H), 1.78-1.76 (m, 2H), 1.71-1.67 (m, 6H), 1.37-1.34 (m, 8H), 0.96-0.90 (m, 6H). ESI-MS $C_{48}H_{65}N_{11}O_6$: 891.5119, found 892 (EM+H$^+$).

To a stirred solution of compound 25-1 (100 mg, 0.11 mmol, 1 eq.) in 0.5 mL of methanol at room temperature, methyl 4-aminobutyrate hydrochloride (85 mg, 0.55 mmol, 5 eq.) and 2-morpholinoethyl isocyanide (110 mg, 0.77 mmol, 7 eq.) and (bicyclo[6.1.0]non-4-yn-9-yl)methyl 4-oxopiperidine-1-carboxylate (61 mg, 0.22 mmol, 2 eq.) were slowly added. The resultant reaction mixture was stirred at room temperature for 15 hours. After removal of MeOH, the resultant residue was extracted with $CH_2Cl_2$ (200 mL). The $CH_2Cl_2$ solution was then washed with a saturated ammonium chloride aqueous solution (200 mL), dried over $MgSO_4$, and concentrated under reduced pressure. The resultant residue was purified by column chromatography over silica gel with MeOH/DCM (1/9) to yield compound 25-2 (79 mg, 50%). $^1$H NMR (400 MHz, CDCl$_3$): δ 8.05 (d, J=8.4 Hz, 2H), 7.63-7.59 (m, 2H), 7.27 (s, 1H), 7.16 (d, J=7.6 Hz, 2H), 6.97 (m, 4H), 6.59 (s, 2H), 3.97 (m, 2H), 3.89 (t, J=5.6 Hz, 2H), 3.71 (s, 4H), 3.69-3.62 (m, 15H), 3.53 (s, 4H), 3.44-3.40 (m, 2H), 3.27-3.22 (m, 4H), 2.65-2.63 (m, 2H), 2.51-2.46 (m, 2H), 2.40-2.31 (m, 18H), 2.26-2.23 (m, 2H), 2.14-2.10 (m, 2H), 1.95-1.90 (m, 2H), 1.78-1.59 (m, 8H), 1.31-1.24 (m, 10H), 0.88-0.81 (m, 8H), 0.73-0.66 (m, 1H). ESI-MS $C_{76}H_{107}N_{15}O_{11}$: 1405.83, found 704 (EM+2H$^+$)/2.

To a stirred solution of compound 25-2 (52 mg, 0.037 mmol, 1 eq.) in 10 mL of DMF at room temperature, intermediate b (46 mg, 0.037 mmol, 1 eq.) was slowly added. The resultant reaction mixture was stirred at room temperature for 1 hour. The resultant residue was extracted with $CH_2Cl_2$ (200 mL). The $CH_2Cl_2$ solution was washed with water (2×200 mL), dried over $MgSO_4$, and concentrated under reduced pressure. The resultant residue was purified by column chromatography over silica gel with MeOH/DCM (1/9) to yield compound 25 (74 mg, 75%). $^1$H NMR (400 MHz, CDCl$_3$): δ 8.04 (d, J=10.0 Hz, 2H), 7.66-7.61 (m, 4H), 7.28-7.26 (m, 3H), 7.20-7.13 (m, 5H), 6.99 (m, 4H), 6.92 (m, 1H), 6.79-6.76 (m, 2H), 6.66-6.61 (m, 3H), 6.47-6.38 (m, 2H), 5.68-5.62 (m, 1H), 5.47-5.42 (m, 1H), 4.73 (d, J=8.8 Hz, 1H), 4.35-4.32 (m, 1H), 4.30-4.25 (m, 1H), 3.94-3.86 (m, 8H), 3.78-3.75 (m, 5H), 3.68-3.64 (m, 16H), 3.56 (s, 4H), 3.50-3.43 (m, 8H), 3.35-3.31 (m, 5H), 3.28-3.25 (m, 6H), 3.08-3.00 (m, 6H), 2.81-2.74 (m, 4H), 2.67-2.65 (m, 3H), 2.60-2.54 (m, 2H), 2.50 (m, 2H), 2.44 (m, 6H), 2.38-2.35 (m, 14H), 2.17-2.13 (m, 3H), 1.95 (m, 2H), 1.77-1.61 (m, 18H), 1.33-1.20 (m, 19H), 0.89-0.73 (m, 15H). ESI-MS $C_{138}H_{186}Cl_2N_{22}O_{25}S$: 2653.3057, found 886 (EM+3H$^+$)/3.

Synthesis of Compound 26

Scheme 42
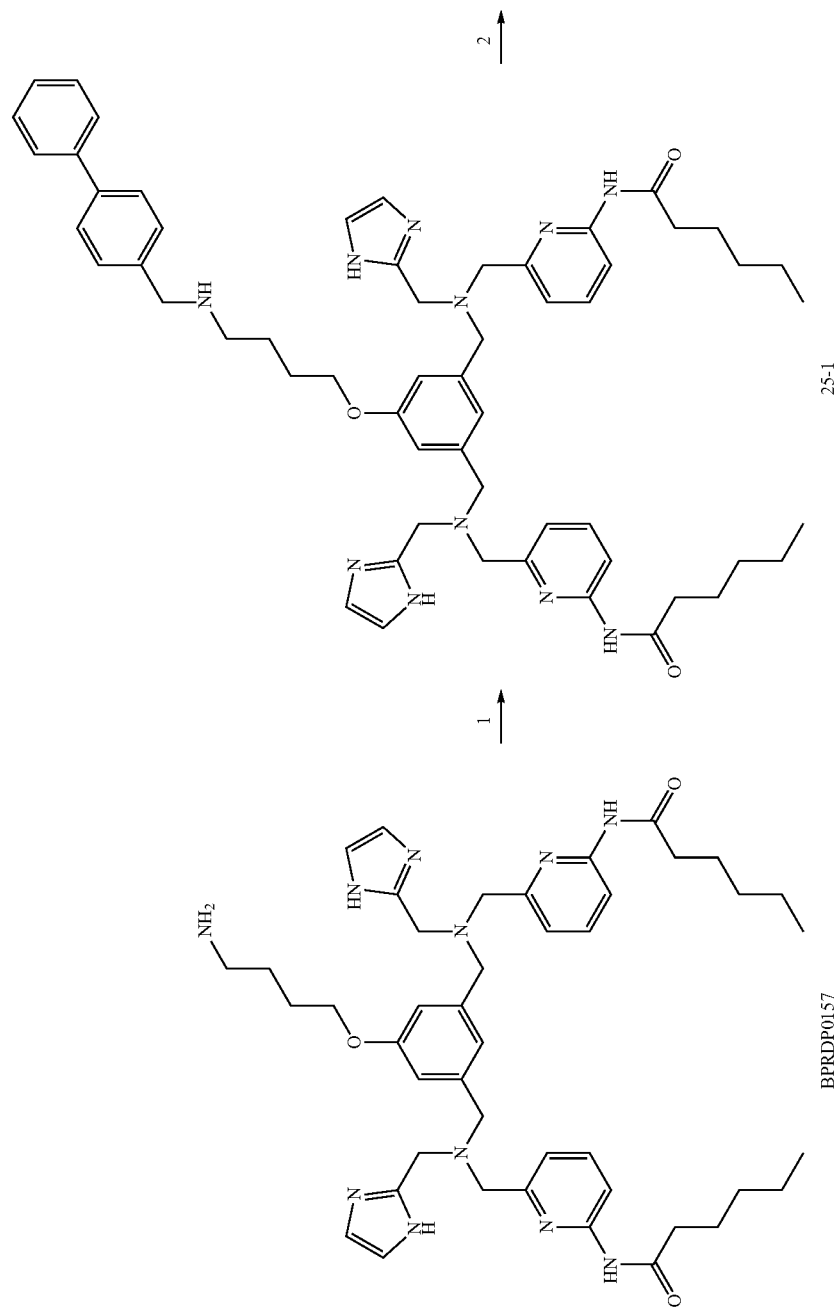

-continued
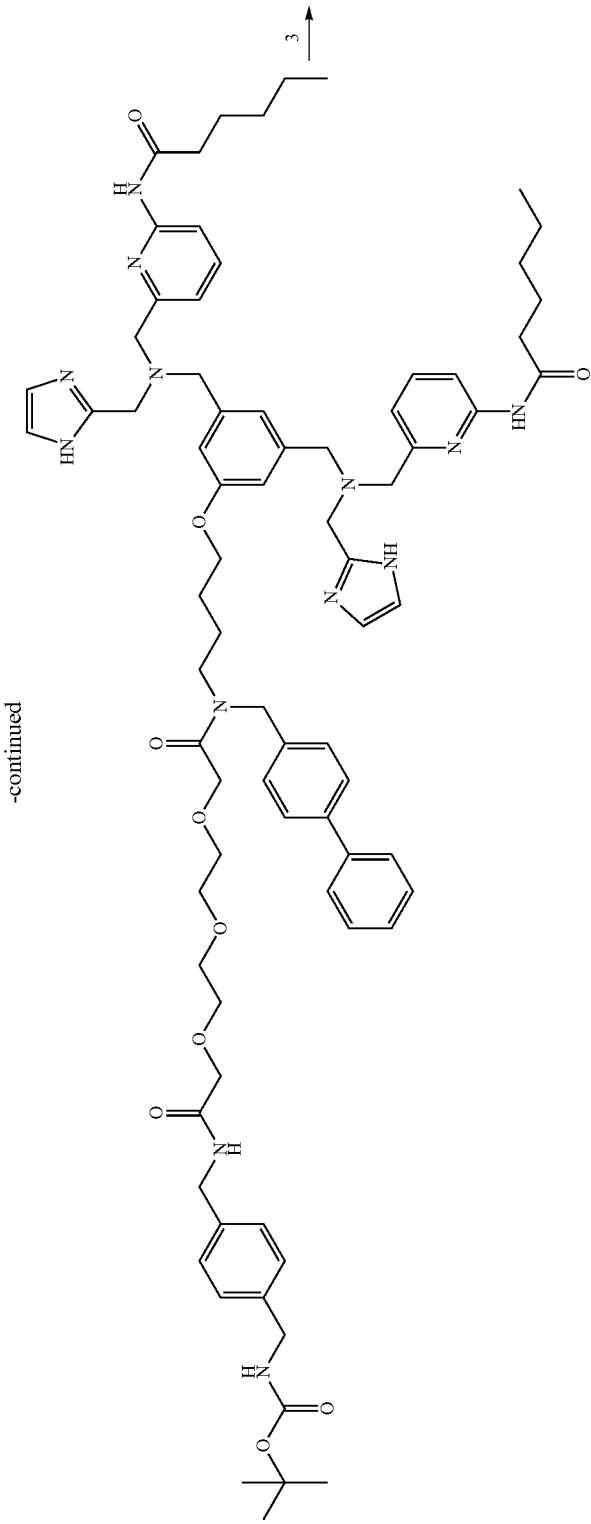
26-2

-continued
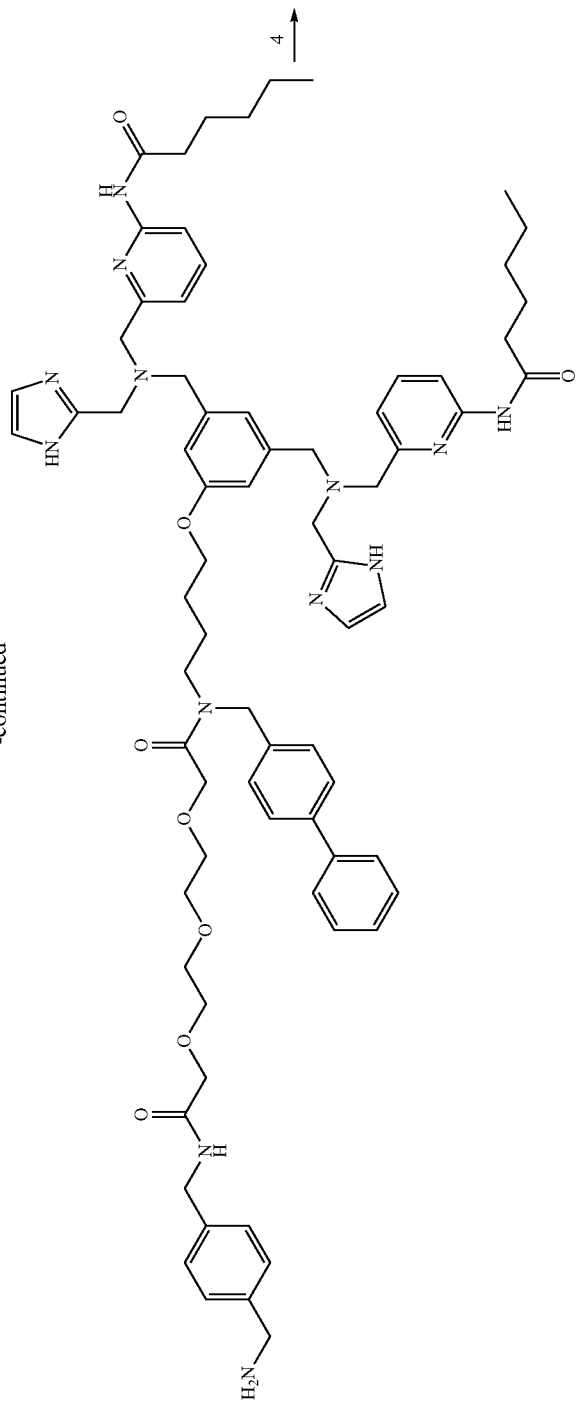
26-3

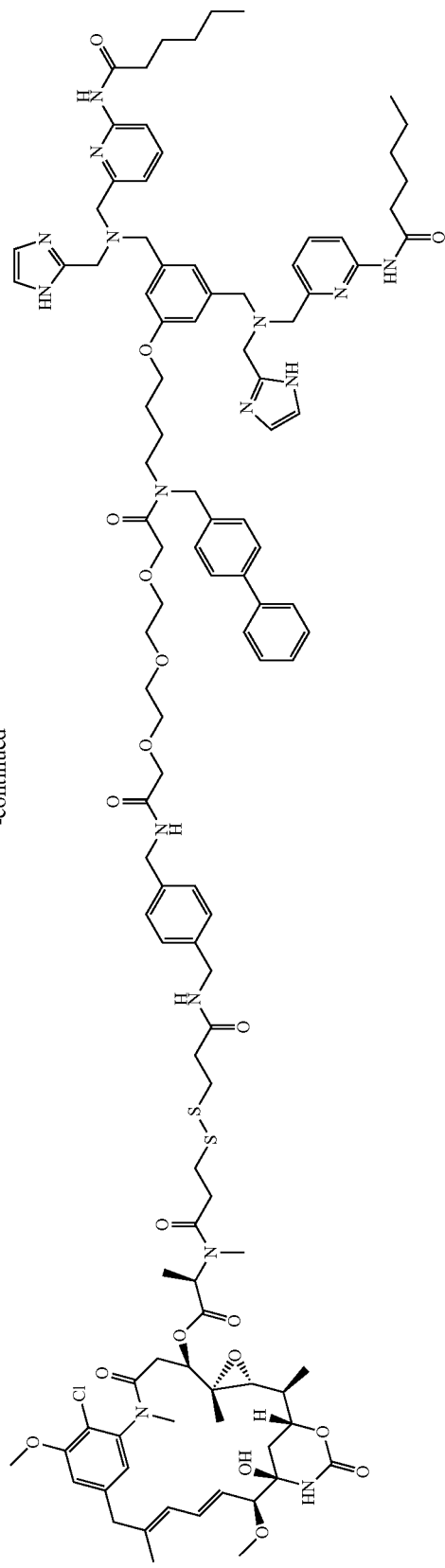

Compound 26

Scheme 42. Reagents and conditions for preparing compound 26: (1) biphenyl-4-carboxaldehyde, NaBH₄, MeOH, 70° C., 24 hr, 65%. (2) 1-(4-(((tert-butoxycarbonyl)amino)methyl)phenyl)-3-oxo-5,8,11-trioxa-2-azatridecan-13-oic acid, HBTU, HOBt, NMM, 18 hr, 83%. (3) TFA, DCM, 2 hr. (4) 3-[(3-{[(2R)-1-{[(1R,2S,3R,6R,16E,18E,20S,21R)-11-chloro-21-hydroxy-12,20-dimethoxy-2,5,9,16-tetramethyl-8,23-dioxo-4,24-dioxa-9,22-diazatetracyclo[19.3.1.1¹⁰,¹⁴.0³,⁵]hexacosa-10(26),11,13,16,18-pentaen-6-yl]oxy}-1-oxopropan-2-yl](methyl)amino}-3-oxopropyl)disulfanyl]propanoic acid, EDCI, HOBt, NMM, 19 hr, 52%.

To a solution of BPRDP0157 (1000 mg, 1.263 mmol) in MeOH (13 mL) at room temperature was added biphenyl-4-carboxaldehyde (460 mg, 2.525 mmol). The reaction solution was then slowly warmed to 70° C. and stirred overnight. After reaction was completed, the reaction mixture was cooled down to 0° C., and sodium borohydride (191 mg, 5.050 mmol) was added into the mixture. The resultant solution was slowly warmed to room temperature and stirred for 4 hours. The reaction mixture was poured into saturated $NH_4Cl_{(aq.)}$. The solvent was removed and the residue was extracted with DCM twice. The combined organic extracts were dried over $Na_2SO_4$, filtered, and concentrated in vacuo. The residue was purified by reverse-phase chromatography (70% MeOH in $H_2O$) to compound 26-1 (784 mg, 65%).

To a solution of 1-(4-(((tert-butoxycarbonyl)amino) methyl)phenyl)-3-oxo-5,8,11-trioxa-2-azatridecan-13-oic acid (433 mg, 0.982 mmol) in DCM (16 mL) at room temperature was added O-(benzotriazol-1-yl)-N,N,N',N'-tetramethyluronium hexafluorophosphate (HBTU, 621 mg, 1.637 mmol) and hydroxybenzotriazole (HOBt, 221 mg, 1.637 mmol). The reaction solution was stirred for 30 mins. Compound 26-1 (784 mg, 0.818 mmol) and N-methylmorpholine (NMM, 0.18 mL, 1.637 mmol) were added consecutively. The reaction solution was stirred for 18 hours, quenched with saturated $NH_4Cl_{(aq.)}$, then extracted with DCM. The organic extracts were dried over $Na_2SO_4$, filtered, and concentrated in vacuo. The residue was purified by flash chromatography over silica gel with 3% MeOH in DCM to afford compound 26-2 (936 mg, 83%).

To a solution of compound 26-2 (450 mg, 0.326 mmol) in DCM (3 mL) at room temperature was added TFA (3 mL). The reaction solution was stirred for 2 hours. After reaction was completed, the excess amount of TFA was removed under reduced pressure to give compound 26-3.

To a solution of 3-[(3-{[(2R)-1-{[(1R,2S,3R,6R,16E,18E,20S,21R)-11-chloro-21-hydroxy-12,20-dimethoxy-2,5,9,16-tetramethyl-8,23-dioxo-4,24-dioxa-9,22-diazatetracyclo [19.3.1.1$^{10,14}$.0$^{3,5}$]hexacosa-10(26),11,13,16,18-pentaen-6-yl]oxy}-1-oxopropan-2-yl](methyl)amino}-3-oxopropyl) disulfanyl]propanoic acid (329 mg, 0.391 mmol) in DCM (7 mL) at room temperature was added 1-(3-dimethylaminopropyl)-3-ethylcarbodiimide hydrochloride (EDC, 125 mg, 0.651 mmol) and HOBt (88 mg, 0.651 mmol). The reaction solution was stirred for 30 mins. Compound 26-3 (417 mg, 0.326 mmol) and NMM (0.3 mL, 2.605 mmol) were added consecutively. The reaction solution was stirred for 19 hours, quenched with saturated $NH_4Cl_{(aq)}$, then extracted with DCM. The organic extracts were dried over $Na_2SO_4$, filtered, and concentrated in vacuo. The residue was purified by flash chromatography over silica gel with 5% MeOH in DCM to afford compound 26 (357 mg, 52%). $^1$H NMR (300 MHz, CDCl$_3$): δ 11.74 (br, 1H), 8.78 (br, 2H), 8.05 (d, J=8.3 Hz, 2H), 7.66-7.25 (m, 17H), 7.22 (s, 1H), 7.09-7.02 (m, 1H), 7.01-6.92 (m, 5H), 6.85-6.80 (m, 1H), 6.71-6.53 (m, 6H), 6.47-6.34 (m, 1H), 5.68 (dd, J=15.3, 8.7 Hz, 1H), 5.32 (br, 1H), 4.84-4.74 (m, 1H), 4.58 (d, J=26.4 Hz, 2H), 4.46-4.24 (m, 5H), 4.17-3.99 (m, 4H), 3.97 (s, 3H), 3.93-3.89 (m, 2H), 3.70-3.41 (m, 22H), 3.28-3.19 (m, 7H), 3.11 (d, J=12.6 Hz, 1H), 3.03-2.92 (m, 2H), 2.83 (s, 3H), 2.69-2.52 (m, 9H), 2.31 (t, J=7.5 Hz, 4H), 1.76-1.61 (m, 12H), 1.52-1.41 (m, 2H), 1.35-1.22 (m, 16H), 0.91-0.84 (m, 6H), 0.80 (s, 3H). ESI-MS $C_{111}H_{143}ClN_{16}O_{19}S_2$: 2105.0, found: 702.7 (M+3H$^+$)$^{3+}$. Purity: 95%.

Synthesis of Compound 27

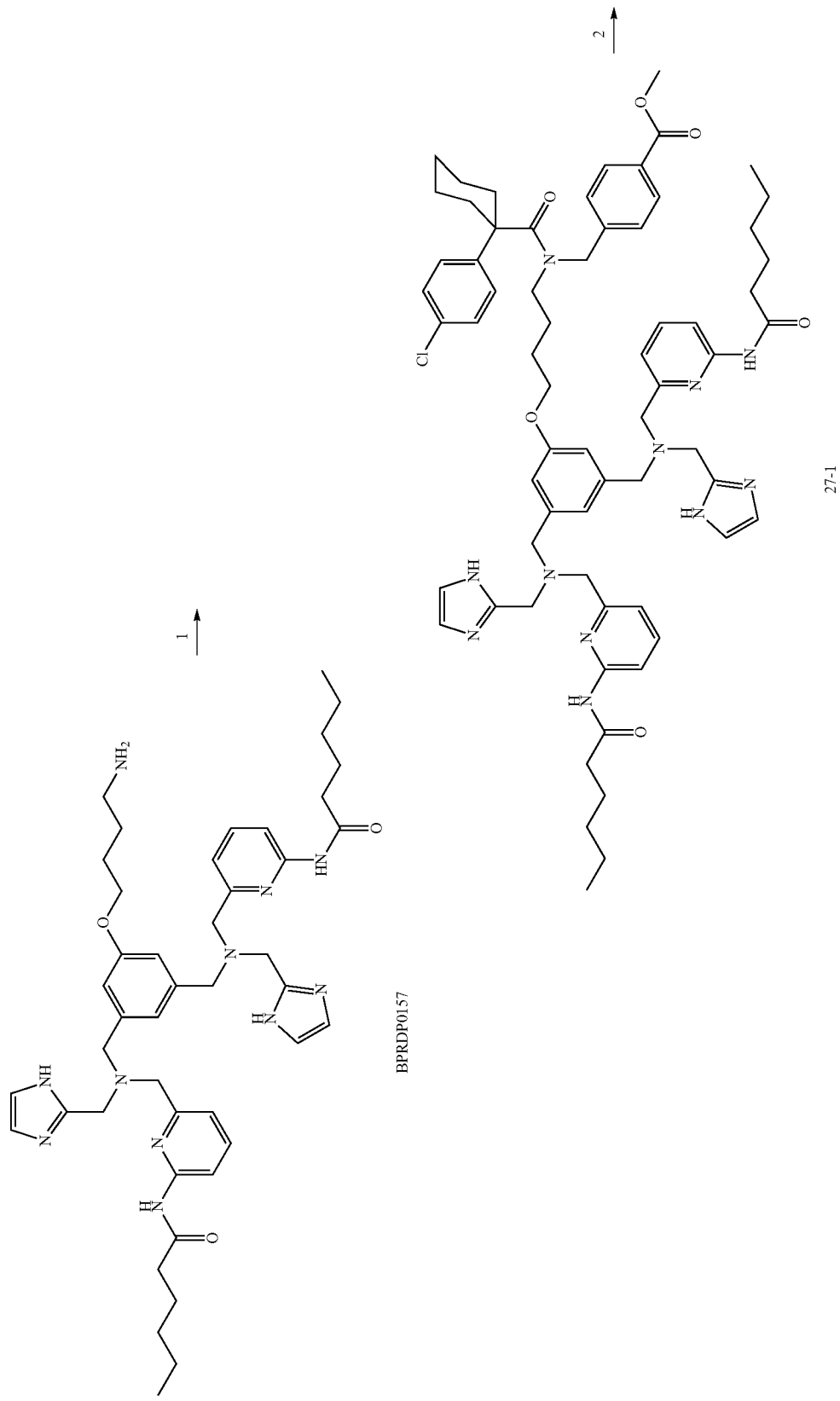

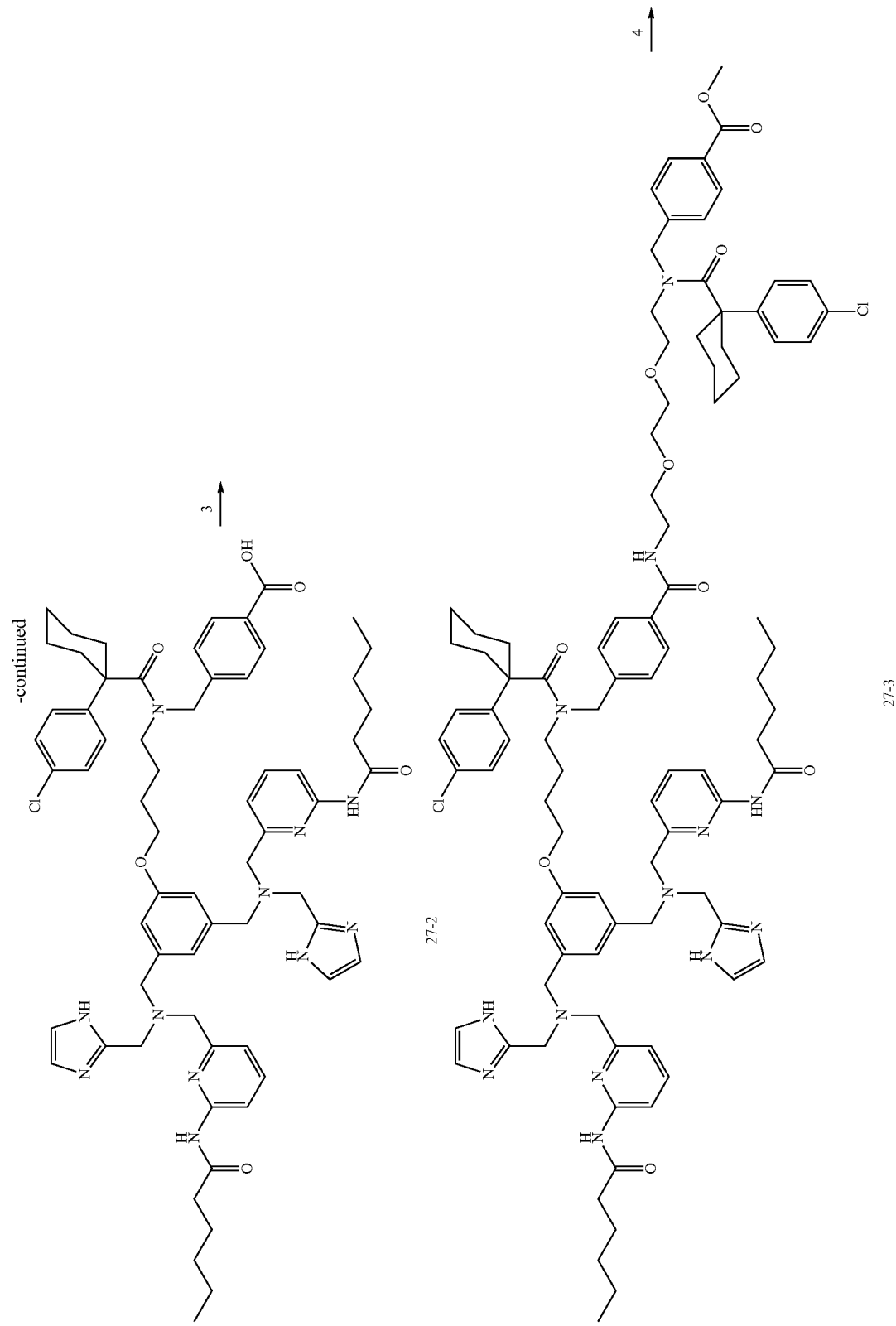

-continued
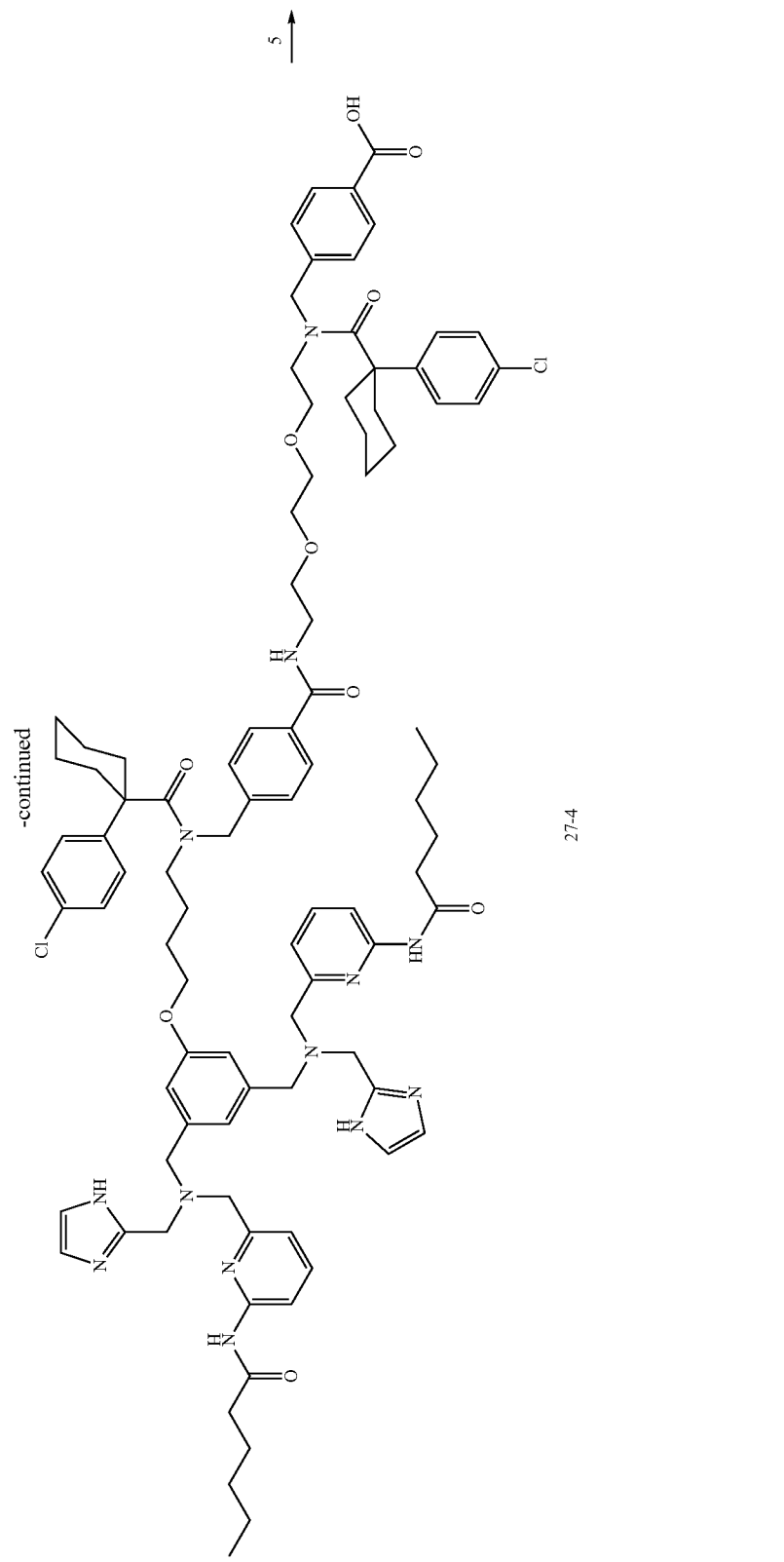
27-4

-continued
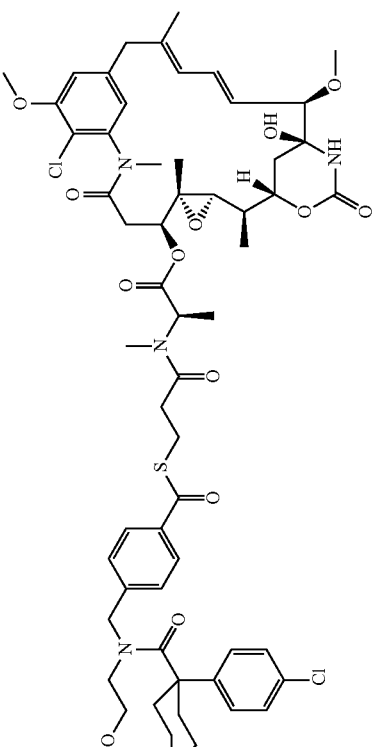
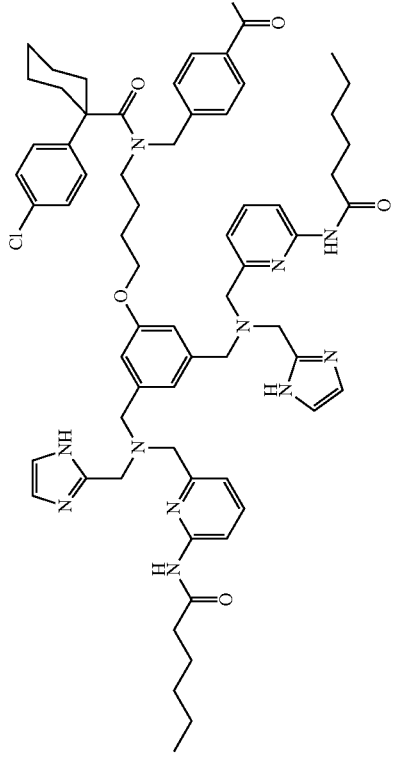
Compound 27
Scheme 43. Reagents and condition for preparing compound 27: (1). Methyl 4-formylbenzoate, MeOH; NaBH₄, MeOH; 1-(4-Chloro-phenyl)-cyclohexanecarbonyl chloride, Et3N, DCM. (2). LiOH, MeOH. (3). 4-({(2-[2-(2-Amino-ethoxy)-ethoxy]-ethyl}-[1-(4-chloro-phenyl)-cyclohexanecarbonyl]-amino}-methyl)-benzoic acid methyl ester, HOBt, EDCI, DCM. (4). LiOH, MeOH. (5). DM-1, DMAP, EDCI, DCM.

BPRDP0157 (300 mg, 0.37 mmol) was added into a solution of methyl 4-formylbenzoate (200 mg, 1.21 mmol) in MeOH. The reaction solution was stirred at room temperature for 2 hours. Sodium borohydride was then added to the resultant solution. MeOH was removed and the residue was dissolved in $CH_2Cl_2$. The protonated products were extracted from $CH_2Cl_2$ with 1 M HCl(aq.). The aqueous extract was neutralized and extracted with $CH_2Cl_2$. The organic extracts were combined, dried with $Na_2SO_4$, filtered, and concentrated. To the residue was added 1-(4-chlorophenyl)cyclohexanecarbonyl chloride and triethylamine in $CH_2Cl_2$. The reaction solution was stirred for 15 hours at room temperature and concentrated. The crude residue was purified by flash chromatography over silica gel to give compound 27-1 (160 mg, 0.13 mmol, 35%).

To a solution of compound 27-1 (160 mg, 0.13 mmol) in MeOH was added 0.5 M LiOH(aq.). The reaction solution was stirred at room temperature for 15 hours. The solvent removed and the residue was re-dissolved in $CH_2Cl_2$. The insoluble solid was filtered. The filtrate was washed with $CH_2Cl_2$, dried over $Na_2SO_4$, and concentrated under vacuum to give compound 27-2 as a yellow powder (137 mg, 0.12 mmol, 92%).

Compound 27-2 (136 mg, 0.12 mmol) was dissolved in $CH_2Cl_2$ at room temperature. 1-Ethyl-3-(3-dimethylaminopropyl)carbodiimide (EDCI, 60 mg, 0.38 mmol), hydroxybenzotriazole (HOBt, 60 mg, 0.44 mmol), and 4-({{2-[2-(2-Amino-ethoxy)-ethoxy]-ethyl}-[1-(4-chloro-phenyl)-cyclohexanecarbonyl]-amino}-methyl)-benzoic acid methyl ester (100 mg, 0.19 mmol) were added to the solution. The resultant reaction solution was stirred at room temperature for 2 hours and the solvent was removed. The crude residue was purified by flash chromatography over silica gel to give compound 27-3 (180 mg, 0.11 mmol, 91%). $^1$H NMR (400 MHz, cdcl$_3$) δ 8.36 (br, 2H), 7.67 (d, J=8.0 Hz, 2H), 7.53 (m, 3H), 7.21 (m, 3H), 6.86 (m, 14H), 6.57 (m, 4H), 6.09 (s, 1H), 4.15 (s, 2H), 3.81 (br, 3H), 3.49 (m, 3H), 3.13 (m, 26H), 1.81 (m, 11H), 1.25 (m, 18H), 0.84 (m, 14H), 0.46 (m, 3H).

To a solution of compound 27-3 (180 mg, 0.11 mmol) in MeOH was added 0.5 M LiOH(aq.). The reaction mixture was stirred at room temperature for 15 hours. The solvent was removed and the residue was re-dissolved in $CH_2Cl_2$. The insoluble solid was filtered. The filtrate was washed with $CH_2Cl_2$, dried over $Na_2SO_4$, and concentrated under vacuum to give compound 27-4 as a yellow powder (140 mg, 0.08 mmol, 72%).

Compound 27-4 (100 mg, 0.06 mmol) was added to a solution of DM-1 (70 mg. 0.09 mmol), DMAP (10 mg, 0.08 mmol), and EDCI (20 mg, 0.10 mmol) in 10 ml $CH_2Cl_2$. The reaction solution was stirred at room temperature for 1 hour, quenched with water, and extracted with $CH_2Cl_2$. The extract was condensed to give a residue. The residue was purified by flash chromatography over silica gel to give compound 27 (20 mg, 0.008 mmol, 13%). $^1$H NMR (400 MHz, cdcl$_3$) δ 8.72 (s, 2H), 8.07 (d, J=8.2 Hz, 2H), 7.74-7.52 (m, 6H), 7.28 (s, 1H), 7.24 (s, 1H), 7.22-7.13 (m, 7H), 6.97 (s, 6H), 6.91-6.83 (m, 2H), 6.77 (d, J=16.9 Hz, 2H), 6.66 (s, 1H), 6.52 (s, 2H), 6.43 (dd, J=13.2, 9.2 Hz, 2H), 5.65 (dd, J=15.2, 9.1 Hz, 1H), 5.43 (d, J=6.7 Hz, 1H), 4.73 (dd, J=12.0, 2.8 Hz, 1H), 4.54 (s, 1H), 4.32-4.02 (m, 4H), 3.95 (s, 3H), 3.88 (s, 1H), 3.79-3.41 (m, 28H), 3.37-3.19 (m, 9H), 3.10 (d, J=25.0 Hz, 5H), 3.00 (d, J=9.7 Hz, 2H), 2.92 (s, 1H), 2.80 (s, 3H), 2.71-2.61 (m, 1H), 2.61-2.51 (m, 1H), 2.32 (t, J=7.5 Hz, 6H), 2.15 (d, J=11.3 Hz, 16H), 1.36-1.17 (m, 23H), 0.87 (t, J=6.6 Hz, 6H), 0.79 (s, 3H). ESI-MS $C_{127}H_{159}Cl_3N_{16}O_{19}S^{2+}$: 1175.54, found: 1177.46. HPLC purity: 95%.

Zn-conjugates of the above-described compounds were prepared following the procedures set forth below. More specifically, each of Compounds 1-27 was mixed with 2 molar equivalents of zinc nitrate in a solution containing a solvent mixture of dichloromethane and methanol (1:1) at room temperature. The reaction mixture was sonicated to give a clear solution. The corresponding Zn-conjugate was obtained either by removal of the solvent under vacuum or by adding ethyl ether into the solution to form a precipitate.

Example 3: Tumor Growth Inhibition in Subcutaneous Xenograft Models

The efficacy of compounds 2 and 11 in inhibiting the growth of human pancreatic cancer cells (MIA PaCa-2) and the efficacy of compounds 1-4, 23, 25, and 26 in inhibiting the growth of human triple-negative breast cancer cells (HCC1806) were assessed as follows.

Male and female athymic NU-Fox1$^{nu}$ nude mice (BioLASCO, Taiwan) at age 4-5 weeks were housed in sterilized cages equipped with an air filter and sterile bedding materials at the Laboratory Animal Center of the National Health Research Institutes (NHRI), which is an AAALAC International accredited facility. All the mice were fed with sterilized water and chow ad libitum under 12-hr light/12-hr dark cycle throughout the study. The procedure and use of the animals were approved by the Institutional Animal Care and Use Committee of the National Health Research Institutes (Zhunan, Miaoli, Taiwan).

The MIA PaCa-2 and HCC1806 cells were suspended in phenol-red-free culture medium/Matrigel™ (1/1) and implanted subcutaneously (s.c.) into the left flank of the nude mice (1×10$^6$ cells/flank) via a 1 mL syringe. Tumor dimensions were measured twice a week using a digital caliper and the tumor volume (mm$^3$) was calculated based on the formula, i.e., volume=(length×width$^2$)/2.

Tumor-bearing mice were randomized (n=7-8 per group) when the average tumor volume reached approximately 200 mm$^3$. The mice were intravenously (i.v.) administered with vehicle (10% DMA/20% Cremophor EL/70% Dextrose 5% solution) as control and compounds (1-5 mg/kg) under two dosage regimens, i.e., once/week and twice/week for 1-3 weeks. Tumor size and body weight of each animal were measured twice a week. Data was expressed as the mean or mean±standard error of the mean (SEM). Statistical differences ($p<0.05$) between the tumor volumes of the vehicle-treated control and compound-treated groups were determined by using ANOVA followed by Student-Newman-Keuls multiple comparison test.

Figure 2:
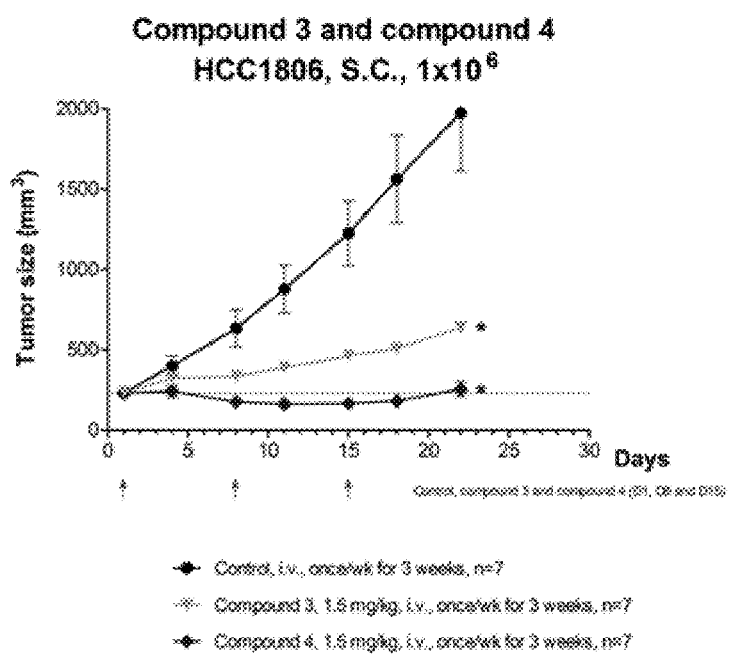
FIG. 2 shows efficacy of compounds 3 and 4 in inhibiting the growth of human triple-negative breast cancer cells lines HCC1806.
Figure 3:
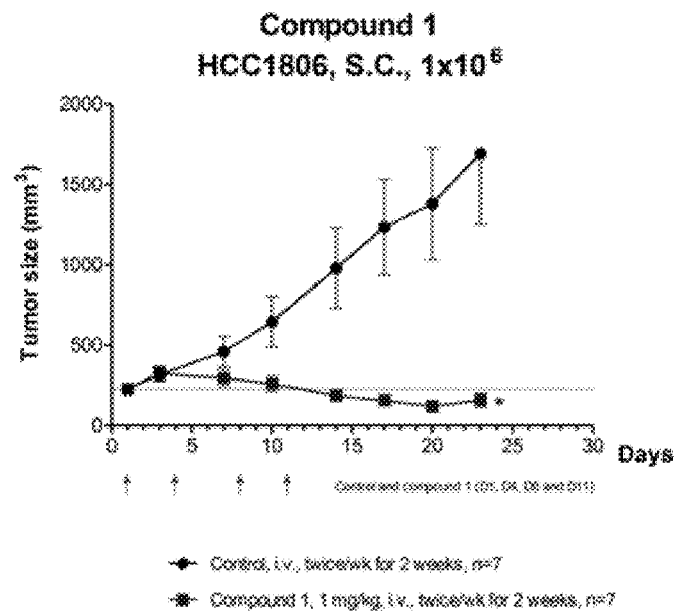
FIG. 3 shows efficacy of compound 1 in inhibiting the growth of human triple-negative breast cancer cells lines HCC1806.
Figure 4:
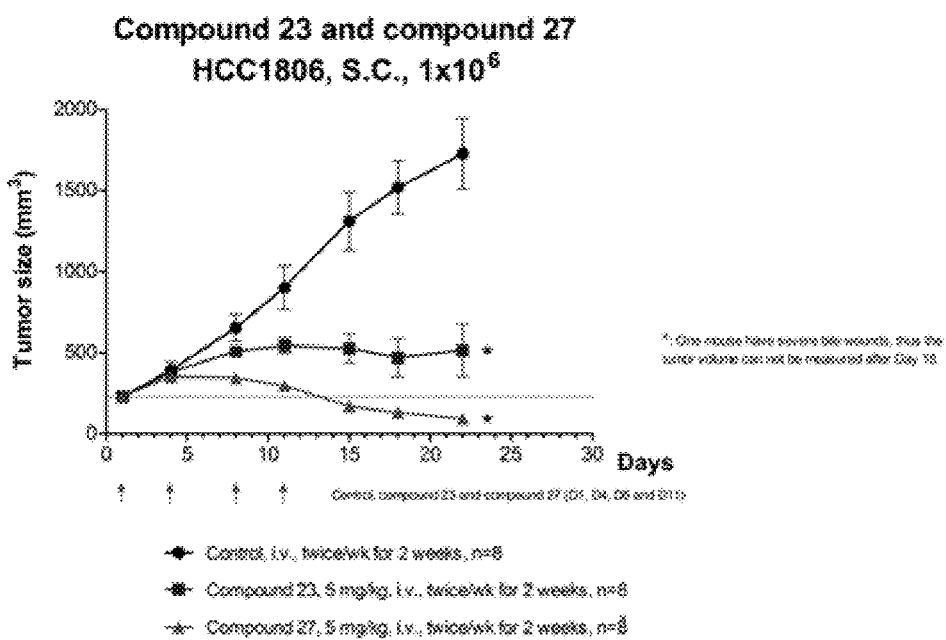
FIG. 4 shows efficacy of compounds 23 and 27 in inhibiting the growth of human triple-negative breast cancer cells lines HCC1806.
Figure 5:
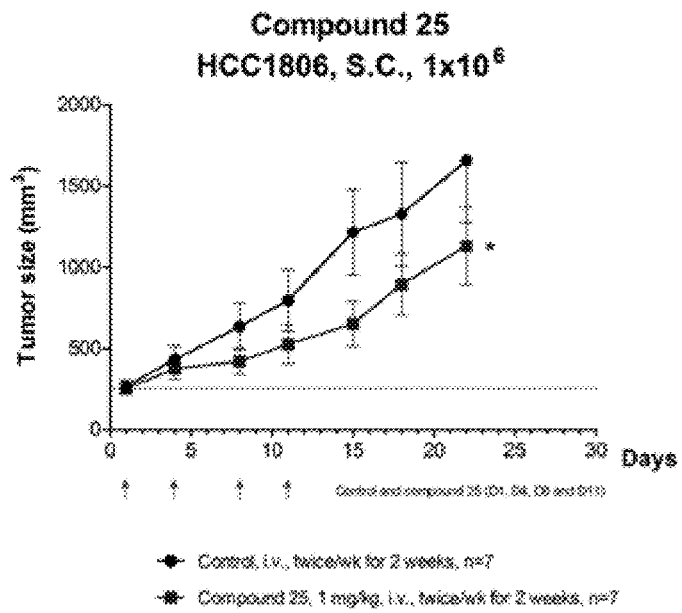
FIG. 5 shows efficacy of compound 25 in inhibiting the growth of human triple-negative breast cancer cells lines HCC1806.
Figure 6:
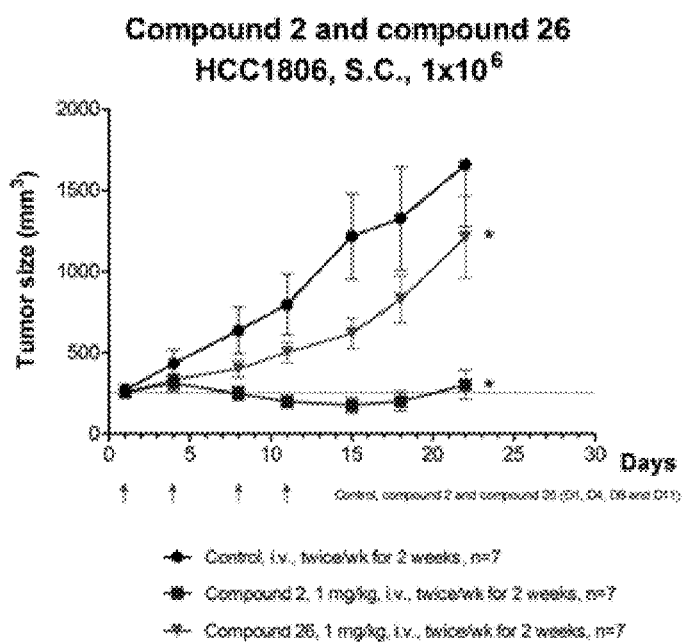
FIG. 6 shows efficacy of compounds 2 and 26 in inhibiting the growth of human triple-negative breast cancer cells lines HCC1806.

As shown in FIGS. 1-6 below, compounds 2 and 11 significantly inhibited the growth of MIA PaCa-2 (see FIG. 1) and compounds 1-4, 23, 25, and 26 significantly inhibited the growth of HCC1806 (see FIGS. 2-6).

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the

US 11,878,986 B2

289 invention to adapt it to various usages and conditions. For example, compounds structurally analogous to the compounds of this invention also can be made, screened for their efficacy in treating a condition that relates to cells containing inside-out phosphatidylserine. Thus, other embodiments are also within the claims.

What is claimed is:

1. A compound of Formula (I):

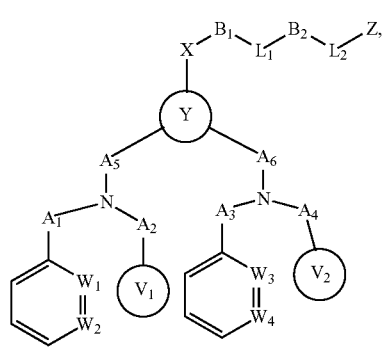

(I)

in which each of $A_1$, $A_2$, $A_3$, $A_4$, $A_5$, and $A_6$, independently, is a $C_1$-$C_6$ bivalent aliphatic radical;

$B_1$ is a bond, $C_1$-$C_6$ bivalent aliphatic radical, a $C_1$-$C_6$ bivalent heteroaliphatic radical, or CHC(O)$R_1$, in which $R_1$ is a $C_1$-$C_6$ monovalent aliphatic radical, a $C_1$-$C_6$ monovalent heteroaliphatic radical, a monovalent aryl radical, a monovalent heteroaryl radical, a $C_1$-$C_{14}$ monovalent aralkyl radical, or a $C_1$-$C_{14}$ monovalent heteroaralkyl radical;

290

-continued

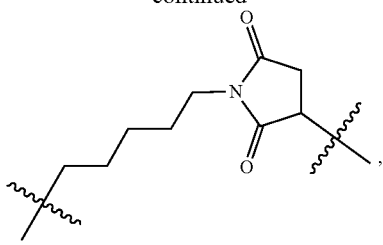

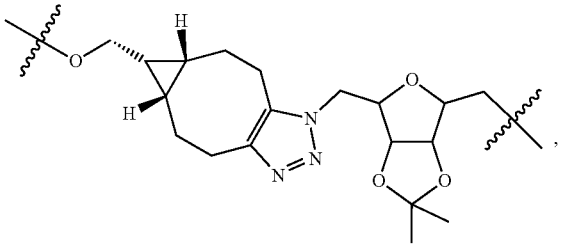

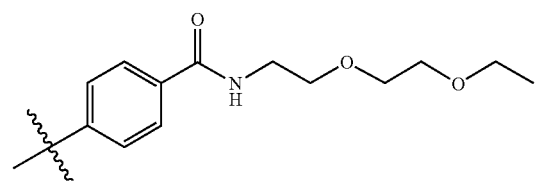

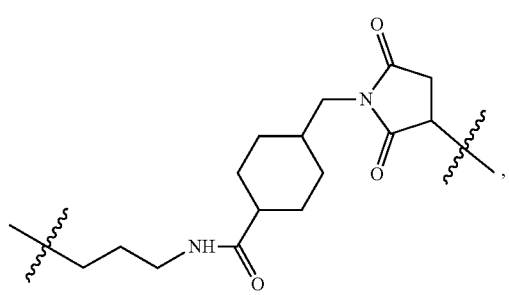

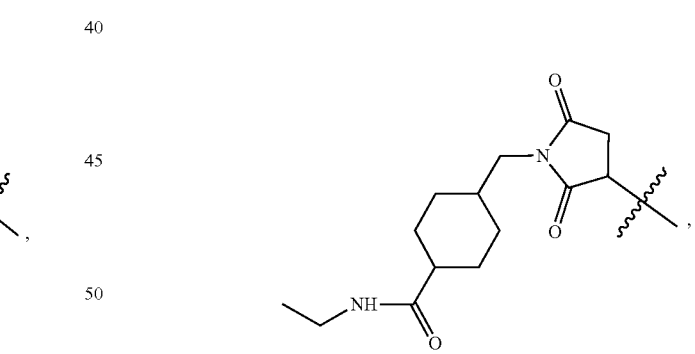

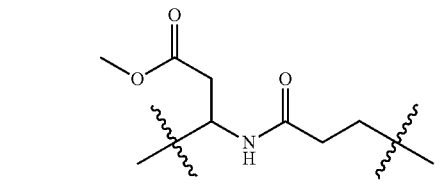

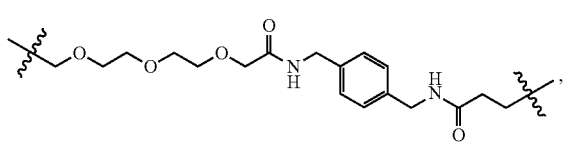

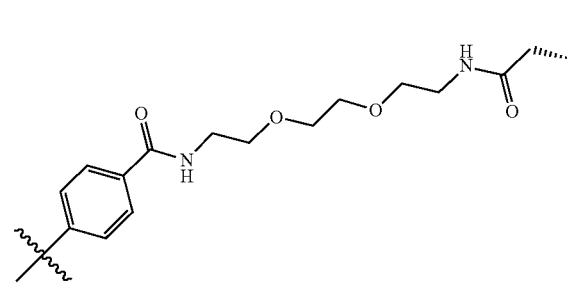

291
-continued
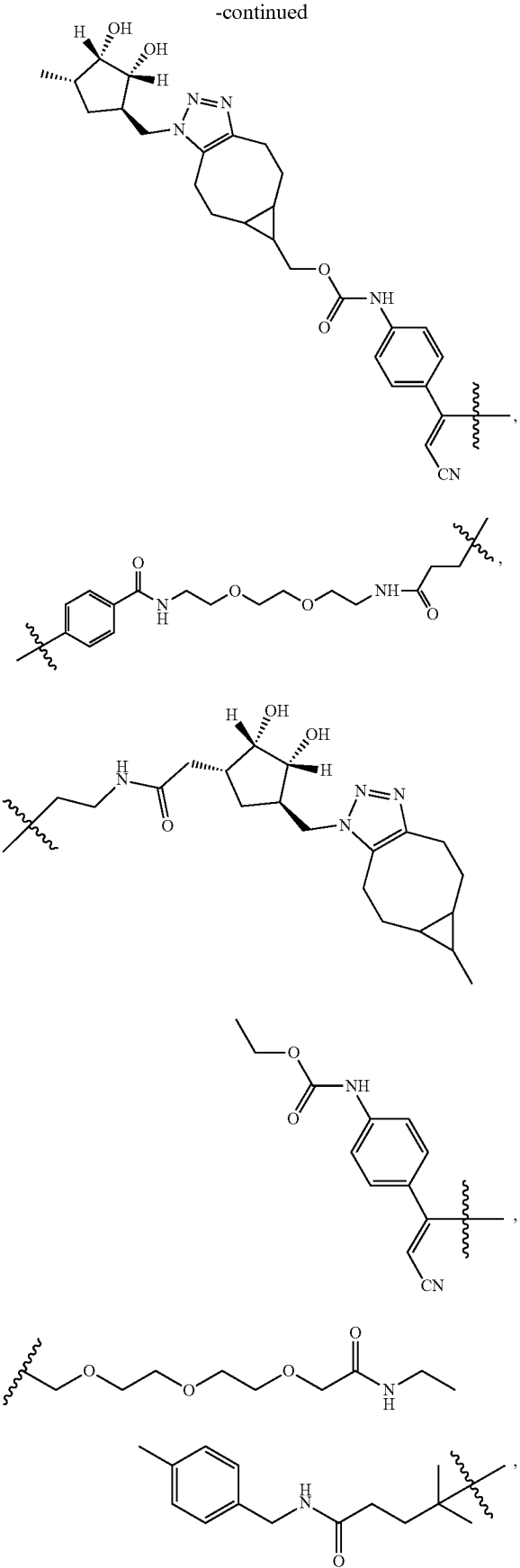
292
-continued
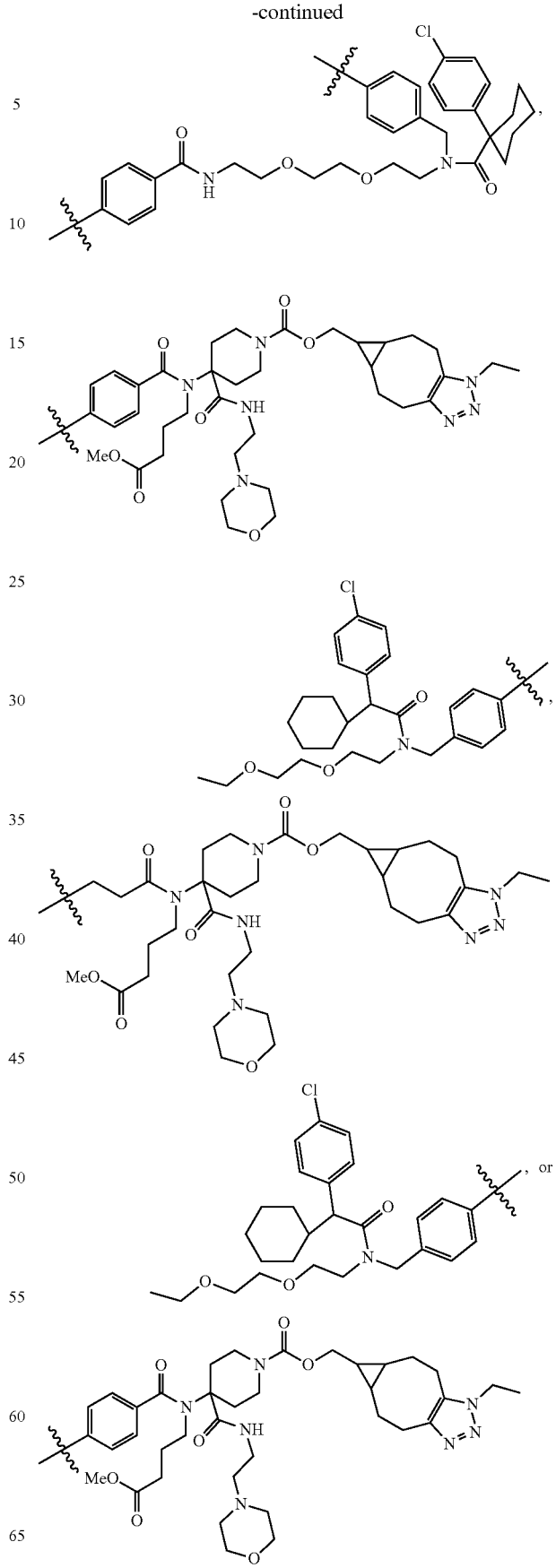

-continued

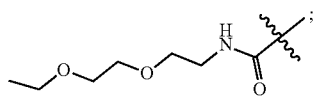

$B_2$ is a bond, ethylene, phenylene, $L_1$ is a bond, $NR_3$, $NR_3C(O)$, or $NR_3CR_4R_5$, each of $R_3$, $R_4$, and $R_5$, independently, being H, a $C_1$-$C_6$ monovalent aliphatic radical, a $C_1$-$C_6$ monovalent heteroaliphatic radical, a monovalent aryl radical, a monovalent heteroaryl radical, a $C_1$-$C_{14}$ monovalent aralkyl radical, a $C_1$-$C_{14}$ monovalent heteroaralkyl radical, or $C(O)R'$, in which $R'$ is a $C_1$-$C_6$ monovalent aliphatic radical, a $C_1$-$C_6$ monovalent heteroaliphatic radical, a monovalent aryl radical, a monovalent heteroaryl radical, a $C_1$-$C_{14}$ monovalent aralkyl radical, or a $C_1$-$C_{14}$ monovalent heteroaralkyl radical;

$L_2$ is

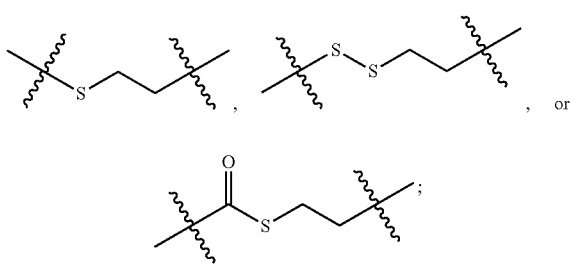

each of $W_1$, $W_2$, $W_3$, and $W_4$, independently, is N or $CR_5'$, $R_5'$ being H, $NHC(O)R_9$, or $NHC(O)NHR_9$, in which $R_9$ is a $C_1$-$C_6$ monovalent aliphatic radical, a $C_1$-$C_6$ monovalent heteroaliphatic radical, a monovalent aryl radical, a monovalent heteroaryl radical, a $C_1$-$C_{14}$ monovalent aralkyl radical, or a $C_1$-$C_{14}$ monovalent heteroaralkyl radical;

X is a bond or O;
Y is a phenyl ring;
each of $V_1$ and $V_2$, independently, is an aryl ring or a heteroaryl ring; and
Z is an anticancer therapeutic moiety;
wherein each of the aliphatic radical, the heteroaliphatic radical, the aralkyl radical, and the heteroaralkyl radical is unsubstituted or substituted with halo, cyano, amino, hydroxyl, nitro, sulfhydryl, $C_1$-$C_6$ alkoxy, $C_1$-$C_6$ alkylamino, $C_1$-$C_{12}$ dialkylamino, or $C_1$-$C_6$ haloalkyl; and
each of the phenyl ring, the aryl radical, and the heteroaryl radical is unsubstituted or substituted with halo, cyano, amino, hydroxyl, nitro, sulfhydryl, a $C_1$-$C_6$ aliphatic radical, a $C_1$-$C_6$ heteroaliphatic radical, or a haloaliphatic radical.

2. The compound of claim 1, in which
each of $A_1$, $A_2$, $A_3$, $A_4$, $A_5$, and $A_6$ is methylene;
$L_1$ is a bond or $NR_3C(O)$;
X is O;
Y is

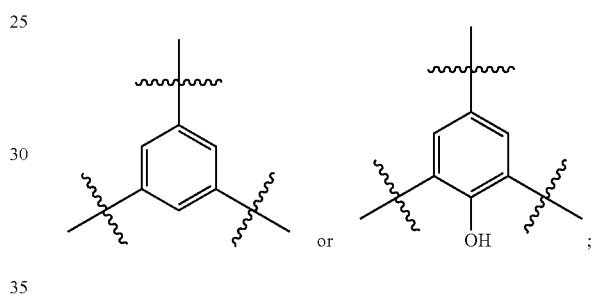

and
each of $V_1$ and $V_2$, independently, is a phenyl ring, a five-member heteroaryl ring, or a six-member heteroaryl ring.

3. The compound of claim 2, in which each of $W_2$ and $W_4$, independently, is $CR_5'$, $R_5'$ being H or $NHC(O)R_9$, and $R_9$ being a $C_4$-$C_6$ monovalent aliphatic radical.

4. The compound of claim 3, in which Z is

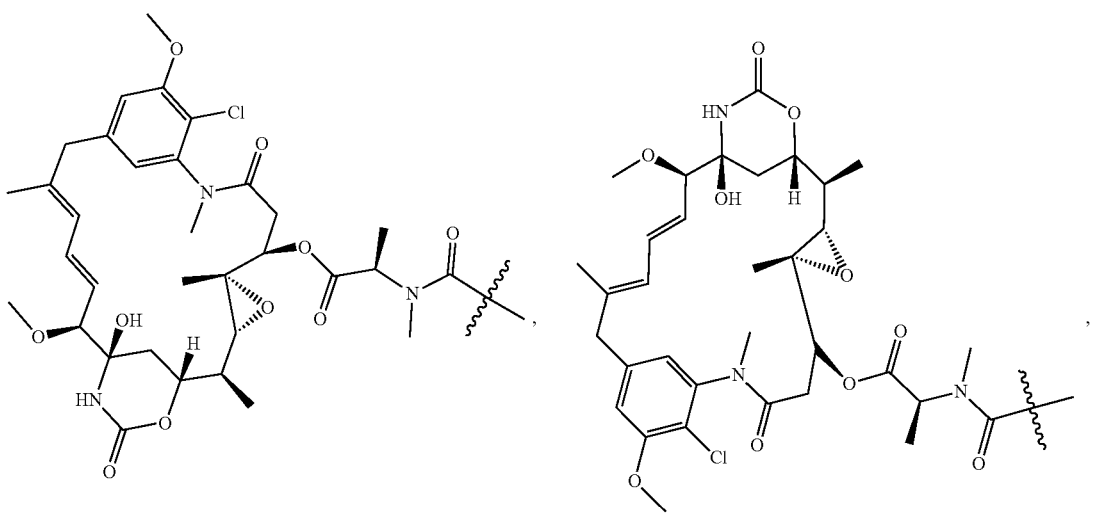

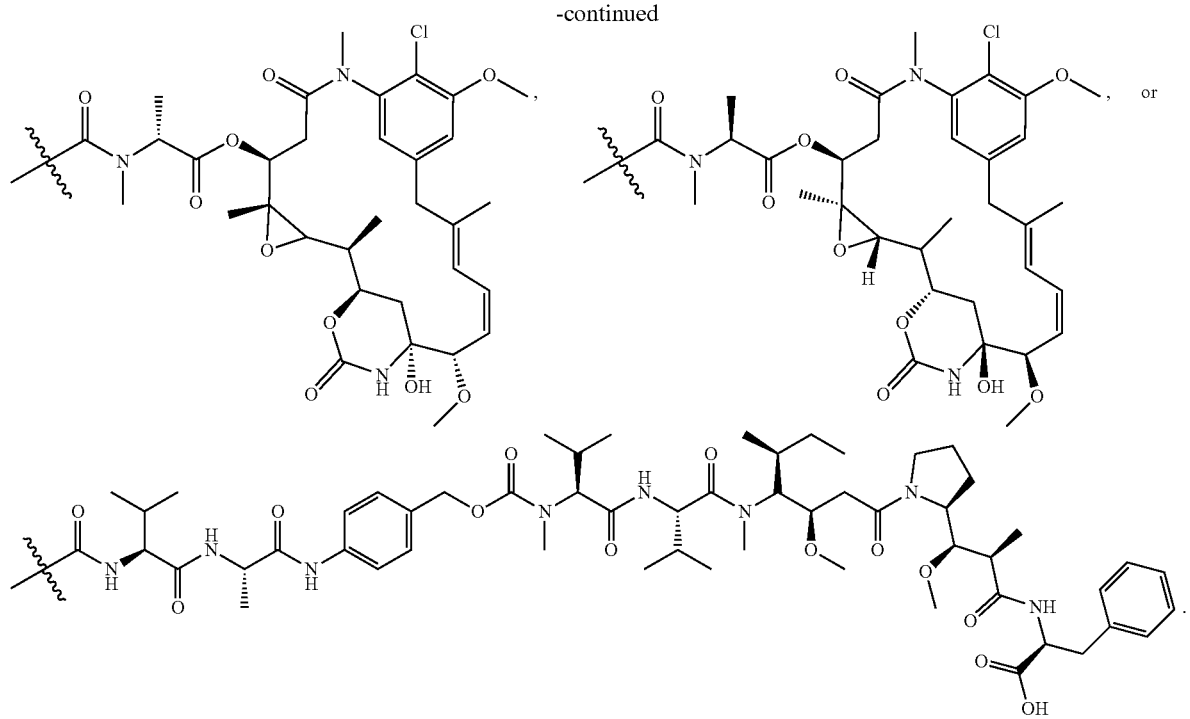

5. The compound of claim 1,
in which
each of $A_1$, $A_2$, $A_3$, $A_4$, $A_5$, and $A_6$ is methylene;
$B_1$ is a $C_1$-$C_6$ bivalent aliphatic radical or a $C_1$-$C_6$ bivalent heteroaliphatic radical;
$L_1$ is $NR_3C(O)$;
$L_2$ is

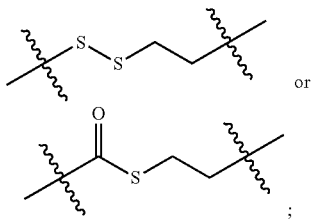

each of $W_1$, $W_2$, $W_3$, and $W_4$, independently, is N or $CR_5'$, $R_5'$ being H or $NHC(O)R_9$, and $R_9$ being a $C_1$-$C_6$ monovalent aliphatic radical;
X is O;
Y is and
each of $V_1$ and $V_2$, independently, is a pyridine ring.

6. The compound of claim 5, in which each of $W_2$ and $W_4$, independently, is $CR_5'$.

7. The compound of claim 6, in which Z is

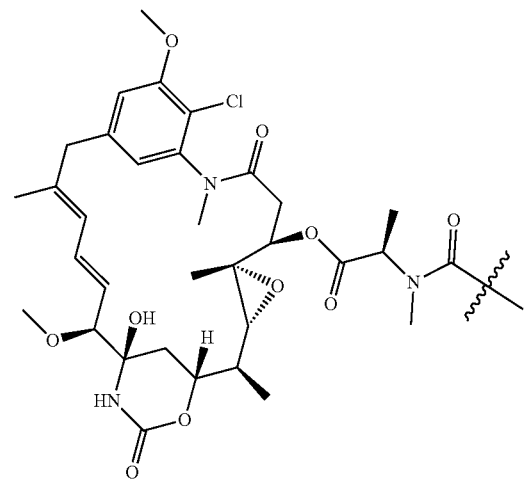

8. The compound of claim 5, in which $B_2$ is
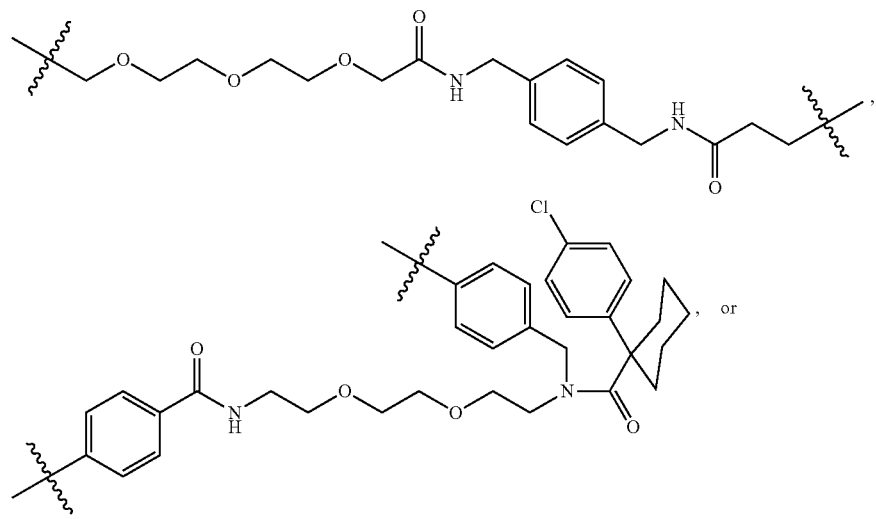
, or
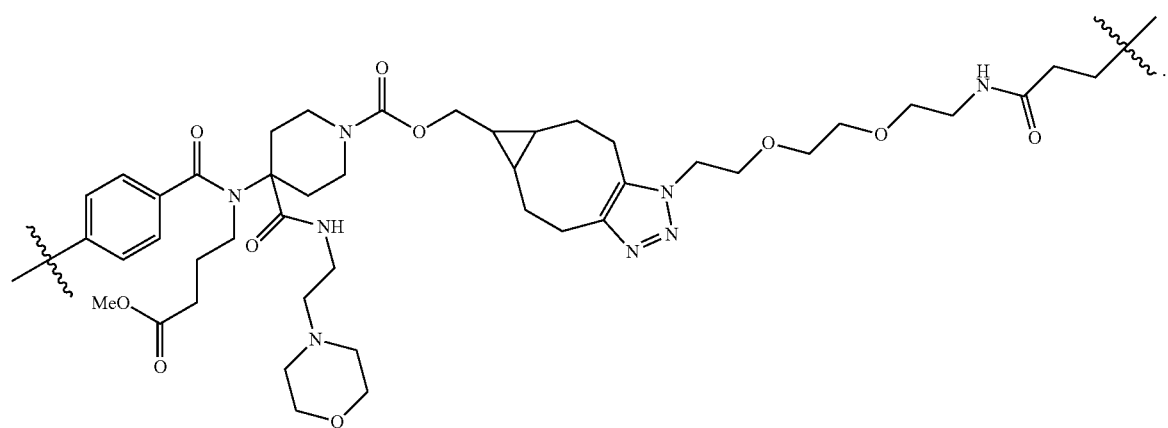
9. A compound having one of the following structures:
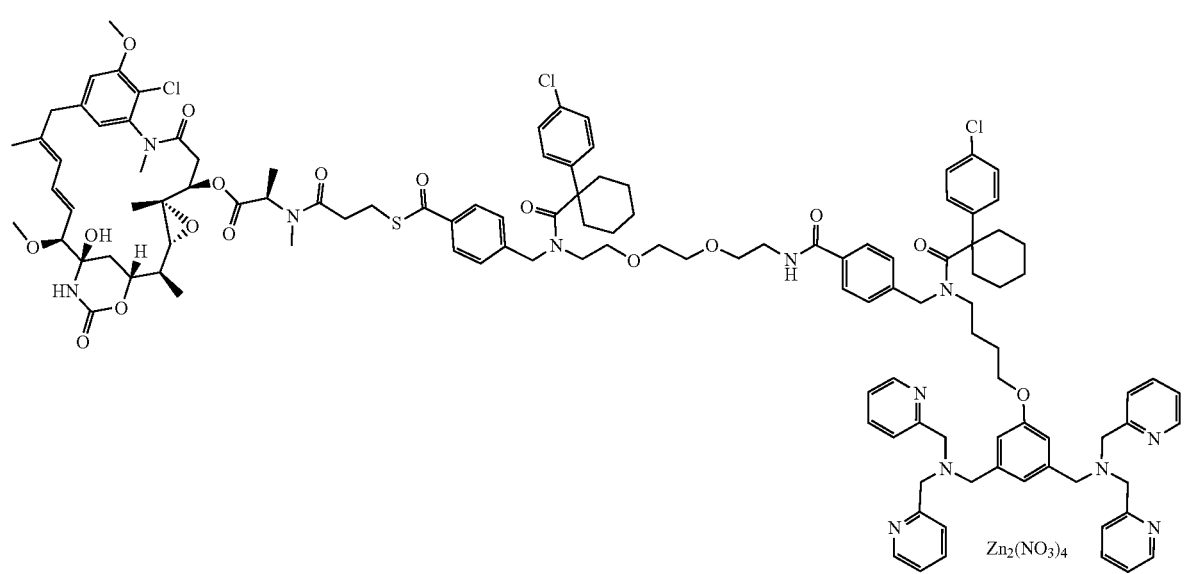

299 300
-continued
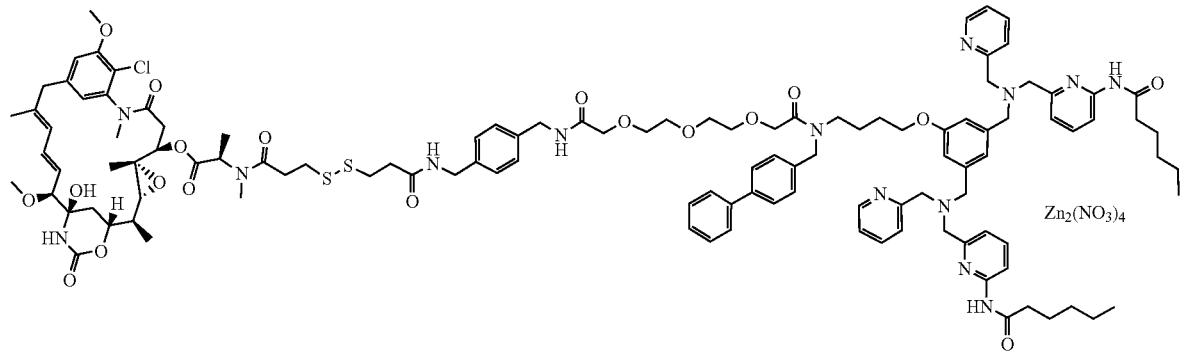
2
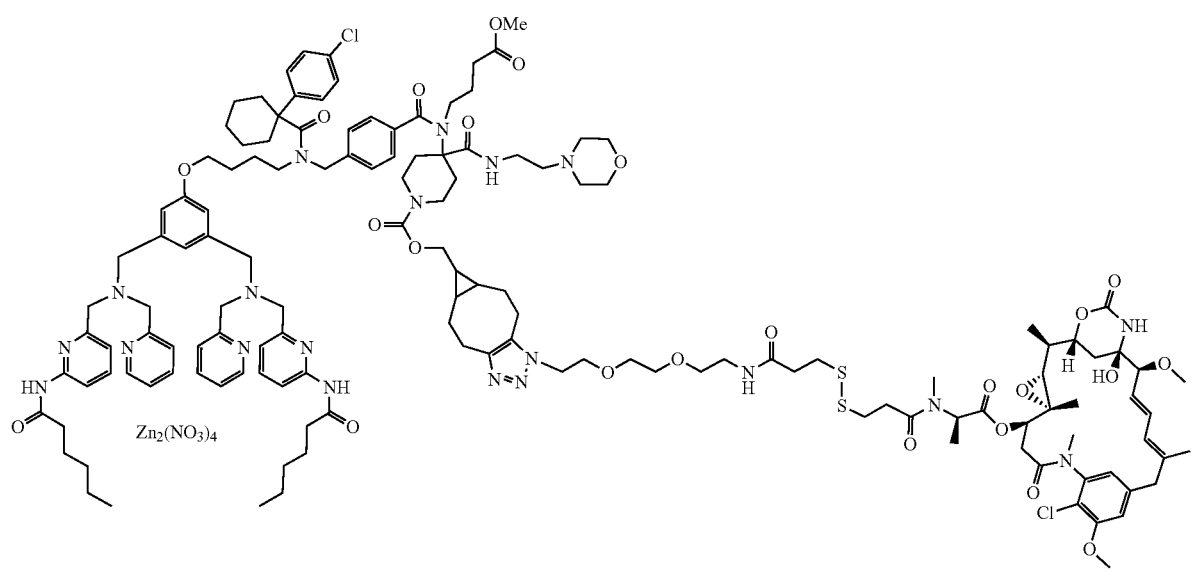
3
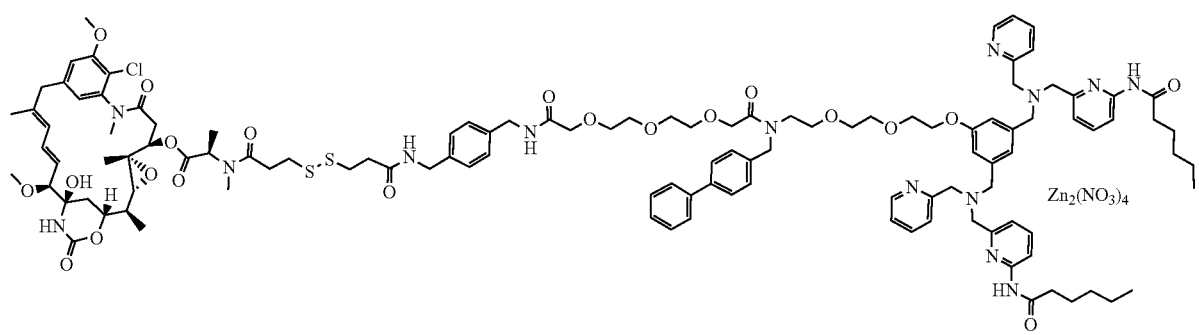
4

-continued
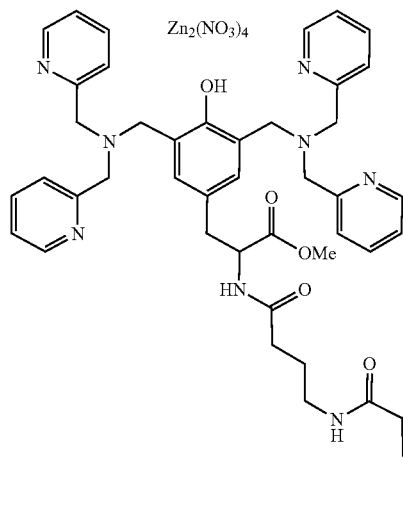
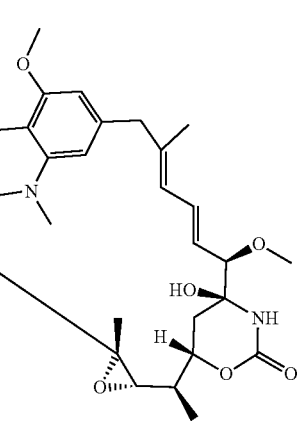
5
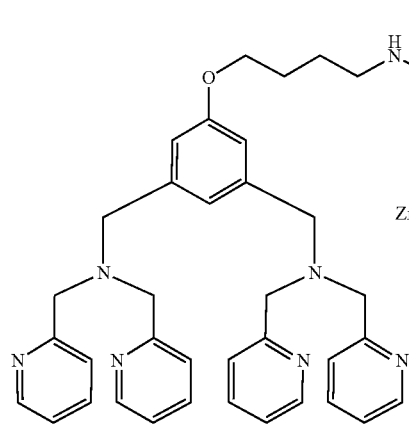
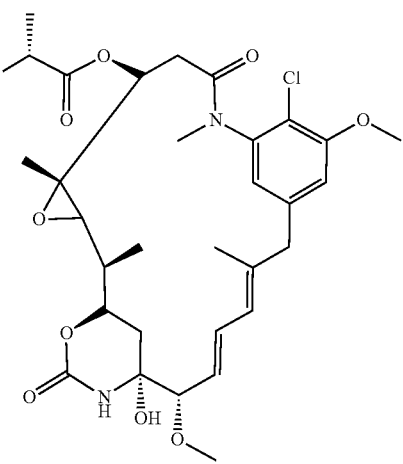
6
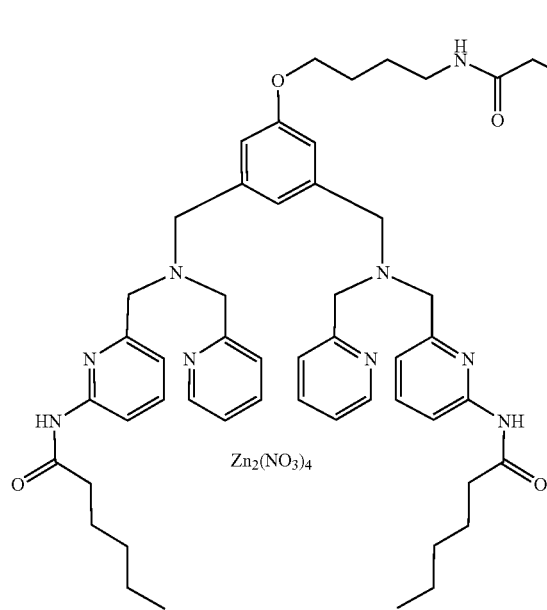
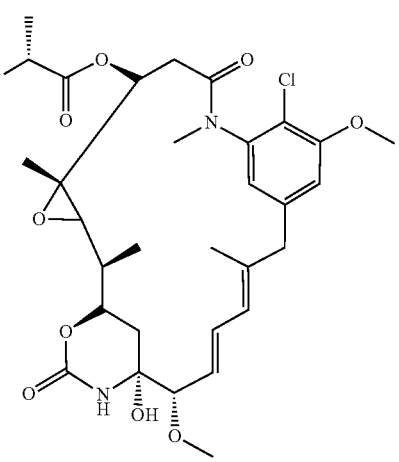
7

-continued
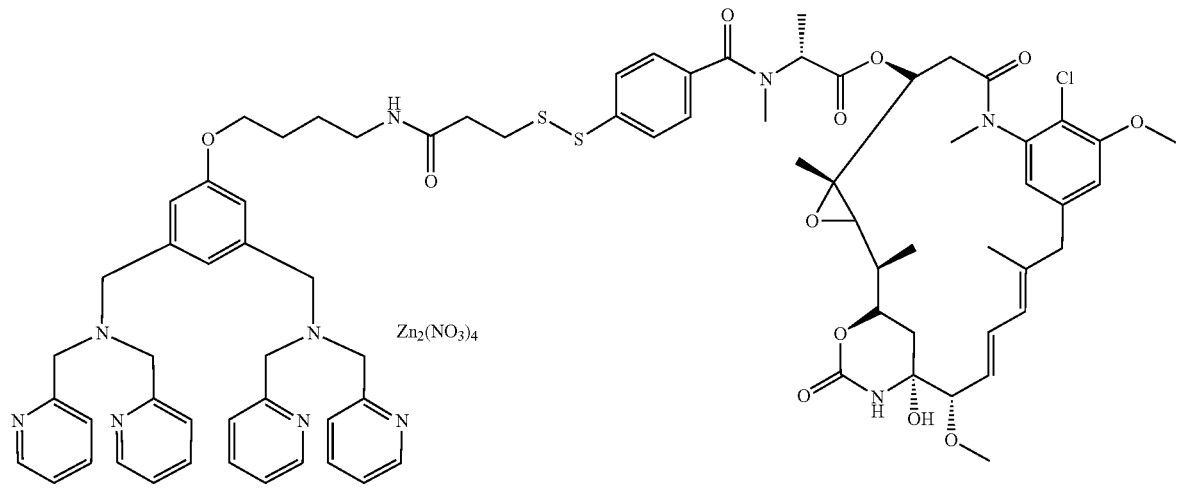
8
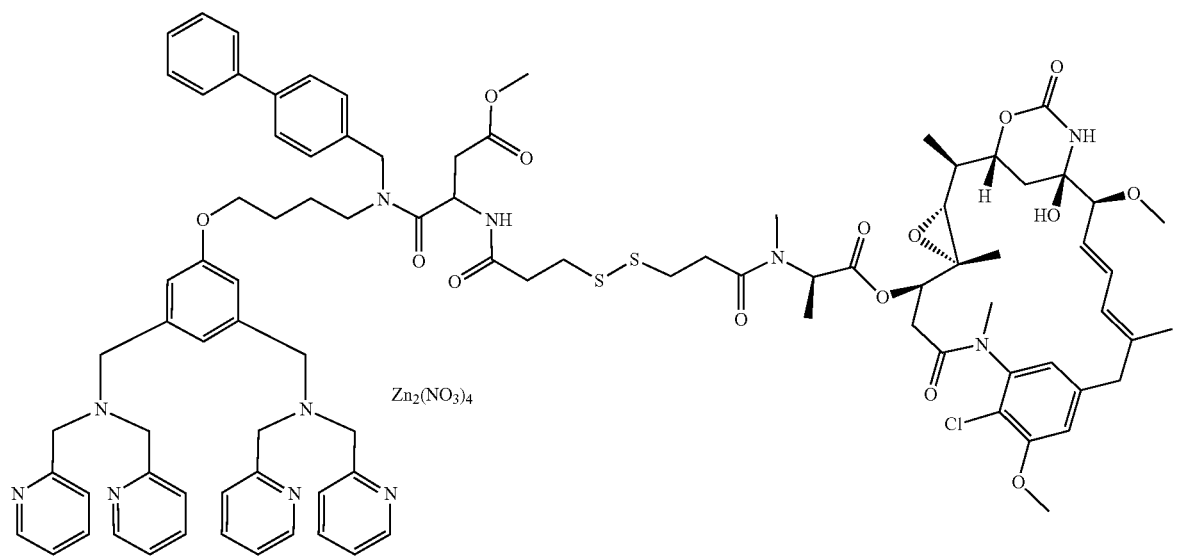
9
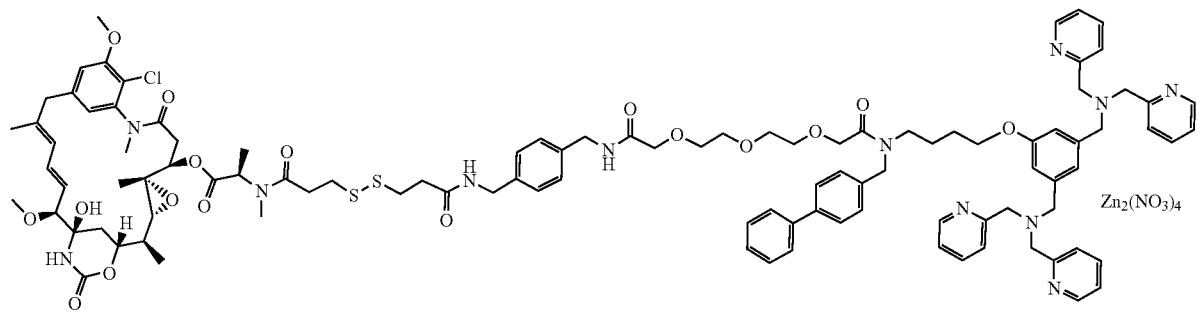
10

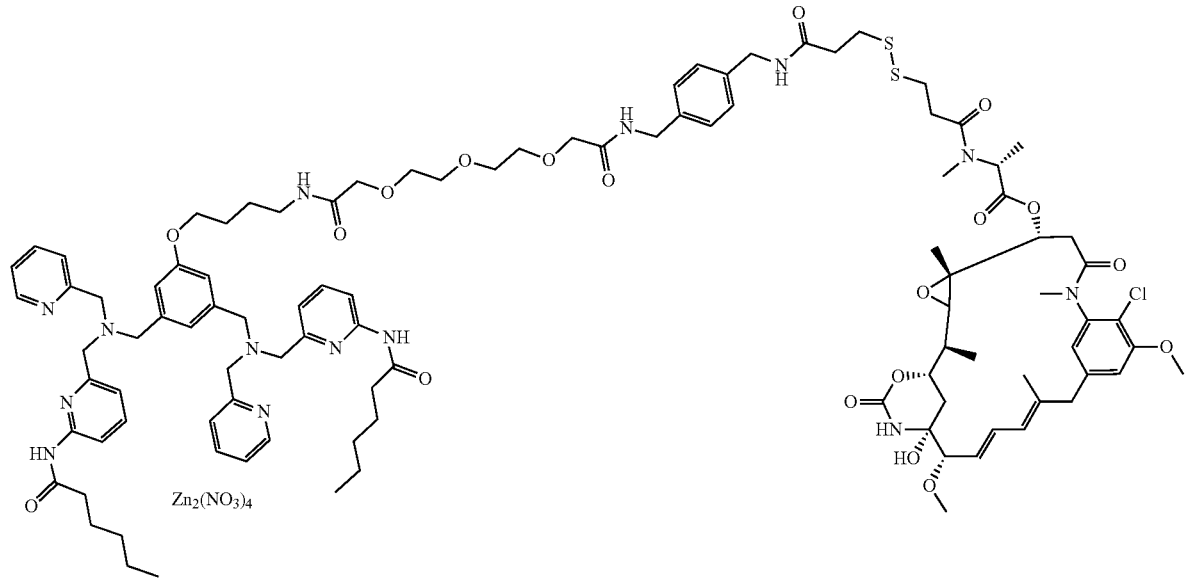
11
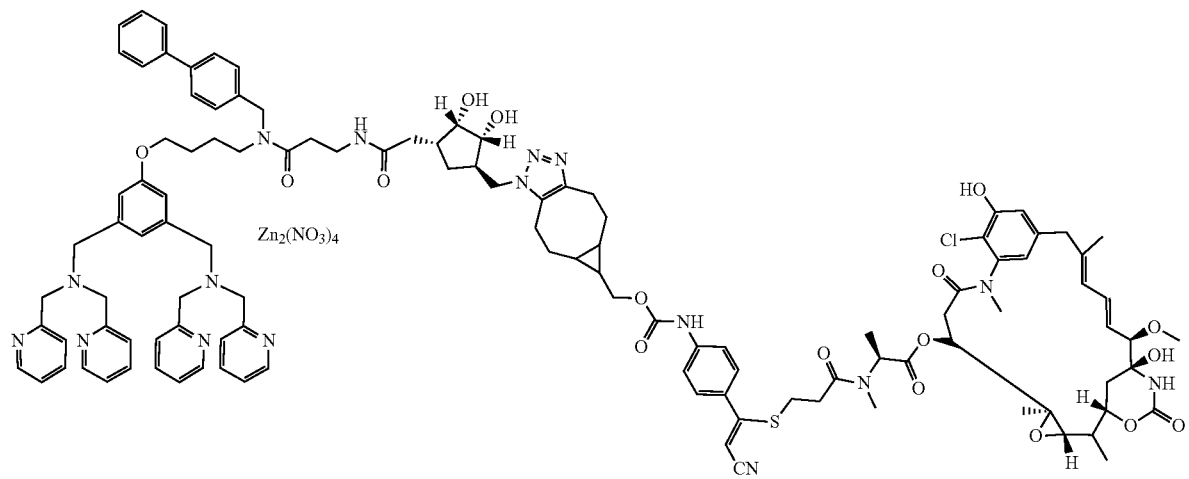
12
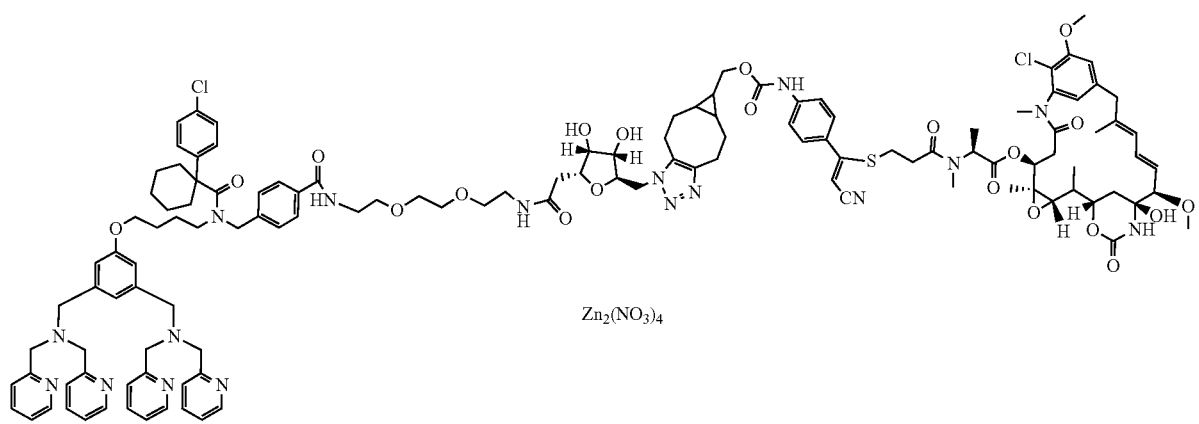
13

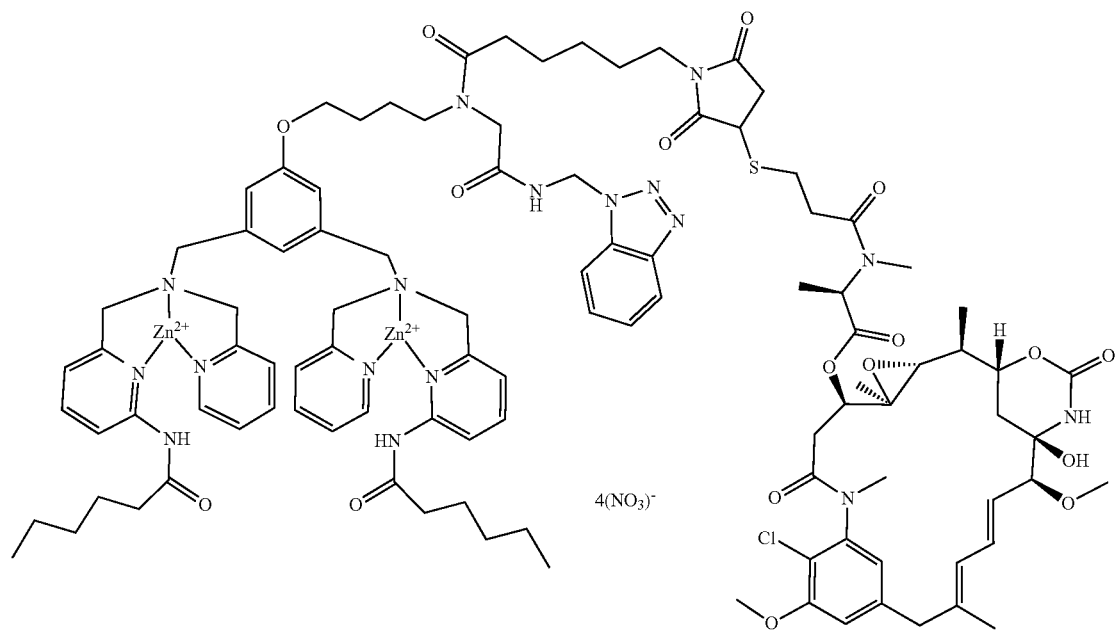
14
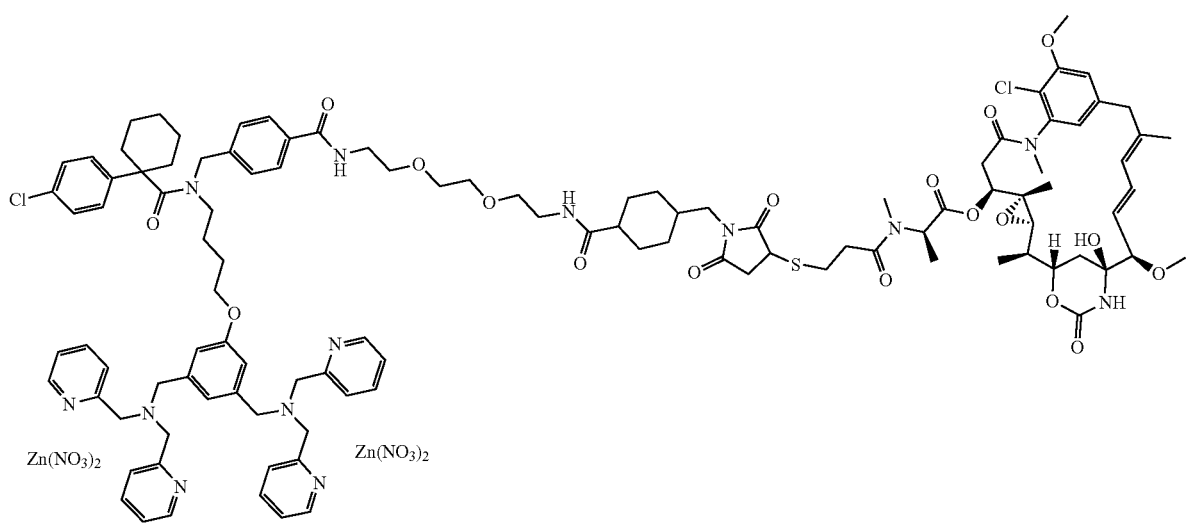
15

-continued
16
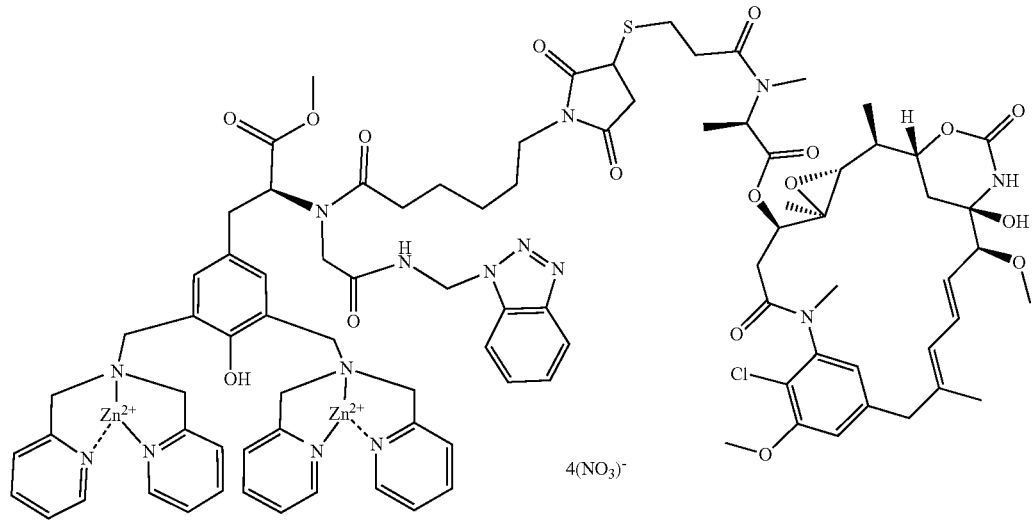
17
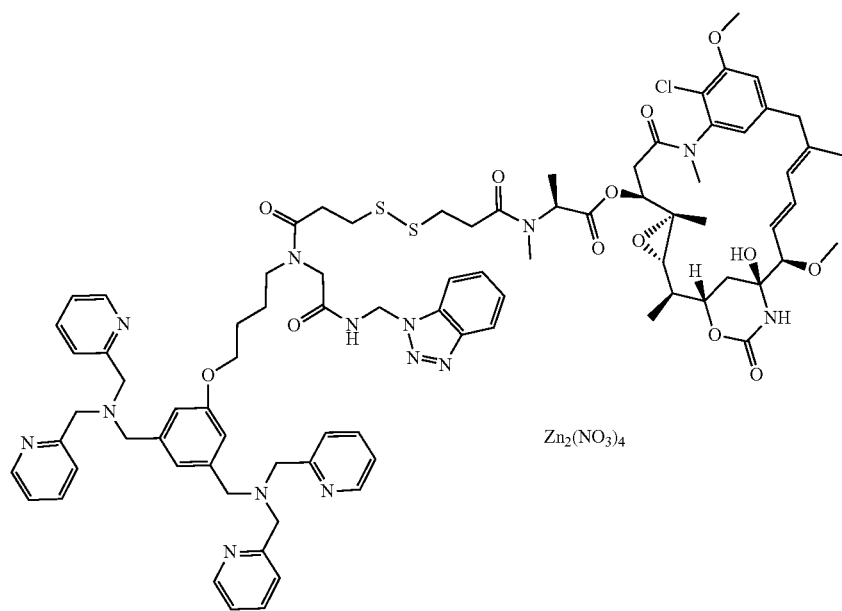
18
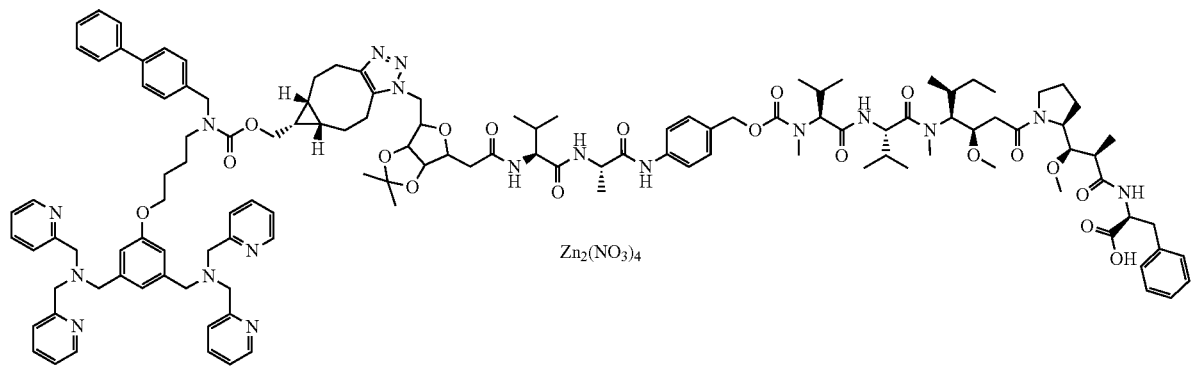

-continued
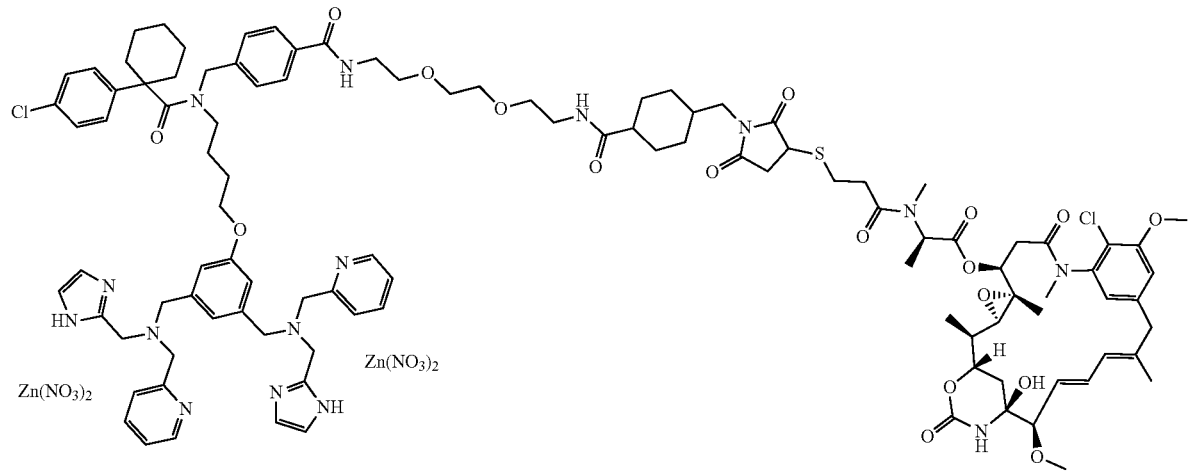
19
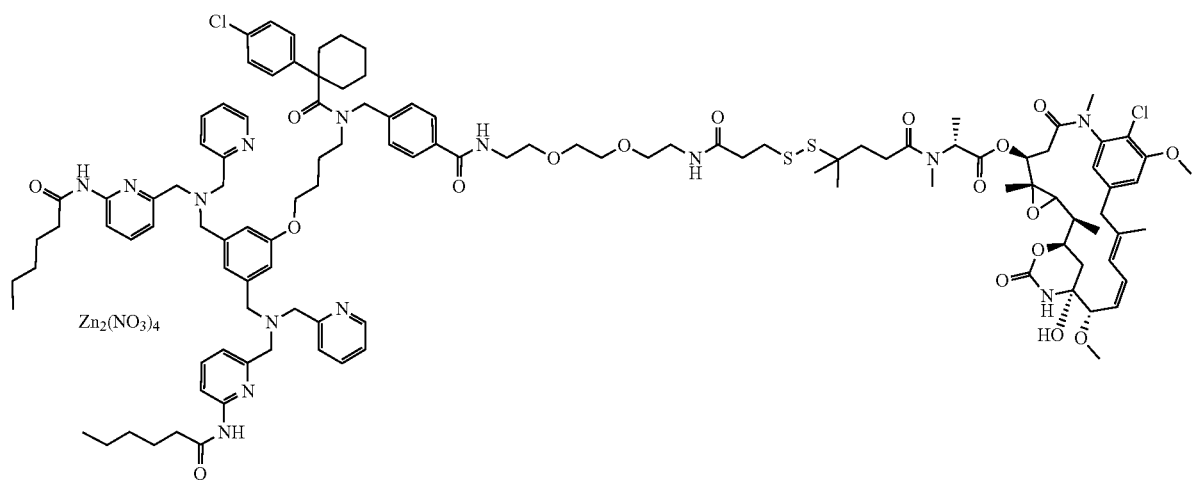
20
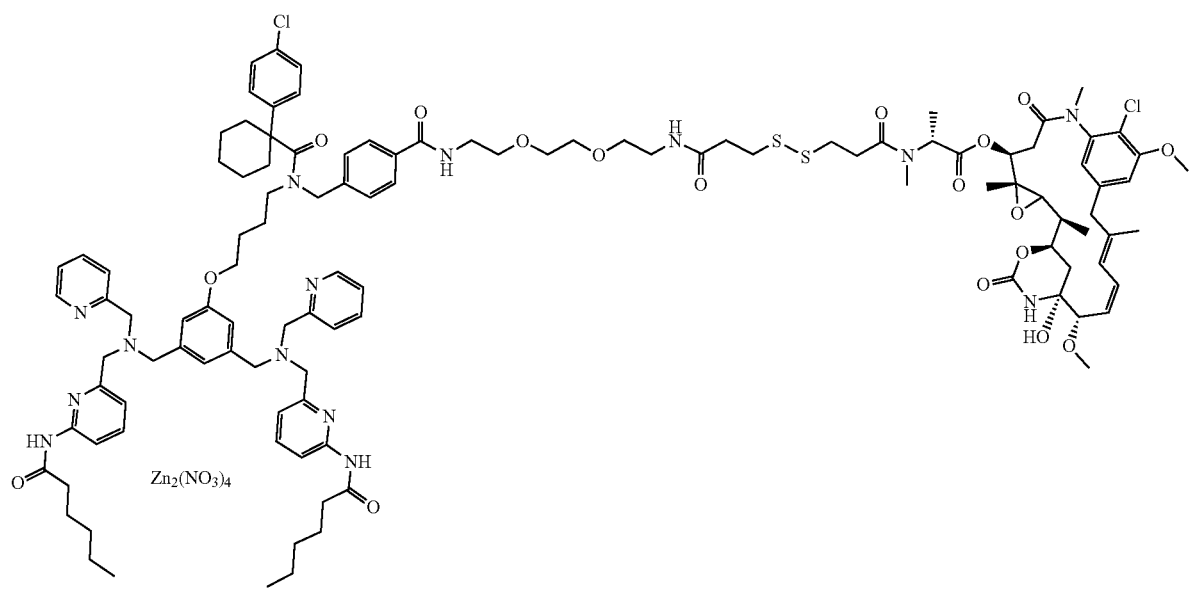
21

-continued
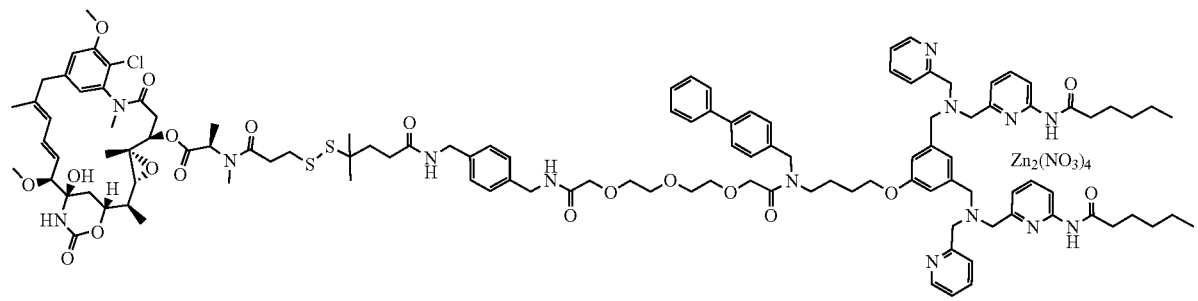
22
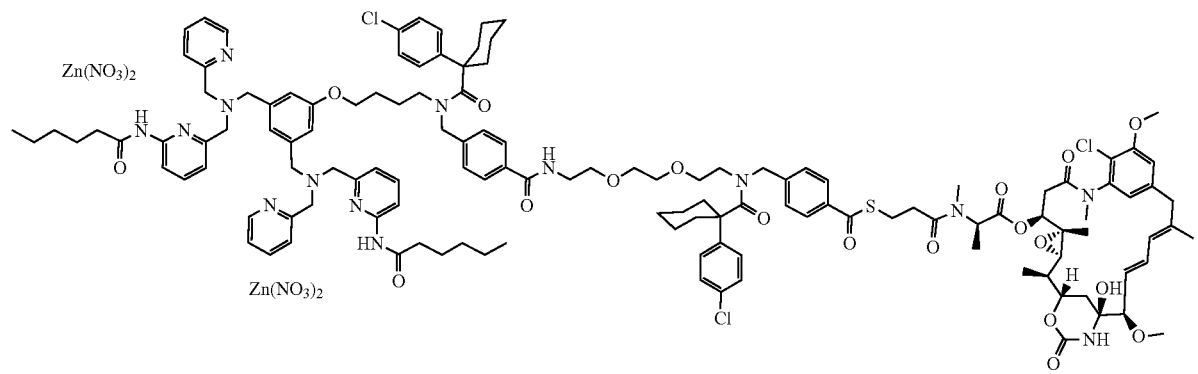
23
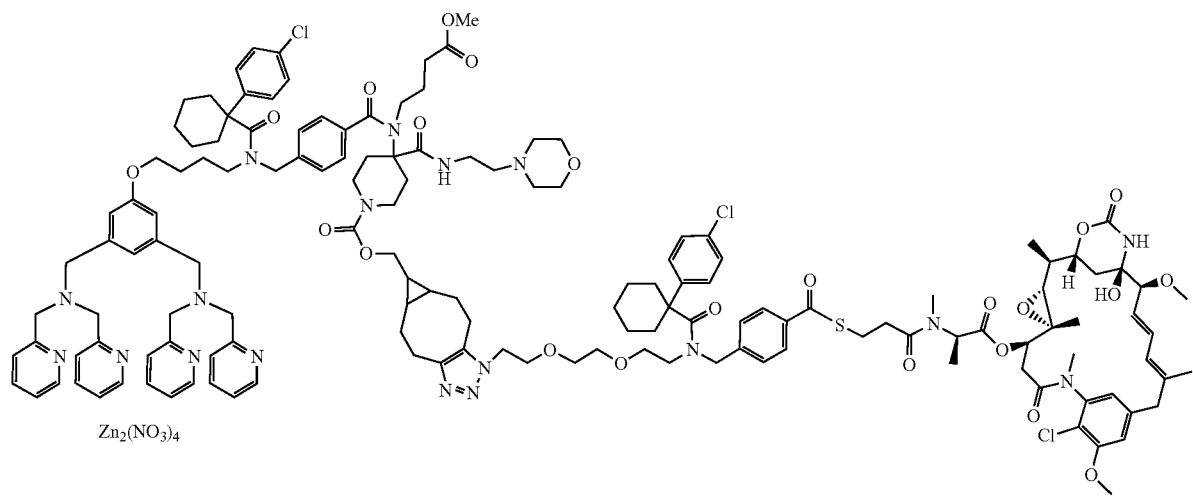
24

-continued
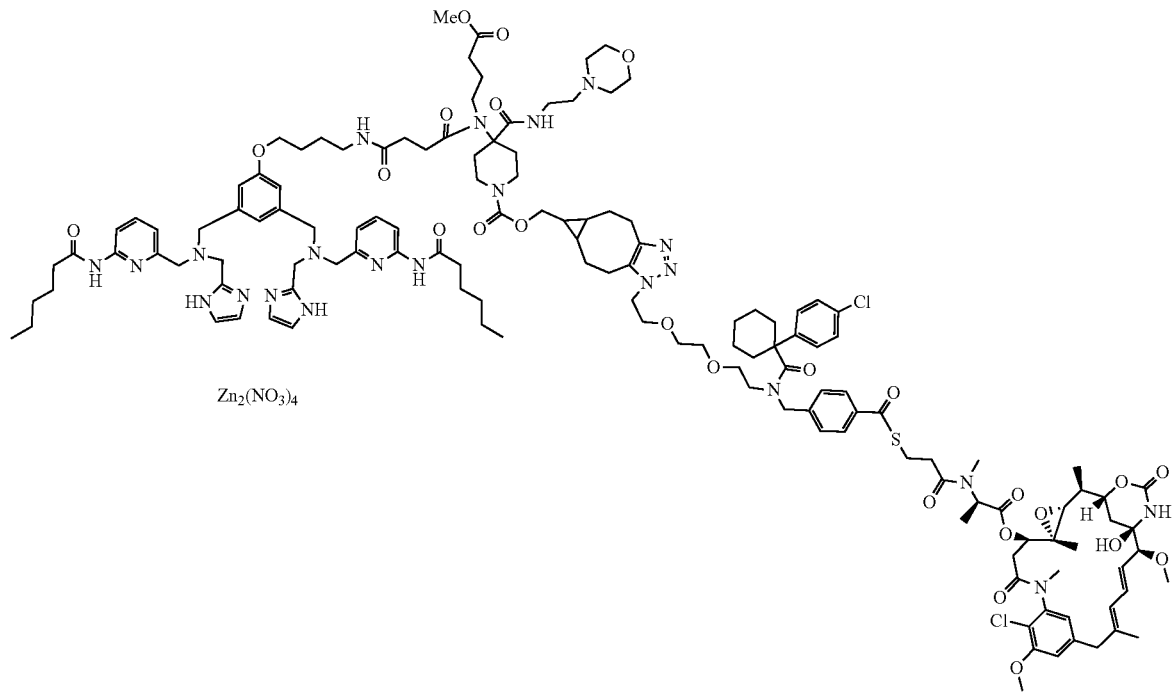
25
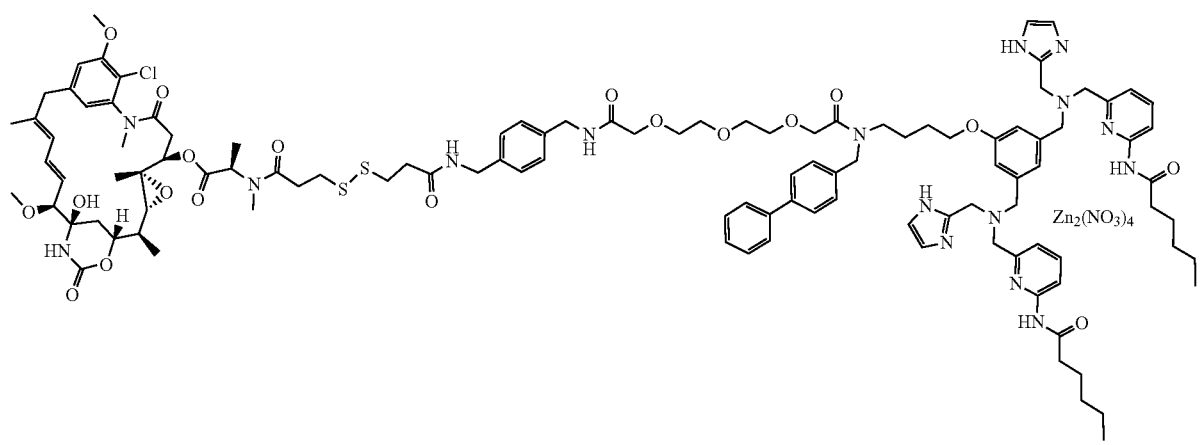
26
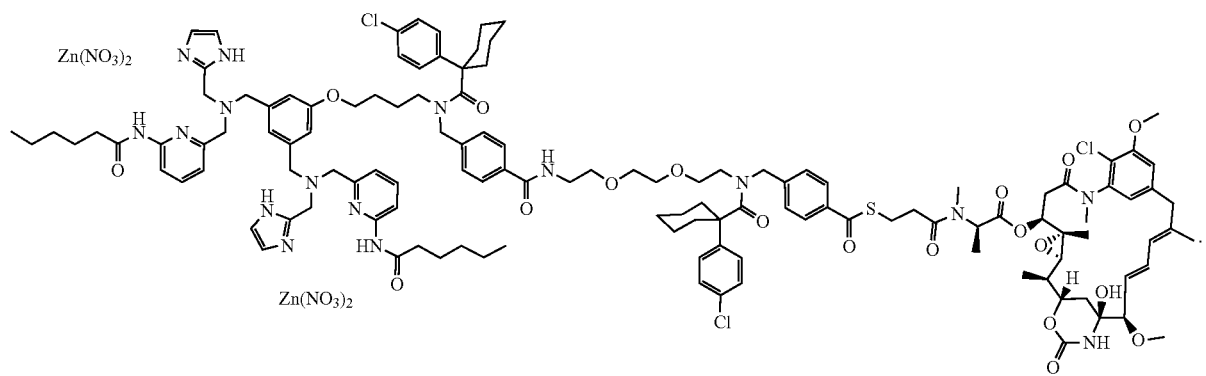
27

10. The compound of claim 9 having one of the following structures:
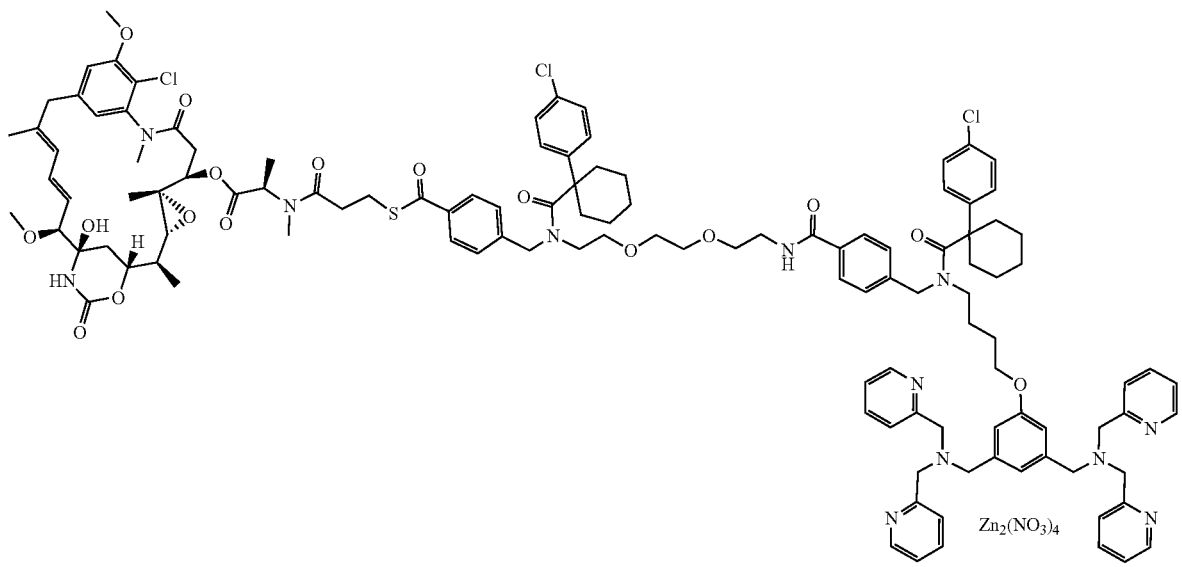
1
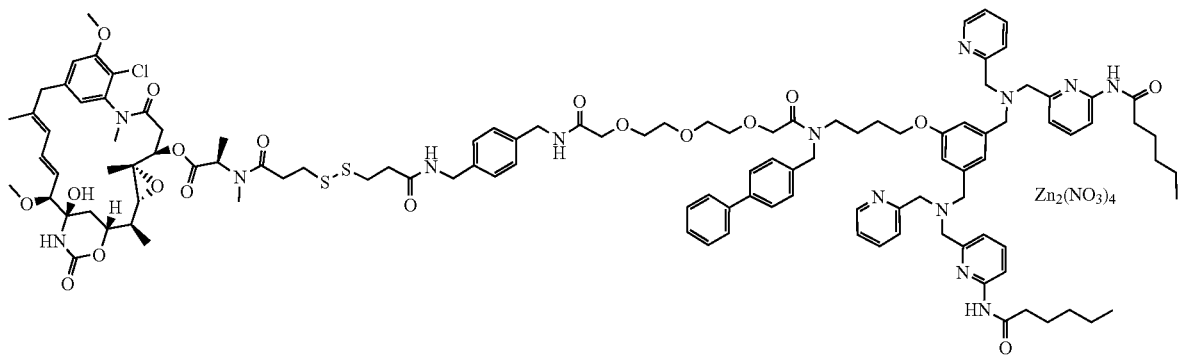
2
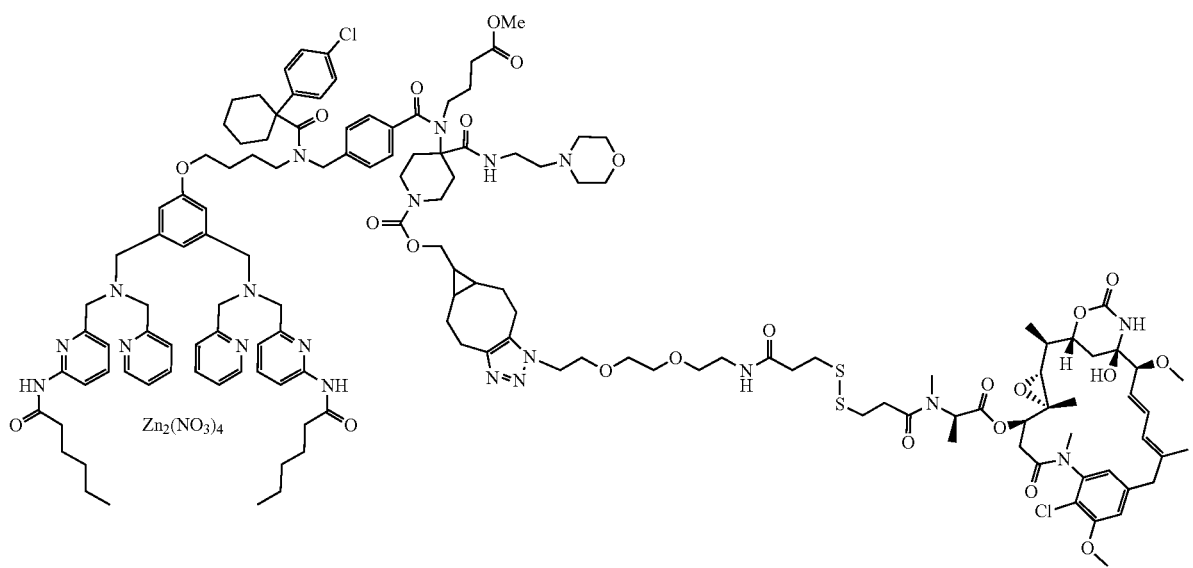
3

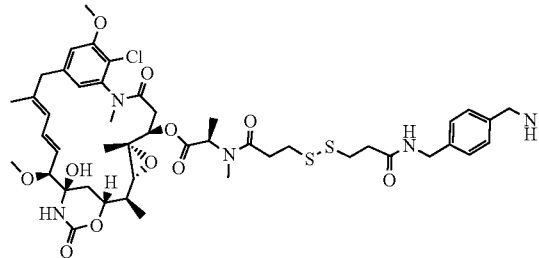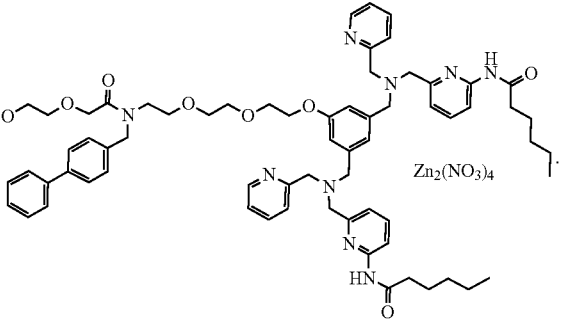

11. A method of treating a condition associated with uncontrolled cell growth, the method comprising administering to a subject in need thereof an effective amount of the compound of claim 1, wherein the condition is pancreatic cancer or triple-negative breast cancer.

12. A pharmaceutical composition comprising the compound of claim 1 and a pharmaceutically acceptable carrier.

13. The compound of claim 1, in which each of $W_2$ and $W_4$, independently, is $CR_5'$, $R_5'$ being $NHC(O)R_9$ and $R_9$ being a $C_4$-$C_6$ monovalent aliphatic radical.

14. A method of treating a condition associated with uncontrolled cell growth, the method comprising administering to a subject in need thereof an effective amount of the compound of claim 9, wherein the condition is pancreatic cancer or triple-negative breast cancer.

15. A pharmaceutical composition comprising the compound of claim 9 and a pharmaceutically acceptable carrier.

* * * * *

UNITED STATES PATENT AND TRADEMARK OFFICE
CERTIFICATE OF CORRECTION

PATENT NO. : 11,878,986 B2  
APPLICATION NO. : 17/349140  
DATED : January 23, 2024  
INVENTOR(S) : Lun Kelvin Tsou et al.

Page 1 of 1

It is certified that error appears in the above-identified patent and that said Letters Patent is hereby corrected as shown below:

In the Claims

Claim 1, Column 293, Line 39, replace "$R_5$' beijng" with "$R_5$' being".

Signed and Sealed this  
Fifteenth Day of April, 2025

Coke Morgan Stewart  
*Acting Director of the United States Patent and Trademark Office*